United States Patent [19]

Pasteris

[11] Patent Number: 4,586,950
[45] Date of Patent: May 6, 1986

[54] NOVEL PHENYL-SUBSTITUTED SULFONAMIDES

[75] Inventor: Robert J. Pasteris, Wilmington, Del.

[73] Assignee: E. I. Du Pont de Nemours & Company, Wilmington, Del.

[21] Appl. No.: 533,341

[22] Filed: Sep. 20, 1983

Related U.S. Application Data

[63] Continuation-in-part of Ser. No. 499,443, May 31, 1982, abandoned, which is a continuation-in-part of Ser. No. 437,632, Oct. 29, 1982, abandoned.

[51] Int. Cl.$^4$ ............... C07D 417/12; A01N 47/36
[52] U.S. Cl. ............................................. 71/92; 71/90; 71/91; 71/93; 544/49; 544/204; 544/212; 544/253; 544/278; 544/321; 544/323; 544/324; 544/331; 544/332

[58] Field of Search ............... 71/92, 90, 91; 544/321, 544/331, 332, 212, 49, 278, 253, 324, 323

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,369,320 | 1/1983 | Levitt et al. | 544/320 |
| 4,492,596 | 1/1985 | Pasteris | 71/90 |

FOREIGN PATENT DOCUMENTS

| | | | |
|---|---|---|---|
| 0079683 | 10/1982 | European Pat. Off. | |
| 99339 | 1/1984 | European Pat. Off. | 71/90 |

*Primary Examiner*—Robert Gerstl

[57] ABSTRACT

Herbicidal sulfonamides are useful as general or selective herbicides, both pre-emergence and post-emergence.

59 Claims, No Drawings

NOVEL PHENYL-SUBSTITUTED SULFONAMIDES

BACKGROUND OF THE INVENTION

This invention relates to 1,2-benzothiazinesulfonamides, 2,1-benzothiazinesulfonamides, 1,2-benzisothiazolesulfonamides, 2,1-benzisothiazolesulfonamides, 1,2-benzoxathiinsulfonamides, 2,1-benzoxathiinsulfonamides, 1,2-benzoxathiolesulfonamides, 2,1-benzoxathiolesulfonamides, 2-quinolonesulfonamides, 1-isoquinolonesulfonamides, 2-oxindolesulfonamides, 1-oxisoindolesulfonamides, benzo[b]pyran-2-onesulfonamides, benzo[c]pyran-1-onesulfonamides, benzo[c]pyran-3-onesulfonamides, benzo[c]thiopyran-1-onesulfonamides, benzo[b]furan-2-onesulfonamides, benzo[c]furan-1-onesulfonamides, benzo[c]thiophen-1-onesulfonamides, 1-tetralonesulfonamides, 2-tetralonesulfonamides, 1-indanonesulfonamides, 2-indanonesulfonamides, benzo[b]-furan-3-onesulfonamides, benzo[b]pyran-4-onesulfonamides, 1,2-benzothiazepinesulfonamides, 2,1-benzothiazepinesulfonamides, 2-benzoxepin-1[5H]-onesulfonamides, 1-benzoxepin-2[3H]-onesulfonamides, 3-benzoxepin-2[1H]-onesulfonamides, 2-benzothiepin-1[5H]-onesulfonamides, 2-benzazepine-1-onesulfonamides, 1-benzazepine-2-onesulfonamides, 2,1-benzoxathiepinsulfonamides, 1,2-benzoxathiepinsulfonamides, benzocyclohepten-5-onesulfonamides, benzocyclohepten-6-onesulfonamides and 1-benzoxepin-5[4H]-onesulfonamides, which are useful as agricultural chemicals and in particular as growth regulants or herbicides.

U.S. Pat. No. 4,127,405 teaches compounds which are useful for controlling weeds in wheat having the formula:

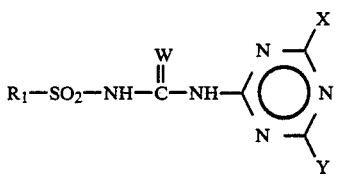
(I)

wherein $R_1$ is

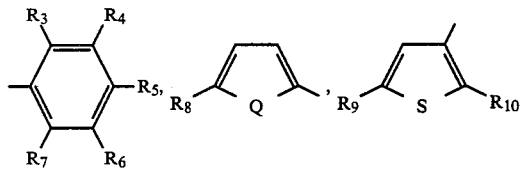

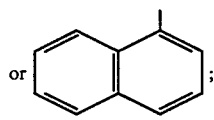

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

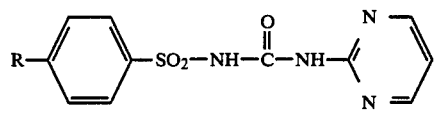

wherein
R=H, halogen, $CF_3$ or alkyl.

Logemann et al., Chem. Ab., 53, 18052 g (1959), disclose a number of sulfonamides, including uracil derivatives and those having the formula:

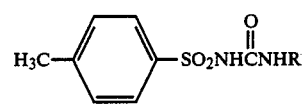

wherein
R is butyl, phenyl or

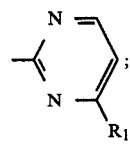

and
$R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

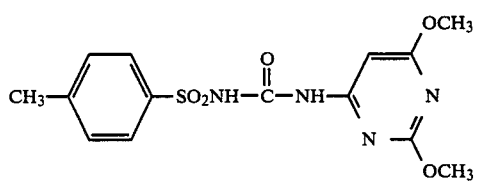

Based upon similarity to a known compound, the author predicted hypoglycemic activity for the foregoing compound.

Netherlands Patent No. 121,788, published Sept. 15, 1966, teaches the preparation of compounds of Formula (i), and their use as general or selective herbicides,

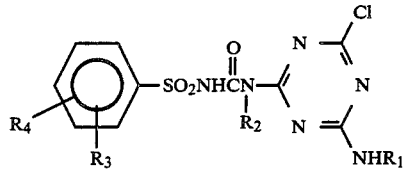

wherein
$R_1$ and $R_2$ may independently be alkyl of 1–4 carbon atoms; and
$R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (19.74),

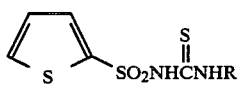

wherein
R is pyridyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, agriculturally suitable compositions containing them, and their method-of-use as pre-emergent or post-emergent herbicides or plant growth regulants.

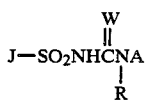

wherein J is

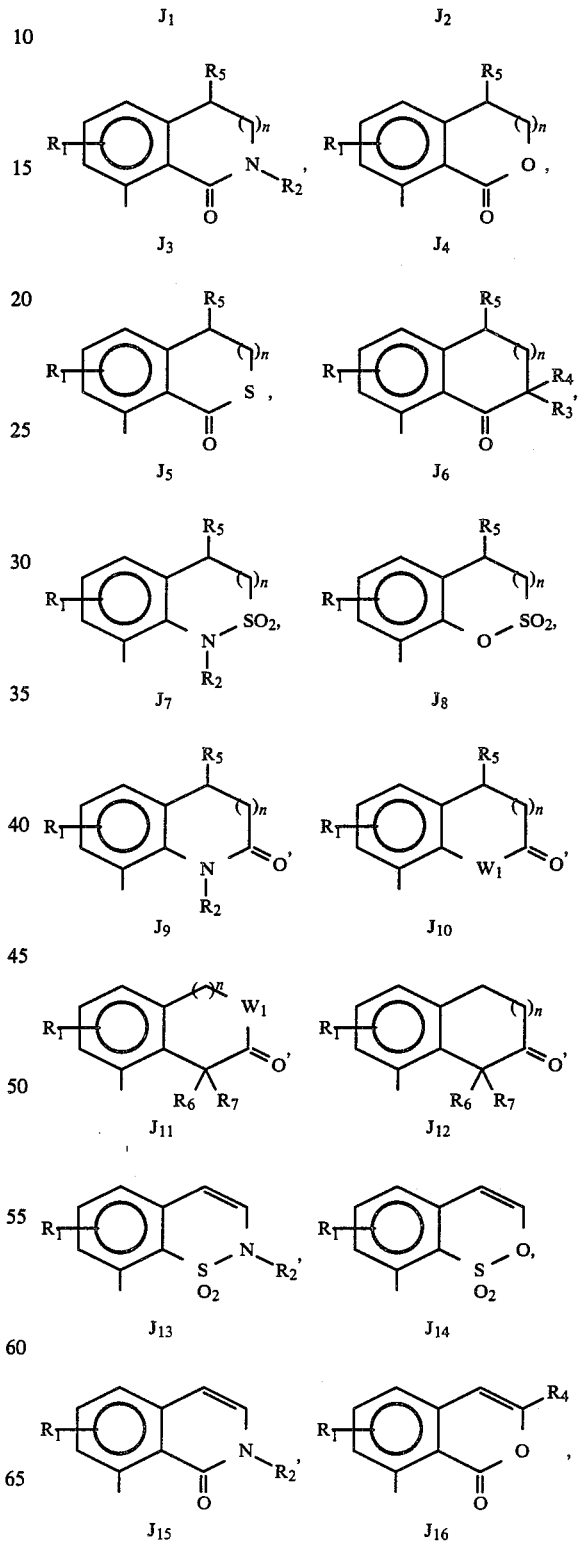

-continued

[Structures J17, J18, J19, J20, J21, J22, J23, J24, J25, J26]

n is 0, 1 or 2;
W is O or S;
$W_1$ is O or S;
R is H or $CH_3$;
$R_1$ is H, F, Cl, Br, $CH_3$, $OCH_3$, $CF_3$, $SCH_3$ or $OCF_2H$;
$R_2$ is H or $C_1$-$C_4$ alkyl;
$R_3$ and $R_4$ are independently H, $C_1$-$C_4$ alkyl, Cl or Br;
$R_5$ is H or $CH_3$;
$R_6$ is H or $CH_3$;
$R_7$ is H or $CH_3$;

[Structures showing A is various pyrimidine/triazine rings with X, Y, Z, $X_1$, $Y_1$, $X_2$, $Y_2$, $X_3$ substituents]

X is $CH_3$, $OCH_3$, $OCH_2CH_3$, Cl, F, Br, $OCF_2H$, $CH_2F$ or $CF_3$;

Y is H, $CH_3$, $OCH_3$, $OC_2H_5$, $CH_2OCH_3$, $NH_2$, $NHCH_3$, $N(CH_3)_2$, $C_2H_5$, $CF_3$, $SCH_3$, $OCH_2CH=CH_2$, $OCH_2C\equiv CH$, $OCH_2CF_3$, CN, $N_3$, $OCH_2CH_2OCH_3$, $CH_2SCH_3$, $CR_6(QCH_3)_2$,

[Structures showing cyclic Q-containing groups with $CR_6$]

$CR_6(QCH_2CH_3)_2$ or $QCF_2T$ where Q is O or S and T is H, CHClF, CHBrF or $CHFCF_3$;
Z is CH, N, $CCH_3$, $CC_2H_5$, CCl or CBr;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
provided that
(a) when W is S, then R is H, A is

[Structure with X, Y, Z substituents on ring with two N atoms]

Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CF_3$, $OCH_2CH_2OCH_3$, $CH(OCH_3)_2$ or

[Cyclic dioxolane-type structure with CH]

(b) the total number of carbon atoms in $R_3$ and $R_4$ is less than or equal to 4;
(c) when X is Cl, F or Br, then Z is CH and Y is $OCH_3$, $OC_2H_5$, $NH_2$, $NHCH_3$, $N(CH_3)_2$ or $OCF_2H$;
(d) when $R_5$ is $CH_3$, then n is 0;
(e) when J is $J_{24}$, then $R_4$ and $R_5$ are not both H and $R_4$ is not Cl or Br;
and their agriculturally suitable salts.

Preferred for reasons of their higher herbicidal activity, greater plant growth regulant activity or more favorable ease of synthesis are:

(1) Compounds of Formula I where W is O, $R_2$ is H or $C_1$-$C_3$ alkyl, $R_3$ and $R_4$ are independently H or $C_1$-$C_3$ alkyl and $R_1$ is bonded to the ortho or meta position of the ring relative to the sulfonylurea moiety.

(2) Compounds of Preferred 1 where $R_1$ is H, F, Cl, Br, $CH_3$, $OCH_3$, $CF_3$ or $SCH_3$; Y is $CH_3$, $OCH_3$, $OC_2H_5$, $CH_2OCH_3$, $NH_2$, $NHCH_3$, $N(CH_3)_2$, $C_2H_5$, $CF_3$, $SCH_3$, $OCH_2CH=CH_2$, $OCH_2C\equiv CH$, $OCH_2CF_3$, $OCH_2CH_2OCH_3$, $CR_6(OCH_3)_2$,

[Cyclic dioxolane structures with $CR_6$]

$CR_6(OCH_2CH_3)_2$ or $OCF_2H$; and Z is CH or N.

(3) Compounds of Preferred 2 where $R_1$ is H, $R_5$ is H, A is $$\begin{array}{c} \phantom{X}\text{X} \\ \text{N} \diagdown \diagup \\ \diagdown \bigcirc \text{Z,} \\ \text{N} \diagup \diagdown \\ \phantom{Y}\text{Y} \end{array}$$

X is $CH_3$, $OCH_3$, Cl, Br, $CH_2F$ or $OCF_2H$; and Y is $CH_3$, $OCH_3$, $OC_2H_5$, $CH_2OCH_3$, $CF_3$, $OCH_2CF_3$, $CH(OCH_3)_2$, $$\begin{array}{c} O \phantom{xx} O \\ \diagup \phantom{xx} \diagup \\ CH \phantom{x}, CH \\ \diagdown \phantom{xx} \diagdown \\ O \phantom{xx} O \end{array}$$

$CH(OCH_2CH_3)_2$ or $OCF_2H$.

(4) Compounds of Preferred 3 where R is H, Y is $CH_3$ or $OCH_3$ and X is $CH_3$, $OCH_3$, Cl or Br.
(5) Compounds of Preferred 4 where J is $J_1$.
(6) Compounds of Preferred 4 where J is $J_2$.
(7) Compounds of Preferred 4 where J is $J_3$.
(8) Compounds of Preferred 4 where J is $J_4$.
(9) Compounds of Preferred 4 where J is $J_5$.
(10) Compounds of Preferred 4 where J is $J_6$.
(11) Compounds of Preferred 4 where J is $J_7$.
(12) Compounds of Preferred 4 where J is $J_8$.
(13) Compounds of Preferred 4 where J is $J_9$.
(14) Compounds of Preferred 4 where J is $J_{10}$.
(15) Compounds of Preferred 4 where J is $J_{11}$.
(16) Compounds of Preferred 4 where J is $J_{12}$.
(17) Compounds of Preferred 4 where J is $J_{13}$.
(18) Compounds of Preferred 4 where J is $J_{14}$.
(19) Compounds of Preferred 4 where J is $J_{15}$.
(20) Compounds of Preferred 4 where J is $J_{16}$.
(21) Compounds of Preferred 4 where J is $J_{17}$.
(22) Compounds of Preferred 4 where J is $J_{18}$.
(23) Compounds of Preferred 4 where J is $J_{19}$.
(24) Compounds of Preferred 4 where J is $J_{20}$.
(25) Compounds of Preferred 4 where J is $J_{21}$.
(26) Compounds of Preferred 4 where J is $J_{22}$.
(27) Compounds of Preferred 4 where J is $J_{23}$.
(28) Compounds of Preferred 4 where J is $J_{24}$.
(29) Compounds of Preferred 4 where J is $J_{25}$.
(30) Compounds of Preferred 4 where J is $J_{26}$.

Specifically preferred for reasons of their highest herbicidal activity, greatest plant growth regulant activity and/or most favorable ease of synthesis are:

N-[(4,6-dimethoxypyrimidin-2-yl)aminocarbonyl]-2,3-dihydro-2-methyl-1,2-benzisothiazole-7-sulfonamide, 1,1-dioxide, m.p. 218°–221° C.;

N-[(4-methoxy-6-methyl-1,3,5-triazin-2-yl)aminocarbonyl]-2,3-dihydro-2-methyl-1,2-benzisothiazole-7-sulfonamide, 1,1-dioxide, m.p. 210°–212° C.;

N-[(4-methoxymethyl-6-methylpyrimidin-2-yl)aminocarbonyl]-2,3-dihydro-2-methyl-1,2-benzisothiazole-7sulfonamide, 1,1-dioxide, m.p. 169°–171° C.;

N-[(4-chloro-6-methoxypyrimidin-2-yl)aminocarbonyl]-2,3-dihydro-2-methyl-1,2-benzisothiazole-7-sulfonamide, 1,1-dioxide, m.p. 206°–208° C.;

N-[(4-methoxy-6-methylpyrimidin-2-yl)aminocarbonyl]-2,3-dihydro-2-(1-methylethyl)-1,2-benzisothiazole-7-sulfonamide, 1,1-dioxide, m.p. 234°–236° C.;

N-[(4-methoxy-6-methyl-1,3,5-triazin-2-yl)aminocarbonyl]-2,3-dihydro-2-(1-methylethyl)-1,2-benzisothiazole-7-sulfonamide, 1,1-dioxide, m.p. 186°–188° C.;

N-[(4-methoxy-6-methylpyrimidin-2-yl)aminocarbonyl]-2,3-dihydro-2-propyl-1,2-benzisothiazole-7-sulfonamide, 1,1-dioxide, m.p. 197°–199° C.;

N-[(4-methoxy-6-methyl-1,3,5-triazin-2-yl)aminocarbonyl-2,3-dihydro-2-ethyl-1,2-benzisothiazole-7-sulfonamide, 1,1-dioxide, m.p. 169°–171° C.;

N-[(4,6-dimethoxy-1,3,5-triazin-2-yl)aminocarbonyl]-2,3-dihydro-2-methyl-2H-1,2-benzisothiazole-8-sulfonamide, 1,1-dioxide, m.p. 258°–266° C.;

N-[(4,6-dimethoxypyrimidin-2-yl)aminocarbonyl]-1,3-dihydro-3-oxoisobenzofuran-4-sulfonamide, m.p. 218°–220° C.;

N-[(4-methoxy-6-methylpyrimidin-2-yl)aminocarbonyl]-1,3-dihydro-2-methyl-1-oxo-1H-isoindole-7-sulfonamide, m.p. 215°–217° C.; and N-[(4-bromo-6-methoxypyrimidin-2-yl)aminocarbonyl]-2,3-dihydro-2-methyl-1,2-benzisothiazole-7-sulfonamide, 1,1-dioxide, m.p. 219°–221° C.

DETAILED DESCRIPTION OF THE INVENTION

Synthesis

The compounds of Formula I can be prepared by one or more of the methods described below in Equations 1, 2, 3 and 4.

As shown in Equation 1, compounds of Formula I where J is other than $J_6$, $J_{12}$, $J_{22}$ and $J_{23}$, can be prepared by reacting a sulfonylisocyanate (W=O) or a sulfonylisothiocyanate (W=S) of Formula II with an appropriate heterocyclic amine of Formula III. R, A and W are as previously defined.

$$\underset{\text{II}}{J-SO_2N=C=W} + \underset{\underset{R}{|}}{\underset{\text{III}}{HN-A}} \longrightarrow \underset{\underset{R}{|}}{\underset{\text{I}}{J-SO_2NHCN-A}}\overset{W}{\overset{\|}{\phantom{x}}} \quad \text{Equation 1}$$

The reaction is carried out at 25° to 100° C. in an inert, aprotic solvent such as methylene chloride or xylene for 0.5 to 24 hours as taught in U.S. Pat. No. 4,127,405.

Compounds of Formula I, where W is S and R is H, (Ia) can be prepared by reacting the appropriate sulfonamide of Formula IV with a heterocyclic isothiocyanate of Formula V, as shown in Equation 2.

$$\underset{\text{IV}}{J-SO_2NH_2} + \underset{\text{V}}{S=C=N-A} \xrightarrow{\text{Base}} \underset{\text{Ia}}{J-SO_2NHCNH-A}\overset{S}{\overset{\|}{\phantom{x}}} \quad \text{Equation 2}$$

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III as taught in EPO Publication No. 35893.

Compounds of Formula I, where W is O (Ib) and J is other than $J_4$, $J_5$, $J_{10}$, $J_{11}$, $J_{16}$, $J_{17}$, $J_{21}$, $J_{24}$ and $J_{25}$, can be prepared by reacting the sulfonamides of Formula IV with an appropriate methylcarbamate of Formula VI in the presence of an equimolar amount of trimethylaluminum, as shown in Equation 3.

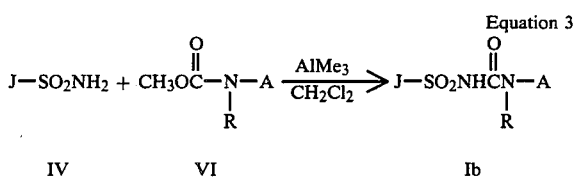

Equation 3

The reaction is carried out at 25° to 40° C. in a solvent such as methylene chloride for 10 to 96 hours under an inert atmosphere as taught in EPO No. 84,244 (7/27/83). The required carbamates VI are prepared by reacting the corresponding amines III with dimethylcarbonate or methyl chloroformate in the presence of a strong base.

Alternatively, compounds of Formula Ib, can be prepared by reacting a sulfonylcarbamate of Formula VII with an appropriate amine of Formula III. as shown in Equation 4.

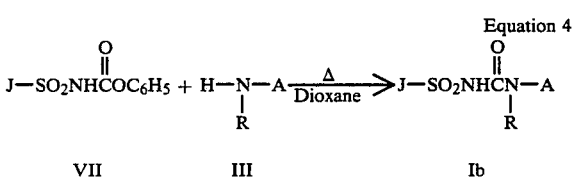

Equation 4

The reaction is carried out at 50° to 100° C. in a solvent such as dioxane for 0.5 to 24 hours as taught in EPO publication No. 44807. The required carbamates VII are prepared by reacting the corresponding sulfonamides IV with diphenylcarbonate in the presence of a strong base.

The intermediate sulfonylisocyanates (W=O) and sulfonylisothiocyanates (W=S) of Formula II from Equation 1 can be prepared as shown in Equations 5, 6 and 7.

As shown in Equation 5, sulfonylisocyanates of Formula IIa where J is other than $J_6$, $J_{12}$, $J_{22}$ and $J_{23}$ can be prepared by the reaction of sulfonamides of Formula IV with phosgene, in the presence of n-butylisocyanate and a tertiary amine catalyst, at reflux in a solvent such as xylene by the method of U.S. Pat. No. 4,238,621.

Equation 5

The sulfonylisocyanates can also be prepared from the sulfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p 223-241, Academic Press, New York and London, W. Foerst Ed.

Alternatively, as shown in Equation 6, the sulfonylisocyanates of Formula IIa can be prepared by reacting the corresponding sulfonyl chlorides VIII with cyanic acid salts.

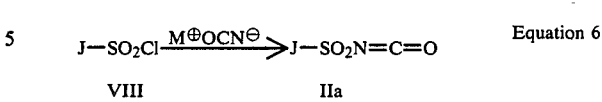

Equation 6

The reaction is carried out at 25° to 100° C. in an inert aprotic solvent such as acetonitrile for 0.5-24 hours in the presence of phosphorus pentoxide and an alkali metal salt such as lithium iodide according to the teachings of Japanese Pat. No. 76/26,816 (*Chem. Abst.*, 85:77892e (1976)).

The sulfonylisothiocyanates of Formula IIb where J is other than $J_6$, $J_{12}$, $J_{22}$ and $J_{23}$ can be prepared, as shown in Equation 7, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

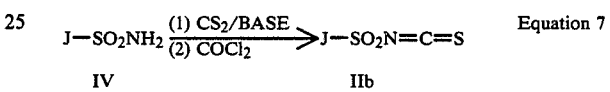

Equation 7

The sulfonamides of Formula IV of Equations 2, 3, 4, 5 and 7 are important intermediates for the preparation of the compounds of this invention. The syntheses of the required sulfonamide intermediates are described in Equations 8 and 9.

As shown in Equation 8, sulfonamides of Formula IV can be prepared from the corresponding sulfonyl chlorides of Formula VIII by contacting with either anhydrous or aqueous ammonia.

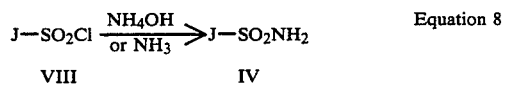

Equation 8

The preparation of sulfonamides from sulfonyl chlorides is widely reported in the literature, for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp., New York, 1948.

The unsaturated sulfonamides of Formula IVa can also be prepared from the corresponding saturated sulfonamides of Formula IVb by the two step procedure shown in Equation 9. $G_1$-$G_2$ is $SO_2$—$NR_2$, $SO_2$—O, CO—$NR_2$, CO—O, CO—S, $NR_2$—$SO_2$, O—$SO_2$, $NR_2$—CO and O—CO, $R_1$ and $R_2$ are as previously defined.

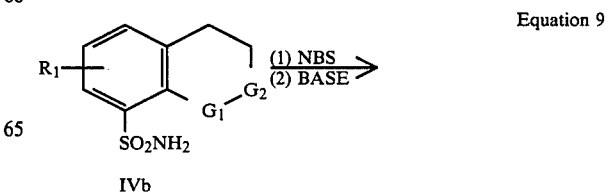

Equation 9

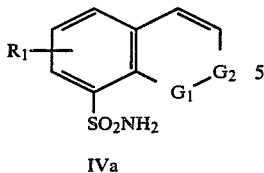

IVa

The first step involves benzylic bromination by N-bromosuccinimide to give a monobromide which is subsequently dehydrobrominated in a second step by reaction with a suitable base such as triethyl amine or potassium-t-butoxide in an inert solvent such as THF. This method has been used to prepare isocoumarins from 3,4-dihydroisocoumarins, see R. Barry, *Chem. Rev.*, 64, 229 (1964). In cases where $R_1$ is a methyl function, competitive bromination at this site may occur resulting in a mixture. The desired bromide may be separated at this stage, or after treatment with the base, by standard methods. A similar method may be used to prepare sulfonamides where J is $J_{23}$ from sulfonamides where J is $J_{22}$ (n=1).

The sulfonyl chlorides of Formula VIII of Equation 6 and 8 can be prepared from the corresponding amines IX by the method shown in Equation 10.

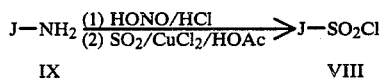
Equation 10

The reaction involves diazotization of the amine IX with sodium nitrite in HCl, followed by reaction of the diazonium salt with sulfur dioxide and cupric chloride in acetic acid analogous to the teachings of Yale and Sowinski, *J. Org. Chem.*, 25, 1824 (1960).

Alternatively, sulfonyl chlorides of Formula VIII can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°–40° C. for 1 to 24 hours.

Some of the sulfonyl chlorides of Formula VIII may best be prepared by direct chlorosulfonation depending on the substitution pattern on the ring and the nature of the substituent as will be known to one skilled in the art.

The sulfonyl chlorides of Formula VIIIa can also be prepared from the chloro compounds X by the two step sequence shown in Equation 11. $R_1$, $R_2$ and n are as previously defined, except that $R_1$ is not halogen when it is para to the sulfonyl group or $SCH_3$. R' is $C_1$–$C_4$ alkyl or benzyl.

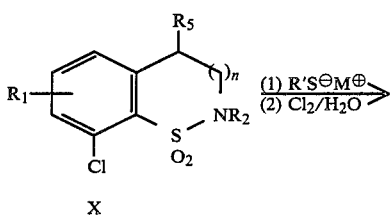
Equation 11

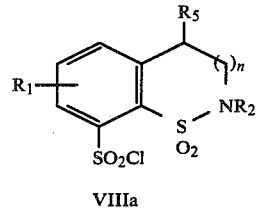

VIIIa

The first step involves nucleophilic displacement of the chlorine atom with an alkyl or benzyl mercaptide to give an intermediate sulfide. The reaction can be carried out at 25° to 80° C. in a polar solvent such as DMF for 0.5–24 hours. The sulfide is then oxidatively chlorinated to the desired sulfonyl chloride VIIIa by the addition of molecular chlorine or a chlorine equivalent to the sulfide in the presence of water at 15° to 80° C. in an aliphatic carboxylic acid solvent such as acetic acid or an inert organic solvent such as dichloroethane for 1 to 24 hours.

Many of the chloro compounds of Formula X in Equation 11, where n=0, can be prepared by the reaction sequence shown in Equation 12. When $R_1$ is para to the sulfonyl group, then it is H, $OCH_3$ or $CF_3$. When $R_1$ is meta to the sulfonyl group, then it is F, Cl, $CH_3$, $OCH_3$ or $CF_3$. $R_2$ and $R_5$ are as previously defined.

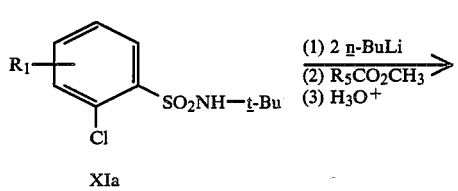
Equation 12

XIa

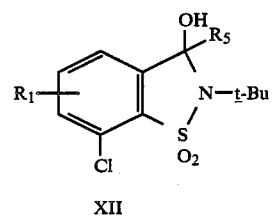

XII

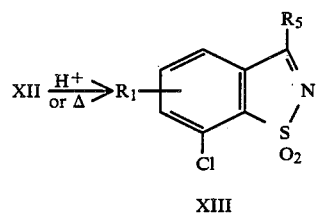

XIII

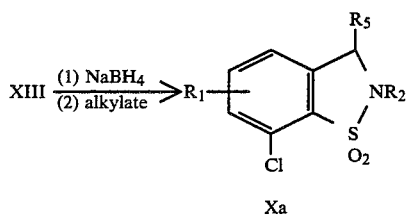

Xa

The sequence begins by contacting an appropriately substituted N-t-butylbenzenesulfonamide XIa with two equivalents of butyl lithium at 0° to 25° C. in an inert solvent such as THF for 2 to 10 hours to give a dianion according to the teachings of J. Lombardino, *J. Org. Chem.*, 36, 1843 (1971). The dianion can then be trapped with an ester or, when R₅ is H, with dimethylformamide at −78° to 25° C. to produce, upon aqueous acid workup, the hemiaminal XII. The hemiaminal XII can be de-t-butylated and dehydrated by a catalytic amount of acid such as p-toluenesulfonic acid in a solvent such as benzene or toluene at reflux. The resulting benzisothiazole XIII can be reduced with a reagent such as sodium borohydride in a suitable solvent such as ethanol to produce a 2,3-dihydrobenzisothiazole which is N-alkylated to give Xa by standard methods known to one skilled in the art.

Many of the chloro compounds of Formula X in Equation 11, where n=1, can be prepared by the reaction sequence shown in Equation 13. $R_1$ and $R_2$ are as defined for Equation 12.

Equation 13

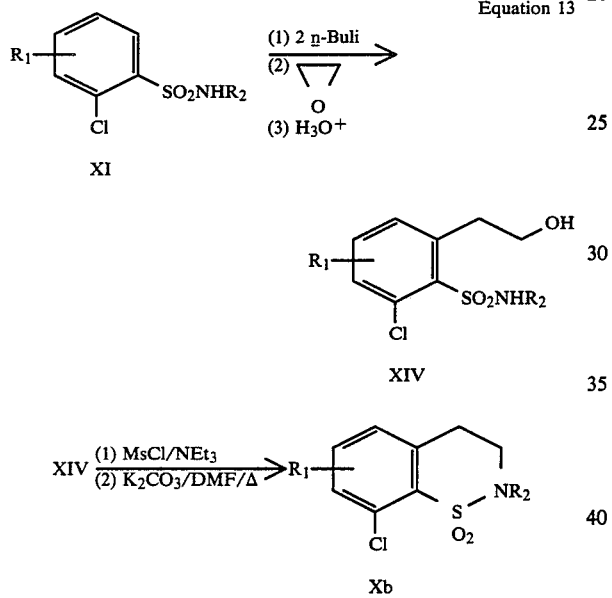

As in Equation 12, the N-substituted-benzenesulfonamides XI is contacted with 2 equivalents of butyl lithium to form a dianion, which is now trapped with ethylene oxide to produce alcohol XIV. The alcohol can be mesylated by treatment of XIV with mesyl chloride in the presence of an equivalent of a tertiary amine at 0° to 25° C. for 1 to 24 hours in a solvent such as methylene chloride. The resulting mesylate is cyclized by heating with a base such as potassium carbonate in a solvent such as DMF to produce the desired compounds Xb.

Many of the sulfonyl chlorides of Formula VIIIb can also be prepared from the thioether compounds A as shown in Equation 13a. $R_1$ is not Br, SCH₃ or OCF₂H. $R_4$ and $R_5$ are as previously defined.

Equation 13a

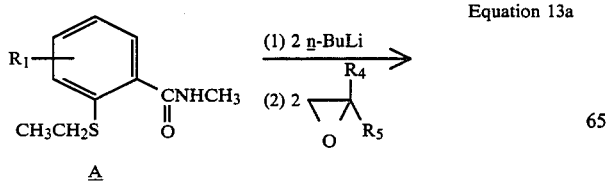

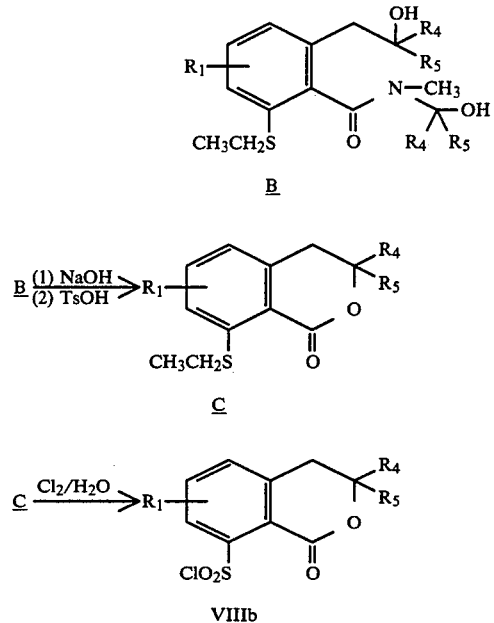

As in Equation 13a, the N-methyl carboxamide A is contacted with 2 equivalents of butyl lithium to form a dianion, which is trapped with 2 equivalents of the appropriate epoxide to produce B. Hydrolysis of the amide to its corresponding carboxylic acid followed by acid catalyzed cyclization gives the lactone C. Oxidative chlorination of C as described previously in Equation 11 produces the desired sulfonyl chloride VIIIb.

The amines of Formula IX in Equation 10, can be prepared by reduction of the corresponding nitro compounds of Formula XV, as shown in Equation 14.

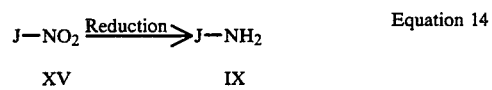

Equation 14

The reduction of nitro compounds to amines can be carried out by any of several known methods as described in *Preparative Organic Chemistry*, 4 Ed., p. 557–563, Jonn Wiley and Sons, New York and London, G. Hilgetag and A. Martini Ed.

The nitro compounds of Formula XV in Equation 14 can be prepared by the procedures outlined in Equations 15 to 41.

As shown in Equation 15, nitro compounds of Formula XV, where J is J₁ (XVa) can be prepared starting from the appropriately substituted nitrobenzenes of Formula XVI. R' is H or CH₂Cl, $R_1$, $R_2$, $R_5$ and n are as previously defined.

Equation 15

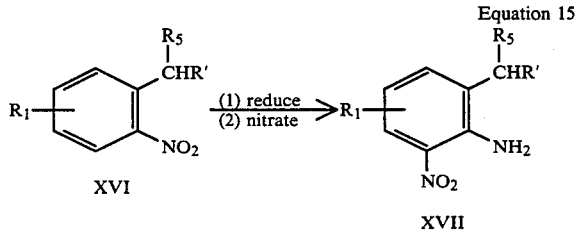

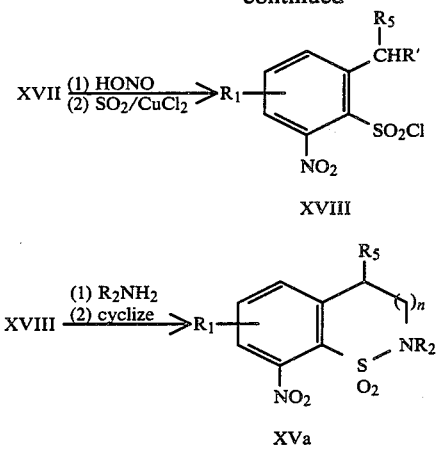

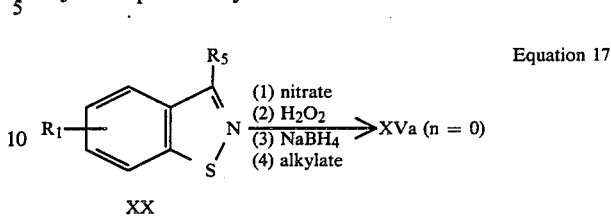

The nitrobenzenes XVI are first reduced to their corresponding amines and nitrated by standard methods to produce, in part, compounds of Formula XVII. In some instances, it may be desirable to first protect the amino group as its acetate prior to nitration as is known to one skilled in the art. The desired nitro compound XVII can be isolated by either fractional crystallization or chromatographic procedures and converted to sulfonyl chlorides XVIII by the method previously discussed in Equation 10. The intermediate sulfonyl chlorides XVIII can be converted into their corresponding sulfonamides by reaction with an appropriate amine (see Equation 8 for references) and subsequently cyclized (a) when R' is CH$_2$Cl, to the nitro-1,2-benzothiazines XVa, where n is 1, by heating in the presence of a base such as potassium carbonate or (b) when R' is H, by contacting the sulfonamide with NBS in a solvent such as carbon tetrachloride to give sulfonamides where R' is Br, followed by contacting this product with a base to give the nitro benzisothiazoles XVa where n is 0. (Note discussion of Equation 9 for NBS brominations when R$_1$ is methyl.)

The procedure of Equation 15 is similar to the method taught by E. Sianesi et al., Chem. Ber., 104, 1880 (1971) for the preparation of substituted 1,2-benzothiazine-1,1-dioxides. The starting nitrobenzenes XVI can be prepared by standard methods known to one skilled in the art.

Alternatively, as shown in Equation 16, the nitro compounds of Formula XVa where n is 1 can be prepared, in part, by contacting the nitro acetamides XIX with fuming sulfuric acid according to the method taught by H. Zenno and T. Mizutani, Japanese Patent No. 44/32,404 (1969) (Chem. Abst.: 72:79122 (1970)) for the preparation of 7-nitro-1,2-benzothiazine-1,1-dioxide. The resulting benzothiazines can be isolated and subsequently alkylated by standard methods known to one skilled in the art.

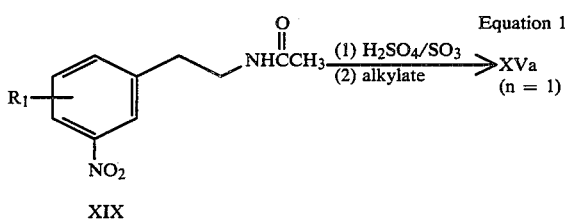

The nitro compounds of Formula XVa where n is 0 can also be prepared from the corresponding 1,2-benzisothiazoles XX as shown in Equation 17. R$_1$, R$_2$ and R$_5$ are as previously defined.

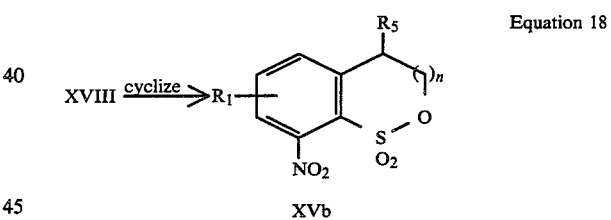

Nitration of XX gives, in part, the 7-nitro derivative which is isolated by standard methods. The derivative is converted to its 1,1-diodide by treatment with hydrogen peroxide. Reduction of the carbon-nitrogen double bond with NaBH$_4$ followed by alkylation of the resulting sulfonamide gives compounds XVa where n is 0. The above reactions are characteristic of 1,2-benzisothiazoles XX. For reviews of their synthesis and reactions, see L. L. Bambas, "The Chemistry of Heterocyclic Compounds," Vol. 4, part III, 1952, p. 223–378, and M. Davis, Adv. Heterocyclic Chem., Vol. 14 (1972) p. 43–98. 1,2-Benzothiazines are also well known in the literature, for a review of their chemistry and alternate methods of their preparation see J. G. Lombardino, D. E. Kuhla, Adv. Heterocyclic Chem., Vol. 28 (1981) p. 73–126.

As shown in Equation 18, nitro compounds of Formula XVb where J=J$_2$ can be prepared from the appropriately substituted nitro sulfonyl chlorides XVIII. R' is H or CH$_2$Cl, R$_1$, R$_5$ and n are as previously defined.

Equation 18

XVIII $\xrightarrow{\text{cyclize}}$

XVb

The nitro sulfonyl chlorides XVIII, previously described in Equation 15, can be (a) cyclized to the nitro benzoxathiins XVb (n=1) by heating in water at 50° to 100° C. for 0.1 to 1 hour when R' is CH$_2$Cl or (b) cyclized to the nitro benzoxathioles XVb (n=0) by brominating with NBS or bromine (see discussion of Equation 9 for brominations when R$_1$ is methyl) followed by heating in water as described above. This is similar to the method taught by Clemo and Turnbull, J. Chem. Soc., 124 (1947) for the preparation of substituted 2,1-benzoxathiins.

2,1-Benzoxathiins and 2,1-benzoxathioles are well known in the literature, for a review of their synthesis and reactions see Chemistry of Heterocyclic Compounds, Vol. 21, John Wiley and Sons, New York, 1966, part 2 and part 1, respectively.

As shown in Equation 19, nitro compounds of Formula XV where J=J$_4$ (XVd) can be prepared from the appropriately substituted amines XVII. R' is H or CH$_2$Cl, R$_1$R$_5$ and n are as previously defined.

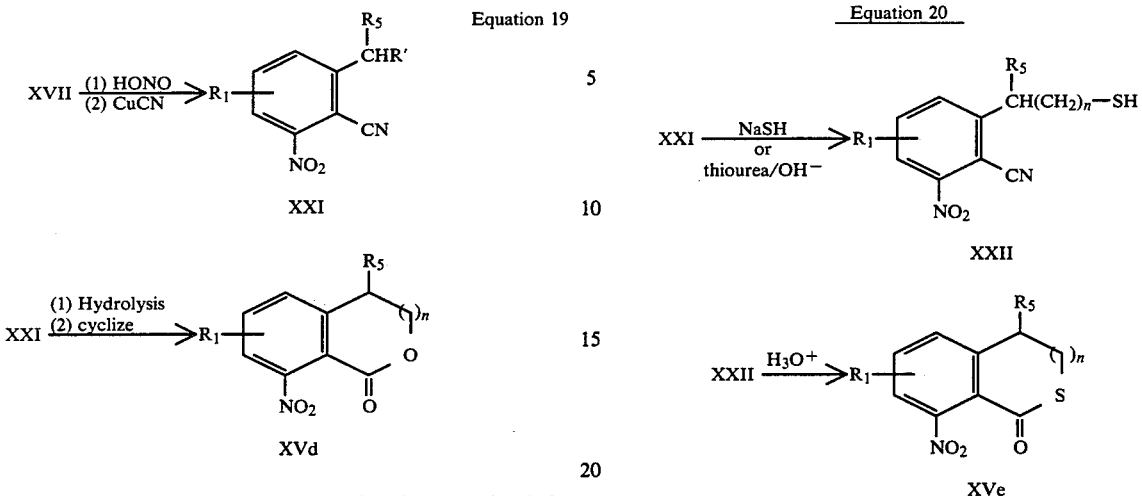

The nitro amines XVII, previously described in Equation 15, can be converted into the corresponding cyano compounds XXI by the "Sandmeyer Reaction" (T. Sandmeyer, *Chem. Ber.*, 17, 1633, 2650 (1884)). The cyano function is hydrolyzed to a carboxylic acid by methods known to one skilled in the art, and the carboxylic acids or their corresponding esters can be (a) cyclized to the nitro isocoumarins XVd (n=1) by heating in the presence of base when R' is CH$_2$Cl, or (b) cyclized to the nitro phthalides XVd (n=0) when R' is H by first brominating with NBS or bromine (note discussion of Equation 9 for brominations when R$_1$ is methyl) followed by heating in a solvent such as aqueous dioxane. The latter method is that taught by J. A. Houbion et al., *Org. Prep. and Procedures Int.*, 11, 27 (1979) for the preparation of 7-nitrophthalide (XVd, n=0, R$_1$=H).

The procedure of Equation 19 is similar to the method of P. Banejce and D. Chaudhury, *J. Org. Chem.*, 26, 4344 (1961) for the preparation of substituted isocoumarins; similar methods can be utilized for the preparation of isocoumarins of the J$_{24}$ type. Isocoumarins are well known in the literature, for a review of their synthesis and reactions see R. Barry, *Chem. Rev.*, 64, 229–260 (1964).

The compounds of Formula XVd, where n=0 can also be prepared by reduction of the corresponding 3-nitrophthalic anhydrides with either sodium borohydride or lithium aluminum hydride in tetrahydrofuran as taught by M. Kayser and P. Morand, *Can. J. Chem.*, 58, 2484 (1980) for the preparation of 7-nitrophthalide (XVd; n=0, R$_1$=H). Phthalides and phthalic anhydrides are well known in the art, for a review of their synthesis and reactions see, S. Wawzonek, *Heterocyclic Compounds*, Vol. 2, John Wiley and Sons, Inc., New York, 1951.

As shown in Equation 20, nitro compounds of Formula XV where J is J$_5$ (XVe) can be prepared from the appropriately substituted cyano compounds XXI. R' is H or CH$_2$Cl, R$_1$, R$_5$ and n are as previously defined.

The nitrobenzonitriles XXI, previously described in Equation 15, can be converted into mercaptans XXII by reacting compounds XXI where R' is Br or CH$_2$Cl with an alkali metal salt of hydrogen sulfide in a polar solvent such as ethanol or DMF according to the teachings of S. Gabriel and E. Leupold, *Chem. Ber.*, 31, 2646 (1898). The cyano mercaptans are cyclized to the thiol ethers by heating in aqueous acid as taught by M. Renson and R. Collienne, *Bull. Soc. Chem. Belges*, 73, 491 (1964) for the preparation of 2-thiophthalide.

Alternatively, as shown in Equation 21, the nitro compounds of Formula XVe can be prepared from the lactones of Formula XVd by reaction with potassium t-butyl mercaptide in a solvent such as DMF at 0° to 100° C. for 0.5 to 24 hours to give the carboxylic acids XXIII, which are then heated in the presence of a catalytic amount of an acid such as p-toluenesulfonic acid in a solvent such as xylene at 100° to 140° C. for 2 to 24 hours.

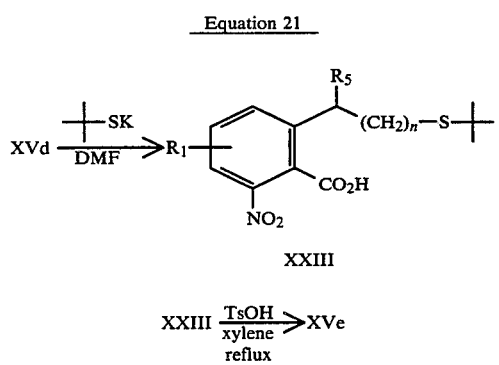

2-Thiophthalides are widely reported in the literature, for a review of their synthesis and reactions see, B. Iddon, *Adv. Heterocyclic Chem.*, Vol. 14 (1972) pp. 368–381.

As shown in Equation 22, nitro compounds of Formula XV, where J is J$_3$ (XVc) can be prepared from the appropriately substituted benzonitriles XXI. R' is H or CH$_2$Cl, R$_1$, R$_2$, R$_5$ and n are as previously defined.

Equation 22

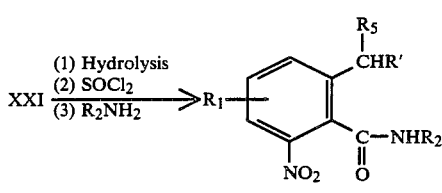

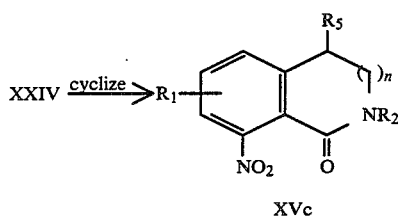

The benzonitriles XXI, previously described in Equation 19, are hydrolyzed to carboxylic acids, converted to their corresponding acid chlorides by contacting with a reagent such as thionyl chloride and subsequently reacted with the appropriate amine, by standard methods, to give the amides XXIV. The intermediate amides XXIV can be cyclized to the nitro compounds XVc by the procedures previously described in Equation 15 for converting sulfonamides of XVIII into nitro compounds XVa.

Alternatively, the nitro compounds of Formula XVc can be prepared from the nitro compounds of Formula XVd as shown in Equation 23. $R_1$, $R_2$, $R_5$ and n are as previously defined.

Equation 23

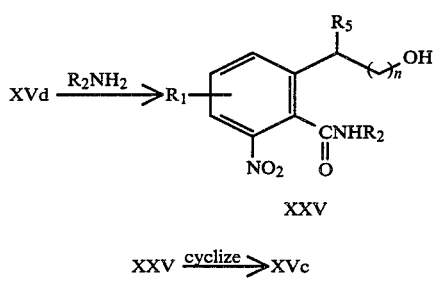

The reactions of phthalides with amines to produce phthalimidines is well known, see C. Hollins, *The Synthesis of Nitrogen Ring Compounds*, Ernest Benn Limited, London, 1924. In these reactions, heating the phthalides (XVd, n=0) with an amine produces the phthalimidines (XVc, n=0) directly, the intermediate alcohols XXV (n=0) are not isolated. With the 3,4-dihydrocoumarins (XVd, n=1) the intermediate amide alcohols XXV (n=1) are formed (see P. Maitte, *Colloq. Intern. Centre Natl. Rech. Sci.* (Paris), 64, 197 (1955), *Chem. Abst.*, 55:10426 (1961)) and can be converted to the dihydroisoquinolines XVc (n=1) by first conversion to the corresponding mesylate followed by heating with a base as described above in Equation 13 for the preparation of compounds Xb from the sulfonamide alcohols XIV. For a comprehensive review of the synthesis and reactions of dihydroisoquinolones see N. J. McCorkindale, *The Chemistry of Heterocyclic Compounds*, Vol. 38, part III, John Wiley and Sons, New York, in press.

As shown in Equation 24, nitro compounds of Formula XV, where J is $J_6$ (XVf) can be prepared, in part, by cyclization of the appropriate arylproprionic (n=0) or arylbutyric (n=1) acids XXVI. $R_1$, $R_3$, $R_4$, $R_5$ and n are as previously defined.

Equation 24

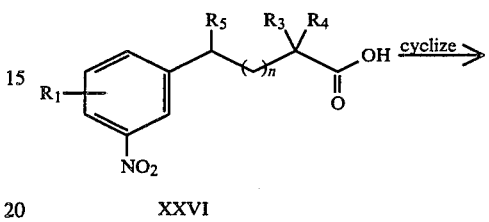

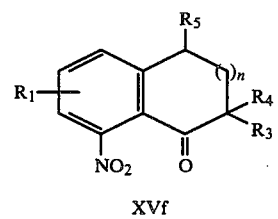

The reaction is carried out by heating the acid with a suitable condensing agent such as polyphosphoric acid, hydrofluoric acid, sulfuric acid or stannic chloride or the acid may be converted to its chloride and heated with a typical Friedel-Crafts reagent such as aluminum chloride or stannic chloride. For a comprehensive review of this and related reactions, see "Friedel-Crafts and Related Reactions", Vols. 1–4, Interscience, New York and London, G. A. Olah, Ed. This procedure has been used to prepare a number of substituted-7-nitro-1-indanones (XVf, n=0), see: H. Jones and T. Y. Shen, German Patent 2,337,120 (1974) and Y. Takahi and Y. Yura, Japanese Patent 78/12,421 (1978) *Chem. Abst.*, 89:101857c.

Alternatively, the nitro compounds of Formula XVf can oe prepared by benzylic oxidation of the corresponding nitroindanes or nitrotetralines as taught by D. Biggs, et al., *J. Med. Chem.*, 19, 472 (1976) for the preparation of 8-nitrotetralone (XVf, n=1, $R_1$, $R_3$, $R_4$ and $R_5$=H). Nitroindanes and nitrotetralines are well known in the literature and can be prepared by methods known to one skilled in the art.

Additionally, ketones of Formula XVf where $R_3$ and/or $R_4$ are other than hydrogen can be prepared from ketones XVf where $R_3$ and/or $R_4$ are hydrogen by standard ketone alkylation and halogenation methods. For a review, see: H. House, *Modern Synthetic Reactions*, 2nd Edition, W. A. Benjamin, Inc., Menlo Park, Calif., 1972, p. 542–570 and 459–478, respectively.

As shown in Equation 25, nitro compounds of Formula XV where J is $J_7$ (XVg) can be prepared from the appropriately substituted nitrobenzenes XVI. R' is Br or $CH_2Br$, $R_1$, $R_2$, $R_5$ and n are as previously defined.

Equation 25

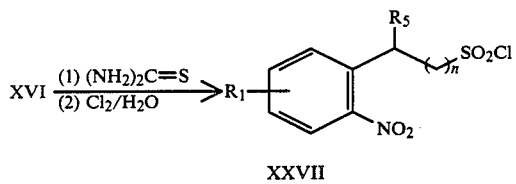

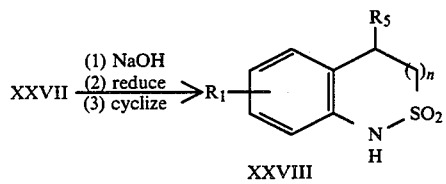

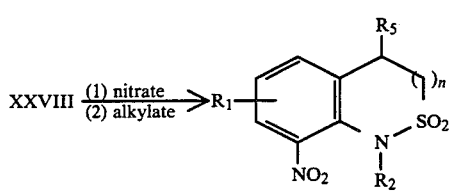

Equation 26

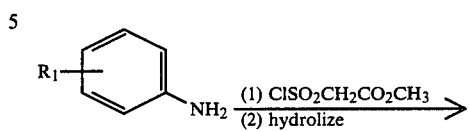

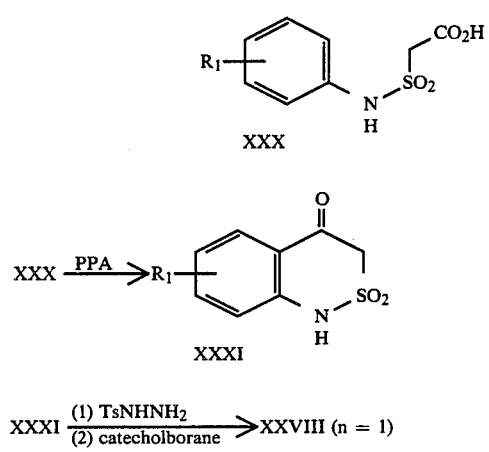

The nitrobenzenes XVI, previously described in Equation 15, are heated with thiourea in a suitable solvent such as ethanol to give thiouronium salts which are oxidatively chlorinated in aqueous acetic acid to give the sulfonyl chlorides XXVII (see also discussion of Equation 11). The sulfonyl chlorides XXVII are dissolved in 10% aqueous sodium hydroxide solution and the nitro groups are catalytically hydrogenated to give intermediate amino sulfonate salts. The salts are cyclized with phosphorous pentachloride and acetyl chloride to give the sultams XXVIII according to the teachings of B. Loev and M. F. Kormendy, *J. Org. Chem.*, 30, 3163 (1965) for the preparation of 3,4-dihydro-2,1-benzothiazine-2,2-dioxide (XXVIII, n=1, $R_1$, $R_5$=H).

Alternatively, the sulfonyl chlorides XXVII can be converted to their corresponding sulfonamides by the methods discussed in Equation 8. Reduction of the nitro group according to procedures of Equation 14 gives the corresponding amino sulfonamides which are cyclized to sultams XXVIII by heating, in the presence of HCl, according to the teachings of E. Sianesi, et al., *Chem. Ber.*, 104, 1880 (1971) for the preparation of 3,4-dihydro-2,1-benzothiazine-2,2-dioxide (XXVIII, n=1, $R_1$, $R_5$=H).

The sultams XXVIII can be nitrated, in part, ortho to the ring nitrogen by standard methods known to one skilled in the art. Isolation by either fractional crystallization or chromatographic methods followed by alkylation of the ring nitrogen under standard conditions gives the nitrosultams XVg as taught by E. Sianesi loc. cit. for the preparation of 1-methyl-8-nitro-3,4-dihydro-2,1-benzothiazine-2,2-dioxide (XVg, n=1, $R_1$, $R_5$=H, $R_2$=CH$_3$).

The sultams of Formula XXVIII of Equation 25 where n=1, can also be prepared from anilines XXIX as shown in Equation 26. $R_1$ is as previously defined.

The substituted anilines XXIX are reacted with methyl chlorosulfonylacetate in the presence of an acid scavenger to give methyl sulfamoyl acetate intermediates which are hydrolized with dilute sodium hydroxide solution to the corresponding carboxylic acids XXX. The carboxylic acids XXX can be cyclized (note discussion of Equation 24) by heating with polyphosphoric acid to give the 4-benzothiazinones XXXI as taught by B. Loev et al., *J. Org. Chem.*, 31, 3531 (1966) for the preparation of 4-keto-3,4-dihydro-2,1-benzothiazine-2,2-dioxide (XXXI, $R_1$=H). When $R_1$ is meta to nitrogen, cyclization may produce an isomeric mixture. The desired compounds XXXI can be isolated by either fractional crystallization or chromatographic methods known to one skilled in the art. The benzothiazines XXVIII (n=1) are prepared by reducing the tosylhydrazone derivative of ketones XXXI with catecholborane in a solvent such as chloroform for 2 to 24 hours at ambient temperatures according to the teachings of G. Kabalka and J. Chandler, *Synthetic Commun.*, 9, 275 (1979).

The synthesis and chemistry of 2,1-benzothiazines has been reviewed, see J. G. Lombardino and D. E. Kuhla, *Adv. Heterocyclic Chem.*, Vol. 28 (1981) p. 73–126. Additionally, for a review of the synthesis and chemistry of benzothiazinone dioxides, see P. Catsoulacos and Ch. Camoutsis, *J. Heterocyclic Chem.*, 16, 1503 (1979).

As shown in Equation 27, nitro compounds of Formula XV where J is J$_8$ (XVh) can be prepared from the appropriately substituted nitrophenols XXXII. R' is Br or CH$_2$Cl, $R_1$, $R_5$ and n are as previously defined.

Equation 27

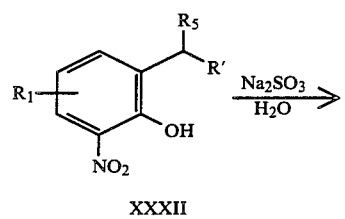

Equation 29

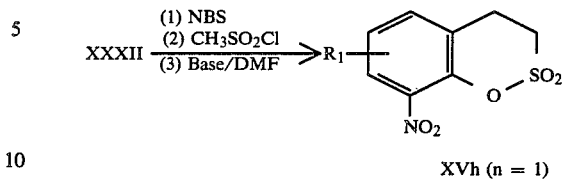

The phenol is brominated with NBS in a solvent such as carbontetrachloride and the hydroxy group is then converted to its methanesulfonate ester by treatment with mesyl chloride in the presence of an acid scavenger such as triethylamine in a solvent such as methylene chloride. The methanesulfonate ester is then cyclized by reacting with a strong base such as sodium hydride or potassium t-butoxide in a polar solvent such as DMF at 0° to 80° C. for 0.5 to 24 hours. For alternative methods of synthesis and the reactions of 1,2-benzoxathiins, see *Chemistry of Heterocyclic Compounds*, Vol. 21, part 2, (1966).

As shown in Equation 30, nitro compounds of Formula XV where J is $J_9$ (XVI) can be prepared from the appropriately substituted nitrobenzenes XVI. R' is Br or $CH_2Br$, $R_1$, $R_2$, $R_5$ and n are as previously defined.

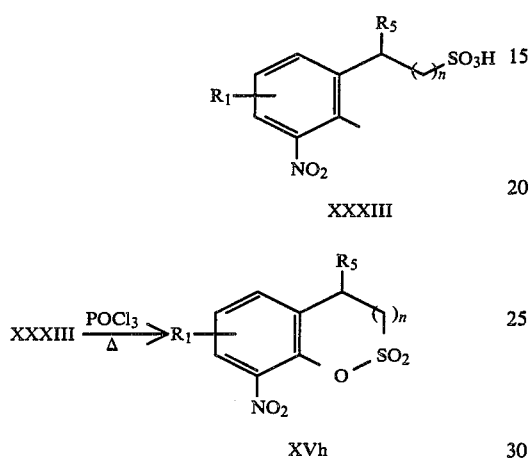

The nitrophenols XXXII, prepared by methods known to one skilled in the art, are heated with aqueous sodium sulfite to give the sulfonic acids XXXIII which are then cyclized by heating with phosphorous oxychloride.

The method is similar to those taught by Marckwald and Frahne, *Chem. Ber.* 31, 1854 (1898) for the preparation of 1,2-benzoxathiole, and Truce and Hoerger, *J. Amer. Chem. Soc.*, 76, 5357 (1954) and 77 2496 (1955) for the preparation of 1,2-benzoxathiin.

Alternatively, compounds of Formula XVh where n=0 can be prepared from nitrophenols XXXIV by the three step sequence shown in Equation 28. This is the method taught by Shearing and Smiles, *J. Chem. Soc.*, 1348 (1937) for the preparation of 5-methyl-1,2-benzoxathiole. For a review of this and alternate methods of synthesis of 1,2-benzoxathioles, see *Chemistry of Heterocyclic Compounds*, Vol. 21, part 1 (1966).

Equation 28

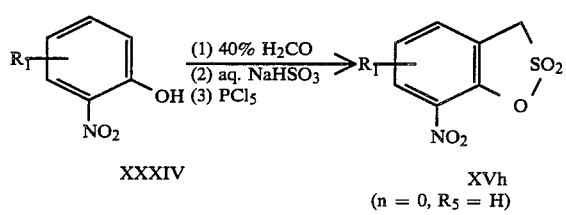

Compounds of Formula XVh where n=1 can be prepared from nitrophenols XXXII where R'=$R_5$=H by the three step sequence shown in Equation 29.

Equation 24

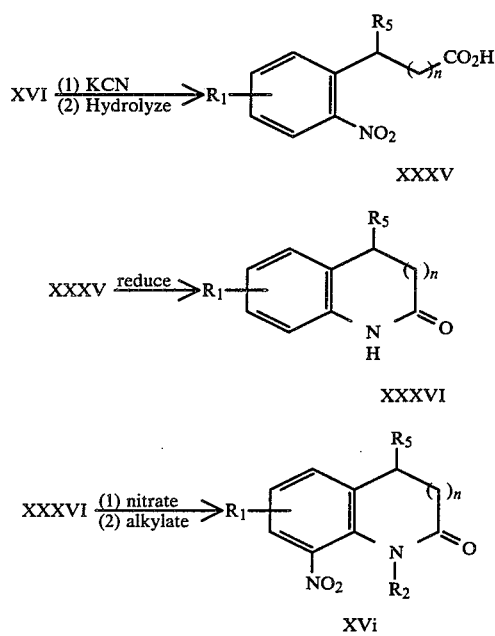

The nitrobenzenes XVI, previously discussed in Equation 15, are reacted with potassium cyanide in a solvent such as acetone to give nitrile intermediates which are hydrolized to the corresponding carboxylic acids XXXV by standard methods known to one skilled in the art. The nitro carboxylic acids XXXV, when reduced by standard methods (see discussion of Equation 14), spontaneously cyclize to give the lactams XXXVI. For a discussion of this reaction when n is 0, see W. Sumpter and F. Miller, *The Chemistry of Heterocyclic Compounds*, Vol. 8, Interscience Publishers, Inc., New York, 1954, p. 134–135, and references cited therein. For a discussion of this reaction when n is 1, see G. Jones, *The Chemistry of Heterocyclic Compounds*, Vol. 32, John Wiley and Sons, New York, 1977, p. 216–217, and references cited therein. The nitro lactams XVi are prepared from lactams XXXVI by the nitration, alkylation sequence described earlier for the preparation of nitro sultams XVg in Equation 25.

Alternatively, lactams XXXVI of Equation 30 can be prepared from the substituted anilines XXIX of Equation 26, as shown in Equation 31. $R_1$ and n are as previously defined.

Equation 31

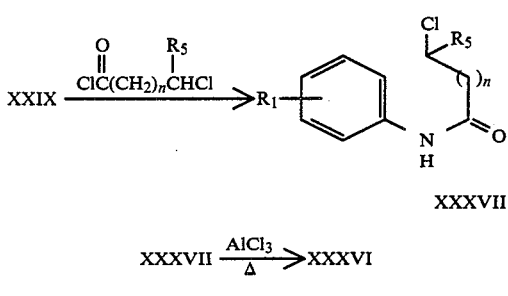

$$XXXVII \xrightarrow{AlCl_3}{\Delta} XXXVI$$

The substituted anilines XXVII are reacted with either a chloroacetyl chloride (n=0) or β-chloropropionyl chloride (n=1, $R_5$=H) in the presence of an acid scavenger to give the chloro amides XXXVII. The amides XXXVII are cyclized by heating in the presence of a suitable Friedel-Crafts reagent such as $AlCl_3$ (see discussion of Equation 24) to give the lactams XXXVI. The method of Equation 31 has been widely used for the preparation of oxindoles (XXXVI, n=0; see W. Sumpter and F. Miller, loc. cit., p. 135–136 for discussion and references) and for the preparation of 3,4-dihydro-2-quinolones (XXXVI, n=1; see G. Jones, loc. cit., p. 164–168 for discussion and references). For a general review of oxindole chemistry see W. Sumpter and F. Miller, loc. cit., p. 134–153.

As shown in Equation 32, nitro compounds of Formula XV where J is $J_{10}$ (XVj) can be prepared from the appropriately substituted phenols XXXII. R' is Br or $CH_2Cl$, $R_1$, $R_5$ and n are as previously defined.

Equation 32

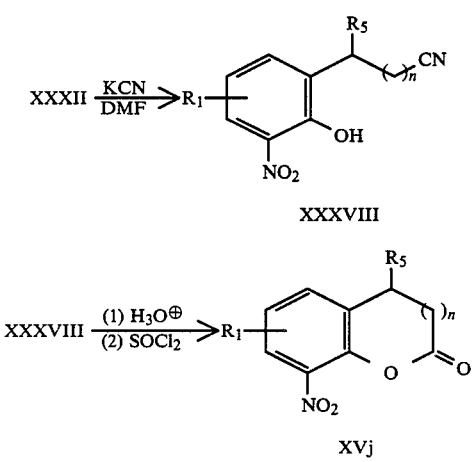

The nitrophenols XXXII, prepared by methods known to one skilled in the art, are reacted with potassium cyanide in a solvent such as DMF at 0° to 80° C. for 0.5 to 24 hours to give the cyanophenols XXXVIII. The cyano function is hydrolyzed to its corresponding carboxylic acid by methods known in the art. For n=0, the carboxylic acids cyclize spontaneously. For n=1, the carboxylic acid is cyclized by heating with a reagent such as thionyl chloride as taught by Wakselman et al. *Tetrahedron*, 30 4069 (1974) for the preparation of substituted dihydrocoumarins and 2-benzofuranones.

Alternatively, as shown in Equation 33, nitro compounds of Formula XVj where n=1 can be prepared by reducing the corresponding coumarins XVp, which are readily prepared from nitrosalicaldehydes XXXIX by heating with, for example where $R_3$ is H, potassium acetate in acetic anhydride according to the teachings of Gqola, et al., *Fort. Hare Pap.*, 6, 197 (1975) (Chem. Abst. 84:150452X (1975)) for the preparation of 8-nitrocoumarin (XVp, $R_1$=H). Coumarins are well known in the literature, for a review see *Comprehensive Organic Chemistry*, Vol. 4, Pergamon Press 1979.

Equation 33

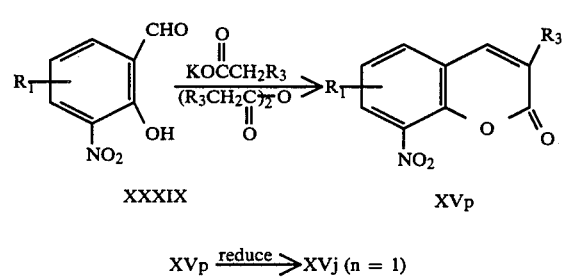

$$XVp \xrightarrow{reduce} XVj \, (n = 1)$$

As shown in Equation 34, nitro compounds of Formula XV where J is $J_{11}$ and n is 0 (XVk) can be prepared from the appropriately substituted nitro phenols XXXX. $R_6$ and $R_7$ are H, $R_1$ is as previously defined.

Equation 34

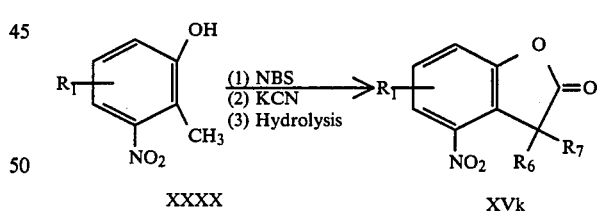

This method is parrallel to that previously discussed for the preparation of Formula XVj in Equation 32. The 2-benzofuranones XVk, where $R_6$ and/or $R_7$ are other than hydrogen, can be prepared from the 2-benzofuranones XVk where $R_6$ and/or $R_7$ are hydrogen by standard alkylation methods known in the art. For a review see: H. House, *Modern Synthetic Reactions*, 2nd Edition, W. A. Benjamin, Inc., Menlo Park, Calif. 1972, p. 542–570.

As shown in Equation 35, nitro compounds of Formula XV where J is $J_{11}$ and n is 1 (XVl) can be prepared from the appropriately substituted nitrophenylacetic acids XXXXI. $R_1$, $R_6$ and $R_7$ are as previously defined.

Equation 35

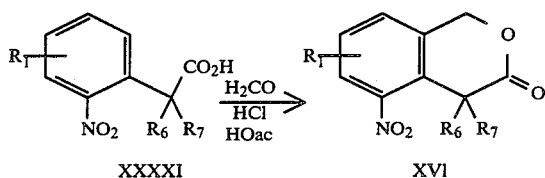

The nitrophenylacetic acids, prepared by methods known to one skilled in the art, are treated with formaldehyde in the presence of a strong acid such as HCl in a solvent such as acetic acid at 25° to 100° C. for 2 to 48 hours. This method has been used to prepare substituted benzo[c]pyran-3-ones, se U.S. Pat. No. 3,480, 634 (*Chem. Abst.* 72:43486s (1970)).

Alternatively, as shown in Equation 36, benzo[c]pyran-3-ones XV1 can be prepared from the appropriately substituted nitrotoluic acids XXXXII. $R_6$ and $R_7$ are H, $R_1$ is as previously defined.

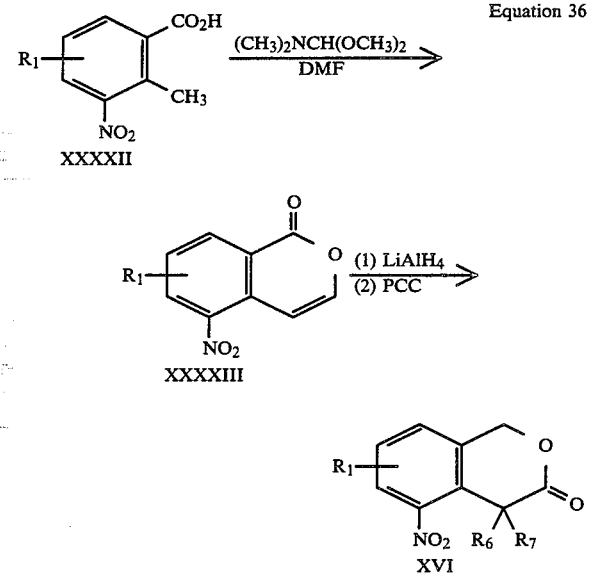

Equation 36

The nitrotoluic acids, prepared by methods known to one skilled in the art, are heated with dimethylformamide dimetheylacetal in DMF to produce, in part, the nitroisocoumarins XXXXIII. The isocoumarins are reduced by lithium aluminum hydride to give a hemiacetal which is then separated and oxidized with pyridinium chlorochromate (PCC) to give the desired benzo[c]pyran-3-ones. This is the method taught by Somei and Shoda, *Heterocycles*, 17, 417 (1982) for the preparation 1,4-dihydro-5-nitrobenzo[c]pyran-3-one (XVl, $R_1$, $R_6$ and $R_7$=H).

The benzo[c]pyran-3-ones XVl where $R_6$ and/or $R_7$ are other than hydrogen can be prepared by the standard alkylation methods discussed for Equation 34.

Additionally, benzo[c]pyran-3-ones XVl, where $R_1$ is other than $SCH_3$, can be prepared by the Baeyer-Villiger oxidation of 2-indanones XVm (n=0) (vide infra). The Baeyer-Villiger oxidation of ketones to esters is well known in the literature, for a review see: *Organic Reactions*, Vol. 9, John Wiley and Sons, New York, 1957, p. 73 to 107. For application of this reaction to 2-indanones see G. Swan *J. Chem. Soc.*, 1720 (1949).

As shown in Equation 37, nitro compounds of Formula XV, where J is $J_{12}$ (XVm), can be prepared from the appropriately substituted indenes and dihydronaphthalenes of Formula XXXXIV. $R_7$ is H, $R_1$, $R_6$ and n are as previously defined.

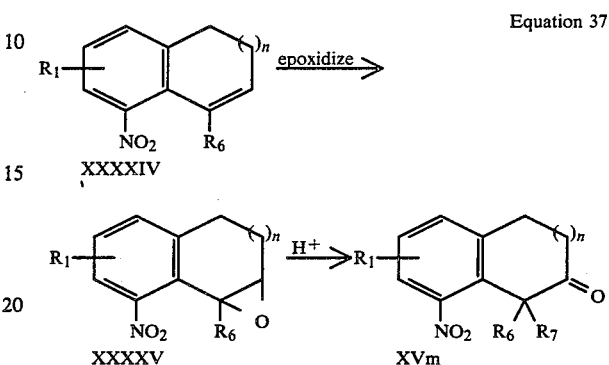

Equation 37

The nitroolefins XXXXIV can be converted to their corresponding epoxides XXXXV by either direct oxidation with a peracid such as m-chloroperbenzoic acid or via hydrobromination followed by treatment with a base as known to one skilled in the art. The epoxides XXXXV are rearranged to the desired 2-indanones (XVm, n=0) or tetralones (XVm, n=1) by reaction with either a protonic acid such as sulfuric acid as taught by Rosen et al., *J. Org. Chem.*, 29, 1723 (1964) or a Lewis Acid such as $BF_3$-etherate as taught by Bondinell and Pendleton, U.S. Pat. No. 4,192,888 (1980).

The starting nitroindenes (XXXXIV, n=0) and nitrodihydronaphthalenes (XXXXIV, n=1) are well known in the literature and can be prepared by methods known to one skilled in the art.

Alternatively, as shown in Equation 38, 2-tetralones of Formula XVm (n=1) can be prepared from the appropriately substituted nitrophenylacetic acids XXXXI discussed previously in Equation 35 by reaction with ethylene under Friedel-Crafts conditions. For a review of this and alternate syntheses of 2-tetralones see Shner and Przhiyaglovskaya, *Russian Chemical Reviews*, 35, 523 (1966).

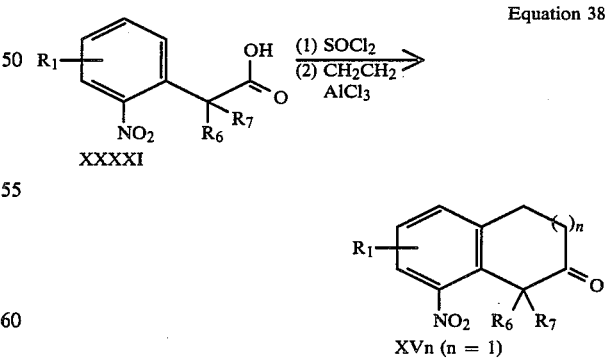

Equation 38

Additionally, the 2-indanones (XVm, n=0) and 2-tetralones (XVm, n=1) can be prepared from the corresponding 1-indanones (XVf, n=0) and 1-tetralones (XVf, n=1), respectively, via a 1,2-carbonyl transposition, as shown in Equation 39. $R_1$, $R_6$ and n are as previously defined.

Equation 39

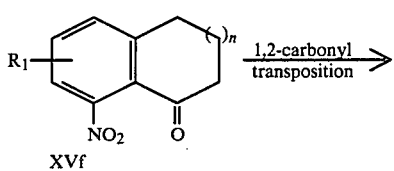
XVf

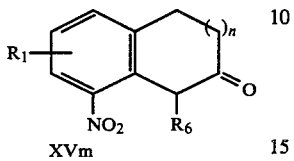
XVm 1,2-Carbonyl transpositions are well known in the literature and can be performed by a wide variety of methods, for a recent review, see: D. G. Morris, *Chem. Soc. Reviews*, II, 397–434 (1983). For application of this method to indanones, see U.S. Pat. No. 4,192,888. For application of the method to tetralones, see Shner and Przhiyaglovskaya loc. cit.

As shown in Equation 40, nitro compounds of Formula XV, where J is $J_{22}$ (XVn), can be prepared from the appropriately substituted nitrophenols XXXXVI. $R_1$, $R_3$, $R_4$ and n are as previously defined.

Equation 40

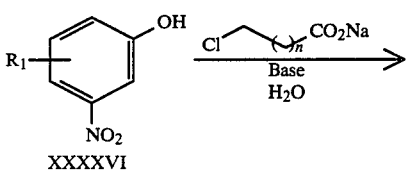
XXXXVI

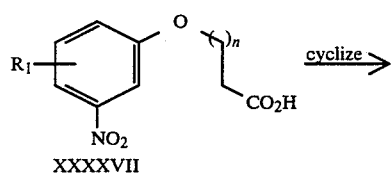
XXXXVII

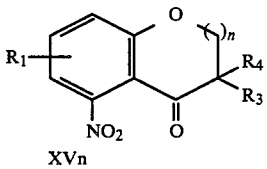
XVn

The reaction of the nitrophenol XXXXVI with the halo-acid salts produces the nitro ethers XXXXVII which are subsequently cyclized, in part, to give XVn ($R_3$, R=H) by heating the acid with a suitable condensing agent such as polyphosphoric acid, hydrofluoric acid, sulfuric acid or stannic chloride, or the acid may be converted to its chloride and heated with a typical Friedel-Crafts reagent such as aluminum chloride or stannic chloride. The ketones of Formula XVn where $R_3$ and/or $R_4$ are other than hydrogen can be prepared from ketones XVn where $R_3$ and/or $R_4$ are hydrogen by standard ketone alkylation and halogenation methods as described previously for compounds of Equation 24.

Alternately, as shown in Equation 41, compounds of Formula XVn where n=0 can be prepared from nitrobenzoates of Formula XXXXVIII. $R_1$, $R_3$ and $R_4$ are as previously defined.

Equation 41

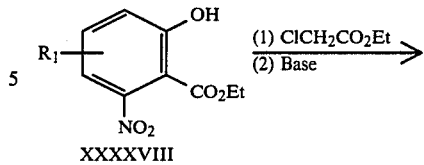
XXXXVIII

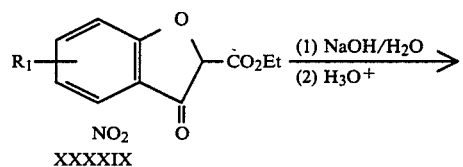
XXXXIX

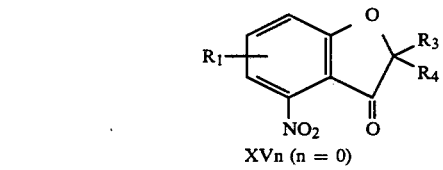
XVn (n = 0)

The phenol XXXXVIII is first alkylated with ethyl chloroacetate in the presence of an acid scavenger followed by reaction with a base to effect cyclization to the ketoester XXXXIX. The ketoester is then saponified and decarboxylated by heating with acid to give the 3-ketobenzofurans XVn (n=0). 3-Ketobenzofurans are well known in the art, for a review of their synthesis and chemistry see *Chemistry of Heterocyclic Compounds*, Vol. 29, Interscience Publishers, Inc., New York, 1974, p. 210–296.

Benzopyran-4-ones are also well known in the art, for a review see *Chemistry of Heterocyclic Compounds*, Vol. 31, Interscience Publishers, Inc., New York, 1977. For a review of the synthesis and chemistry of benzoxepin-5-ones see *Chemistry of Heterocyclic Compounds*, Vol. 26, Interscience Publishers, Inc., New York, 1972.

The nitro compounds of Formula XV in Equation 14, where J is $J_{13}$, $J_{14}$, $J_{15}$, $J_{16}$, $J_{17}$, $J_{18}$, $J_{19}$, $J_{20}$, $J_{21}$ or $J_{23}$ can be prepared from the nitro compounds of Formula XV where J is $J_1$, $J_2$, $J_3$, $J_4$ ($J_{24}$), $J_5$, $J_7$, $J_8$, $J_9$, $J_{10}$ or $J_{22}$, respectively, (n=1) by the bromination/dehydrobromination sequence described above for sulfonamides IV in Equation 9.

Alternately, nitro compounds of Formula XV in Equation 14 where J is $J_{15}$ can be prepared from nitro compounds of Formula XV where J is $J_{16}$ by treatment with the appropriate amines $R_2NH_2$ as taught by J. Jones and A. Pinder, *J. Chem. Soc.*, 2612 (1958). Additionally, the nitro compounds of Formula XV where J is $J_{21}$ can be prepared as discussed in Equation 33.

The nitro compounds of Formula XV in Equation 14 where J is $J_{18}$ can also be prepared from ketones XXXI by base treatment of its tosylhydrazone derivative as taught by B. Loev, et al., *J. Org. Chem.*, 31, 3531 (1966).

The preparation of compounds of Formula I where J is $J_1$ to $J_{12}$ and $J_{22}$ and n=2 can be prepared using the procedures outlined above for the analogous compounds where n=1.

The amines of Formula III in Equations 1 and 4 are also important intermediates for the preparation of the compounds of this invention and are described below.

The pyrimidines and triazines of Formula (IIIa) to (IIId) below are either known or can be prepared by obvious methods by one skilled in the art.

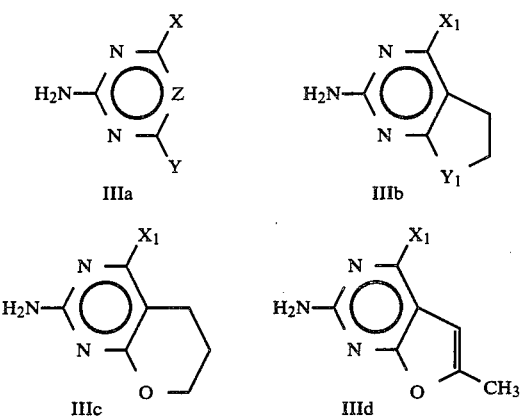

For a review of the synthesis and reactions of 2-aminopyrimidines (IIIa, Z=CR') see *The Chemistry of Heterocyclic Compounds*, Vol. 16, John Wiley and Sons, New York (1962). For a review of the synthesis and reactions of 2-amino-s-triazines (IIIa, Z=N) see *The Chemistry of Heterocyclic Compounds*, Vol. 13, John Wiley, New York (1959), F. C. Schaefer, U.S. Pat. No. 3,154,547 and F. C. Schaefer and K. R. Huffman, *J. Org. Chem.*, 28, 1812 (1963). The synthesis of the bicyclic amines IIIb and IIIc is taught in European Patent Application No. 803,005,05.7. The synthesis of bicyclic amines IIId is taught in European Patent Publication No. 46,677.

The amines of Formula III where X is $OCF_2H$, $OCH_2F$, $OCF_3$ or $CF_3$; or $X_1$ is $OCF_2H$ and/or Y is $OCH_2F$, $OCF_3$, $SCH_2F$, $SCF_3$ or $GCF_2T$ wherein G is O or S and T is H, CHClF, CHBrF or $CHFCF_3$ can be prepared by methods taught in South African Patent Application No. 825,045, or by suitable modifications that would be obvious to one skilled in the art.

The pyrimidines of Formula IIIa (Z=CH) where Y is —$CR_6(OCH_3)_2$, —$CR_6(OCH_2CH_3)_2$,

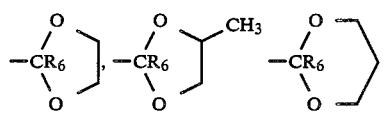

can be prepared according to the methods taught in European Patent Application No. 82-306,492.8 or suitable modifications thereof known to one skilled in the art.

The triazine amines of Formula IIIe where $X_3$ is $CH_3$ or $OCH_3$ and R is H or $CH_3$ can be prepared according to the teachings of U.S. Ser. No. 472,879, filed 14, 1983.

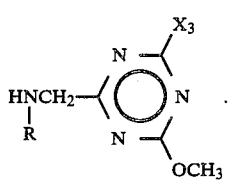

Preparations of 3-amino-1,2,4-triazoles of Formula (IIIf) are known in the art and 1,2,4-triazoles are reviewed in *The Chemistry of Heterocyclic Compounds* "Triazoles 1,2,4" (John Wiley and Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature synthesis are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); *Berichte*, 96, 1064 (1963).

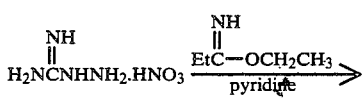

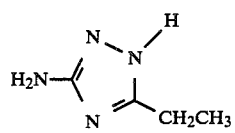

Condensation of hydrazine with ethyl N-cyanoacetimidate yields 3-amino-5-methyltriazole; *Journal of Organic Chemistry*, 28, 1816 (1963).

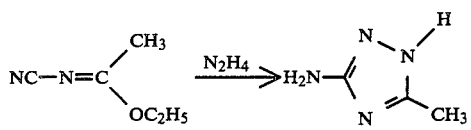

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

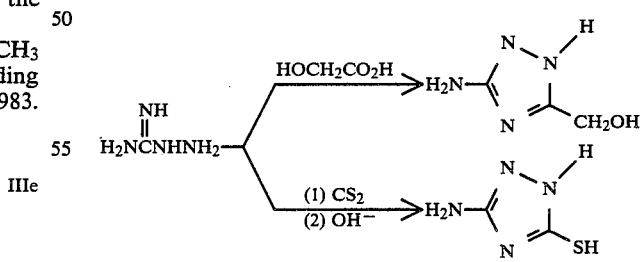

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry*, 39, 1522 (1974).

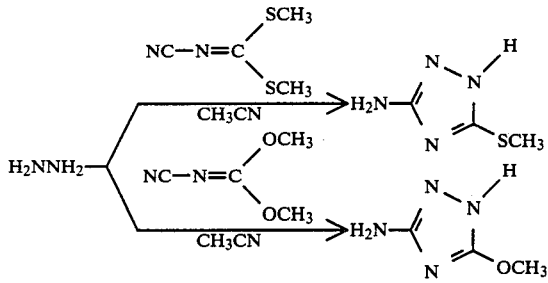

Reaction of substituted hydrazines with N-cyanothioimidocarbonates (prepared according to the procedure given in D. M. Wieland, Ph.D. Thesis, 1971, pp. 123-124) yields disubstituted aminotriazoles as shown below.

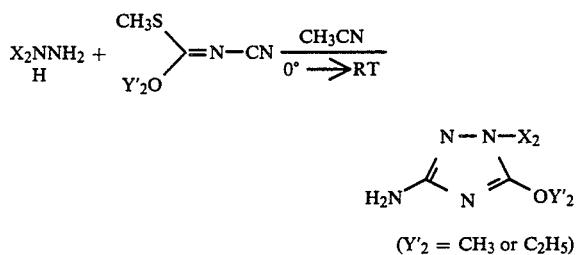

(Y′$_2$ = CH$_3$ or C$_2$H$_5$)

Many of the aminoheterocyclic intermediates of Formula (III) where R is methyl may be prepared by a two-step procedure as described for IIIi in Equation 42. X, Y and Z are as previously defined.

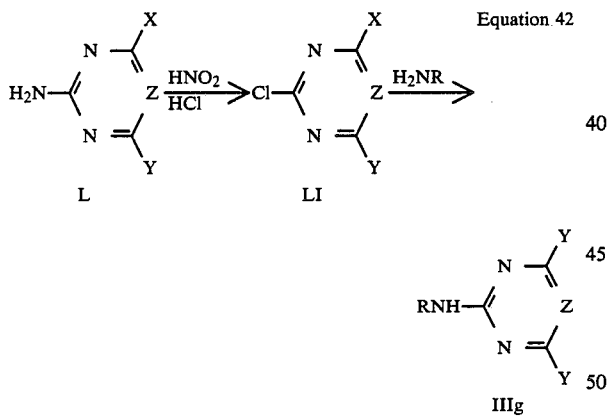

A solution of the amine L in concentrated hydrochloric acid is treated with sodium nitrite solution and the chloro compound LI is isolated in the usual manner by filtration of the acidic solution. A representative procedure is described by Bee and Rose in *J. Chem. Soc. C*, 2031 (1966), for the case in which Z=CH, and X=Y=OCH$_3$. Displacement of the chlorine of LI may be accomplished by heating with an excess of methylamine in water to obtain the methylamino heterocycle (IIIg).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

EXAMPLE 1

2-t-Butyl-3-hydroxy-7-chloro-2,3-dihydro-1,2-benzisothiazole-1,1-dioxide

To a solution of 49.5 g of N-t-butyl-2-chlorobenzenesulfonamide in 875 mls of dry THF was added 262 ml of a 1.6M hexane solution of n-butyl lithium at −20° to −5° C. under an inert atmosphere. The mixture was stirred at 0° C. for 1 hour, room temperature for 2 hours, recooled to −78° C. and contacted with 38 mls of dry dimethylformamide. The mixture was allowed to warm to room temperature overnight, poured into water, acidified to a ph of ~3 and ether extracted. The extract was washed with water and brine, dried over MgSO$_4$ and concentrated to give a yellow oil. The oil was dissolved in 50% ether in hexane solution and allowed to stand, giving, after filtration, 38 g of the title compound as colorless crystals, m.p. 139°–141° C.

90 MHz NMR (CDCl$_3$)δ: 7.7–7.2 (m, 3H, arom); 5.9 (br. d, J=11 Hz, 1H, CH or OH); 4.2 (br. d, J=11 Hz, 1H, OH or CH); and 1.5 (s, 9H, CH$_3$'s).

IR (nujol) 3440 cm$^{-1}$.

EXAMPLE 2

7-Chloro-1,2-benzisothiazole-1,1-dioxide

A solution of 37 g of 2-t-butyl-3-hydroxy-7-chloro-2,3-dihydro-1,2-benzisothiazole-1,1-dioxide and 0.2 g of tosic acid in 370 mls of benzene was refluxed through a Dean-Stark water separator for 16 hours, cooled in ice and filtered to give 18.9 g of the title compound as colorless crystals, m.p. 162°–164° C.

90 MHz NMR (CDCl$_3$)δ: 9.15 (s, 1H, CH); and 8.0–7.7 (m, 3H, arom).

IR (nujol) 1445, 1320, 1170 cm$^{-1}$.

EXAMPLE 3

7-Chloro-2,3-dihydro-1,2-benzisothiazole-1,1-dioxide

A suspension of 17.9 g of 7-chloro-1,2-benzisothiazole-1,1-dioxide in 180 ml of absolute etnanol was cooled to 0° C. and treated with 3.33 g of sodium borohydride at such a rate that the temperature remained below 5° C. The mixture was warmed to room temperature for 30 minutes, recooled to 0° C. and treated with glacial acetic acid to destroy excess hydride. The mixture was concentrated to dryness, the resulting solid suspended in water, filtered, washed with water and dried in vacuo at 50° C. for 16 hours to give 17.6 g of the title compound as a white powder, m.p. 159°–161° C.

90 MHz NMR (CDCl$_3$/DMSO)δ: 7.9–7.2 (m, 3H, arom;; 6.9 (br, 1H, NH); and 4.4 (s, 2H, CH$_2$).

IR (nujol) 3220 cm$^{-1}$.

EXAMPLE 4

2-Methyl-7-chloro-2,3-dihydro-1,2-benzisothiazole-1,1-dioxide

A solution of 16.6 g of 7-chloro-2,3-dihydro-1,2-benzisothiazole-1,1-dioxide in 85 mls of dry dimethylformamide was cooled and treated with 10 g of potassium t-butoxide at such a rate that the temperature remained below 6° C. The resulting suspension was stirred at 5° to 10° C. for 30 minutes, treated with 6.1 mls of methyl iodide at 10° to 15° C. and stirred at room temperature for 16 hours. The mixture was poured into ice water and the resulting solid was filtered, washed with water and dried in vacuo at 50° C. for 1.5 hours to give 15.4 g of the title compound as a pinkish solid, m.p. 95°–97° C.

90 MHz NMR (CDCl$_3$)δ: 7.8–7.2 (m, 3H, arom); 4.4 (s, 2H, CH$_2$); and 3.0 (s, 3H, CH$_3$).

IR (nujol) 1460, 1300, 1165, 1152 cm$^{-1}$.

EXAMPLE 5

2-Methyl-7-(phenylmethylthio)-2,3-dihydro-1,2-benzisothiazole-1,1-dioxide

To a solution of 12 g of potassium-t-butoxide in 100 ml of dry dimethylformamide was added 12.9 mls of benzyl mercaptan at −5°, to 0° C. under an inert atmosphere followed by 12.2 g of 2-methyl-7-chloro-2,3-dihydro-1,2-benzisothiazole-1,1-dioxide. The mixture was stirred at room temperature for 16 hours and poured into water to give a gummy solid. The water was decanted and extracted with ethyl acetate. The gummy solid was slurried in ethyl acetate and filtered to give 5.9 g of the title compound as a light orange solid, m.p. 119°–122° C. The combined ethyl acetate extract and filtrate were washed with water and brine, dried over MgSO$_4$ and concentrated to a solid which was slurried in ether and filtered to give an additional 7.6 g of product, m.p. 121°–124° C. Total yield was 13.5 g.

90 MHz NMR (CDCl$_3$)δ: 7.5–7.3 (m, 8H, arom); 4.3 (br. s, 4H, CH$_2$'s); and 2.9 (s, 3H, CH$_3$).

IR (nujol) 1455, 1290, 1155 cm$^{-1}$.

EXAMPLE 6

2-Methyl-2,3-dihydro-1,2-benzisothiazole-7-sulfonamide-1,1-dioxide

To a solution of 9.8 g of 2-methyl-7-(phenylmethylthio)-2,3-dihydro-1,2-benzisothiazole-1,1-dioxide and 1.44 mls of water in 200 mls of 1,2-dichloroethane was added a solution of 12.9 mls of sulfuryl chloride in 50 mls of 1,2-dichloroethane, dropwise, at 65° C. to 70° C. The mixture was heated at 70° to 75° C. for 2 hours, cooled to room temperature and concentrated. The residue was dissolved in 100 ml of methylene chloride and added to a solution of 4.0 ml of liquified ammonia in 200 mls of methylene chloride at −78° to −40° C. The mixture was warmed to room temperature, stirred for 16 hours, concentrated and the resulting white solid was suspended in 150 mls of 1N HCl, filtered, washed with water and ether and dried in vacuo at 70° C. to 5.0 g of the title compound as a white powder, m.p. 195°–197° C. (a similar preparation had m.p. 203°–205° C.).

90 MHz NMR (CDCl$_3$/DMSO)δ: 8.2–7.7 (m, 3H, arom); 7.5 (b, 2H NH$_2$); 4.4 (s, 2H, CH$_2$); and 2.9 (s, 3H, CH$_3$).

IR (nujol) 3330, 3230 cm$^{-1}$.

EXAMPLE 7

N-(Butylaminocarbonyl)-2-methyl-2,3-dihydro-1,2-benzisothiazole-7-sulfonamide-1,1-dioxide A suspension of 13.0 g of 2-methyl-2,3-dihydro-1,2-benzisothiazole-7-sulfonamide-1,1-dioxide, 11.2 ml of butyl isocyanate and 13.8 g of potassium carbonate in 200 ml of dry methyl ethyl ketone was heated at reflux for 2 hours. 13.8 g of potassium carbonate was added and heating was continued for an additional 16 hours. The mixture was cooled, the solvent was decanted from the solids, concentrated in vacuo, the residue dissolved in ethyl acetate and washed with saturated aq. NaHCO$_3$. The aqueous wash was added to the original solids diluted with water and acidified to pH ∼3 with dilute HCl. The mixture was extracted with methylene chloride, the extract was washed with water and brine, dried and concentrated in vacuo leaving a solid which was slurried in ether and filtered to give 13.24 g of the title compound as a white powder, m.p. 162°–164° C.

90 MHz NMR (CDCl$_3$)δ: 8.4–7.5 (m, 3H, arom); 6.4 (b, t, 1H, NH); 5.8 (b, 1H, NH); 4.4 (s, 2H, CH$_2$); 3.1 (m, 2H, CH$_2$); 3.0 (s, 3H, CH$_3$); and 1.7–0.7 (m, 7H, alkyl).

IR (nujol) 3350, 3240, 1680 cm$^{-1}$.

EXAMPLE 8

N-((4,6-Dimethoxypyrimidin-2-yl)aminocarbonyl)-2-methyl-2,3-dihydro-1,2-benzisothiazole-7-sulfonamide-1,1-dioxide A mixture of 13.2 g N-(butylaminocarbonyl)-2-methyl-2,3-dihydro-1,2-benzisothiazole-7-sulfonamide-1,1-dioxide, 3.7 ml of butyl isocyanate and 0.1 g of DABCO was treated with 3.5 ml of phosgene at 135°–138° C. for 2 hours, purged with N$_2$ and cooled to 0° C. depositing a solid which was filtered under nitrogen to give 5.5 g of 2-methyl-2,3-dihydro-1,2-benzisothiazole-7-sulfonyl isocyanate-1,1-dioxide as a cream colored solid, m.p. 176°–180° C., IR (nujol) 2220 cm$^{-1}$.

To a solution of 0.69 g of the isocyanate in 10 ml of dry methylene chloride was added 0.31 g of 2-amino-4,6-dimethoxypyrimidine. The mixture was heated to reflux for 1 minute and stirred at 25° C. for 16 hours. The resulting solid was filtered, washed with methylene chloride and ether to give 0.81 g of the title compound as a white powder, m.p. 229°–231° C.

90 MHz NMR (TFA-d)δ: 8.7–7.9 (m, 3H, aromatic); 6.3 (s, 1H, CH); 4.6 (s, 2H, CH$_2$); 4.2 (s, 6H, OCH$_3$); and 3.15 (s, 3H, CH$_3$).

IR (nujol) 1710 cm$^{-1}$.

EXAMPLE 9

N-((4,6-Dimethoxypyrimidin-2-yl)aminocarbonyl)benzo[c]furan-1-one-7-sulfonamide

A slurry of 0.8 g of crude phthalide-7-sulfonylisocyanate in 10 ml of dry acetonitrile was combined with 0.53 g of 2-amino-4,6-dimethoxypyrimidine and the mixture stirred at ambient temperature for 18 hours. The mixture was then diluted with 15 ml of acetonitrile, heated to a boil, filtered hot, the filtrate concentrated to 10 ml, allowed to cool, the crystals collected and washed with acetonitrile. Yield 0.69 g, m.p. 210°–215° C. (dec.). Recrystallization from acetonitrile improved the m.p. to 219°–221° C.(d).

NMR (CDCl$_3$): δ4.06 (s, 6H, OCH$_3$'s); 5.40 (s, 2H, CH$_2$); 5.84 (s, 1H, pyrimidine C$_5$—H); 7.2 (broad s, 1H, NH); 7.8–8.1 (m, 2H); 8. (broad d, J=8, 1H); and 13.0 (broad s, 1H, NH).

IR (nujol) 3430 cm$^{-1}$ (NH); 1765 (lactone); and 1728, 1708 (sulfonylurea).

The following compounds can be prepared according to the procedures of Examples 1–9 and Equations 1–42.

TABLE 1a

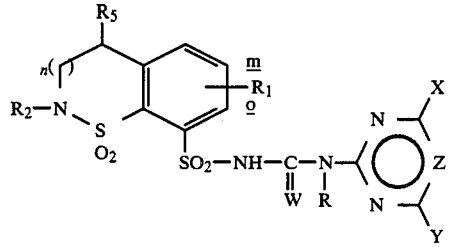

| W | n | R | R$_1$ | R$_2$ | R$_5$ | X | Y | Z | m.p. (°C.) |
|---|---|---|---|---|---|---|---|---|---|
| O | 0 | H | H | CH$_3$ | H | CH$_3$ | CH$_3$ | CH | 227–229 |
| O | 0 | H | H | CH$_3$ | H | CH$_3$ | OCH$_3$ | CH | 235–237 |
| O | 0 | H | H | CH$_3$ | H | OCH$_3$ | OCH$_3$ | CH | 229–231 |
| O | 0 | H | H | CH$_3$ | H | Cl | OCH$_3$ | CH | 206–208 |
| O | 0 | H | H | CH$_3$ | H | CH$_3$ | OCH$_3$ | N | 210–212 |
| O | 0 | H | H | CH$_3$ | H | OCH$_3$ | OCH$_3$ | N | 207–209 |
| O | 0 | H | H | CH$_2$CH$_3$ | H | CH$_3$ | CH$_3$ | CH | 215–217 |
| O | 0 | H | H | CH$_2$CH$_3$ | H | CH$_3$ | OCH$_3$ | CH | 221–222 |
| O | 0 | H | H | CH$_2$CH$_3$ | H | OCH$_3$ | OCH$_3$ | CH | 219–221 |
| O | 0 | H | H | CH$_2$CH$_3$ | H | Cl | OCH$_3$ | CH | 224–226 |
| O | 0 | H | H | CH$_2$CH$_3$ | H | CH$_3$ | OCH$_3$ | N | 169–171 |
| O | 0 | H | H | CH$_2$CH$_3$ | H | OCH$_3$ | OCH$_3$ | N | 180–183 |
| O | 0 | H | H | CH(CH$_3$)$_2$ | H | CH$_3$ | OCH$_3$ | CH | 234–236 |
| O | 0 | H | H | CH(CH$_3$)$_2$ | H | OCH$_3$ | OCH$_3$ | CH | 237–239 |
| O | 0 | H | H | CH(CH$_3$)$_2$ | H | CH$_3$ | CH$_3$ | CH | 206–210 |
| O | 0 | H | H | CH(CH$_3$)$_2$ | H | Cl | OCH$_3$ | CH | 239–241 |
| O | 0 | H | H | CH(CH$_3$)$_2$ | H | F | OCH$_3$ | CH | 221–223 |
| O | 0 | H | H | CH(CH$_3$)$_2$ | H | CH$_3$ | OCH$_3$ | N | 186–188 |
| O | 0 | H | H | CH(CH$_3$)$_2$ | H | OCH$_3$ | OCH$_3$ | N | 199–201 |
| O | 0 | H | H | CH(CH$_3$)$_2$ | H | CH$_3$ | CH(OCH$_3$)$_2$ | CH | 170–175 |
| O | 0 | CH$_3$ | H | CH(CH$_3$)$_2$ | H | OCH$_3$ | OCH$_3$ | CH | 200–204 |
| O | 0 | CH$_3$ | H | CH(CH$_3$)$_2$ | H | OCH$_3$ | OCH$_3$ | N | 192–195 |
| O | 1 | H | H | CH$_3$ | H | CH$_3$ | CH$_3$ | CH | |
| O | 1 | H | H | CH$_3$ | H | CH$_3$ | OCH$_3$ | CH | |
| O | 1 | H | H | CH$_3$ | H | OCH$_3$ | OCH$_3$ | CH | 230–235 |
| O | 1 | H | H | CH$_3$ | H | CH$_3$ | CH$_3$ | N | >215 |
| O | 1 | H | H | CH$_3$ | H | CH$_3$ | OCH$_3$ | N | |
| O | 1 | H | H | CH$_3$ | H | OCH$_3$ | OCH$_3$ | N | 258–266 |
| O | 1 | H | H | CH$_2$CH$_3$ | H | CH$_3$ | CH$_3$ | CH | |
| O | 1 | H | H | CH$_2$CH$_3$ | H | CH$_3$ | OCH$_3$ | CH | |
| O | 1 | H | H | CH$_2$CH$_3$ | H | OCH$_3$ | OCH$_3$ | CH | 199–200 |
| O | 1 | H | H | CH$_2$CH$_3$ | H | CH$_3$ | CH$_3$ | N | |
| O | 1 | H | H | CH$_2$CH$_3$ | H | CH$_3$ | OCH$_3$ | N | |
| O | 1 | H | H | CH$_2$CH$_3$ | H | OCH$_3$ | OCH$_3$ | N | |
| S | 0 | H | H | CH$_3$ | H | OCH$_3$ | OCH$_3$ | CH | |
| S | 1 | H | H | CH$_3$ | H | OCH$_3$ | OCH$_3$ | CH | |
| O | 0 | CH$_3$ | H | CH$_3$ | H | OCH$_3$ | OCH$_3$ | N | 182–188 |
| O | 0 | H | o-F | CH$_3$ | H | OCH$_3$ | OCH$_3$ | CH | |
| O | 0 | H | m-Cl | CH$_3$ | H | OCH$_3$ | OCH$_3$ | CH | |
| O | 0 | H | o-Br | CH$_3$ | H | OCH$_3$ | OCH$_3$ | CH | |
| O | 0 | H | m-CH$_3$ | CH$_3$ | H | OCH$_3$ | OCH$_3$ | CH | |
| O | 0 | H | o-OCH$_3$ | CH$_3$ | H | OCH$_3$ | OCH$_3$ | CH | |
| O | 0 | H | m-CF$_3$ | CH$_3$ | H | OCH$_3$ | OCH$_3$ | CH | |
| O | 0 | H | H | CH$_3$ | H | Cl | OCH$_3$ | CH | |
| O | 0 | H | H | CH$_3$ | H | CH$_3$ | OCH$_2$CH$_3$ | CH | |
| O | 0 | H | H | CH$_3$ | H | CH$_3$ | NH$_2$ | CH | |
| O | 0 | H | H | CH$_3$ | H | CH$_3$ | NHCH$_3$ | CH | |
| O | 0 | H | H | CH$_3$ | H | CH$_3$ | N(CH$_3$)$_2$ | CH | |
| O | 0 | H | H | CH$_3$ | H | CH$_3$ | CH$_2$CH$_3$ | CH | |
| O | 0 | H | H | CH$_3$ | H | CH$_3$ | CF$_3$ | CH | |
| O | 0 | H | H | CH$_3$ | H | CH$_3$ | SCH$_3$ | CH | |
| O | 0 | H | H | CH$_3$ | H | CH$_3$ | OCH$_2$CH=CH$_2$ | CH | |
| O | 0 | H | H | CH$_3$ | H | CH$_3$ | OCH$_2$C≡CH | CH | |
| O | 0 | H | H | CH$_3$ | H | CH$_3$ | OCH$_2$CF$_3$ | CH | 193–195 |
| O | 0 | H | H | CH$_3$ | H | CH$_3$ | OCH$_2$CH$_2$OCH$_3$ | CH | |
| O | 0 | H | H | CH$_3$ | H | CH$_3$ | CH(OCH$_3$)$_2$ | CH | |
| O | 1 | H | H | CH(CH$_3$)$_2$ | H | CH$_3$ | CH$_3$ | CH | |
| O | 1 | H | H | CH(CH$_3$)$_2$ | H | OCH$_3$ | CH$_3$ | CH | |
| O | 1 | H | H | CH(CH$_3$)$_2$ | H | OCH$_3$ | OCH$_3$ | CH | 211–214 |
| O | 1 | H | H | CH(CH$_3$)$_2$ | H | Cl | OCH$_3$ | CH | |

TABLE 1a-continued

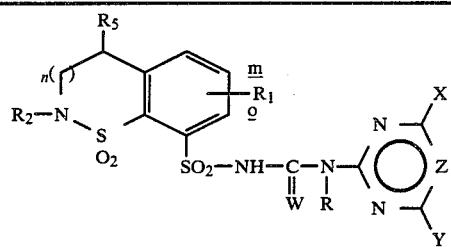

| W | n | R | R₁ | R₂ | R₅ | X | Y | Z | m.p. (°C.) |
|---|---|---|---|---|---|---|---|---|---|
| O | 1 | H | H | CH(CH₃)₂ | H | OCH₃ | CH₃ | N | |
| O | 1 | H | H | CH(CH₃)₂ | H | OCH₃ | OCH₃ | N | |
| O | 0 | H | H | CH₃ | H | CH₃ | (O-CH(-)-O cyclic) | CH | |
| O | 0 | H | H | CH₃ | H | CH₃ | CH₂OCH₃ | CH | 169–171 |
| O | 0 | H | H | CH₃ | H | CH₃ | CH₃ | CCH₃ | |
| O | 0 | H | H | CH₃ | H | CH₃ | CH₃ | CCH₂CH₃ | |
| O | 0 | H | H | CH₃ | H | CH₃ | CH₃ | CCl | |
| O | 0 | H | H | CH₃ | H | CH₃ | CH₃ | CBr | |
| O | 1 | H | H | CH₃ | H | CH₃ | CH₂OCH₃ | CH | |
| O | 1 | H | H | CH₃ | H | Cl | OCH₃ | CH | |
| O | 0 | H | H | CH₂CH₂CH₃ | H | CH₃ | CH₃ | CH | 195–198 |
| O | 0 | H | H | CH₂CH₂CH₃ | H | CH₃ | OCH₃ | CH | 197–199 |
| O | 0 | H | H | CH₂CH₂CH₃ | H | OCH₃ | OCH₃ | CH | 206–208 |
| O | 0 | H | H | CH₂CH₂CH₃ | H | Cl | OCH₃ | CH | 199–201 |
| O | 0 | H | H | CH₂CH₂CH₃ | H | CH₃ | OCH₃ | N | |
| O | 0 | H | H | CH₂CH₂CH₃ | H | OCH₃ | OCH₃ | N | 187–190 |
| O | 0 | H | H | CH₂CH₂CH₂CH₃ | H | OCH₃ | OCH₃ | N | 185–187 |
| O | 0 | H | H | CH₂CH₂CH₂CH₃ | H | CH₃ | CH₃ | CH | 193–195 |
| O | 0 | H | H | CH₂CH₂CH₂CH₃ | H | CH₃ | OCH₃ | CH | 167–170 |
| O | 0 | H | H | CH₂CH₂CH₂CH₃ | H | OCH₃ | OCH₃ | CH | 214–216 |
| O | 0 | H | H | CH₂CH₂CH₂CH₃ | H | Cl | OCH₃ | CH | 195–197 |
| O | 0 | H | H | CH₂CH₂CH₂CH₃ | H | CH₃ | OCH₃ | N | 165–168 |
| O | 0 | H | H | H | H | OCH₃ | OCH₃ | CH | |
| O | 0 | H | H | CH₃ | CH₃ | OCH₃ | OCH₃ | CH | |
| O | 0 | H | m-SCH₃ | CH₃ | H | OCH₃ | OCH₃ | CH | |
| O | 0 | H | m-OCF₂H | CH₃ | H | OCH₃ | OCH₃ | CH | |
| O | 0 | H | H | CH₃ | H | F | OCH₃ | CH | 224–226 |
| O | 0 | H | H | CH₃ | H | Br | OCH₃ | CH | 219–221 |
| O | 0 | H | H | CH₃ | H | CH₂F | OCH₃ | CH | |
| O | 0 | H | H | CH₃ | H | OCF₂H | CH₃ | CH | 228–230 |
| O | 0 | H | H | CH₃ | H | CF₃ | OCH₃ | CH | |
| O | 0 | H | H | CH₂CH₂CH₃ | H | OCF₂H | OCH₃ | CH | 185–189 |
| O | 0 | H | H | CH₂CH₂CH₃ | H | OCF₂H | OCF₂H | CH | 207–210 |
| O | 0 | H | H | CH₂CH₂CH₃ | H | Br | OCH₃ | CH | 190–192 |
| O | 0 | H | H | CH(CH₃)CH₂CH₃ | H | CH₃ | CH₃ | CH | |
| O | 0 | H | H | CH(CH₃)CH₂CH₃ | H | CH₃ | OCH₃ | CH | |
| O | 0 | H | H | CH(CH₃)CH₂CH₃ | H | OCH₃ | OCH₃ | CH | 220–222 |
| O | 0 | H | H | CH(CH₃)CH₂CH₃ | H | Cl | OCH₃ | CH | 221–224 |
| O | 0 | H | H | CH(CH₃)CH₂CH₃ | H | CH₃ | OCH₃ | N | 151–153 |
| O | 0 | H | H | CH(CH₃)CH₂CH₃ | H | OCH₃ | OCH₃ | N | 139–142 |
| O | 0 | H | H | CH₃ | H | CH₃ | (O-C(CH₃)(-)-O cyclic, 6-membered) | CH | |
| O | 0 | H | H | CH₃ | H | CH₃ | (O-CH(-)-O cyclic with CH₃ branch) | CH | |
| O | 0 | H | H | CH₃ | H | CH₃ | H | CH | |
| O | 0 | H | H | CH₃ | H | CH₃ | CN | CH | |
| O | 0 | H | H | CH₃ | H | CH₃ | CH(OCH₂CH₃)₂ | CH | |
| O | 0 | H | H | CH₃ | H | CH₃ | OCH₂F | CH | |
| O | 0 | H | H | CH₃ | H | CH₃ | OCF₃ | CH | |
| O | 0 | H | H | CH₃ | H | CH₃ | SCH₂F | CH | |
| O | 0 | H | H | CH₃ | H | CH₃ | SCF₃ | CH | |

TABLE 1a-continued

| W | n | R | $R_1$ | $R_2$ | $R_5$ | X | Y | Z | m.p. (°C.) |
|---|---|---|---|---|---|---|---|---|---|
| O | 0 | H | H | $CH_3$ | H | $CH_3$ | $OCF_2H$ | CH | |
| O | 0 | H | H | $CH_3$ | H | $CH_3$ | $OCF_2CHClF$ | CH | |
| O | 0 | H | H | $CH_3$ | H | $CH_3$ | $OCF_2CHBrF$ | CH | |
| O | 0 | H | H | $CH_3$ | H | $CH_3$ | $OCF_2CHFCF_3$ | CH | |
| O | 0 | H | H | $CH_3$ | H | $CH_3$ | $SCF_2H$ | CH | |
| O | 0 | H | H | $CH_3$ | H | $CH_3$ | $SCF_2CHClF$ | CH | |
| O | 0 | H | H | $CH_3$ | H | $CH_3$ | $SCF_2CHBrF$ | CH | |
| O | 0 | H | H | $CH_3$ | H | $CH_3$ | $SCF_2CHFCF_3$ | CH | |
| O | 2 | H | H | $CH_3$ | H | $CH_3$ | $CH_3$ | CH | |
| O | 2 | H | H | $CH_3$ | H | $CH_3$ | $OCH_3$ | CH | |
| O | 2 | H | H | $CH_3$ | H | $OCH_3$ | $OCH_3$ | CH | |
| O | 2 | H | H | $CH_3$ | H | Cl | $OCH_3$ | CH | |
| O | 2 | H | H | $CH_3$ | H | $CH_3$ | $OCH_3$ | N | |
| O | 2 | H | H | $CH_3$ | H | $OCH_3$ | $OCH_3$ | N | |
| O | 0 | $CH_3$ | H | $CH_3$ | H | $OCH_3$ | $OCH_3$ | CH | 192–194 |
| O | 0 | H | H | $CH_3$ | H | $OCH_3$ | $CH(OCH_3)_2$ | CH | 167–168 |
| O | 0 | H | H | $CH_3$ | H | $OCH_2CH_3$ | $CH_3$ | CH | |
| O | 0 | H | H | $CH_3$ | H | $OCH_3$ | $N_3$ | CH | |

TABLE 2a

| W | n | R | $R_1$ | $R_5$ | X | Y | Z | m.p. (°C.) |
|---|---|---|---|---|---|---|---|---|
| O | 0 | H | H | H | $CH_3$ | $CH_3$ | CH | |
| O | 0 | H | H | H | $CH_3$ | $OCH_3$ | CH | |
| O | 0 | H | H | H | $OCH_3$ | $OCH_3$ | CH | |
| O | 0 | H | H | H | $CH_3$ | $CH_3$ | N | |
| O | 0 | H | H | H | $CH_3$ | $OCH_3$ | N | |
| O | 0 | H | H | H | $OCH_3$ | $OCH_3$ | N | |
| O | 1 | H | H | H | $CH_3$ | $CH_3$ | CH | |
| O | 1 | H | H | H | $CH_3$ | $OCH_3$ | CH | |
| O | 1 | H | H | H | $OCH_3$ | $OCH_3$ | CH | |
| O | 1 | H | H | H | $CH_3$ | $CH_3$ | N | |
| O | 1 | H | H | H | $CH_3$ | $OCH_3$ | N | |
| O | 1 | H | H | H | $OCH_3$ | $OCH_3$ | N | |
| S | 0 | H | H | H | $OCH_3$ | $OCH_3$ | CH | |
| S | 1 | H | H | H | $OCH_3$ | $OCH_3$ | CH | |
| O | 0 | $CH_3$ | H | H | $OCH_3$ | $OCH_3$ | N | |
| O | 0 | H | o-F | H | $OCH_3$ | $OCH_3$ | CH | |
| O | 0 | H | m-Cl | H | $OCH_3$ | $OCH_3$ | CH | |
| O | 0 | H | o-Br | H | $OCH_3$ | $OCH_3$ | CH | |
| O | 0 | H | m-$CH_3$ | H | $OCH_3$ | $OCH_3$ | CH | |
| O | 0 | H | o-$OCH_3$ | H | $OCH_3$ | $OCH_3$ | CH | |
| O | 0 | H | m-$CF_3$ | H | $OCH_3$ | $OCH_3$ | CH | |
| O | 0 | H | H | H | Cl | $OCH_3$ | CH | |
| O | 0 | H | H | H | $CH_3$ | $OCH_2CH_3$ | CH | |
| O | 0 | H | H | H | $CH_3$ | $NH_2$ | CH | |
| O | 0 | H | H | H | $CH_3$ | $NHCH_3$ | CH | |
| O | 0 | H | H | H | $CH_3$ | $N(CH_3)_2$ | CH | |
| O | 0 | H | H | H | $CH_3$ | $CH_2CH_3$ | CH | |
| O | 0 | H | H | H | $CH_3$ | $CF_3$ | CH | |
| O | 0 | H | H | H | $CH_3$ | $SCH_3$ | CH | |
| O | 0 | H | H | H | $CH_3$ | $OCH_2CH=CH_2$ | CH | |
| O | 0 | H | H | H | $CH_3$ | $OCH_2C\equiv CH$ | CH | |
| O | 0 | H | H | H | $CH_3$ | $OCH_2CF_3$ | CH | |

TABLE 2a-continued

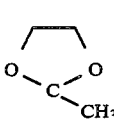

| W | n | R | R₁ | R₅ | X | Y | Z | m.p. (°C.) |
|---|---|---|---|---|---|---|---|---|
| O | 0 | H | H | H | CH₃ | OCH₂CH₂OCH₃ | CH | |
| O | 0 | H | H | H | CH₃ | CH(OCH₃)₂ | CH | |
| O | 0 | H | H | H | CH₃ | 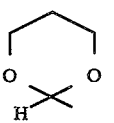 | CH | |
| O | 0 | H | H | H | CH₃ | CH₂OCH₃ | CH | |
| O | 0 | H | H | H | CH₃ | CH₃ | CCH₃ | |
| O | 0 | H | H | H | CH₃ | CH₃ | CCH₂CH₃ | |
| O | 0 | H | H | H | CH₃ | CH₃ | CCl | |
| O | 0 | H | H | H | CH₃ | CH₃ | CBr | |
| O | 1 | H | H | H | CH₃ | CH₂OCH₃ | CH | |
| O | 1 | H | H | H | Cl | OCH₃ | CH | |
| O | 0 | H | H | CH₃ | OCH₃ | OCH₃ | CH | |
| O | 0 | H | m-SCH₃ | H | OCH₃ | OCH₃ | CH | |
| O | 0 | H | m-OCF₂H | H | OCH₃ | OCH₃ | CH | |
| O | 0 | H | H | H | F | OCH₃ | CH | |
| O | 0 | H | H | H | CH₂F | OCH₃ | CH | |
| O | 0 | H | H | H | OCF₂H | OCH₃ | CH | |
| O | 0 | H | H | H | OCF₃ | OCH₃ | CH | |
| O | 0 | H | H | H | CF₃ | OCH₃ | CH | |
| O | 0 | H | H | H | CH₃ | 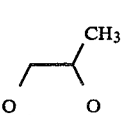 | CH | |
| O | 0 | H | H | H | Br | OCH₃ | CH | |
| O | 0 | H | H | H | CH₃ | 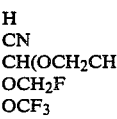 | CH | |
| O | 0 | H | H | H | CH₃ | H | CH | |
| O | 0 | H | H | H | CH₃ | CN | CH | |
| O | 0 | H | H | H | CH₃ | CH(OCH₂CH₃)₂ | CH | |
| O | 0 | H | H | H | CH₃ | OCH₂F | CH | |
| O | 0 | H | H | H | CH₃ | OCF₃ | CH | |
| O | 0 | H | H | H | CH₃ | SCH₂F | CH | |
| O | 0 | H | H | H | CH₃ | SCF₃ | CH | |
| O | 0 | H | H | H | CH₃ | OCF₂H | CH | |
| O | 0 | H | H | H | CH₃ | OCF₂CHClF | CH | |
| O | 0 | H | H | H | CH₃ | OCF₂CHBrF | CH | |
| O | 0 | H | H | H | CH₃ | OCF₂CHFCF₃ | CH | |
| O | 0 | H | H | H | CH₃ | SCF₂H | CH | |
| O | 0 | H | H | H | CH₃ | SCF₂CHClF | CH | |
| O | 0 | H | H | H | CH₃ | SCF₂CHBrF | CH | |
| O | 0 | H | H | H | CH₃ | SCF₂CHFCF₃ | CH | |
| O | 2 | H | H | H | CH₃ | CH₃ | CH | |
| O | 2 | H | H | H | CH₃ | OCH₃ | CH | |
| O | 2 | H | H | H | OCH₃ | OCH₃ | CH | |
| O | 2 | H | H | H | Cl | OCH₃ | CH | |
| O | 2 | H | H | H | CH₃ | OCH₃ | N | |
| O | 2 | H | H | H | OCH₃ | OCH₃ | N | |

TABLE 3a

[Structure: substituted isoquinolinone sulfonylurea with pyrimidine/triazine ring bearing substituents X, Y, Z; R5 on CH group, n(CH2) linker, R2-N, R1 on aromatic ring, SO2-NH-C(=W)-N(R)- linkage]

| W | n | R | R₁ | R₂ | R₅ | X | Y | Z | m.p. (°C.) |
|---|---|---|---|---|---|---|---|---|---|
| O | 0 | H | H | CH₃ | H | CH₃ | CH₃ | CH | 215–216 |
| O | 0 | H | H | CH₃ | H | CH₃ | OCH₃ | CH | 215–217 |
| O | 0 | H | H | CH₃ | H | OCH₃ | OCH₃ | CH | 202–204 |
| O | 0 | H | H | CH₃ | H | Cl | OCH₃ | CH | 211–213 |
| O | 0 | H | H | CH₃ | H | CH₃ | OCH₃ | N | 192–193 |
| O | 0 | H | H | CH₃ | H | OCH₃ | OCH₃ | N | 198–200 |
| O | 0 | H | H | CH(CH₃)₂ | H | CH₃ | CH₃ | CH | 150–153 |
| O | 0 | H | H | CH(CH₃)₂ | H | CH₃ | OCH₃ | CH | 195–197 |
| O | 0 | H | H | CH(CH₃)₂ | H | OCH₃ | OCH₃ | CH | 199–203 |
| O | 0 | H | H | CH(CH₃)₂ | H | Cl | OCH₃ | CH | 180–183 |
| O | 0 | H | H | CH(CH₃)₂ | H | CH₃ | OCH₃ | N | 181–183 |
| O | 0 | H | H | CH(CH₃)₂ | H | OCH₃ | OCH₃ | N | 203–206 |
| O | 0 | H | H | CH₂CH₃ | H | CH₃ | OCH₃ | CH | |
| O | 0 | H | H | CH₂CH₃ | H | OCH₃ | OCH₃ | CH | |
| O | 1 | H | H | CH₃ | H | CH₃ | CH₃ | CH | |
| O | 1 | H | H | CH₃ | H | CH₃ | OCH₃ | CH | |
| O | 1 | H | H | CH₃ | H | OCH₃ | OCH₃ | CH | |
| O | 1 | H | H | CH₃ | H | CH₃ | CH₃ | N | |
| O | 1 | H | H | CH₃ | H | CH₃ | OCH₃ | N | |
| O | 1 | H | H | CH₃ | H | OCH₃ | OCH₃ | N | |
| O | 1 | H | H | CH₂CH₃ | H | CH₃ | CH₃ | CH | |
| O | 1 | H | H | CH₂CH₃ | H | CH₃ | OCH₃ | CH | |
| O | 1 | H | H | CH₂CH₃ | H | OCH₃ | OCH₃ | CH | |
| O | 1 | H | H | CH₂CH₃ | H | CH₃ | CH₃ | N | |
| O | 1 | H | H | CH₂CH₃ | H | CH₃ | OCH₃ | N | |
| O | 1 | H | H | CH₂CH₃ | H | OCH₃ | OCH₃ | N | |
| S | 0 | H | H | CH₃ | H | OCH₃ | OCH₃ | CH | |
| S | 1 | H | H | CH₃ | H | OCH₃ | OCH₃ | CH | |
| O | 0 | CH₃ | H | CH₃ | H | OCH₃ | OCH₃ | N | |
| O | 0 | H | o-F | CH₃ | H | OCH₃ | OCH₃ | CH | |
| O | 0 | H | m-Cl | CH₃ | H | OCH₃ | OCH₃ | CH | |
| O | 0 | H | o-Br | CH₃ | H | OCH₃ | OCH₃ | CH | |
| O | 0 | H | m-CH₃ | CH₃ | H | OCH₃ | OCH₃ | CH | |
| O | 0 | H | o-OCH₃ | CH₃ | H | OCH₃ | OCH₃ | CH | |
| O | 0 | H | m-CF₃ | CH₃ | H | OCH₃ | OCH₃ | CH | |
| O | 0 | H | H | CH₃ | H | Cl | OCH₃ | CH | |
| O | 0 | H | H | CH₃ | H | CH₃ | OCH₂CH₃ | CH | |
| O | 0 | H | H | CH₃ | H | CH₃ | NH₂ | CH | |
| O | 0 | H | H | CH₃ | H | CH₃ | NHCH₃ | CH | |
| O | 0 | H | H | CH₃ | H | CH₃ | N(CH₃)₂ | CH | |
| O | 0 | H | H | CH₃ | H | CH₃ | CH₂CH₃ | CH | |
| O | 0 | H | H | CH₃ | H | CH₃ | CF₃ | CH | |
| O | 0 | H | H | CH₃ | H | CH₃ | SCH₃ | CH | |
| O | 0 | H | H | CH₃ | H | CH₃ | OCH₂CH=CH₂ | CH | |
| O | 0 | H | H | CH₃ | H | CH₃ | OCH₂C≡CH | CH | |
| O | 0 | H | H | CH₃ | H | CH₃ | OCH₂CF₃ | CH | |
| O | 0 | H | H | CH₃ | H | CH₃ | OCH₂CH₂OCH₃ | CH | |
| O | 0 | H | H | CH₃ | H | CH₃ | CH(OCH₃)₂ | CH | |
| O | 0 | H | H | CH₃ | H | CH₃ | [1,3-dioxolan-2-yl: CH(OCH₂CH₂O)] | CH | |
| O | 0 | H | H | CH₃ | H | CH₃ | CH₂OCH₃ | CH | |
| O | 0 | H | H | CH₃ | H | CH₃ | CH₃ | CCH₃ | |
| O | 0 | H | H | CH₃ | H | CH₃ | CH₃ | CCH₂CH₃ | |
| O | 0 | H | H | CH₃ | H | CH₃ | CH₃ | CCl | |
| O | 0 | H | H | CH₃ | H | CH₃ | CH₃ | CBr | |
| O | 1 | H | H | CH₃ | H | CH₃ | CH₂OCH₃ | CH | |
| O | 1 | H | H | CH₃ | H | Cl | OCH₃ | CH | |
| O | 0 | H | H | CH₂CH₂CH₃ | H | CH₃ | CH₃ | CH | |
| O | 0 | H | H | CH₂CH₂CH₃ | H | CH₃ | OCH₃ | CH | |
| O | 0 | H | H | CH₂CH₂CH₃ | H | OCH₃ | OCH₃ | CH | |
| O | 0 | H | H | CH₂CH₂CH₃ | H | Cl | OCH₃ | CH | |
| O | 0 | H | H | CH₂CH₂CH₃ | H | CH₃ | OCH₃ | N | |
| O | 0 | H | H | CH₂CH₂CH₃ | H | OCH₃ | OCH₃ | N | |

TABLE 3a-continued

| W | n | R | R$_1$ | R$_2$ | R$_5$ | X | Y | Z | m.p. (°C.) |
|---|---|---|---|---|---|---|---|---|---|
| O | 0 | H | H | CH$_2$CH$_2$CH$_2$CH$_3$ | H | OCH$_3$ | OCH$_3$ | N | |
| O | 0 | H | H | H | H | CH$_3$ | CH$_3$ | CH | |
| O | 0 | H | H | H | H | CH$_3$ | OCH$_3$ | CH | |
| O | 0 | H | H | H | H | OCH$_3$ | OCH$_3$ | CH | |
| O | 0 | H | H | H | H | Cl | OCH$_3$ | CH | |
| O | 0 | H | H | H | H | CH$_3$ | OCH$_3$ | N | |
| O | 0 | H | H | H | H | OCH$_3$ | OCH$_3$ | N | |
| O | 0 | H | H | CH$_3$ | CH$_3$ | OCH$_3$ | OCH$_3$ | CH | |
| O | 0 | H | m-SCH$_3$ | CH$_3$ | H | OCH$_3$ | OCH$_3$ | CH | |
| O | 0 | H | m-OCF$_2$H | CH$_3$ | H | OCH$_3$ | OCH$_3$ | CH | |
| O | 0 | H | H | CH$_3$ | H | F | OCH$_3$ | CH | |
| O | 0 | H | H | CH$_3$ | H | Br | OCH$_3$ | CH | |
| O | 0 | H | H | CH$_3$ | H | CH$_2$F | OCH$_3$ | CH | |
| O | 0 | H | H | CH$_3$ | H | OCF$_2$H | OCH$_3$ | CH | |
| O | 0 | H | H | CH$_3$ | H | OCF$_3$ | OCH$_3$ | CH | |
| O | 0 | H | H | CH$_3$ | H | CF$_3$ | OCH$_3$ | CH | |
| O | 0 | H | H | CH$_3$ | H | CH$_3$ | (1,3-dioxan-2-yl) | CH | |
| O | 0 | H | H | CH$_3$ | H | CH$_3$ | (5-methyl-1,3-dioxan-2-yl) | CH | |
| O | 0 | H | H | CH$_3$ | H | CH$_3$ | H | CH | |
| O | 0 | H | H | CH$_3$ | H | CH$_3$ | CN | CH | |
| O | 0 | H | H | CH$_3$ | H | CH$_3$ | CH(OCH$_2$CH$_3$)$_2$ | CH | |
| O | 0 | H | H | CH$_3$ | H | CH$_3$ | OCH$_2$F | CH | |
| O | 0 | H | H | CH$_3$ | H | CH$_3$ | OCF$_3$ | CH | |
| O | 0 | H | H | CH$_3$ | H | CH$_3$ | SCH$_2$F | CH | |
| O | 0 | H | H | CH$_3$ | H | CH$_3$ | SCF$_3$ | CH | |
| O | 0 | H | H | CH$_3$ | H | CH$_3$ | OCF$_2$H | CH | |
| O | 0 | H | H | CH$_3$ | H | CH$_3$ | OCF$_2$CHClF | CH | |
| O | 0 | H | H | CH$_3$ | H | CH$_3$ | OCF$_2$CHBrF | CH | |
| O | 0 | H | H | CH$_3$ | H | CH$_3$ | OCF$_2$CHFCF$_3$ | CH | |
| O | 0 | H | H | CH$_3$ | H | CH$_3$ | SCF$_2$H | CH | |
| O | 0 | H | H | CH$_3$ | H | CH$_3$ | SCF$_2$CHClF | CH | |
| O | 0 | H | H | CH$_3$ | H | CH$_3$ | SCF$_2$CHBrF | CH | |
| O | 0 | H | H | CH$_3$ | H | CH$_3$ | SCF$_2$CHFCF$_3$ | CH | |
| O | 2 | H | H | CH$_3$ | H | CH$_3$ | CH$_3$ | CH | |
| O | 2 | H | H | CH$_3$ | H | CH$_3$ | OCH$_3$ | CH | |
| O | 2 | H | H | CH$_3$ | H | OCH$_3$ | OCH$_3$ | CH | |
| O | 2 | H | H | CH$_3$ | H | Cl | OCH$_3$ | CH | |
| O | 2 | H | H | CH$_3$ | H | CH$_3$ | OCH$_3$ | N | |
| O | 2 | H | H | CH$_3$ | H | OCH$_3$ | OCH$_3$ | N | |

TABLE 4a

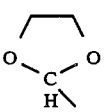

| W | n | R | $R_1$ | $R_5$ | X | Y | Z | m.p. (°C.) |
|---|---|---|---|---|---|---|---|---|
| O | 0 | H | H | H | $CH_3$ | $CH_3$ | CH | 185–200 |
| O | 0 | H | H | H | $CH_3$ | $OCH_3$ | CH | 209–211 |
| O | 0 | H | H | H | $OCH_3$ | $OCH_3$ | CH | 219–221 |
| O | 0 | H | H | H | $CH_3$ | $CH_3$ | N | |
| O | 0 | H | H | H | $CH_3$ | $OCH_3$ | N | 194–196 |
| O | 0 | H | H | H | $OCH_3$ | $OCH_3$ | N | |
| O | 1 | H | H | H | $CH_3$ | $CH_3$ | CH | 218–220 |
| O | 1 | H | H | H | $CH_3$ | $OCH_3$ | CH | 219–222 |
| O | 1 | H | H | H | $OCH_3$ | $OCH_3$ | CH | 210–214 |
| O | 1 | H | H | H | $CH_3$ | $CH_3$ | N | 202–204 |
| O | 1 | H | H | H | $CH_3$ | $OCH_3$ | N | 190–197 |
| O | 1 | H | H | H | $OCH_3$ | $OCH_3$ | N | 204–207 |
| S | 0 | H | H | H | $OCH_3$ | $OCH_3$ | CH | |
| S | 1 | H | H | H | $OCH_3$ | $OCH_3$ | CH | |
| O | 0 | $CH_3$ | H | H | $OCH_3$ | $OCH_3$ | N | 198–200 |
| O | 0 | H | o-F | H | $OCH_3$ | $OCH_3$ | CH | |
| O | 0 | H | m-Cl | H | $OCH_3$ | $OCH_3$ | CH | |
| O | 0 | H | o-Br | H | $OCH_3$ | $OCH_3$ | CH | |
| O | 0 | H | m-$CH_3$ | H | $OCH_3$ | $OCH_3$ | CH | |
| O | 0 | H | o-$OCH_3$ | H | $OCH_3$ | $OCH_3$ | CH | |
| O | 0 | H | m-$CF_3$ | H | $OCH_3$ | $OCH_3$ | CH | |
| O | 0 | H | H | H | Cl | $OCH_3$ | CH | 210–213 |
| O | 0 | H | H | H | $CH_3$ | $OCH_2CH_3$ | CH | |
| O | 0 | H | H | H | $CH_3$ | $NH_2$ | CH | |
| O | 0 | H | H | H | $CH_3$ | $NHCH_3$ | CH | |
| O | 0 | H | H | H | $CH_3$ | $N(CH_3)_2$ | CH | |
| O | 0 | H | H | H | $CH_3$ | $CH_2CH_3$ | CH | |
| O | 0 | H | H | H | $CH_3$ | $CF_3$ | CH | |
| O | 0 | H | H | H | $CH_3$ | $SCH_3$ | CH | |
| O | 0 | H | H | H | $OCH_3$ | $OCH_2CH=CH_2$ | CH | |
| O | 0 | H | H | H | $OCH_3$ | $OCH_2C\equiv CH$ | CH | |
| O | 0 | H | H | H | $OCH_3$ | $OCH_2CF_3$ | CH | |
| O | 0 | H | H | H | $CH_3$ | $OCH_2CH_2OCH_3$ | CH | |
| O | 0 | H | H | H | $CH_3$ | $CH(OCH_3)_2$ | CH | 149–151 |
| O | 0 | H | H | H | $CH_3$ | 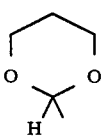 | CH | |
| O | 0 | H | H | H | $CH_3$ | $CH_2OCH_3$ | CH | |
| O | 0 | H | H | H | $CH_3$ | $CH_3$ | $CCH_3$ | |
| O | 0 | H | H | H | $CH_3$ | $CH_3$ | $CCH_2CH_3$ | |
| O | 0 | H | H | H | $CH_3$ | $CH_3$ | CCl | |
| O | 0 | H | H | H | $CH_3$ | $CH_3$ | CBr | |
| O | 1 | H | H | H | Cl | $OCH_3$ | CH | 175–182 |
| O | 1 | H | H | H | Br | $OCH_3$ | CH | 182–190 |
| O | 0 | H | H | $CH_3$ | $OCH_3$ | $OCH_3$ | CH | |
| O | 0 | H | m-$SCH_3$ | H | $OCH_3$ | $OCH_3$ | CH | |
| O | 0 | H | m-$OCF_2H$ | H | $OCH_3$ | $OCH_3$ | CH | |
| O | 0 | H | H | H | F | $OCH_3$ | CH | |
| O | 0 | H | H | H | $CH_2F$ | $OCH_3$ | CH | |
| O | 0 | H | H | H | $OCF_2H$ | $OCH_3$ | CH | 230 |
| O | 0 | H | H | H | $OCF_3$ | $OCH_3$ | CH | |
| O | 0 | H | H | H | $CF_3$ | $OCH_3$ | CH | |
| O | 0 | H | H | H | $CH_3$ | | CH | |
| O | 0 | H | H | H | Br | $OCH_3$ | CH | |

TABLE 4a-continued

| W | n | R | R₁ | R₅ | X | Y | Z | m.p. (°C.) |
|---|---|---|---|---|---|---|---|---|
| O | 0 | H | H | H | CH₃ | CH(CH₃)-O-CH(H)-O (4-methyl-1,3-dioxolan-2-yl) | CH | |
| O | 0 | H | H | H | CH₃ | H | CH | |
| O | 0 | H | H | H | CH₃ | CN | CH | |
| O | 0 | H | H | H | CH₃ | CH(OCH₂CH₃)₂ | CH | |
| O | 0 | H | H | H | CH₃ | OCH₂F | CH | |
| O | 0 | H | H | H | CH₃ | OCF₃ | CH | |
| O | 0 | H | H | H | CH₃ | SCH₂F | CH | |
| O | 0 | H | H | H | CH₃ | SCF₃ | CH | |
| O | 0 | H | H | H | CH₃ | OCF₂H | CH | 208–209 |
| O | 0 | H | H | H | CH₃ | OCF₂CHClF | CH | |
| O | 0 | H | H | H | CH₃ | OCF₂CHBrF | CH | |
| O | 0 | H | H | H | CH₃ | OCF₂CHFCF₃ | CH | |
| O | 0 | H | H | H | CH₃ | SCF₂H | CH | |
| O | 0 | H | H | H | CH₃ | SCF₂CHClF | CH | |
| O | 0 | H | H | H | CH₃ | SCF₂CHBrF | CH | |
| O | 0 | H | H | H | CH₃ | SCF₂CHFCF₃ | CH | |
| O | 2 | H | H | H | CH₃ | CH₃ | CH | |
| O | 2 | H | H | H | CH₃ | OCH₃ | CH | |
| O | 2 | H | H | H | OCH₃ | OCH₃ | CH | |
| O | 2 | H | H | H | Cl | OCH₃ | CH | |
| O | 2 | H | H | H | CH₃ | OCH₃ | N | |
| O | 2 | H | H | H | OCH₃ | OCH₃ | N | |
| O | 0 | CH₃ | H | H | OCH₃ | OCH₃ | CH | 230–232 |
| O | 0 | H | H | H | OCH₃ | CH(OCH₃)₂ | CH | 143–145 |
| O | 0 | H | H | H | OCF₂H | OCF₂H | CH | |
| O | 1 | CH₃ | H | H | CH₃ | OCH₃ | CH | 203–209 |

TABLE 5a

| W | n | R | R₁ | R₅ | X | Y | Z | m.p. (°C.) |
|---|---|---|---|---|---|---|---|---|
| O | 0 | H | H | H | CH₃ | CH₃ | CH | |
| O | 0 | H | H | H | CH₃ | OCH₃ | CH | 210–212 |
| O | 0 | H | H | H | OCH₃ | OCH₃ | CH | 232–233 |
| O | 0 | H | H | H | CH₃ | CH₃ | N | |
| O | 0 | H | H | H | CH₃ | OCH₃ | N | 193–195 |
| O | 0 | H | H | H | OCH₃ | OCH₃ | N | |
| O | 1 | H | H | H | CH₃ | CH₃ | CH | |
| O | 1 | H | H | H | CH₃ | OCH₃ | CH | |
| O | 1 | H | H | H | OCH₃ | OCH₃ | CH | |
| O | 1 | H | H | H | CH₃ | CH₃ | N | |
| O | 1 | H | H | H | CH₃ | OCH₃ | N | |
| O | 1 | H | H | H | OCH₃ | OCH₃ | N | |
| S | 0 | H | H | H | OCH₃ | OCH₃ | CH | |
| S | 1 | H | H | H | OCH₃ | OCH₃ | CH | |
| O | 0 | CH₃ | H | H | OCH₃ | OCH₃ | N | |
| O | 0 | H | o-F | H | OCH₃ | OCH₃ | CH | |
| O | 0 | H | m-Cl | H | OCH₃ | OCH₃ | CH | |

TABLE 5a-continued

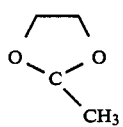

| W | n | R | R₁ | R₅ | X | Y | Z | m.p. (°C.) |
|---|---|---|---|---|---|---|---|---|
| O | 0 | H | o-Br | H | OCH₃ | OCH₃ | CH | |
| O | 0 | H | m-CH₃ | H | OCH₃ | OCH₃ | CH | |
| O | 0 | H | o-OCH₃ | H | OCH₃ | OCH₃ | CH | |
| O | 0 | H | m-CF₃ | H | OCH₃ | OCH₃ | CH | |
| O | 0 | H | H | H | Cl | OCH₃ | CH | 218–219 |
| O | 0 | H | H | H | CH₃ | OCH₂CH₃ | CH | |
| O | 0 | H | H | H | CH₃ | NH₂ | CH | |
| O | 0 | H | H | H | CH₃ | NHCH₃ | CH | |
| O | 0 | H | H | H | CH₃ | N(CH₃)₂ | CH | |
| O | 0 | H | H | H | CH₃ | CH₂CH₃ | CH | |
| O | 0 | H | H | H | CH₃ | CF₃ | CH | |
| O | 0 | H | H | H | CH₃ | SCH₃ | CH | |
| O | 0 | H | H | H | CH₃ | OCH₂CH=CH₂ | CH | |
| O | 0 | H | H | H | CH₃ | OCH₂C≡CH | CH | |
| O | 0 | H | H | H | CH₃ | OCH₂CF₃ | CH | |
| O | 0 | H | H | H | CH₃ | OCH₂CH₂OCH₃ | CH | |
| O | 0 | H | H | H | CH₃ | CH(OCH₃)₂ | CH | |
| O | 0 | H | H | H | CH₃ | 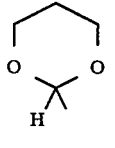 | CH | |
| O | 0 | H | H | H | CH₃ | CH₂OCH₃ | CH | |
| O | 0 | H | H | H | CH₃ | CH₃ | CCH₃ | |
| O | 0 | H | H | H | CH₃ | CH₃ | CCH₂CH₃ | |
| O | 0 | H | H | H | CH₃ | CH₃ | CCl | |
| O | 0 | H | H | H | CH₃ | CH₃ | CBr | |
| O | 1 | H | H | H | CH₃ | CH₂OCH₃ | CH | |
| O | 1 | H | H | H | Cl | OCH₃ | CH | |
| O | 0 | H | H | CH₃ | OCH₃ | OCH₃ | CH | |
| O | 0 | H | m-SCH₃ | H | OCH₃ | OCH₃ | CH | |
| O | 0 | H | m-OCF₂H | H | OCH₃ | OCH₃ | CH | |
| O | 0 | H | H | H | F | OCH₃ | CH | |
| O | 0 | H | H | H | CH₂F | OCH₃ | CH | |
| O | 0 | H | H | H | OCF₂H | OCH₂ | CH | |
| O | 0 | H | H | H | OCF₃ | OCH₃ | CH | |
| O | 0 | H | H | H | CF₃ | OCH₃ | CH | |
| O | 0 | H | H | H | CH₃ | 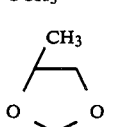 | CH | |
| O | 0 | H | H | H | Br | OCH₃ | CH | |
| O | 0 | H | H | H | CH₃ | 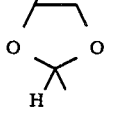 | CH | |
| O | 0 | H | H | H | CH₃ | H | CH | |
| O | 0 | H | H | H | CH₃ | CN | CH | |
| O | 0 | H | H | H | CH₃ | CH(OCH₂CH₃)₂ | CH | |
| O | 0 | H | H | H | CH₃ | OCH₂F | CH | |
| O | 0 | H | H | H | CH₃ | OCF₃ | CH | |
| O | 0 | H | H | H | CH₃ | SCH₂F | CH | |
| O | 0 | H | H | H | CH₃ | SCF₃ | CH | |
| O | 0 | H | H | H | CH₃ | OCF₂H | CH | |
| O | 0 | H | H | H | CH₃ | OCF₂CHClF | CH | |

TABLE 5a-continued

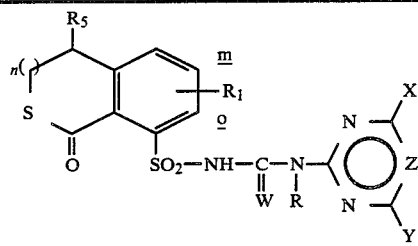

| W | n | R | R₁ | R₅ | X | Y | Z | m.p. (°C.) |
|---|---|---|----|----|----|---|---|------------|
| O | 0 | H | H | H | CH₃ | OCF₂CHBrF | CH | |
| O | 0 | H | H | H | CH₃ | OCF₂CHFCF₃ | CH | |
| O | 0 | H | H | H | CH₃ | SCF₂H | CH | |
| O | 0 | H | H | H | CH₃ | SCF₂CHClF | CH | |
| O | 0 | H | H | H | CH₃ | SCF₂CHBrF | CH | |
| O | 0 | H | H | H | CH₃ | SCF₂CHFCF₃ | CH | |
| O | 2 | H | H | H | CH₃ | CH₃ | CH | |
| O | 2 | H | H | H | CH₃ | OCH₃ | CH | |
| O | 2 | H | H | H | OCH₃ | OCH₃ | CH | |
| O | 2 | H | H | H | Cl | OCH₃ | CH | |
| O | 2 | H | H | H | CH₃ | OCH₃ | N | |
| O | 2 | H | H | H | OCH₃ | OCH₃ | N | |

TABLE 6a

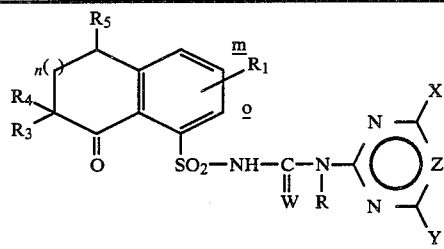

| W | n | R | R₁ | R₃ | R₄ | R₅ | X | Y | Z | m.p. (°C.) |
|---|---|---|----|----|----|----|---|---|---|------------|
| O | 0 | H | H | H | H | H | CH₃ | CH₃ | CH | |
| O | 0 | H | H | H | H | H | CH₃ | OCH₃ | CH | |
| O | 0 | H | H | H | H | H | OCH₃ | OCH₃ | CH | |
| O | 0 | H | H | H | H | H | Cl | OCH₃ | CH | |
| O | 0 | H | H | H | H | H | CH₃ | OCH₃ | N | |
| O | 0 | H | H | H | H | H | OCH₃ | OCH₃ | N | |
| O | 0 | H | H | CH₃ | H | H | CH₃ | CH₃ | CH | |
| O | 0 | H | H | CH₃ | H | H | CH₃ | OCH₃ | CH | |
| O | 0 | H | H | CH₃ | H | H | OCH₃ | OCH₃ | CH | |
| O | 0 | H | H | CH₃ | H | H | Cl | OCH₃ | CH | |
| O | 0 | H | H | CH₃ | H | H | CH₃ | OCH₃ | N | |
| O | 0 | H | H | CH₃ | H | H | OCH₃ | OCH₃ | N | |
| O | 0 | H | H | CH₃ | CH₃ | H | CH₃ | CH₃ | CH | |
| O | 0 | H | H | CH₃ | CH₃ | H | CH₃ | OCH₃ | CH | |
| O | 0 | H | H | CH₃ | CH₃ | H | OCH₃ | OCH₃ | CH | |
| O | 0 | H | H | CH₃ | CH₃ | H | Cl | OCH₃ | CH | |
| O | 0 | H | H | CH₃ | CH₃ | H | CH₃ | OCH₃ | N | |
| O | 0 | H | H | CH₃ | CH₃ | H | OCH₃ | OCH₃ | N | |
| O | 1 | H | H | H | H | H | CH₃ | CH₃ | CH | |
| O | 1 | H | H | H | H | H | CH₃ | OCH₃ | CH | |
| O | 1 | H | H | H | H | H | OCH₃ | OCH₃ | CH | |
| O | 1 | H | H | H | H | H | Cl | CH₃ | CH | |
| O | 1 | H | H | H | H | H | CH₃ | OCH₃ | N | |
| O | 1 | H | H | H | H | H | OCH₃ | OCH₃ | N | |
| O | 1 | H | H | CH₃ | H | H | CH₃ | CH₃ | CH | |
| O | 1 | H | H | CH₃ | H | H | CH₃ | OCH₃ | CH | |
| O | 1 | H | H | CH₃ | H | H | OCH₃ | OCH₃ | CH | |
| O | 1 | H | H | CH₃ | H | H | Cl | CH₃ | CH | |
| O | 1 | H | H | CH₃ | H | H | CH₃ | OCH₃ | N | |
| O | 1 | H | H | CH₃ | H | H | OCH₃ | OCH₃ | N | |
| O | 1 | H | H | CH₃ | CH₃ | H | CH₃ | CH₃ | CH | |
| O | 1 | H | H | CH₃ | CH₃ | H | CH₃ | OCH₃ | CH | |
| O | 1 | H | H | CH₃ | CH₃ | H | OCH₃ | OCH₃ | CH | |
| O | 1 | H | H | CH₃ | CH₃ | H | Cl | CH₃ | CH | |
| O | 1 | H | H | CH₃ | CH₃ | H | CH₃ | OCH₃ | N | |
| O | 1 | H | H | CH₃ | CH₃ | H | OCH₃ | OCH₃ | N | |
| S | 0 | H | H | H | H | H | OCH₃ | OCH₃ | CH | |
| O | 0 | CH₃ | H | H | H | H | OCH₃ | OCH₃ | N | |

TABLE 6a-continued

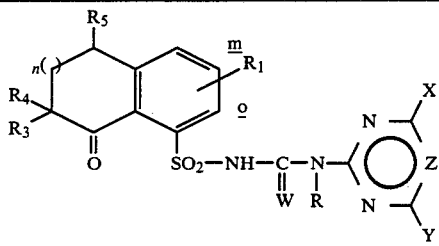

| W | n | R | R1 | R3 | R4 | R5 | X | Y | Z | m.p. (°C.) |
|---|---|---|---|---|---|---|---|---|---|---|
| O | 0 | H | o-F | H | H | H | OCH3 | OCH3 | CH | |
| O | 0 | H | m-Cl | H | H | H | OCH3 | OCH3 | CH | |
| O | 0 | H | o-Br | H | H | H | OCH3 | OCH3 | CH | |
| O | 0 | H | m-CH3 | H | H | H | OCH3 | OCH3 | CH | |
| O | 0 | H | o-OCH3 | H | H | H | OCH3 | OCH3 | CH | |
| O | 0 | H | m-CF3 | H | H | H | OCH3 | OCH3 | CH | |
| O | 0 | H | H | H | H | CH2CH3 | OCH3 | OCH3 | CH | |
| O | 0 | H | H | CH2CH2CH3 | H | H | OCH3 | OCH3 | CH | |
| O | 0 | H | H | H | H | H | CH3 | CH3 | N | |
| O | 0 | H | H | H | H | H | CH3 | OCH2CH3 | CH | |
| O | 0 | H | H | H | H | H | CH3 | CH2OCH3 | CH | |
| O | 1 | H | H | H | H | H | CH3 | CH2OCH3 | CH | |
| O | 0 | H | H | H | H | H | CH3 | NH2 | CH | |
| O | 0 | H | H | H | H | H | CH3 | NHCH3 | CH | |
| O | 0 | H | H | H | H | H | CH3 | N(CH3)2 | CH | |
| O | 0 | H | H | H | H | H | CH3 | CH2CH3 | CH | |
| O | 0 | H | H | H | H | H | CH3 | CF3 | CH | |
| O | 0 | H | H | H | H | H | CH3 | SCH3 | CH | |
| O | 0 | H | H | H | H | H | CH3 | OCH2CH=CH2 | CH | |
| O | 0 | H | H | H | H | H | CH3 | OCH2C≡CH | CH | |
| O | 0 | H | H | H | H | H | CH3 | OCH2CF3 | CH | |
| O | 0 | H | H | H | H | H | CH3 | OCH2CH2OCH3 | CH | |
| O | 0 | H | H | H | H | H | CH3 | CH(OCH3)2 | CH | |
| O | 0 | H | H | H | H | H | CH3 | 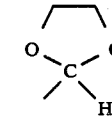 | CH | |
| O | 0 | H | H | H | H | H | OCH3 | OCH3 | CCH3 | |
| O | 0 | H | H | H | H | H | OCH3 | OCH3 | CC2H5 | |
| O | 0 | H | H | H | H | H | OCH3 | OCH3 | CCl | |
| O | 0 | H | H | H | H | H | OCH3 | OCH3 | CBr | |
| O | 0 | H | H | H | H | H | F | OCH3 | CH | |
| O | 0 | H | H | H | H | H | Br | OCH3 | CH | |
| O | 0 | H | H | H | H | H | CH2F | OCH3 | CH | |
| O | 0 | H | H | H | H | H | OCF2H | OCH3 | CH | |
| O | 0 | H | H | H | H | H | OCF3 | OCH3 | CH | |
| O | 0 | H | H | H | H | H | CF3 | OCH3 | CH | |
| O | 0 | H | H | H | H | H | CH3 | 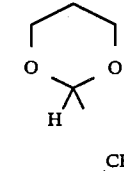 | | |
| O | 0 | H | H | H | H | H | CH3 | 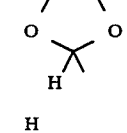 | CH | |
| O | 0 | H | H | H | H | H | CH3 | H | CH | |
| O | 0 | H | H | H | H | H | CH3 | CN | CH | |
| O | 0 | H | H | H | H | H | CH3 | CH(OCH2CH3)2 | CH | |
| O | 0 | H | H | H | H | H | CH3 | OCH2F | CH | |
| O | 0 | H | H | H | H | H | CH3 | OCF3 | CH | |
| O | 0 | H | H | H | H | H | CH3 | SCH2F | CH | |
| O | 0 | H | H | H | H | H | CH3 | SCF3 | CH | |
| O | 0 | H | H | H | H | H | CH3 | OCF2H | CH | |
| O | 0 | H | H | H | H | H | CH3 | OCF2CHClF | CH | |
| O | 0 | H | H | H | H | H | CH3 | OCF2CHBrF | CH | |
| O | 0 | H | H | H | H | H | CH3 | OCF2CHFCF3 | CH | |

TABLE 6a-continued

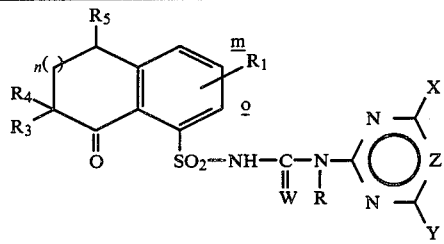

| W | n | R | R₁ | R₃ | R₄ | R₅ | X | Y | Z | m.p. (°C.) |
|---|---|---|---|---|---|---|---|---|---|---|
| O | 0 | H | H | H | H | H | CH₃ | SCF₂H | CH | |
| O | 0 | H | H | H | H | H | CH₃ | SCF₂CHClF | CH | |
| O | 0 | H | H | H | H | H | CH₃ | SCF₂CHBrF | CH | |
| O | 0 | H | H | H | H | H | CH₃ | SCF₂CHFCF₃ | CH | |
| O | 0 | H | H | H | H | CH₃ | OCH₃ | OCH₃ | CH | |
| O | 0 | H | H | H | CH₂CH₂CH₃ | H | OCH₃ | OCH₃ | CH | |
| O | 0 | H | H | H | CH₂CH₂CH₂CH₃ | H | OCH₃ | OCH₃ | CH | |
| O | 0 | H | m-SCH₃ | H | H | H | OCH₃ | OCH₃ | CH | |
| O | 0 | H | o-CF₂H | H | H | H | OCH₃ | OCH₃ | CH | |
| O | 2 | H | H | H | H | H | CH₃ | CH₃ | CH | |
| O | 2 | H | H | H | H | H | CH₃ | OCH₃ | CH | |
| O | 2 | H | H | H | H | H | OCH₃ | OCH₃ | CH | |
| O | 2 | H | H | H | H | H | Cl | OCH₃ | CH | |
| O | 2 | H | H | H | H | H | CH₃ | OCH₃ | N | |
| O | 2 | H | H | H | H | H | OCH₃ | OCH₃ | N | |
| O | 2 | H | H | CH₃ | H | H | CH₃ | CH₃ | CH | |
| O | 2 | H | H | CH₃ | H | H | CH₃ | OCH₃ | CH | |
| O | 2 | H | H | CH₃ | H | H | OCH₃ | OCH₃ | CH | |
| O | 2 | H | H | CH₃ | H | H | Cl | OCH₃ | CH | |
| O | 2 | H | H | CH₃ | H | H | CH₃ | OCH₃ | N | |
| O | 2 | H | H | CH₃ | H | H | OCH₃ | OCH₃ | N | |
| O | 0 | H | H | Cl | Cl | H | CH₃ | CH₃ | CH | 197–199 |
| O | 0 | H | H | Cl | Cl | H | CH₃ | OCH₃ | CH | 198–201 |
| O | 0 | H | H | Cl | Cl | H | OCH₃ | OCH₃ | CH | 154–166 |
| O | 0 | H | H | Br | Br | H | OCH₃ | OCH₃ | CH | |
| O | 0 | H | H | Cl | Cl | H | OCH₃ | CH₃ | N | 178–182 |

TABLE 7a

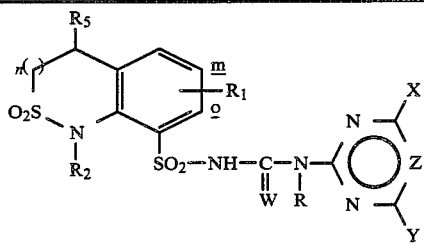

| W | n | R | R₁ | R₂ | R₅ | X | Y | Z | m.p. (°C.) |
|---|---|---|---|---|---|---|---|---|---|
| O | 0 | H | H | CH₃ | H | CH₃ | CH₃ | CH | |
| O | 0 | H | H | CH₃ | H | CH₃ | OCH₃ | CH | |
| O | 0 | H | H | CH₃ | H | OCH₃ | OCH₃ | CH | |
| O | 0 | H | H | CH₃ | H | Cl | OCH₃ | CH | |
| O | 0 | H | H | CH₃ | H | CH₃ | OCH₃ | N | |
| O | 0 | H | H | CH₃ | H | OCH₃ | OCH₃ | N | |
| O | 0 | H | H | CH₂CH₃ | H | CH₃ | CH₃ | CH | |
| O | 0 | H | H | CH₂CH₃ | H | CH₃ | OCH₃ | CH | |
| O | 0 | H | H | CH₂CH₃ | H | OCH₃ | OCH₃ | CH | |
| O | 0 | H | H | CH₂CH₃ | H | Cl | OCH₃ | CH | |
| O | 0 | H | H | CH₂CH₃ | H | CH₃ | OCH₃ | N | |
| O | 0 | H | H | CH₂CH₃ | H | OCH₃ | OCH₃ | N | |
| O | 0 | H | H | CH(CH₃)₂ | H | CH₃ | OCH₃ | CH | |
| O | 0 | H | H | CH(CH₃)₂ | H | OCH₃ | OCH₃ | CH | |
| O | 1 | H | H | CH₃ | H | CH₃ | CH₃ | CH | |
| O | 1 | H | H | CH₃ | H | CH₃ | OCH₃ | CH | |
| O | 1 | H | H | CH₃ | H | OCH₃ | OCH₃ | CH | |
| O | 1 | H | H | CH₃ | H | CH₃ | CH₃ | N | |
| O | 1 | H | H | CH₃ | H | CH₃ | OCH₃ | N | |
| O | 1 | H | H | CH₃ | H | OCH₃ | OCH₃ | N | |
| O | 1 | H | H | CH₂CH₃ | H | CH₃ | CH₃ | CH | |
| O | 1 | H | H | CH₂CH₃ | H | CH₃ | OCH₃ | CH | |
| O | 1 | H | H | CH₂CH₃ | H | OCH₃ | OCH₃ | CH | |
| O | 1 | H | H | CH₂CH₃ | H | CH₃ | CH₃ | N | |

TABLE 7a-continued

| W | n | R | R₁ | R₂ | R₅ | X | Y | Z | m.p. (°C.) |
|---|---|---|---|---|---|---|---|---|---|
| O | 1 | H | H | CH$_2$CH$_3$ | H | CH$_3$ | OCH$_3$ | N | |
| O | 1 | H | H | CH$_2$CH$_3$ | H | OCH$_3$ | OCH$_3$ | N | |
| S | 0 | H | H | CH$_3$ | H | OCH$_3$ | OCH$_3$ | CH | |
| S | 1 | H | H | CH$_3$ | H | OCH$_3$ | OCH$_3$ | CH | |
| O | 0 | CH$_3$ | H | CH$_3$ | H | OCH$_3$ | OCH$_3$ | N | |
| O | 0 | H | o-F | CH$_3$ | H | OCH$_3$ | OCH$_3$ | CH | |
| O | 0 | H | m-Cl | CH$_3$ | H | OCH$_3$ | OCH$_3$ | CH | |
| O | 0 | H | o-Br | CH$_3$ | H | OCH$_3$ | OCH$_3$ | CH | |
| O | 0 | H | m-CH$_3$ | CH$_3$ | H | OCH$_3$ | OCH$_3$ | CH | |
| O | 0 | H | o-OCH$_3$ | CH$_3$ | H | OCH$_3$ | OCH$_3$ | CH | |
| O | 0 | H | m-CF$_3$ | CH$_3$ | H | OCH$_3$ | OCH$_3$ | CH | |
| O | 0 | H | H | CH$_3$ | H | Cl | OCH$_3$ | CH | |
| O | 0 | H | H | CH$_3$ | H | CH$_3$ | OCH$_2$CH$_3$ | CH | |
| O | 0 | H | H | CH$_3$ | H | CH$_3$ | NH$_2$ | CH | |
| O | 0 | H | H | CH$_3$ | H | CH$_3$ | NHCH$_3$ | CH | |
| O | 0 | H | H | CH$_3$ | H | CH$_3$ | N(CH$_3$)$_2$ | CH | |
| O | 0 | H | H | CH$_3$ | H | CH$_3$ | CH$_2$CH$_3$ | CH | |
| O | 0 | H | H | CH$_3$ | H | CH$_3$ | CF$_3$ | CH | |
| O | 0 | H | H | CH$_3$ | H | CH$_3$ | SCH$_3$ | CH | |
| O | 0 | H | H | CH$_3$ | H | CH$_3$ | OCH$_2$CH=CH$_2$ | CH | |
| O | 0 | H | H | CH$_3$ | H | CH$_3$ | OCH$_2$C≡CH | CH | |
| O | 0 | H | H | CH$_3$ | H | CH$_3$ | OCH$_2$CF$_3$ | CH | |
| O | 0 | H | H | CH$_3$ | H | CH$_3$ | OCH$_2$CH$_2$OCH$_3$ | CH | |
| O | 0 | H | H | CH$_3$ | H | CH$_3$ | CH(OCH$_3$)$_2$ | CH | |
| O | 0 | H | H | CH$_3$ | H | CH$_3$ | 1,3-dioxolan-2-yl | CH | |
| O | 0 | H | H | CH$_3$ | H | CH$_3$ | CH$_2$OCH$_3$ | CH | |
| O | 0 | H | H | CH$_3$ | H | CH$_3$ | CH$_3$ | CCH$_3$ | |
| O | 0 | H | H | CH$_3$ | H | CH$_3$ | CH$_3$ | CCH$_2$CH$_3$ | |
| O | 0 | H | H | CH$_3$ | H | CH$_3$ | CH$_3$ | CCl | |
| O | 0 | H | H | CH$_3$ | H | CH$_3$ | CH$_3$ | CBr | |
| O | 1 | H | H | CH$_3$ | H | CH$_3$ | CH$_2$OCH$_3$ | CH | |
| O | 1 | H | H | CH$_3$ | H | Cl | OCH$_3$ | CH | |
| O | 0 | H | H | CH$_2$CH$_2$CH$_3$ | H | CH$_3$ | CH$_3$ | CH | |
| O | 0 | H | H | CH$_2$CH$_2$CH$_3$ | H | CH$_3$ | OCH$_3$ | CH | |
| O | 0 | H | H | CH$_2$CH$_2$CH$_3$ | H | OCH$_3$ | OCH$_3$ | CH | |
| O | 0 | H | H | CH$_2$CH$_2$CH$_3$ | H | Cl | OCH$_3$ | CH | |
| O | 0 | H | H | CH$_2$CH$_2$CH$_3$ | H | CH$_3$ | OCH$_3$ | N | |
| O | 0 | H | H | CH$_2$CH$_2$CH$_3$ | H | OCH$_3$ | OCH$_3$ | N | |
| O | 0 | H | H | CH$_2$CH$_2$CH$_2$CH$_3$ | H | OCH$_3$ | OCH$_3$ | N | |
| O | 0 | H | H | H | H | CH$_3$ | CH$_3$ | CH | |
| O | 0 | H | H | H | H | CH$_3$ | OCH$_3$ | CH | |
| O | 0 | H | H | H | H | OCH$_3$ | OCH$_3$ | CH | |
| O | 0 | H | H | H | H | Cl | OCH$_3$ | CH | |
| O | 0 | H | H | H | H | CH$_3$ | OCH$_3$ | N | |
| O | 0 | H | H | H | H | OCH$_3$ | OCH$_3$ | N | |
| O | 0 | H | H | CH$_3$ | CH$_3$ | OCH$_3$ | OCH$_3$ | CH | |
| O | 0 | H | m-SCH$_3$ | CH$_3$ | H | OCH$_3$ | OCH$_3$ | CH | |
| O | 0 | H | m-OCF$_2$H | CH$_3$ | H | OCH$_3$ | OCH$_3$ | CH | |
| O | 0 | H | H | CH$_3$ | H | F | OCH$_3$ | CH | |
| O | 0 | H | H | CH$_3$ | H | Br | OCH$_3$ | CH | |
| O | 0 | H | H | CH$_3$ | H | CH$_2$F | OCH$_3$ | CH | |
| O | 0 | H | H | CH$_3$ | H | OCF$_2$H | OCH$_3$ | CH | |
| O | 0 | H | H | CH$_3$ | H | OCF$_3$ | OCH$_3$ | CH | |
| O | 0 | H | H | CH$_3$ | H | CF$_3$ | OCH$_3$ | CH | |
| O | 0 | H | H | CH$_3$ | H | CH$_3$ | 1,3-dioxan-2-yl | CH | |

TABLE 7a-continued

| W | n | R | $R_1$ | $R_2$ | $R_5$ | X | Y | Z | m.p. (°C.) |
|---|---|---|---|---|---|---|---|---|---|
| O | 0 | H | H | $CH_3$ | H | $CH_3$ | (structure: $CH_3$-CH with O-CH(H)-O ring) | CH | |
| O | 0 | H | H | $CH_3$ | H | $CH_3$ | H | CH | |
| O | 0 | H | H | $CH_3$ | H | $CH_3$ | CN | CH | |
| O | 0 | H | H | $CH_3$ | H | $CH_3$ | $CH(OCH_2CH_3)_2$ | CH | |
| O | 0 | H | H | $CH_3$ | H | $CH_3$ | $OCH_2F$ | CH | |
| O | 0 | H | H | $CH_3$ | H | $CH_3$ | $OCF_3$ | CH | |
| O | 0 | H | H | $CH_3$ | H | $CH_3$ | $SCH_2F$ | CH | |
| O | 0 | H | H | $CH_3$ | H | $CH_3$ | $SCF_3$ | CH | |
| O | 0 | H | H | $CH_3$ | H | $CH_3$ | $OCF_2H$ | CH | |
| O | 0 | H | H | $CH_3$ | H | $CH_3$ | $OCF_2CHClF$ | CH | |
| O | 0 | H | H | $CH_3$ | H | $CH_3$ | $OCF_2CHBrF$ | CH | |
| O | 0 | H | H | $CH_3$ | H | $CH_3$ | $OCF_2CHFCF_3$ | CH | |
| O | 0 | H | H | $CH_3$ | H | $CH_3$ | $SCF_2H$ | CH | |
| O | 0 | H | H | $CH_3$ | H | $CH_3$ | $SCF_2CHClF$ | CH | |
| O | 0 | H | H | $CH_3$ | H | $CH_3$ | $SCF_2CHBrF$ | CH | |
| O | 0 | H | H | $CH_3$ | H | $CH_3$ | $SCF_2CHFCF_3$ | CH | |
| O | 2 | H | H | $CH_3$ | H | $CH_3$ | $CH_3$ | CH | |
| O | 2 | H | H | $CH_3$ | H | $CH_3$ | $OCH_3$ | CH | |
| O | 2 | H | H | $CH_3$ | H | $OCH_3$ | $OCH_3$ | CH | |
| O | 2 | H | H | $CH_3$ | H | Cl | $OCH_3$ | CH | |
| O | 2 | H | H | $CH_3$ | H | $CH_3$ | $OCH_3$ | N | |
| O | 2 | H | H | $CH_3$ | H | $OCH_3$ | $OCH_3$ | N | |

TABLE 8a

| W | n | R | $R_1$ | $R_5$ | X | Y | Z | m.p. (°C.) |
|---|---|---|---|---|---|---|---|---|
| O | 0 | H | H | H | $CH_3$ | $CH_3$ | CH | |
| O | 0 | H | H | H | $CH_3$ | $OCH_3$ | CH | |
| O | 0 | H | H | H | $OCH_3$ | $OCH_3$ | CH | |
| O | 0 | H | H | H | $CH_3$ | $CH_3$ | N | |
| O | 0 | H | H | H | $CH_3$ | $OCH_3$ | N | |
| O | 0 | H | H | H | $OCH_3$ | $OCH_3$ | N | |
| O | 1 | H | H | H | $CH_3$ | $CH_3$ | CH | |
| O | 1 | H | H | H | $CH_3$ | $OCH_3$ | CH | |
| O | 1 | H | H | H | $OCH_3$ | $OCH_3$ | CH | |
| O | 1 | H | H | H | $CH_3$ | $CH_3$ | N | |
| O | 1 | H | H | H | $CH_3$ | $OCH_3$ | N | |
| O | 1 | H | H | H | $OCH_3$ | $OCH_3$ | N | |
| S | 0 | H | H | H | $OCH_3$ | $OCH_3$ | CH | |
| S | 1 | H | H | H | $OCH_3$ | $OCH_3$ | CH | |
| O | 0 | $CH_3$ | H | H | $OCH_3$ | $OCH_3$ | N | |
| O | 0 | H | o-F | H | $OCH_3$ | $OCH_3$ | CH | |
| O | 0 | H | m-Cl | H | $OCH_3$ | $OCH_3$ | CH | |
| O | 0 | H | o-Br | H | $OCH_3$ | $OCH_3$ | CH | |
| O | 0 | H | m-$CH_3$ | H | $OCH_3$ | $OCH_3$ | CH | |
| O | 0 | H | o-$OCH_3$ | H | $OCH_3$ | $OCH_3$ | CH | |

TABLE 8a-continued

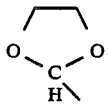

| W | n | R | R₁ | R₅ | X | Y | Z | m.p. (°C.) |
|---|---|---|---|---|---|---|---|---|
| O | 0 | H | m-CF₃ | H | OCH₃ | OCH₃ | CH | |
| O | 0 | H | H | H | Cl | OCH₃ | CH | |
| O | 0 | H | H | H | CH₃ | OCH₂CH₃ | CH | |
| O | 0 | H | H | H | CH₃ | NH₂ | CH | |
| O | 0 | H | H | H | CH₃ | NHCH₃ | CH | |
| O | 0 | H | H | H | CH₃ | N(CH₃)₂ | CH | |
| O | 0 | H | H | H | CH₃ | CH₂CH₃ | CH | |
| O | 0 | H | H | H | CH₃ | CF₃ | CH | |
| O | 0 | H | H | H | CH₃ | SCH₃ | CH | |
| O | 0 | H | H | H | CH₃ | OCH₂CH=CH₂ | CH | |
| O | 0 | H | H | H | CH₃ | OCH₂C≡CH | CH | |
| O | 0 | H | H | H | CH₃ | OCH₂CF₃ | CH | |
| O | 0 | H | H | H | CH₃ | OCH₂CH₂OCH₃ | CH | |
| O | 0 | H | H | H | CH₃ | CH(OCH₃)₂ | CH | |
| O | 0 | H | H | H | CH₃ | 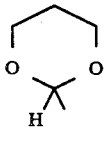 | CH | |
| O | 0 | H | H | H | CH₃ | CH₂OCH₃ | CH | |
| O | 0 | H | H | H | CH₃ | CH₃ | CCH₃ | |
| O | 0 | H | H | H | CH₃ | CH₃ | CCH₂CH₃ | |
| O | 0 | H | H | H | CH₃ | CH₃ | CCl | |
| O | 0 | H | H | H | CH₃ | CH₃ | CBr | |
| O | 1 | H | H | H | CH₃ | CH₂OCH₃ | CH | |
| O | 1 | H | H | H | Cl | OCH₃ | CH | |
| O | 0 | H | H | CH₃ | OCH₃ | OCH₃ | CH | |
| O | 0 | H | m-SCH₃ | H | OCH₃ | OCH₃ | CH | |
| O | 0 | H | m-OCF₂H | H | OCH₃ | OCH₃ | CH | |
| O | 0 | H | H | H | F | OCH₃ | CH | |
| O | 0 | H | H | H | CH₂F | OCH₃ | CH | |
| O | 0 | H | H | H | OCF₂H | OCH₃ | CH | |
| O | 0 | H | H | H | OCF₃ | OCH₃ | CH | |
| O | 0 | H | H | H | CF₃ | OCH₃ | CH | |
| O | 0 | H | H | H | CH₃ | 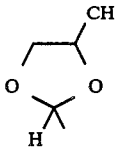 | CH | |
| O | 0 | H | H | H | Br | OCH₃ | CH | |
| O | 0 | H | H | H | CH₃ | | CH | |
| O | 0 | H | H | H | CH₃ | H | CH | |
| O | 0 | H | H | H | CH₃ | CN | CH | |
| O | 0 | H | H | H | CH₃ | CH(OCH₂CH₃)₂ | CH | |
| O | 0 | H | H | H | CH₃ | OCH₂F | CH | |
| O | 0 | H | H | H | CH₃ | OCF₃ | CH | |
| O | 0 | H | H | H | CH₃ | SCH₂F | CH | |
| O | 0 | H | H | H | CH₃ | SCF₃ | CH | |
| O | 0 | H | H | H | CH₃ | OCF₂H | CH | |
| O | 0 | H | H | H | CH₃ | OCF₂CHClF | CH | |
| O | 0 | H | H | H | CH₃ | OCF₂CHBrF | CH | |
| O | 0 | H | H | H | CH₃ | OCF₂CHFCF₃ | CH | |
| O | 0 | H | H | H | CH₃ | SCF₂H | CH | |
| O | 0 | H | H | H | CH₃ | SCF₂CHClF | CH | |

TABLE 8a-continued

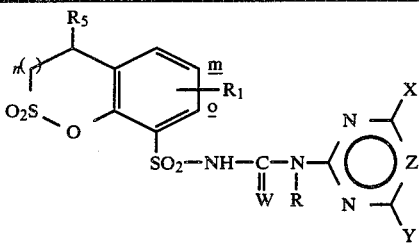

| W | n | R | R₁ | R₅ | X | Y | Z | m.p. (°C.) |
|---|---|---|---|---|---|---|---|---|
| O | 0 | H | H | H | CH₃ | SCF₂CHBrF | CH | |
| O | 0 | H | H | H | CH₃ | SCF₂CHFCF₃ | CH | |
| O | 2 | H | H | H | CH₃ | CH₃ | CH | |
| O | 2 | H | H | H | CH₃ | OCH₃ | CH | |
| O | 2 | H | H | H | OCH₃ | OCH₃ | CH | |
| O | 2 | H | H | H | Cl | OCH₃ | CH | |
| O | 2 | H | H | H | CH₃ | OCH₃ | N | |
| O | 2 | H | H | H | OCH₃ | OCH₃ | N | |

TABLE 9a

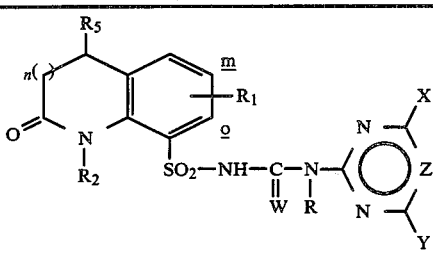

| W | n | R | R₁ | R₂ | R₅ | X | Y | Z | m.p. (°C.) |
|---|---|---|---|---|---|---|---|---|---|
| O | 0 | H | H | CH₃ | H | CH₃ | CH₃ | CH | |
| O | 0 | H | H | CH₃ | H | CH₃ | OCH₃ | CH | |
| O | 0 | H | H | CH₃ | H | OCH₃ | OCH₃ | CH | |
| O | 0 | H | H | CH₃ | H | Cl | OCH₃ | CH | |
| O | 0 | H | H | CH₃ | H | CH₃ | OCH₃ | N | |
| O | 0 | H | H | CH₃ | H | OCH₃ | OCH₃ | N | |
| O | 0 | H | H | CH₂CH₃ | H | CH₃ | CH₃ | CH | |
| O | 0 | H | H | CH₂CH₃ | H | CH₃ | OCH₃ | CH | |
| O | 0 | H | H | CH₂CH₃ | H | OCH₃ | OCH₃ | CH | |
| O | 0 | H | H | CH₂CH₃ | H | Cl | OCH₃ | CH | |
| O | 0 | H | H | CH₂CH₃ | H | CH₃ | OCH₃ | N | |
| O | 0 | H | H | CH₂CH₃ | H | OCH₃ | OCH₃ | N | |
| O | 0 | H | H | CH(CH₃)₂ | H | CH₃ | OCH₃ | CH | |
| O | 0 | H | H | CH(CH₃)₂ | H | OCH₃ | OCH₃ | CH | |
| O | 1 | H | H | CH₃ | H | CH₃ | CH₃ | CH | |
| O | 1 | H | H | CH₃ | H | CH₃ | OCH₃ | CH | |
| O | 1 | H | H | CH₃ | H | OCH₃ | OCH₃ | CH | |
| O | 1 | H | H | CH₃ | H | CH₃ | CH₃ | N | |
| O | 1 | H | H | CH₃ | H | CH₃ | OCH₃ | N | |
| O | 1 | H | H | CH₃ | H | OCH₃ | OCH₃ | N | |
| O | 1 | H | H | CH₂CH₃ | H | CH₃ | CH₃ | CH | |
| O | 1 | H | H | CH₂CH₃ | H | CH₃ | OCH₃ | CH | |
| O | 1 | H | H | CH₂CH₃ | H | OCH₃ | OCH₃ | CH | |
| O | 1 | H | H | CH₂CH₃ | H | CH₃ | CH₃ | N | |
| O | 1 | H | H | CH₂CH₃ | H | CH₃ | OCH₃ | N | |
| O | 1 | H | H | CH₂CH₃ | H | OCH₃ | OCH₃ | N | |
| S | 0 | H | H | CH₃ | H | OCH₃ | OCH₃ | CH | |
| S | 1 | H | H | CH₃ | H | OCH₃ | OCH₃ | CH | |
| O | 0 | CH₃ | H | CH₃ | H | OCH₃ | OCH₃ | N | |
| O | 0 | H | o-F | CH₃ | H | OCH₃ | OCH₃ | CH | |
| O | 0 | H | m-Cl | CH₃ | H | OCH₃ | OCH₃ | CH | |
| O | 0 | H | o-Br | CH₃ | H | OCH₃ | OCH₃ | CH | |
| O | 0 | H | m-CH₃ | CH₃ | H | OCH₃ | OCH₃ | CH | |
| O | 0 | H | o-OCH₃ | CH₃ | H | OCH₃ | OCH₃ | CH | |
| O | 0 | H | m-CF₃ | CH₃ | H | OCH₃ | OCH₃ | CH | |
| O | 0 | H | H | CH₃ | H | Cl | OCH₃ | CH | |
| O | 0 | H | H | CH₃ | H | CH₃ | OCH₂CH₃ | CH | |
| O | 0 | H | H | CH₃ | H | CH₃ | NH₂ | CH | |
| O | 0 | H | H | CH₃ | H | CH₃ | NHCH₃ | CH | |
| O | 0 | H | H | CH₃ | H | CH₃ | N(CH₃)₂ | CH | |
| O | 0 | H | H | CH₃ | H | CH₃ | CH₂CH₃ | CH | |
| O | 0 | H | H | CH₃ | H | CH₃ | CF₃ | CH | |

TABLE 9a-continued

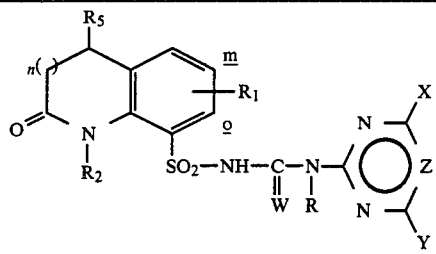

| W | n | R | R₁ | R₂ | R₅ | X | Y | Z | m.p. (°C.) |
|---|---|---|---|---|---|---|---|---|---|
| O | 0 | H | H | CH₃ | H | CH₃ | SCH₃ | CH | |
| O | 0 | H | H | CH₃ | H | CH₃ | OCH₂CH=CH₂ | CH | |
| O | 0 | H | H | CH₃ | H | CH₃ | OCH₂C≡CH | CH | |
| O | 0 | H | H | CH₃ | H | CH₃ | OCH₂CF₃ | CH | |
| O | 0 | H | H | CH₃ | H | CH₃ | OCH₂CH₂OCH₃ | CH | |
| O | 0 | H | H | CH₃ | H | CH₃ | CH(OCH₃)₂ | CH | |
| O | 0 | H | H | CH₃ | H | CH₃ | (1,3-dioxolan-2-yl) | CH | |
| O | 0 | H | H | CH₃ | H | CH₃ | CH₂OCH₃ | CH | |
| O | 0 | H | H | CH₃ | H | CH₃ | CH₃ | CCH₃ | |
| O | 0 | H | H | CH₃ | H | CH₃ | CH₃ | CCH₂CH₃ | |
| O | 0 | H | H | CH₃ | H | CH₃ | CH₃ | CCl | |
| O | 0 | H | H | CH₃ | H | CH₃ | CH₃ | CBr | |
| O | 1 | H | H | CH₃ | H | CH₃ | CH₂OCH₃ | CH | |
| O | 1 | H | H | CH₃ | H | Cl | OCH₃ | CH | |
| O | 0 | H | H | CH₂CH₂CH₃ | H | CH₃ | CH₃ | CH | |
| O | 0 | H | H | CH₂CH₂CH₃ | H | CH₃ | OCH₃ | CH | |
| O | 0 | H | H | CH₂CH₂CH₃ | H | OCH₃ | OCH₃ | CH | |
| O | 0 | H | H | CH₂CH₂CH₃ | H | Cl | OCH₃ | CH | |
| O | 0 | H | H | CH₂CH₂CH₃ | H | CH₃ | OCH₃ | N | |
| O | 0 | H | H | CH₂CH₂CH₃ | H | OCH₃ | OCH₃ | N | |
| O | 0 | H | H | CH₂CH₂CH₂CH₃ | H | OCH₃ | OCH₃ | N | |
| O | 0 | H | H | H | H | CH₃ | CH₃ | CH | |
| O | 0 | H | H | H | H | CH₃ | OCH₃ | CH | |
| O | 0 | H | H | H | H | OCH₃ | OCH₃ | CH | |
| O | 0 | H | H | H | H | Cl | OCH₃ | CH | |
| O | 0 | H | H | H | H | CH₃ | OCH₃ | N | |
| O | 0 | H | H | H | H | OCH₃ | OCH₃ | N | |
| O | 0 | H | H | CH₃ | CH₃ | OCH₃ | OCH₃ | CH | |
| O | 0 | H | m-SCH₃ | CH₃ | H | OCH₃ | OCH₃ | CH | |
| O | 0 | H | m-OCF₂H | CH₃ | H | OCH₃ | OCH₃ | CH | |
| O | 0 | H | H | CH₃ | H | F | OCH₃ | CH | |
| O | 0 | H | H | CH₃ | H | Br | OCH₃ | CH | |
| O | 0 | H | H | CH₃ | H | CH₂F | OCH₃ | CH | |
| O | 0 | H | H | CH₃ | H | OCF₂H | OCH₃ | CH | |
| O | 0 | H | H | CH₃ | H | OCF₃ | OCH₃ | CH | |
| O | 0 | H | H | CH₃ | H | CF₃ | OCH₃ | CH | |
| O | 0 | H | H | CH₃ | H | CH₃ | (1,3-dioxan-2-yl) | CH | |
| O | 0 | H | H | CH₃ | H | CH₃ | (4-methyl-1,3-dioxan-2-yl) | CH | |
| O | 0 | H | H | CH₃ | H | CH₃ | H | CH | |
| O | 0 | H | H | CH₃ | H | CH₃ | CN | CH | |
| O | 0 | H | H | CH₃ | H | CH₃ | CH(OCH₂CH₃)₂ | CH | |
| O | 0 | H | H | CH₃ | H | CH₃ | OCH₂F | CH | |
| O | 0 | H | H | CH₃ | H | CH₃ | OCF₃ | CH | |
| O | 0 | H | H | CH₃ | H | CH₃ | SCH₂F | CH | |
| O | 0 | H | H | CH₃ | H | CH₃ | SCF₃ | CH | |
| O | 0 | H | H | CH₃ | H | CH₃ | OCF₂H | CH | |
| O | 0 | H | H | CH₃ | H | CH₃ | OCF₂CHClF | CH | |
| O | 0 | H | H | CH₃ | H | CH₃ | OCF₂CHBrF | CH | |
| O | 0 | H | H | CH₃ | H | CH₃ | OCF₂CHFCF₃ | CH | |
| O | 0 | H | H | CH₃ | H | CH₃ | SCF₂H | CH | |

TABLE 9a-continued

| W | n | R | $R_1$ | $R_2$ | $R_5$ | X | Y | Z | m.p. (°C.) |
|---|---|---|---|---|---|---|---|---|---|
| O | 0 | H | H | $CH_3$ | H | $CH_3$ | $SCF_2CHClF$ | CH | |
| O | 0 | H | H | $CH_3$ | H | $CH_3$ | $SCF_2CHBrF$ | CH | |
| O | 0 | H | H | $CH_3$ | H | $CH_3$ | $SCF_2CHFCF_3$ | CH | |
| O | 2 | H | H | $CH_3$ | H | $CH_3$ | $CH_3$ | CH | |
| O | 2 | H | H | $CH_3$ | H | $CH_3$ | $OCH_3$ | CH | |
| O | 2 | H | H | $CH_3$ | H | $OCH_3$ | $OCH_3$ | CH | |
| O | 2 | H | H | $CH_3$ | H | Cl | $OCH_3$ | CH | |
| O | 2 | H | H | $CH_3$ | H | $CH_3$ | $OCH_3$ | N | |
| O | 2 | H | H | $CH_3$ | H | $OCH_3$ | $OCH_3$ | N | |

TABLE 10a

| W | n | R | $R_1$ | $R_5$ | X | Y | Z | m.p. (°C.) |
|---|---|---|---|---|---|---|---|---|
| O | 0 | H | H | H | $CH_3$ | $CH_3$ | CH | |
| O | 0 | H | H | H | $CH_3$ | $OCH_3$ | CH | |
| O | 0 | H | H | H | $OCH_3$ | $OCH_3$ | CH | |
| O | 0 | H | H | H | $CH_3$ | $CH_3$ | N | |
| O | 0 | H | H | H | $CH_3$ | $OCH_3$ | N | |
| O | 0 | H | H | H | $OCH_3$ | $OCH_3$ | N | |
| O | 1 | H | H | H | $CH_3$ | $CH_3$ | CH | |
| O | 1 | H | H | H | $CH_3$ | $OCH_3$ | CH | |
| O | 1 | H | H | H | $OCH_3$ | $OCH_3$ | CH | |
| O | 1 | H | H | H | $CH_3$ | $CH_3$ | N | |
| O | 1 | H | H | H | $CH_3$ | $OCH_3$ | N | |
| O | 1 | H | H | H | $OCH_3$ | $OCH_3$ | N | |
| S | 0 | H | H | H | $OCH_3$ | $OCH_3$ | CH | |
| S | 1 | H | H | H | $OCH_3$ | $OCH_3$ | CH | |
| O | 0 | $CH_3$ | H | H | $OCH_3$ | $OCH_3$ | N | |
| O | 0 | H | o-F | H | $OCH_3$ | $OCH_3$ | CH | |
| O | 0 | H | m-Cl | H | $OCH_3$ | $OCH_3$ | CH | |
| O | 0 | H | o-Br | H | $OCH_3$ | $OCH_3$ | CH | |
| O | 0 | H | m-$CH_3$ | H | $OCH_3$ | $OCH_3$ | CH | |
| O | 0 | H | o-$OCH_3$ | H | $OCH_3$ | $OCH_3$ | CH | |
| O | 0 | H | m-$CF_3$ | H | $OCH_3$ | $OCH_3$ | CH | |
| O | 0 | H | H | H | Cl | $OCH_3$ | CH | |
| O | 0 | H | H | H | $CH_3$ | $OCH_2CH_3$ | CH | |
| O | 0 | H | H | H | $CH_3$ | $NH_2$ | CH | |
| O | 0 | H | H | H | $CH_3$ | $NHCH_3$ | CH | |
| O | 0 | H | H | H | $CH_3$ | $N(CH_3)_2$ | CH | |
| O | 0 | H | H | H | $CH_3$ | $CH_2CH_3$ | CH | |
| O | 0 | H | H | H | $CH_3$ | $CF_3$ | CH | |
| O | 0 | H | H | H | $CH_3$ | $SCH_3$ | CH | |
| O | 0 | H | H | H | $CH_3$ | $OCH_2CH=CH_2$ | CH | |
| O | 0 | H | H | H | $CH_3$ | $OCH_2C\equiv CH$ | CH | |
| O | 0 | H | H | H | $CH_3$ | $OCH_2CF_3$ | CH | |
| O | 0 | H | H | H | $CH_3$ | $OCH_2CH_2OCH_3$ | CH | |
| O | 0 | H | H | H | $CH_3$ | $CH(OCH_3)_2$ | CH | |
| O | 0 | H | H | H | $CH_3$ | (1,3-dioxolan-2-yl) | CH | |

TABLE 10a-continued

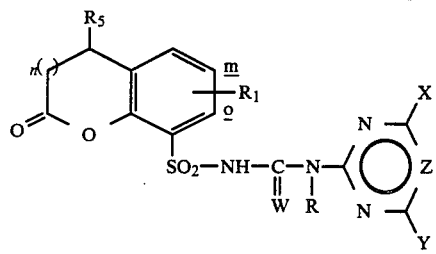

| W | n | R | R₁ | R₅ | X | Y | Z | m.p. (°C.) |
|---|---|---|---|---|---|---|---|---|
| O | 0 | H | H | H | CH₃ | CH₂OCH₃ | CH | |
| O | 0 | H | H | H | CH₃ | CH₃ | CCH₃ | |
| O | 0 | H | H | H | CH₃ | CH₃ | CCH₂CH₃ | |
| O | 0 | H | H | H | CH₃ | CH₃ | CCl | |
| O | 0 | H | H | H | CH₃ | CH₃ | CBr | |
| O | 1 | H | H | H | CH₃ | CH₂OCH₃ | CH | |
| O | 1 | H | H | H | Cl | OCH₃ | CH | |
| O | 0 | H | H | CH₃ | OCH₃ | OCH₃ | CH | |
| O | 0 | H | m-SCH₃ | H | OCH₃ | OCH₃ | CH | |
| O | 0 | H | m-OCF₂H | H | OCH₃ | OCH₃ | CH | |
| O | 0 | H | H | H | F | OCH₃ | CH | |
| O | 0 | H | H | H | CH₂F | OCH₃ | CH | |
| O | 0 | H | H | H | OCF₂H | OCH₃ | CH | |
| O | 0 | H | H | H | OCF₃ | OCH₃ | CH | |
| O | 0 | H | H | H | CF₃ | OCH₃ | CH | |
| O | 0 | H | H | H | CH₃ | 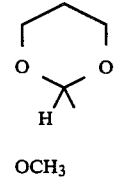 | CH | |
| O | 0 | H | H | H | Br | OCH₃ | CH | |
| O | 0 | H | H | H | CH₃ | 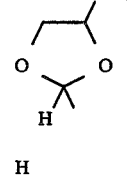 | CH | |
| O | 0 | H | H | H | CH₃ | H | CH | |
| O | 0 | H | H | H | CH₃ | CN | CH | |
| O | 0 | H | H | H | CH₃ | CH(OCH₂CH₃)₂ | CH | |
| O | 0 | H | H | H | CH₃ | OCH₂F | CH | |
| O | 0 | H | H | H | CH₃ | OCF₃ | CH | |
| O | 0 | H | H | H | CH₃ | SCH₂F | CH | |
| O | 0 | H | H | H | CH₃ | SCF₃ | CH | |
| O | 0 | H | H | H | CH₃ | OCF₂H | CH | |
| O | 0 | H | H | H | CH₃ | OCF₂CHClF | CH | |
| O | 0 | H | H | H | CH₃ | OCF₂CHBrF | CH | |
| O | 0 | H | H | H | CH₃ | OCF₂CHFCF₃ | CH | |
| O | 0 | H | H | H | CH₃ | SCF₂H | CH | |
| O | 0 | H | H | H | CH₃ | SCF₂CHClF | CH | |
| O | O | H | H | H | CH₃ | SCF₂CHBrF | CH | |
| O | 0 | H | H | H | CH₃ | SCF₂CHFCF₃ | CH | |
| O | 2 | H | H | H | CH₃ | CH₃ | CH | |
| O | 2 | H | H | H | CH₃ | OCH₃ | CH | |
| O | 2 | H | H | H | OCH₃ | OCH₃ | CH | |
| O | 2 | H | H | H | Cl | OCH₃ | CH | |
| O | 2 | H | H | H | CH₃ | OCH₃ | N | |
| O | 2 | H | H | H | OCH₃ | OCH₃ | N | |

TABLE 10b

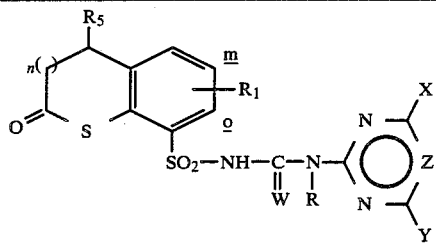

| W | n | R | R₁ | R₅ | X | Y | Z | m.p. (°C.) |
|---|---|---|---|---|---|---|---|---|
| O | 0 | H | H | H | $CH_3$ | $CH_3$ | CH | |
| O | 0 | H | H | H | $CH_3$ | $OCH_3$ | CH | |
| O | 0 | H | H | H | $OCH_3$ | $OCH_3$ | CH | |
| O | 0 | H | H | H | $CH_3$ | $CH_3$ | N | |
| O | 0 | H | H | H | $CH_3$ | $OCH_3$ | N | |
| O | 0 | H | H | H | $OCH_3$ | $OCH_3$ | N | |
| O | 1 | H | H | H | $CH_3$ | $CH_3$ | CH | |
| O | 1 | H | H | H | $CH_3$ | $OCH_3$ | CH | |
| O | 1 | H | H | H | $OCH_3$ | $OCH_3$ | CH | |
| O | 1 | H | H | H | $CH_3$ | $CH_3$ | N | |
| O | 1 | H | H | H | $CH_3$ | $OCH_3$ | N | |
| O | 1 | H | H | H | $OCH_3$ | $OCH_3$ | N | |
| S | 0 | H | H | H | $OCH_3$ | $OCH_3$ | CH | |
| S | 1 | H | H | H | $OCH_3$ | $OCH_3$ | CH | |
| O | 0 | $CH_3$ | H | H | $OCH_3$ | $OCH_3$ | N | |
| O | 0 | H | o-F | H | $OCH_3$ | $OCH_3$ | CH | |
| O | 0 | H | m-Cl | H | $OCH_3$ | $OCH_3$ | CH | |
| O | 0 | H | o-Br | H | $OCH_3$ | $OCH_3$ | CH | |
| O | 0 | H | m-$CH_3$ | H | $OCH_3$ | $OCH_3$ | CH | |
| O | 0 | H | o-$OCH_3$ | H | $OCH_3$ | $OCH_3$ | CH | |
| O | 0 | H | m-$CF_3$ | H | $OCH_3$ | $OCH_3$ | CH | |
| O | 0 | H | H | H | Cl | $OCH_3$ | CH | |
| O | 0 | H | H | H | $CH_3$ | $OCH_2CH_3$ | CH | |
| O | 0 | H | H | H | $CH_3$ | $NH_2$ | CH | |
| O | 0 | H | H | H | $CH_3$ | $NHCH_3$ | CH | |
| O | 0 | H | H | H | $CH_3$ | $N(CH_3)_2$ | CH | |
| O | 0 | H | H | H | $CH_3$ | $CH_2CH_3$ | CH | |
| O | 0 | H | H | H | $CH_3$ | $CF_3$ | CH | |
| O | 0 | H | H | H | $CH_3$ | $SCH_3$ | CH | |
| O | 0 | H | H | H | $CH_3$ | $OCH_2CH=CH_2$ | CH | |
| O | 0 | H | H | H | $CH_3$ | $OCH_2C\equiv CH$ | CH | |
| O | 0 | H | H | H | $CH_3$ | $OCH_2CF_3$ | CH | |
| O | 0 | H | H | H | $CH_3$ | $OCH_2CH_2OCH_3$ | CH | |
| O | 0 | H | H | H | $CH_3$ | $CH(OCH_3)_2$ | CH | |
| O | 0 | H | H | H | $CH_3$ | (1,3-dioxolan-2-yl) | CH | |
| O | 0 | H | H | H | $CH_3$ | $CH_2OCH_3$ | CH | |
| O | 0 | H | H | H | $CH_3$ | $CH_3$ | $CCH_3$ | |
| O | 0 | H | H | H | $CH_3$ | $CH_3$ | $CCH_2CH_3$ | |
| O | 0 | H | H | H | $CH_3$ | $CH_3$ | CCl | |
| O | 0 | H | H | H | $CH_3$ | $CH_3$ | CBr | |
| O | 1 | H | H | H | $CH_3$ | $CH_2OCH_3$ | CH | |
| O | 1 | H | H | H | Cl | $OCH_3$ | CH | |
| O | 0 | H | H | $CH_3$ | $OCH_3$ | $OCH_3$ | CH | |
| O | 0 | H | m-$SCH_3$ | H | $OCH_3$ | $OCH_3$ | CH | |
| O | 0 | H | m-$OCF_2H$ | H | $OCH_3$ | $OCH_3$ | CH | |
| O | 0 | H | H | H | F | $OCH_3$ | CH | |
| O | 0 | H | H | H | $CH_2F$ | $OCH_3$ | CH | |
| O | 0 | H | H | H | $OCF_2H$ | $OCH_3$ | CH | |
| O | 0 | H | H | H | $OCF_3$ | $OCH_3$ | CH | |
| O | 0 | H | H | H | $CF_3$ | $OCH_3$ | CH | |
| O | 0 | H | H | H | $CH_3$ | (1,3-dioxan-2-yl) | CH | |
| O | 0 | H | H | H | Br | $OCH_3$ | CH | |

TABLE 10b-continued

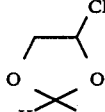

| W | n | R | R1 | R5 | X | Y | Z | m.p. (°C.) |
|---|---|---|---|---|---|---|---|---|
| O | 0 | H | H | H | CH3 | CH3-CH(-O-CH(H)-O-) | CH | |
| O | 0 | H | H | H | CH3 | H | CH | |
| O | 0 | H | H | H | CH3 | CN | CH | |
| O | 0 | H | H | H | CH3 | CH(OCH2CH3)2 | CH | |
| O | 0 | H | H | H | CH3 | OCH2F | CH | |
| O | 0 | H | H | H | CH3 | OCF3 | CH | |
| O | 0 | H | H | H | CH3 | SCH2F | CH | |
| O | 0 | H | H | H | CH3 | SCF3 | CH | |
| O | 0 | H | H | H | CH3 | OCF2H | CH | |
| O | 0 | H | H | H | CH3 | OCF2CHClF | CH | |
| O | 0 | H | H | H | CH3 | OCF2CHBrF | CH | |
| O | 0 | H | H | H | CH3 | OCF2CHFCF3 | CH | |
| O | 0 | H | H | H | CH3 | SCF2H | CH | |
| O | 0 | H | H | H | CH3 | SCF2CHClF | CH | |
| O | 0 | H | H | H | CH3 | SCF2CHBrF | CH | |
| O | 0 | H | H | H | CH3 | SCF2CHFCF3 | CH | |
| O | 2 | H | H | H | CH3 | CH3 | CH | |
| O | 2 | H | H | H | CH3 | OCH3 | CH | |
| O | 2 | H | H | H | OCH3 | OCH3 | CH | |
| O | 2 | H | H | H | Cl | OCH3 | CH | |
| O | 2 | H | H | H | CH3 | OCH3 | N | |
| O | 2 | H | H | H | OCH3 | OCH3 | N | |

TABLE 11a

| W | n | R | R1 | R6 | R7 | X | Y | Z | m.p. (°C.) |
|---|---|---|---|---|---|---|---|---|---|
| O | 0 | H | H | H | H | CH3 | CH3 | CH | |
| O | 0 | H | H | H | H | CH3 | OCH3 | CH | |
| O | 0 | H | H | H | H | OCH3 | OCH3 | CH | |
| O | 0 | H | H | H | H | Cl | OCH3 | CH | |
| O | 0 | H | H | H | H | CH3 | OCH3 | N | |
| O | 0 | H | H | H | H | OCH3 | OCH3 | N | |
| O | 0 | H | H | CH3 | H | CH3 | CH3 | CH | |
| O | 0 | H | H | H | CH3 | CH3 | OCH3 | CH | |
| O | 0 | H | H | CH3 | H | OCH3 | OCH3 | CH | |
| O | 0 | H | H | H | CH3 | Cl | OCH3 | CH | |
| O | 0 | H | H | CH3 | H | CH3 | OCH3 | N | |
| O | 0 | H | H | H | CH3 | OCH3 | OCH3 | N | |
| O | 0 | H | H | CH3 | CH3 | CH3 | CH3 | CH | |
| O | 0 | H | H | CH3 | CH3 | CH3 | OCH3 | CH | |
| O | 0 | H | H | CH3 | CH3 | OCH3 | OCH3 | CH | |
| O | 0 | H | H | CH3 | CH3 | Cl | OCH3 | CH | |
| O | 0 | H | H | CH3 | CH3 | CH3 | OCH3 | N | |
| O | 0 | H | H | CH3 | CH3 | OCH3 | OCH3 | N | |
| O | 0 | H | H | H | H | CH3 | OCH2CH3 | CH | |
| O | 0 | H | m-F | H | H | CH3 | CH2OCH3 | CH | |
| O | 0 | H | o-Cl | H | H | CH3 | NH2 | CH | |
| O | 0 | H | m-Br | H | H | CH3 | NHCH3 | CH | |
| O | 0 | H | o-CH3 | H | H | CH3 | N(CH3)2 | CH | |

TABLE 11a-continued

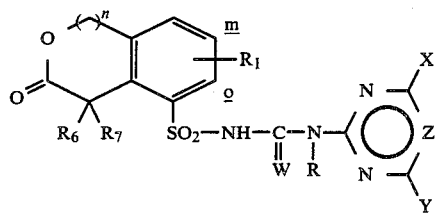

| W | n | R | R₁ | R₆ | R₇ | X | Y | Z | m.p. (°C.) |
|---|---|---|---|---|---|---|---|---|---|
| O | 0 | H | m-OCH₃ | H | H | CH₃ | C₂H₅ | CH | |
| O | 0 | H | o-CF₃ | H | H | CH₃ | CF₃ | CH | |
| O | 0 | H | m-SCH₃ | H | H | CH₃ | SCH₃ | CH | |
| O | 0 | H | o-OCF₂H | H | H | CH₃ | OCH₂CH=CH₂ | CH | |
| O | 0 | H | o-OCF₂H | H | H | CH₃ | OCH₂C≡CH | CH | |
| O | 0 | H | H | H | H | CH₃ | OCH₂CF₃ | CH | |
| O | 0 | H | H | H | H | CH₃ | OCH₂CH₂OCH₃ | CH | |
| O | 0 | H | H | H | H | CH₃ | CH(OCH₃)₂ | CH | |
| O | 0 | H | H | H | H | CH₃ | (1,3-dioxolan-2-yl) | CH | |
| O | 0 | H | H | H | H | CH₃ | (1,3-dioxan-2-yl) | CH | |
| O | 0 | H | H | H | H | CH₃ | (5-methyl-1,3-dioxan-2-yl) | CH | |
| O | 0 | H | H | H | H | CH₃ | H | CH | |
| O | 0 | H | H | H | H | CH₃ | CN | CH | |
| O | 0 | H | H | H | H | CH₃ | CH(OCH₂CH₃)₂ | CH | |
| O | 0 | H | H | H | H | CH₃ | OCH₂F | CH | |
| O | 0 | H | H | H | H | CH₃ | OCF₃ | CH | |
| O | 0 | H | H | H | H | CH₃ | SCH₂F | CH | |
| O | 0 | H | H | H | H | CH₃ | SCF₃ | CH | |
| O | 0 | H | H | H | H | CH₃ | OCF₂H | CH | |
| O | 0 | H | H | H | H | CH₃ | OCF₂CHClF | CH | |
| O | 0 | H | H | H | H | CH₃ | OCF₂CHBrF | CH | |
| O | 0 | H | H | H | H | CH₃ | OCF₂CHFCF₃ | CH | |
| O | 0 | H | H | H | H | CH₃ | SCF₂H | CH | |
| O | 0 | H | H | H | H | CH₃ | SCF₂CHClF | CH | |
| O | 0 | H | H | H | H | CH₃ | SCF₂CHBrF | CH | |
| O | 0 | H | H | H | H | CH₃ | SCF₂CHFCF₃ | CH | |
| O | 0 | H | H | H | H | CH₂F | CH₃ | CH | |
| O | 0 | H | H | H | H | F | OCH₃ | CH | |
| O | 0 | H | H | H | H | Br | OCH₃ | CH | |
| O | 0 | H | H | H | H | OCF₂H | CH₃ | CH | |
| O | 0 | H | H | H | H | OCF₃ | CH₃ | CH | |
| O | 0 | H | H | H | H | CF₃ | CH₃ | CH | |
| S | 0 | H | H | H | H | OCH₃ | OCH₃ | CH | |
| O | 0 | CH₃ | H | H | H | OCH₃ | OCH₃ | N | |
| O | 1 | H | H | H | H | CH₃ | CH₃ | CH | |
| O | 1 | H | H | H | H | CH₃ | OCH₃ | CH | |
| O | 1 | H | H | H | H | OCH₃ | OCH₃ | CH | |
| O | 1 | H | H | H | H | Cl | OCH₃ | CH | |
| O | 1 | H | H | H | H | CH₃ | OCH₃ | N | |
| O | 1 | H | H | H | H | OCH₃ | OCH₃ | N | |
| O | 1 | H | H | CH₃ | H | CH₃ | CH₃ | CH | |
| O | 1 | H | H | H | CH₃ | CH₃ | OCH₃ | CH | |
| O | 1 | H | H | CH₃ | H | OCH₃ | OCH₃ | CH | |
| O | 1 | H | H | H | CH₃ | Cl | OCH₃ | CH | |
| O | 1 | H | H | CH₃ | H | CH₃ | OCH₃ | N | |
| O | 1 | H | H | H | CH₃ | OCH₃ | OCH₃ | N | |
| O | 1 | H | H | CH₃ | CH₃ | CH₃ | CH₃ | CH | |
| O | 1 | H | H | CH₃ | CH₃ | CH₃ | OCH₃ | CH | |
| O | 1 | H | H | CH₃ | CH₃ | OCH₃ | OCH₃ | CH | |
| O | 1 | H | H | CH₃ | CH₃ | Cl | OCH₃ | CH | |
| O | 1 | H | H | CH₃ | CH₃ | CH₃ | OCH₃ | N |

TABLE 11a-continued

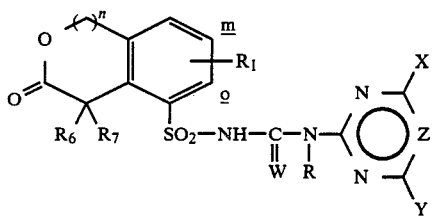

| W | n | R | R1 | R6 | R7 | X | Y | Z | m.p. (°C.) |
|---|---|---|----|----|----|---|---|---|------------|
| O | 1 | H | H | CH3 | CH3 | OCH3 | OCH3 | N | |
| O | 2 | H | H | H | H | CH3 | CH3 | CH | |
| O | 2 | H | H | H | H | CH3 | OCH3 | CH | |
| O | 2 | H | H | H | H | OCH3 | OCH3 | CH | |
| O | 2 | H | H | H | H | Cl | OCH3 | CH | |
| O | 2 | H | H | H | H | CH3 | OCH3 | N | |
| O | 2 | H | H | H | H | OCH3 | OCH3 | N | |

TABLE 11b

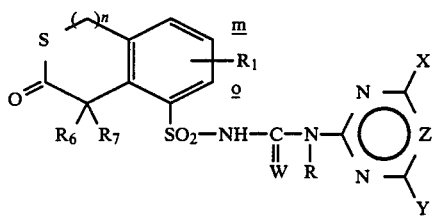

| W | n | R | R1 | R6 | R7 | X | Y | Z | m.p. (°C.) |
|---|---|---|----|----|----|---|---|---|------------|
| O | 0 | H | H | H | H | CH3 | CH3 | CH | |
| O | 0 | H | H | H | H | CH3 | OCH3 | CH | |
| O | 0 | H | H | H | H | OCH3 | OCH3 | CH | |
| O | 0 | H | H | H | H | Cl | OCH3 | CH | |
| O | 0 | H | H | H | H | CH3 | OCH3 | N | |
| O | 0 | H | H | H | H | OCH3 | OCH3 | N | |
| O | 0 | H | H | CH3 | H | CH3 | CH3 | CH | |
| O | 0 | H | H | H | CH3 | CH3 | OCH3 | CH | |
| O | 0 | H | H | CH3 | H | OCH3 | OCH3 | CH | |
| O | 0 | H | H | H | CH3 | Cl | OCH3 | CH | |
| O | 0 | H | H | CH3 | H | CH3 | OCH3 | N | |
| O | 0 | H | H | H | CH3 | OCH3 | OCH3 | N | |
| O | 0 | H | H | CH3 | CH3 | CH3 | CH3 | CH | |
| O | 0 | H | H | CH3 | CH3 | CH3 | OCH3 | CH | |
| O | 0 | H | H | CH3 | CH3 | OCH3 | OCH3 | CH | |
| O | 0 | H | H | CH3 | CH3 | Cl | OCH3 | CH | |
| O | 0 | H | H | CH3 | CH3 | CH3 | OCH3 | N | |
| O | 0 | H | H | CH3 | CH3 | OCH3 | OCH3 | N | |
| O | 0 | H | H | H | H | CH3 | OCH2CH3 | CH | |
| O | 0 | H | m-F | H | H | CH3 | CH2OCH3 | CH | |
| O | 0 | H | o-Cl | H | H | CH3 | NH2 | CH | |
| O | 0 | H | m-Br | H | H | CH3 | NHCH3 | CH | |
| O | 0 | H | o-CH3 | H | H | CH3 | N(CH3)2 | CH | |
| O | 0 | H | m-OCH3 | H | H | CH3 | C2H5 | CH | |
| O | 0 | H | o-CF3 | H | H | CH3 | CF3 | CH | |
| O | 0 | H | m-SCH3 | H | H | CH3 | SCH3 | CH | |
| O | 0 | H | o-OCF2H | H | H | CH3 | OCH2CH=CH2 | CH | |
| O | 0 | H | o-OCF2H | H | H | CH3 | OCH2C≡CH | CH | |
| O | 0 | H | H | H | H | CH3 | OCH2CF3 | CH | |
| O | 0 | H | H | H | H | CH3 | OCH2CH2OCH3 | CH | |
| O | 0 | H | H | H | H | CH3 | CH(OCH3)2 | CH | |
| O | 0 | H | H | H | H | CH3 | 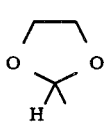 | CH | |
| O | 0 | H | H | H | H | CH3 | 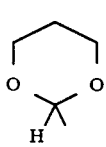 | CH | |

TABLE 11b-continued

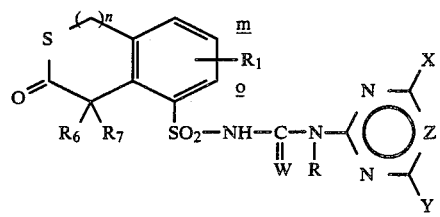

| W | n | R | $R_1$ | $R_6$ | $R_7$ | X | Y | Z | m.p. (°C.) |
|---|---|---|---|---|---|---|---|---|---|
| O | 0 | H | H | H | H | $CH_3$ | 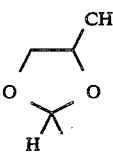 | CH | |
| O | 0 | H | H | H | H | $CH_3$ | H | CH | |
| O | 0 | H | H | H | H | $CH_3$ | CN | CH | |
| O | 0 | H | H | H | H | $CH_3$ | $CH(OCH_2CH_3)_2$ | CH | |
| O | 0 | H | H | H | H | $CH_3$ | $OCH_2F$ | CH | |
| O | 0 | H | H | H | H | $CH_3$ | $OCF_3$ | CH | |
| O | 0 | H | H | H | H | $CH_3$ | $SCH_2F$ | CH | |
| O | 0 | H | H | H | H | $CH_3$ | $SCF_3$ | CH | |
| O | 0 | H | H | H | H | $CH_3$ | $OCF_2H$ | CH | |
| O | 0 | H | H | H | H | $CH_3$ | $OCF_2CHClF$ | CH | |
| O | 0 | H | H | H | H | $CH_3$ | $OCF_2CHBrF$ | CH | |
| O | 0 | H | H | H | H | $CH_3$ | $OCF_2CHFCF_3$ | CH | |
| O | 0 | H | H | H | H | $CH_3$ | $SCF_2H$ | CH | |
| O | 0 | H | H | H | H | $CH_3$ | $SCF_2CHClF$ | CH | |
| O | 0 | H | H | H | H | $CH_3$ | $SCF_2CHBrF$ | CH | |
| O | 0 | H | H | H | H | $CH_3$ | $SCF_2CHFCF_3$ | CH | |
| O | 0 | H | H | H | H | $CH_2F$ | $CH_3$ | CH | |
| O | 0 | H | H | H | H | F | $OCH_3$ | CH | |
| O | 0 | H | H | H | H | Br | $OCH_3$ | CH | |
| O | 0 | H | H | H | H | $OCF_2H$ | $CH_3$ | CH | |
| O | 0 | H | H | H | H | $OCF_3$ | $CH_3$ | CH | |
| O | 0 | H | H | H | H | $CF_3$ | $CH_3$ | CH | |
| S | 0 | H | H | H | H | $OCH_3$ | $OCH_3$ | CH | |
| O | 0 | $CH_3$ | H | H | H | $OCH_3$ | $OCH_3$ | N | |
| O | 1 | H | H | H | H | $CH_3$ | $CH_3$ | CH | |
| O | 1 | H | H | H | H | $CH_3$ | $OCH_3$ | CH | |
| O | 1 | H | H | H | H | $OCH_3$ | $OCH_3$ | CH | |
| O | 1 | H | H | H | H | Cl | $OCH_3$ | CH | |
| O | 1 | H | H | H | H | $CH_3$ | $OCH_3$ | N | |
| O | 1 | H | H | H | H | $OCH_3$ | $OCH_3$ | N | |
| O | 1 | H | H | $CH_3$ | H | $CH_3$ | $CH_3$ | CH | |
| O | 1 | H | H | H | $CH_3$ | $CH_3$ | $CH_3$ | CH | |
| O | 1 | H | H | $CH_3$ | H | $OCH_3$ | $OCH_3$ | CH | |
| O | 1 | H | H | H | $CH_3$ | Cl | $OCH_3$ | CH | |
| O | 1 | H | H | $CH_3$ | H | $CH_3$ | $OCH_3$ | N | |
| O | 1 | H | H | H | $CH_3$ | $OCH_3$ | $OCH_3$ | N | |
| O | 1 | H | H | $CH_3$ | $CH_3$ | $CH_3$ | $CH_3$ | CH | |
| O | 1 | H | H | $CH_3$ | $CH_3$ | $CH_3$ | $OCH_3$ | CH | |
| O | 1 | H | H | $CH_3$ | $CH_3$ | $OCH_3$ | $OCH_3$ | CH | |
| O | 1 | H | H | $CH_3$ | $CH_3$ | Cl | $OCH_3$ | CH | |
| O | 1 | H | H | $CH_3$ | $CH_3$ | $CH_3$ | $OCH_3$ | N | |
| O | 1 | H | H | $CH_3$ | $CH_3$ | $OCH_3$ | $OCH_3$ | N | |
| O | 2 | H | H | H | H | $CH_3$ | $CH_3$ | CH | |
| O | 2 | H | H | H | H | $CH_3$ | $OCH_3$ | CH | |
| O | 2 | H | H | H | H | $OCH_3$ | $OCH_3$ | CH | |
| O | 2 | H | H | H | H | Cl | $OCH_3$ | CH | |
| O | 2 | H | H | H | H | $CH_3$ | $OCH_3$ | N | |
| O | 2 | H | H | H | H | $OCH_3$ | $OCH_3$ | N | |

TABLE 12a

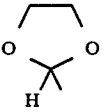

| W | n | R | R₁ | R₅ | R₆ | R₇ | X | Y | Z | m.p. (°C.) |
|---|---|---|---|---|---|---|---|---|---|---|
| O | 0 | H | H | H | H | H | CH₃ | CH₃ | CH | |
| O | 0 | H | H | H | H | H | CH₃ | OCH₃ | CH | |
| O | 0 | H | H | H | H | H | OCH₃ | OCH₃ | CH | |
| O | 0 | H | H | H | H | H | Cl | OCH₃ | CH | |
| O | 0 | H | H | H | H | H | CH₃ | OCH₃ | N | |
| O | 0 | H | H | H | H | H | OCH₃ | OCH₃ | N | |
| O | 0 | H | H | H | CH₃ | H | CH₃ | CH₃ | CH | |
| O | 0 | H | H | H | H | CH₃ | CH₃ | OCH₃ | CH | |
| O | 0 | H | H | H | CH₃ | H | OCH₃ | OCH₃ | CH | |
| O | 0 | H | H | H | H | CH₃ | Cl | OCH₃ | CH | |
| O | 0 | H | H | H | CH₃ | H | CH₃ | OCH₃ | N | |
| O | 0 | H | H | H | H | CH₃ | OCH₃ | OCH₃ | N | |
| O | 0 | H | H | H | CH₃ | CH₃ | CH₃ | CH₃ | CH | |
| O | 0 | H | H | H | CH₃ | CH₃ | CH₃ | OCH₃ | CH | |
| O | 0 | H | H | H | CH₃ | CH₃ | OCH₃ | OCH₃ | CH | |
| O | 0 | H | H | H | CH₃ | CH₃ | Cl | OCH₃ | CH | |
| O | 0 | H | H | H | CH₃ | CH₃ | CH₃ | OCH₃ | N | |
| O | 0 | H | H | H | CH₃ | CH₃ | OCH₃ | OCH₃ | N | |
| O | 0 | H | H | CH₃ | H | H | CH₃ | OCH₂CH₃ | CH | |
| O | 0 | H | m-F | H | H | H | CH₃ | CH₂OCH₃ | CH | |
| O | 0 | H | o-Cl | H | H | H | CH₃ | NH₂ | CH | |
| O | 0 | H | m-Br | H | H | H | CH₃ | NHCH₃ | CH | |
| O | 0 | H | o-CH₃ | H | H | H | CH₃ | N(CH₃)₂ | CH | |
| O | 0 | H | m-OCH₃ | H | H | H | CH₃ | C₂H₅ | CH | |
| O | 0 | H | o-CF₃ | H | H | H | CH₃ | CF₃ | CH | |
| O | 0 | H | m-SCH₃ | H | H | H | CH₃ | SCH₃ | CH | |
| O | 0 | H | o-OCF₂H | H | H | H | CH₃ | OCH₂CH=CH₂ | CH | |
| O | 0 | H | o-OCF₂H | H | H | H | CH₃ | OCH₂C≡CH | CH | |
| O | 0 | H | H | H | H | H | CH₃ | OCH₂CF₃ | CH | |
| O | 0 | H | H | H | H | H | CH₃ | OCH₂CH₂OCH₃ | CH | |
| O | 0 | H | H | H | H | H | CH₃ | CH(OCH₃)₂ | CH | |
| O | 0 | H | H | H | H | H | CH₃ | 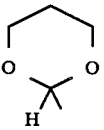 | CH | |
| O | 0 | H | H | H | H | H | CH₃ | 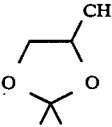 | CH | |
| O | 0 | H | H | H | H | H | CH₃ |  | CH | |
| O | 0 | H | H | H | H | H | CH₃ | H | CH | |
| O | 0 | H | H | H | H | H | CH₃ | CN | CH | |
| O | 0 | H | H | H | H | H | CH₃ | CH(OCH₂CH₃)₂ | CH | |
| O | 0 | H | H | H | H | H | CH₃ | OCH₂F | CH | |
| O | 0 | H | H | H | H | H | CH₃ | OCF₃ | CH | |
| O | 0 | H | H | H | H | H | CH₃ | SCH₂F | CH | |
| O | 0 | H | H | H | H | H | CH₃ | SCF₃ | CH | |
| O | 0 | H | H | H | H | H | CH₃ | OCF₂H | CH | |
| O | 0 | H | H | H | H | H | CH₃ | OCF₂CHClF | CH | |
| O | 0 | H | H | H | H | H | CH₃ | OCF₂CHBrF | CH | |
| O | 0 | H | H | H | H | H | CH₃ | OCF₂CHFCF₃ | CH | |
| O | 0 | H | H | H | H | H | CH₃ | SCF₂H | CH | |
| O | 0 | H | H | H | H | H | CH₃ | SCF₂CHClF | CH | |
| O | 0 | H | H | H | H | H | CH₃ | SCF₂CHBrF | CH | |

TABLE 12a-continued

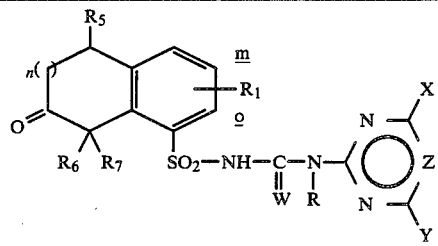

| W | n | R | R₁ | R₅ | R₆ | R₇ | X | Y | Z | m.p. (°C.) |
|---|---|---|----|----|----|----|----|----|----|------------|
| O | 0 | H | H | H | H | H | CH₃ | SCF₂CHFCF₃ | CH | |
| O | 0 | H | H | H | H | H | CH₂F | CH₃ | CH | |
| O | 0 | H | H | H | H | H | F | OCH₃ | CH | |
| O | 0 | H | H | H | H | H | Br | OCH₃ | CH | |
| O | 0 | H | H | H | H | H | OCF₂H | CH₃ | CH | |
| O | 0 | H | H | H | H | H | OCF₃ | CH₃ | CH | |
| O | 0 | H | H | H | H | H | CF₃ | CH₃ | CH | |
| S | 0 | H | H | H | H | H | OCH₃ | OCH₃ | CH | |
| O | 0 | CH₃ | H | H | H | H | OCH₃ | OCH₃ | N | |
| O | 1 | H | H | H | H | H | CH₃ | CH₃ | CH | |
| O | 1 | H | H | H | H | H | CH₃ | OCH₃ | CH | |
| O | 1 | H | H | H | H | H | OCH₃ | OCH₃ | CH | |
| O | 1 | H | H | H | H | H | Cl | OCH₃ | CH | |
| O | 1 | H | H | H | H | H | CH₃ | OCH₃ | N | |
| O | 1 | H | H | H | H | H | OCH₃ | OCH₃ | N | |
| O | 1 | H | H | H | CH₃ | H | CH₃ | CH₃ | CH | |
| O | 1 | H | H | H | H | CH₃ | CH₃ | OCH₃ | CH | |
| O | 1 | H | H | H | CH₃ | H | OCH₃ | OCH₃ | CH | |
| O | 1 | H | H | H | H | CH₃ | Cl | OCH₃ | CH | |
| O | 1 | H | H | H | CH₃ | H | CH₃ | OCH₃ | N | |
| O | 1 | H | H | H | H | CH₃ | OCH₃ | OCH₃ | N | |
| O | 1 | H | H | H | CH₃ | CH₃ | CH₃ | CH₃ | CH | |
| O | 1 | H | H | H | CH₃ | CH₃ | CH₃ | OCH₃ | CH | |
| O | 1 | H | H | H | CH₃ | CH₃ | OCH₃ | OCH₃ | CH | |
| O | 1 | H | H | H | CH₃ | CH₃ | Cl | OCH₃ | CH | |
| O | 1 | H | H | H | CH₃ | CH₃ | CH₃ | OCH₃ | N | |
| O | 1 | H | H | H | CH₃ | CH₃ | OCH₃ | OCH₃ | N | |
| O | 2 | H | H | H | H | H | CH₃ | CH₃ | CH | |
| O | 2 | H | H | H | H | H | CH₃ | OCH₃ | CH | |
| O | 2 | H | H | H | H | H | OCH₃ | OCH₃ | CH | |
| O | 2 | H | H | H | H | H | Cl | OCH₃ | CH | |
| O | 2 | H | H | H | H | H | CH₃ | OCH₃ | N | |
| O | 2 | H | H | H | H | H | OCH₃ | OCH₃ | N | |

TABLE 13a

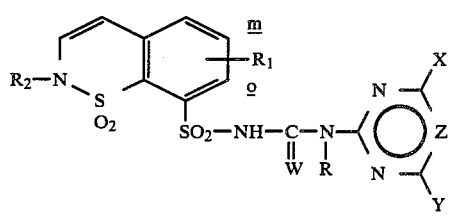

| W | R | R₁ | R₂ | X | Y | Z | m.p. (°C.) |
|---|---|----|----|----|----|----|------------|
| S | H | H | CH₃ | OCH₃ | OCH₃ | CH | |
| O | H | H | CH₃ | CH₃ | OCH₂CH₃ | CH | |
| O | H | H | CH₃ | CH₃ | CH₂OCH₃ | CH | |
| O | H | H | CH₃ | CH₃ | NH₂ | CH | |
| O | H | H | CH₃ | CH₃ | NHCH₃ | CH | |
| O | H | H | CH₃ | CH₃ | N(CH₃)₂ | CH | |
| O | H | H | CH₃ | CH₃ | CH₂CH₃ | CH | |
| O | H | H | CH₃ | CH₃ | CF₃ | CH | |
| O | H | H | CH₃ | CH₃ | SCH₃ | CH | |
| O | H | H | CH₃ | CH₃ | OCH₂CH=CH₂ | CH | |
| O | H | H | CH₃ | CH₃ | OCH₂C≡CH | CH | |
| O | H | H | CH₃ | CH₃ | OCH₂CF₃ | CH | |
| O | H | H | CH₃ | CH₃ | OCH₂CH₂OCH₃ | CH | |
| O | H | H | CH₃ | CH₃ | CH(OCH₃)₂ | CH | |

TABLE 13a-continued

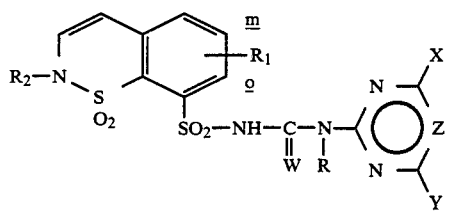

| W | R | R₁ | R₂ | X | Y | Z | m.p. (°C.) |
|---|---|----|----|----|----|----|----|
| O | H | H | CH₃ | CH₃ | (1,3-dioxolan-2-yl) | CH | |
| O | H | H | CH₃ | CH₃ | (1,3-dioxan-2-yl) | CH | |
| O | H | H | CH₃ | CH₃ | (4-methyl-1,3-dioxolan-2-yl) | CH | |
| O | H | H | CH₃ | CH₃ | H | CH | |
| O | H | H | CH₃ | CH₃ | CN | CH | |
| O | H | H | CH₃ | CH₃ | CH(OCH₂CH₃)₂ | CH | |
| O | H | H | CH₃ | CH₃ | OCH₂F | CH | |
| O | H | H | CH₃ | CH₃ | OCF₃ | CH | |
| O | H | H | CH₃ | CH₃ | SCH₂F | CH | |
| O | H | H | CH₃ | CH₃ | SCF₃ | CH | |
| O | H | H | CH₃ | CH₃ | OCF₂H | CH | |
| O | H | H | CH₃ | CH₃ | OCF₂CHClF | CH | |
| O | H | H | CH₃ | CH₃ | OCF₂CHBrF | CH | |
| O | H | H | CH₃ | CH₃ | OCF₂CHFCF₃ | CH | |
| O | H | H | CH₃ | CH₃ | SCF₂H | CH | |
| O | H | H | CH₃ | CH₃ | SCF₂CHClF | CH | |
| O | H | H | CH₃ | CH₃ | SCF₂CHBrF | CH | |
| O | H | H | CH₃ | CH₃ | SCF₂CHFCF₃ | CH | |
| O | H | H | CH₃ | CH₃ | OCH₃ | CCH₃ | |
| O | H | H | CH₃ | CH₃ | OCH₃ | CCH₂CH₃ | |
| O | H | H | CH₃ | CH₃ | OCH₃ | CCl | |
| O | H | H | CH₃ | CH₃ | OCH₃ | CBr | |
| O | H | H | CH₃ | F | OCH₃ | CH | |
| O | H | H | CH₃ | Br | OCH₃ | CH | |
| O | H | H | CH₃ | CH₂F | OCH₃ | CH | |
| O | H | H | CH₃ | OCF₂H | OCH₃ | CH | |
| O | H | H | CH₃ | OCF₃ | OCH₃ | CH | |
| O | H | H | CH₃ | CF₃ | OCH₃ | CH | |
| O | H | m-F | CH₃ | CH₃ | OCH₃ | CH | |
| O | H | o-Cl | CH₃ | CH₃ | OCH₃ | CH | |
| O | H | m-Br | CH₃ | CH₃ | OCH₃ | CH | |
| O | H | o-CH₃ | CH₃ | CH₃ | OCH₃ | CH | |
| O | H | m-CF₃ | CH₃ | CH₃ | OCH₃ | CH | |
| O | H | o-SCH₃ | CH₃ | CH₃ | OCH₃ | CH | |
| O | H | m-OCH₃ | CH₃ | CH₃ | OCH₃ | CH | |
| O | H | o-OCF₂H | CH₃ | CH₃ | OCH₃ | CH | |
| O | CH₃ | H | H | CH₃ | OCH₃ | CH | |
| O | H | H | H | CH₃ | CH₃ | CH | |
| O | H | H | H | CH₃ | OCH₃ | CH | |
| O | H | H | H | OCH₃ | OCH₃ | CH | |
| O | H | H | H | Cl | OCH₃ | CH | |
| O | H | H | H | CH₃ | OCH₃ | N | |
| O | H | H | H | OCH₃ | OCH₃ | N | |
| O | H | H | CH₃ | CH₃ | CH₃ | CH | |
| O | H | H | CH₃ | CH₃ | OCH₃ | CH | |
| O | H | H | CH₃ | OCH₃ | OCH₃ | CH | 205–210 |
| O | H | H | CH₃ | Cl | OCH₃ | CH | |
| O | H | H | CH₃ | CH₃ | OCH₃ | N | |
| O | H | H | CH₃ | OCH₃ | OCH₃ | N | |
| O | H | H | CH₂CH₃ | CH₃ | CH₃ | CH | |

TABLE 13a-continued

| W | R | R₁ | R₂ | X | Y | Z | m.p. (°C.) |
|---|---|----|----|---|---|---|------------|
| O | H | H | CH₂CH₃ | CH₃ | OCH₃ | CH | |
| O | H | H | CH₂CH₃ | OCH₃ | OCH₃ | CH | |
| O | H | H | CH₂CH₃ | Cl | OCH₃ | CH | |
| O | H | H | CH₂CH₃ | CH₃ | OCH₃ | N | |
| O | H | H | CH₂CH₃ | OCH₃ | OCH₃ | N | |
| O | H | H | CH₂CH₂CH₃ | OCH₃ | OCH₃ | CH | |
| O | H | H | CH₂CH₂CH₂CH₃ | OCH₃ | OCH₃ | CH | |

TABLE 14a

| W | R | R₁ | X | Y | Z | m.p. (°C.) |
|---|---|----|---|---|---|------------|
| S | H | H | OCH₃ | OCH₃ | CH | |
| O | H | H | CH₃ | OCH₂CH₃ | CH | |
| O | H | H | CH₃ | CH₂OCH₃ | CH | |
| O | H | H | CH₃ | NH₂ | CH | |
| O | H | H | CH₃ | NHCH₃ | CH | |
| O | H | H | CH₃ | N(CH₃)₂ | CH | |
| O | H | H | CH₃ | CH₂CH₃ | CH | |
| O | H | H | CH₃ | CF₃ | CH | |
| O | H | H | CH₃ | SCH₃ | CH | |
| O | H | H | CH₃ | OCH₂CH=CH₂ | CH | |
| O | H | H | CH₃ | OCH₂C≡CH | CH | |
| O | H | H | CH₃ | OCH₂CF₃ | CH | |
| O | H | H | CH₃ | OCH₂CH₂OCH₃ | CH | |
| O | H | H | CH₃ | CH(OCH₃)₂ | CH | |
| O | H | H | CH₃ | (1,3-dioxolan-2-yl) | CH | |
| O | H | H | CH₃ | (1,3-dioxan-2-yl) | CH | |
| O | H | H | CH₃ | (4-methyl-1,3-dioxan-2-yl) | CH | |
| O | H | H | CH₃ | H | CH | |
| O | H | H | CH₃ | CN | CH | |
| O | H | H | CH₃ | CH(OCH₂CH₃)₂ | CH | |
| O | H | H | CH₃ | OCH₂F | CH | |
| O | H | H | CH₃ | OCF₃ | CH | |
| O | H | H | CH₃ | SCH₂F | CH | |
| O | H | H | CH₃ | SCF₃ | CH | |
| O | H | H | CH₃ | OCF₂H | CH | |
| O | H | H | CH₃ | OCF₂CHClF | CH | |
| O | H | H | CH₃ | OCF₂CHBrF | CH | |
| O | H | H | CH₃ | OCF₂CHFCF₃ | CH | |
| O | H | H | CH₃ | SCF₂H | CH | |
| O | H | H | CH₃ | SCF₂CHClF | CH | |
| O | H | H | CH₃ | SCF₂CHBrF | CH | |
| O | H | H | CH₃ | SCF₂CHFCF₃ | CH | |
| O | H | H | CH₃ | OCH₃ | CCH₃ | |
| O | H | H | CH₃ | OCH₃ | CCH₂CH₃ | |
| O | H | H | CH₃ | OCH₃ | CCl | |
| O | H | H | CH₃ | OCH₃ | CBr | |
| O | H | H | F | OCH₃ | CH | |
| O | H | H | Br | OCH₃ | CH | |
| O | H | H | CH₂F | OCH₃ | CH | |
| O | H | H | OCF₂H | OCH₃ | CH | |
| O | H | H | OCF₃ | OCH₃ | CH | |
| O | H | H | CF₃ | OCH₃ | CH | |
| O | H | m-F | CH₃ | OCH₃ | CH | |
| O | H | o-Cl | CH₃ | OCH₃ | CH | |
| O | H | m-Br | CH₃ | OCH₃ | CH | |
| O | H | o-CH₃ | CH₃ | OCH₃ | CH | |
| O | H | m-CF₃ | CH₃ | OCH₃ | CH | |
| O | H | o-SCH₃ | CH₃ | OCH₃ | CH | |
| O | H | m-OCH₃ | CH₃ | OCH₃ | CH | |
| O | H | o-OCF₂H | CH₃ | OCH₃ | CH | |
| O | CH₃ | H | CH₃ | OCH₃ | CH | |
| O | H | H | CH₃ | CH₃ | CH | |
| O | H | H | CH₃ | OCH₃ | CH | |
| O | H | H | OCH₃ | OCH₃ | CH | |
| O | H | H | Cl | OCH₃ | CH | |
| O | H | H | CH₃ | OCH₃ | N | |
| O | H | H | OCH₃ | OCH₃ | N | |

TABLE 15a

| W | R | R₁ | R₂ | X | Y | Z | m.p. (°C.) |
|---|---|---|---|---|---|---|---|
| S | H | H | CH₃ | OCH₃ | OCH₃ | CH | |
| O | H | H | CH₃ | CH₃ | OCH₂CH₃ | CH | |
| O | H | H | CH₃ | CH₃ | CH₂OCH₃ | CH | |
| O | H | H | CH₃ | CH₃ | NH₂ | CH | |
| O | H | H | CH₃ | CH₃ | NHCH₃ | CH | |
| O | H | H | CH₃ | CH₃ | N(CH₃)₂ | CH | |
| O | H | H | CH₃ | CH₃ | CH₂CH₃ | CH | |
| O | H | H | CH₃ | CH₃ | CF₃ | CH | |
| O | H | H | CH₃ | CH₃ | SCH₃ | CH | |
| O | H | H | CH₃ | CH₃ | OCH₂CH=CH₂ | CH | |
| O | H | H | CH₃ | CH₃ | OCH₂C≡CH | CH | |
| O | H | H | CH₃ | CH₃ | OCH₂CF₃ | CH | |
| O | H | H | CH₃ | CH₃ | OCH₂CH₂OCH₃ | CH | |
| O | H | H | CH₃ | CH₃ | CH(OCH₃)₂ | CH | |
| O | H | H | CH₃ | CH₃ | (1,3-dioxolan-2-yl) | CH | |
| O | H | H | CH₃ | CH₃ | (1,3-dioxan-2-yl) | CH | |
| O | H | H | CH₃ | CH₃ | (4-methyl-1,3-dioxolan-2-yl) | CH | |
| O | H | H | CH₃ | CH₃ | H | CH | |
| O | H | H | CH₃ | CH₃ | CN | CH | |
| O | H | H | CH₃ | CH₃ | CH(OCH₂CH₃)₂ | CH | |
| O | H | H | CH₃ | CH₃ | OCH₂F | CH | |
| O | H | H | CH₃ | CH₃ | OCF₃ | CH | |
| O | H | H | CH₃ | CH₃ | SCH₂F | CH | |
| O | H | H | CH₃ | CH₃ | SCF₃ | CH | |
| O | H | H | CH₃ | CH₃ | OCF₂H | CH | |
| O | H | H | CH₃ | CH₃ | OCF₂CHClF | CH | |
| O | H | H | CH₃ | CH₃ | OCF₂CHBrF | CH | |
| O | H | H | CH₃ | CH₃ | OCF₂CHFCF₃ | CH | |
| O | H | H | CH₃ | CH₃ | SCF₂H | CH | |
| O | H | H | CH₃ | CH₃ | SCF₂CHClF | CH | |
| O | H | H | CH₃ | CH₃ | SCF₂CHBrF | CH | |
| O | H | H | CH₃ | CH₃ | SCF₂CHFCF₃ | CH | |
| O | H | H | CH₃ | CH₃ | OCH₃ | CCH₃ | |
| O | H | H | CH₃ | CH₃ | OCH₃ | CCH₂CH₃ | |
| O | H | H | CH₃ | CH₃ | OCH₃ | CCl | |
| O | H | H | CH₃ | CH₃ | OCH₃ | CBr | |
| O | H | H | CH₃ | F | OCH₃ | CH | |
| O | H | H | CH₃ | Br | OCH₃ | CH | |
| O | H | H | CH₃ | CH₂F | OCH₃ | CH | |
| O | H | H | CH₃ | OCF₂H | OCH₃ | CH | |
| O | H | H | CH₃ | OCF₃ | OCH₃ | CH | |
| O | H | H | CH₃ | CF₃ | OCH₃ | CH | |
| O | H | m-F | CH₃ | CH₃ | OCH₃ | CH | |
| O | H | o-Cl | CH₃ | CH₃ | OCH₃ | CH | |
| O | H | m-Br | CH₃ | CH₃ | OCH₃ | CH | |
| O | H | o-CH₃ | CH₃ | CH₃ | OCH₃ | CH | |
| O | H | m-CF₃ | CH₃ | CH₃ | OCH₃ | CH | |
| O | H | o-SCH₃ | CH₃ | CH₃ | OCH₃ | CH | |
| O | H | m-OCH₃ | CH₃ | CH₃ | OCH₃ | CH | |

TABLE 15a-continued

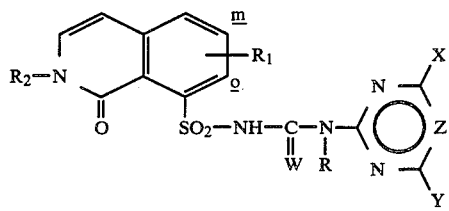

| W | R | R1 | R2 | X | Y | Z | m.p. (°C.) |
|---|---|----|----|---|---|---|-----------|
| O | H | o-OCF2H | CH3 | CH3 | OCH3 | CH | |
| O | CH3 | H | H | CH3 | OCH3 | CH | |
| O | H | H | H | CH3 | CH3 | CH | |
| O | H | H | H | CH3 | OCH3 | CH | |
| O | H | H | H | OCH3 | OCH3 | CH | |
| O | H | H | H | Cl | OCH3 | CH | |
| O | H | H | H | CH3 | OCH3 | N | |
| O | H | H | H | OCH3 | OCH3 | N | |
| O | H | H | CH3 | CH3 | CH3 | CH | |
| O | H | H | CH3 | CH3 | OCH3 | CH | |
| O | H | H | CH3 | OCH3 | OCH3 | CH | |
| O | H | H | CH3 | Cl | OCH3 | CH | |
| O | H | H | CH3 | CH3 | OCH3 | N | |
| O | H | H | CH3 | OCH3 | OCH3 | N | |
| O | H | H | CH2CH3 | CH3 | CH3 | CH | |
| O | H | H | CH2CH3 | CH3 | OCH3 | CH | |
| O | H | H | CH2CH3 | OCH3 | OCH3 | CH | |
| O | H | H | CH2CH3 | Cl | OCH3 | CH | |
| O | H | H | CH2CH3 | CH3 | OCH3 | N | |
| O | H | H | CH2CH3 | OCH3 | OCH3 | N | |
| O | H | H | CH2CH2CH3 | OCH3 | OCH3 | CH | |
| O | H | H | CH2CH2CH2CH3 | OCH3 | OCH3 | CH | |

TABLE 16a

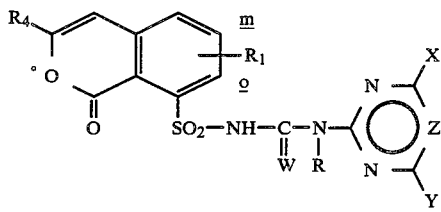

| W | R | R1 | R4 | X | Y | Z | m.p. (°C.) |
|---|---|----|----|---|---|---|-----------|
| S | H | H | H | OCH3 | OCH3 | CH | |
| O | H | H | H | CH3 | OCH2CH3 | CH | |
| O | H | H | H | CH3 | CH2OCH3 | CH | |
| O | H | H | H | CH3 | NH2 | CH | |
| O | H | H | H | CH3 | NHCH3 | CH | |
| O | H | H | H | CH3 | N(CH3)2 | CH | |
| O | H | H | H | CH3 | CH2CH3 | CH | |
| O | H | H | H | CH3 | CF3 | CH | |
| O | H | H | H | CH3 | SCH3 | CH | |
| O | H | H | H | CH3 | OCH2CH=CH2 | CH | |
| O | H | H | H | CH3 | OCH2C≡CH | CH | |
| O | H | H | H | CH3 | OCH2CF3 | CH | |
| O | H | H | H | CH3 | OCH2CH2OCH3 | CH | |
| O | H | H | H | CH3 | CH(OCH3)2 | CH | |
| O | H | H | H | CH3 | (1,3-dioxolan-2-yl) | CH | |
| O | H | H | H | CH3 | (1,3-dioxan-2-yl) | CH | |

TABLE 16a-continued

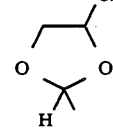

| W | R | R₁ | R₄ | X | Y | Z | m.p. (°C.) |
|---|---|----|----|---|---|---|---|
| O | H | H | H | CH₃ | (CH₃-substituted 1,3-dioxolane) | CH | |
| O | H | H | H | CH₃ | H | CH | |
| O | H | H | H | CH₃ | CN | CH | |
| O | H | H | H | CH₃ | CH(OCH₂CH₃)₂ | CH | |
| O | H | H | H | CH₃ | OCH₂F | CH | |
| O | H | H | H | CH₃ | OCF₃ | CH | |
| O | H | H | H | CH₃ | SCH₂F | CH | |
| O | H | H | H | CH₃ | SCF₃ | CH | |
| O | H | H | H | CH₃ | OCF₂H | CH | |
| O | H | H | H | CH₃ | OCF₂CHClF | CH | |
| O | H | H | H | CH₃ | OCF₂CHBrF | CH | |
| O | H | H | H | CH₃ | OCF₂CHFCF₃ | CH | |
| O | H | H | H | CH₃ | SCF₂H | CH | |
| O | H | H | H | CH₃ | SCF₂CHClF | CH | |
| O | H | H | H | CH₃ | SCF₂CHBrF | CH | |
| O | H | H | H | CH₃ | SCF₂CHFCF₃ | CH | |
| O | H | H | H | CH₃ | OCH₃ | CCH₃ | |
| O | H | H | H | CH₃ | OCH₃ | CCH₂CH₃ | |
| O | H | H | H | CH₃ | OCH₃ | CCl | |
| O | H | H | H | CH₃ | OCH₃ | CBr | |
| O | H | H | H | F | OCH₃ | CH | |
| O | H | H | H | Br | OCH₃ | CH | |
| O | H | H | H | CH₂F | OCH₃ | CH | |
| O | H | H | H | OCF₂H | OCH₃ | CH | |
| O | H | H | H | OCF₃ | OCH₃ | CH | |
| O | H | H | H | CF₃ | OCH₃ | CH | |
| O | H | m-F | H | CH₃ | OCH₃ | CH | |
| O | H | o-Cl | H | CH₃ | OCH₃ | CH | |
| O | H | m-Br | H | CH₃ | OCH₃ | CH | |
| O | H | o-CH₃ | H | CH₃ | OCH₃ | CH | |
| O | H | m-CF₃ | H | CH₃ | OCH₃ | CH | |
| O | H | o-SCH₃ | H | CH₃ | OCH₃ | CH | |
| O | H | m-OCH₃ | H | CH₃ | OCH₃ | CH | |
| O | H | o-OCF₂H | H | CH₃ | OCH₃ | CH | |
| O | CH₃ | H | H | CH₃ | OCH₃ | CH | |
| O | H | H | H | CH₃ | CH₃ | CH | |
| O | H | H | H | CH₃ | OCH₃ | CH | |
| O | H | H | H | OCH₃ | OCH₃ | CH | 226–236° |
| O | H | H | H | Cl | OCH₃ | CH | |
| O | H | H | H | CH₃ | OCH₃ | N | |
| O | H | H | H | OCH₃ | OCH₃ | N | |
| O | H | H | CH₃ | OCH₃ | OCH₃ | CH | |
| O | H | H | CH₂CH₃ | OCH₃ | OCH₃ | CH | |
| O | H | H | CH₂CH₂CH₃ | OCH₃ | OCH₃ | CH | |
| O | H | H | CH₂CH₂CH₂CH₃ | OCH₃ | OCH₃ | CH | |

TABLE 17a

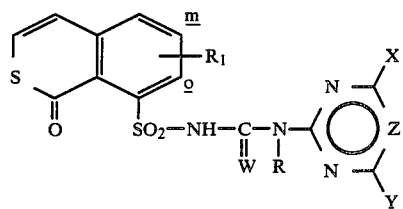

| W | R | R₁ | X | Y | Z | m.p. (°C.) |
|---|---|---|---|---|---|---|
| S | H | H | OCH₃ | OCH₃ | CH | |
| O | H | H | CH₃ | OCH₂CH₃ | CH | |
| O | H | H | CH₃ | CH₂OCH₃ | CH | |
| O | H | H | CH₃ | NH₂ | CH | |
| O | H | H | CH₃ | NHCH₃ | CH | |
| O | H | H | CH₃ | N(CH₃)₂ | CH | |
| O | H | H | CH₃ | CH₂CH₃ | CH | |
| O | H | H | CH₃ | CF₃ | CH | |
| O | H | H | CH₃ | SCH₃ | CH | |
| O | H | H | CH₃ | OCH₂CH=CH₂ | CH | |
| O | H | H | CH₃ | OCH₂C≡CH | CH | |
| O | H | H | CH₃ | OCH₂CF₃ | CH | |
| O | H | H | CH₃ | OCH₂CH₂OCH₃ | CH | |
| O | H | H | CH₃ | CH(OCH₃)₂ | CH | |
| O | H | H | CH₃ | (1,3-dioxolan-2-yl) | CH | |
| O | H | H | CH₃ | (1,3-dioxan-2-yl) | CH | |
| O | H | H | CH₃ | (4-methyl-1,3-dioxolan-2-yl) | CH | |
| O | H | H | CH₃ | H | CH | |
| O | H | H | CH₃ | CN | CH | |
| O | H | H | CH₃ | CH(OCH₂CH₃)₂ | CH | |
| O | H | H | CH₃ | OCH₂F | CH | |
| O | H | H | CH₃ | OCF₃ | CH | |
| O | H | H | CH₃ | SCH₂F | CH | |
| O | H | H | CH₃ | SCF₃ | CH | |
| O | H | H | CH₃ | OCF₂H | CH | |
| O | H | H | CH₃ | OCF₂CHClF | CH | |
| O | H | H | CH₃ | OCF₂CHBrF | CH | |
| O | H | H | CH₃ | OCF₂CHFCF₃ | CH | |
| O | H | H | CH₃ | SCF₂H | CH | |
| O | H | H | CH₃ | SCF₂CHClF | CH | |
| O | H | H | CH₃ | SCF₂CHBrF | CH | |
| O | H | H | CH₃ | SCF₂CHFCF₃ | CH | |
| O | H | H | CH₃ | OCH₃ | CCH₃ | |
| O | H | H | CH₃ | OCH₃ | CCH₂CH₃ | |
| O | H | H | CH₃ | OCH₃ | CCl | |
| O | H | H | CH₃ | OCH₃ | CBr | |
| O | H | H | F | OCH₃ | CH | |
| O | H | H | Br | OCH₃ | CH | |
| O | H | H | CH₂F | OCH₃ | CH | |
| O | H | H | OCF₂H | OCH₃ | CH | |
| O | H | H | OCF₃ | OCH₃ | CH | |
| O | H | H | CF₃ | OCH₃ | CH | |
| O | H | m-F | CH₃ | OCH₃ | CH | |
| O | H | o-Cl | CH₃ | OCH₃ | CH | |
| O | H | m-Br | CH₃ | OCH₃ | CH | |
| O | H | o-CH₃ | CH₃ | OCH₃ | CH | |
| O | H | m-CF₃ | CH₃ | OCH₃ | CH | |
| O | H | o-SCH₃ | CH₃ | OCH₃ | CH | |
| O | H | m-OCH₃ | CH₃ | OCH₃ | CH | |
| O | H | o-OCF₂H | CH₃ | OCH₃ | CH | |
| O | CH₃ | H | CH₃ | OCH₃ | CH | |
| O | H | H | CH₃ | CH₃ | CH | |
| O | H | H | CH₃ | OCH₃ | CH | |
| O | H | H | OCH₃ | OCH₃ | CH | |
| O | H | H | Cl | OCH₃ | CH | |
| O | H | H | CH₃ | OCH₃ | N | |
| O | H | H | OCH₃ | OCH₃ | N | |

TABLE 18a

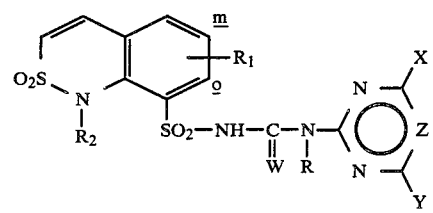

| W | R | R₁ | R₂ | X | Y | Z | m.p. (°C.) |
|---|---|---|---|---|---|---|---|
| S | H | H | CH₃ | OCH₃ | OCH₃ | CH | |
| O | H | H | CH₃ | CH₃ | OCH₂CH₃ | CH | |
| O | H | H | CH₃ | CH₃ | CH₂OCH₃ | CH | |
| O | H | H | CH₃ | CH₃ | NH₂ | CH | |
| O | H | H | CH₃ | CH₃ | NHCH₃ | CH | |
| O | H | H | CH₃ | CH₃ | N(CH₃)₂ | CH | |
| O | H | H | CH₃ | CH₃ | CH₂CH₃ | CH | |
| O | H | H | CH₃ | CH₃ | CF₃ | CH | |
| O | H | H | CH₃ | CH₃ | SCH₃ | CH | |
| O | H | H | CH₃ | CH₃ | OCH₂CH=CH₂ | CH | |
| O | H | H | CH₃ | CH₃ | OCH₂C≡CH | CH | |
| O | H | H | CH₃ | CH₃ | OCH₂CF₃ | CH | |
| O | H | H | CH₃ | CH₃ | OCH₂CH₂OCH₃ | CH | |
| O | H | H | CH₃ | CH₃ | CH(OCH₃)₂ | CH | |

TABLE 18a-continued

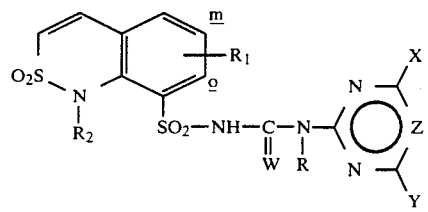

| W | R | R₁ | R₂ | X | Y | Z | m.p. (°C.) |
|---|---|---|---|---|---|---|---|
| O | H | H | CH₃ | CH₃ | (1,3-dioxolan-2-yl) | CH | |
| O | H | H | CH₃ | CH₃ | (1,3-dioxan-2-yl) | CH | |
| O | H | H | CH₃ | CH₃ | (5-methyl-1,3-dioxan-2-yl) | CH | |
| O | H | H | CH₃ | CH₃ | H | CH | |
| O | H | H | CH₃ | CH₃ | CN | CH | |
| O | H | H | CH₃ | CH₃ | CH(OCH₂CH₃)₂ | CH | |
| O | H | H | CH₃ | CH₃ | OCH₂F | CH | |
| O | H | H | CH₃ | CH₃ | OCF₃ | CH | |
| O | H | H | CH₃ | CH₃ | SCH₂F | CH | |
| O | H | H | CH₃ | CH₃ | SCF₃ | CH | |
| O | H | H | CH₃ | CH₃ | OCF₂H | CH | |
| O | H | H | CH₃ | CH₃ | OCF₂CHClF | CH | |
| O | H | H | CH₃ | CH₃ | OCF₂CHBrF | CH | |
| O | H | H | CH₃ | CH₃ | OCF₂CHFCF₃ | CH | |
| O | H | H | CH₃ | CH₃ | SCF₂H | CH | |
| O | H | H | CH₃ | CH₃ | SCF₂CHClF | CH | |
| O | H | H | CH₃ | CH₃ | SCF₂CHBrF | CH | |
| O | H | H | CH₃ | CH₃ | SCF₂CHFCF₃ | CH | |
| O | H | H | CH₃ | CH₃ | OCH₃ | CCH₃ | |
| O | H | H | CH₃ | CH₃ | OCH₃ | CCH₂CH₃ | |
| O | H | H | CH₃ | CH₃ | OCH₃ | CCl | |
| O | H | H | CH₃ | CH₃ | OCH₃ | CBr | |
| O | H | H | CH₃ | F | OCH₃ | CH | |
| O | H | H | CH₃ | Br | OCH₃ | CH | |
| O | H | H | CH₃ | CH₂F | OCH₃ | CH | |
| O | H | H | CH₃ | OCF₂H | OCH₃ | CH | |
| O | H | H | CH₃ | OCF₃ | OCH₃ | CH | |
| O | H | H | CH₃ | CF₃ | OCH₃ | CH | |
| O | H | m-F | CH₃ | CH₃ | OCH₃ | CH | |
| O | H | o-Cl | CH₃ | CH₃ | OCH₃ | CH | |
| O | H | m-Br | CH₃ | CH₃ | OCH₃ | CH | |
| O | H | o-CH₃ | CH₃ | CH₃ | OCH₃ | CH | |
| O | H | m-CF₃ | CH₃ | CH₃ | OCH₃ | CH | |
| O | H | o-SCH₃ | CH₃ | CH₃ | OCH₃ | CH | |
| O | H | m-OCH₃ | CH₃ | CH₃ | OCH₃ | CH | |
| O | H | o-OCF₂H | CH₃ | CH₃ | OCH₃ | CH | |
| O | CH₃ | H | H | CH₃ | OCH₃ | CH | |
| O | H | H | H | CH₃ | CH₃ | CH | |
| O | H | H | H | CH₃ | OCH₃ | CH | |
| O | H | H | H | OCH₃ | OCH₃ | CH | |
| O | H | H | H | Cl | OCH₃ | CH | |
| O | H | H | H | CH₃ | OCH₃ | N | |
| O | H | H | H | OCH₃ | OCH₃ | N | |
| O | H | H | CH₃ | CH₃ | CH₃ | CH | |
| O | H | H | CH₃ | CH₃ | OCH₃ | CH | |
| O | H | H | CH₃ | OCH₃ | OCH₃ | CH | |
| O | H | H | CH₃ | Cl | OCH₃ | CH | |
| O | H | H | CH₃ | CH₃ | OCH₃ | N | |
| O | H | H | CH₃ | OCH₃ | OCH₃ | N | |

TABLE 18a-continued

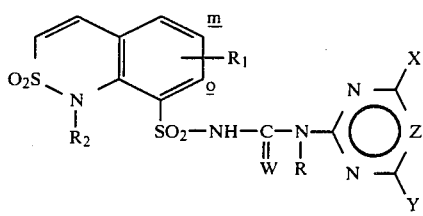

| W | R | R₁ | R₂ | X | Y | Z | m.p. (°C.) |
|---|---|----|----|---|---|---|-----------|
| O | H | H | CH₂CH₃ | CH₃ | CH₃ | CH | |
| O | H | H | CH₂CH₃ | CH₃ | OCH₃ | CH | |
| O | H | H | CH₂CH₃ | OCH₃ | OCH₃ | CH | |
| O | H | H | CH₂CH₃ | Cl | OCH₃ | CH | |
| O | H | H | CH₂CH₃ | CH₃ | OCH₃ | N | |
| O | H | H | CH₂CH₃ | OCH₃ | OCH₃ | N | |
| O | H | H | CH₂CH₂CH₃ | OCH₃ | OCH₃ | CH | |
| O | H | H | CH₂CH₂CH₂CH₃ | OCH₃ | OCH₃ | CH | |

TABLE 19a

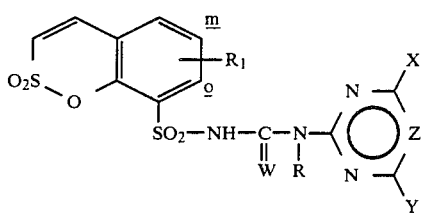

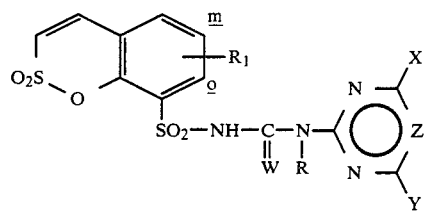

| W | R | R₁ | X | Y | Z | m.p. (°C.) |
|---|---|----|---|---|---|-----------|
| S | H | H | OCH₃ | OCH₃ | CH | |
| O | H | H | CH₃ | OCH₂CH₃ | CH | |
| O | H | H | CH₃ | CH₂OCH₃ | CH | |
| O | H | H | CH₃ | NH₂ | CH | |
| O | H | H | CH₃ | NHCH₃ | CH | |
| O | H | H | CH₃ | N(CH₃)₂ | CH | |
| O | H | H | CH₃ | CH₂CH₃ | CH | |
| O | H | H | CH₃ | CF₃ | CH | |
| O | H | H | CH₃ | SCH₃ | CH | |
| O | H | H | CH₃ | OCH₂CH=CH₂ | CH | |
| O | H | H | CH₃ | OCH₂C≡CH | CH | |
| O | H | H | CH₃ | OCH₂CF₃ | CH | |
| O | H | H | CH₃ | OCH₂CH₂OCH₃ | CH | |
| O | H | H | CH₃ | CH(OCH₃)₂ | CH | |
| O | H | H | CH₃ | (1,3-dioxolan-2-yl) | CH | |
| O | H | H | CH₃ | (1,3-dioxan-2-yl) | CH | |
| O | H | H | CH₃ | (4-methyl-1,3-dioxan-2-yl) | CH | |
| O | H | H | CH₃ | H | CH | |
| O | H | H | CH₃ | CN | CH | |
| O | H | H | CH₃ | CH(OCH₂CH₃)₂ | CH | |
| O | H | H | CH₃ | OCH₂F | CH | |
| O | H | H | CH₃ | OCF₃ | CH | |
| O | H | H | CH₃ | SCH₂F | CH | |
| O | H | H | CH₃ | SCF₃ | CH | |
| O | H | H | CH₃ | OCF₂H | CH | |
| O | H | H | CH₃ | OCF₂CHClF | CH | |
| O | H | H | CH₃ | OCF₂CHBrF | CH | |
| O | H | H | CH₃ | OCF₂CHFCF₃ | CH | |
| O | H | H | CH₃ | SCF₂H | CH | |
| O | H | H | CH₃ | SCF₂CHClF | CH | |
| O | H | H | CH₃ | SCF₂CHBrF | CH | |
| O | H | H | CH₃ | SCF₂CHFCF₃ | CH | |
| O | H | H | CH₃ | OCH₃ | CCH₃ | |
| O | H | H | CH₃ | OCH₃ | CCH₂CH₃ | |
| O | H | H | CH₃ | OCH₃ | CCl | |
| O | H | H | CH₃ | OCH₃ | CBr | |
| O | H | H | F | OCH₃ | CH | |
| O | H | H | Br | OCH₃ | CH | |
| O | H | H | CH₂F | OCH₃ | CH | |
| O | H | H | OCF₂H | OCH₃ | CH | |
| O | H | H | OCF₃ | OCH₃ | CH | |
| O | H | H | CF₃ | OCH₃ | CH | |
| O | H | m-F | CH₃ | OCH₃ | CH | |
| O | H | o-Cl | CH₃ | OCH₃ | CH | |
| O | H | m-Br | CH₃ | OCH₃ | CH | |
| O | H | o-CH₃ | CH₃ | OCH₃ | CH | |
| O | H | m-CF₃ | CH₃ | OCH₃ | CH | |
| O | H | o-SCH₃ | CH₃ | OCH₃ | CH | |
| O | H | m-OCH₃ | CH₃ | OCH₃ | CH | |
| O | H | o-OCF₂H | CH₃ | OCH₃ | CH | |
| O | CH₃ | H | CH₃ | OCH₃ | CH | |
| O | H | H | CH₃ | CH₃ | CH | |
| O | H | H | CH₃ | OCH₃ | CH | |
| O | H | H | OCH₃ | OCH₃ | CH | |
| O | H | H | Cl | OCH₃ | CH | |
| O | H | H | CH₃ | OCH₃ | N | |
| O | H | H | OCH₃ | OCH₃ | N | |

TABLE 20a

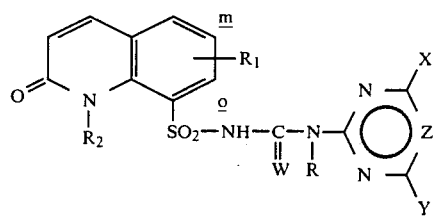

| W | R | R₁ | R₂ | X | Y | Z | m.p. (°C.) |
|---|---|---|---|---|---|---|---|
| S | H | H | CH₃ | OCH₃ | OCH₃ | CH | |
| O | H | H | CH₃ | CH₃ | OCH₂CH₃ | CH | |
| O | H | H | CH₃ | CH₃ | CH₂OCH₃ | CH | |
| O | H | H | CH₃ | CH₃ | NH₂ | CH | |
| O | H | H | CH₃ | CH₃ | NHCH₃ | CH | |
| O | H | H | CH₃ | CH₃ | N(CH₃)₂ | CH | |
| O | H | H | CH₃ | CH₃ | CH₂CH₃ | CH | |
| O | H | H | CH₃ | CH₃ | CF₃ | CH | |
| O | H | H | CH₃ | CH₃ | SCH₃ | CH | |
| O | H | H | CH₃ | CH₃ | OCH₂CH=CH₂ | CH | |
| O | H | H | CH₃ | CH₃ | OCH₂C≡CH | CH | |
| O | H | H | CH₃ | CH₃ | OCH₂CF₃ | CH | |
| O | H | H | CH₃ | CH₃ | OCH₂CH₂OCH₃ | CH | |
| O | H | H | CH₃ | CH₃ | CH(OCH₃)₂ | CH | |
| O | H | H | CH₃ | CH₃ | (1,3-dioxolan-2-yl) | CH | |
| O | H | H | CH₃ | CH₃ | (1,3-dioxan-2-yl) | CH | |
| O | H | H | CH₃ | CH₃ | (4-methyl-1,3-dioxolan-2-yl) | CH | |
| O | H | H | CH₃ | CH₃ | H | CH | |
| O | H | H | CH₃ | CH₃ | CN | CH | |
| O | H | H | CH₃ | CH₃ | CH(OCH₂CH₃)₂ | CH | |
| O | H | H | CH₃ | CH₃ | OCH₂F | CH | |
| O | H | H | CH₃ | CH₃ | OCF₃ | CH | |
| O | H | H | CH₃ | CH₃ | SCH₂F | CH | |
| O | H | H | CH₃ | CH₃ | SCF₃ | CH | |
| O | H | H | CH₃ | CH₃ | OCF₂H | CH | |
| O | H | H | CH₃ | CH₃ | OCF₂CHClF | CH | |
| O | H | H | CH₃ | CH₃ | OCF₂CHBrF | CH | |
| O | H | H | CH₃ | CH₃ | OCF₂CHFCF₃ | CH | |
| O | H | H | CH₃ | CH₃ | SCF₂H | CH | |
| O | H | H | CH₃ | CH₃ | SCF₂CHClF | CH | |
| O | H | H | CH₃ | CH₃ | SCF₂CHBrF | CH | |
| O | H | H | CH₃ | CH₃ | SCF₂CHFCF₃ | CH | |
| O | H | H | CH₃ | CH₃ | OCH₃ | CCH₃ | |
| O | H | H | CH₃ | CH₃ | OCH₃ | CCH₂CH₃ | |
| O | H | H | CH₃ | CH₃ | OCH₃ | CCl | |
| O | H | H | CH₃ | CH₃ | OCH₃ | CBr | |
| O | H | H | CH₃ | F | OCH₃ | CH | |
| O | H | H | CH₃ | Br | OCH₃ | CH | |
| O | H | H | CH₃ | CH₂F | OCH₃ | CH | |
| O | H | H | CH₃ | OCF₂H | OCH₃ | CH | |
| O | H | H | CH₃ | OCF₃ | OCH₃ | CH | |
| O | H | H | CH₃ | CF₃ | OCH₃ | CH | |
| O | H | m-F | CH₃ | CH₃ | OCH₃ | CH | |
| O | H | o-Cl | CH₃ | CH₃ | OCH₃ | CH | |
| O | H | m-Br | CH₃ | CH₃ | OCH₃ | CH | |
| O | H | o-CH₃ | CH₃ | CH₃ | OCH₃ | CH | |
| O | H | m-CF₃ | CH₃ | CH₃ | OCH₃ | CH | |
| O | H | o-SCH₃ | CH₃ | CH₃ | OCH₃ | CH | |
| O | H | m-OCH₃ | CH₃ | CH₃ | OCH₃ | CH | |

TABLE 20a-continued

| W | R | R₁ | R₂ | X | Y | Z | m.p. (°C.) |
|---|---|---|---|---|---|---|---|
| O | H | o-OCF₂H | CH₃ | CH₃ | OCH₃ | CH | |
| O | CH₃ | H | H | CH₃ | OCH₃ | CH | |
| O | H | H | H | CH₃ | CH₃ | CH | |
| O | H | H | H | CH₃ | OCH₃ | CH | |
| O | H | H | H | OCH₃ | OCH₃ | CH | |
| O | H | H | H | Cl | OCH₃ | CH | |
| O | H | H | H | CH₃ | OCH₃ | N | |
| O | H | H | H | OCH₃ | OCH₃ | N | |
| O | H | H | CH₃ | CH₃ | CH₃ | CH | |
| O | H | H | CH₃ | CH₃ | OCH₃ | CH | |
| O | H | H | CH₃ | OCH₃ | OCH₃ | CH | |
| O | H | H | CH₃ | Cl | OCH₃ | CH | |
| O | H | H | CH₃ | CH₃ | OCH₃ | N | |
| O | H | H | CH₃ | OCH₃ | OCH₃ | N | |
| O | H | H | CH₂CH₃ | CH₃ | CH₃ | CH | |
| O | H | H | CH₂CH₃ | CH₃ | OCH₃ | CH | |
| O | H | H | CH₂CH₃ | OCH₃ | OCH₃ | CH | |
| O | H | H | CH₂CH₃ | Cl | OCH₃ | CH | |
| O | H | H | CH₂CH₃ | CH₃ | OCH₃ | N | |
| O | H | H | CH₂CH₃ | OCH₃ | OCH₃ | N | |
| O | H | H | CH₂CH₂CH₃ | OCH₃ | OCH₃ | CH | |
| O | H | H | CH₂CH₂CH₂CH₃ | OCH₃ | OCH₃ | CH | |

TABLE 21a

| W | R | R₁ | R₃ | X | Y | Z | m.p. (°C.) |
|---|---|---|---|---|---|---|---|
| S | H | H | H | OCH₃ | OCH₃ | CH | |
| O | H | H | H | CH₃ | OCH₂CH₃ | CH | |
| O | H | H | H | CH₃ | CH₂OCH₃ | CH | |
| O | H | H | H | CH₃ | NH₂ | CH | |
| O | H | H | H | CH₃ | NHCH₃ | CH | |
| O | H | H | H | CH₃ | N(CH₃)₂ | CH | |
| O | H | H | H | CH₃ | CH₂CH₃ | CH | |
| O | H | H | H | CH₃ | CF₃ | CH | |
| O | H | H | H | CH₃ | SCH₃ | CH | |
| O | H | H | H | CH₃ | OCH₂CH=CH₂ | CH | |
| O | H | H | H | CH₃ | OCH₂C≡CH | CH | |
| O | H | H | H | CH₃ | OCH₂CF₃ | CH | |
| O | H | H | H | CH₃ | OCH₂CH₂OCH₃ | CH | |
| O | H | H | H | CH₃ | CH(OCH₃)₂ | CH | |
| O | H | H | H | CH₃ | 1,3-dioxolan-2-yl | CH | |
| O | H | H | H | CH₃ | 1,3-dioxan-2-yl | CH | |

TABLE 21a-continued

| W | R | R₁ | R₃ | X | Y | Z | m.p. (°C.) |
|---|---|---|---|---|---|---|---|
| O | H | H | H | CH₃ | CH(CH₃)-O-CH(H)-O (cyclic acetal) | CH | |
| O | H | H | H | CH₃ | H | CH | |
| O | H | H | H | CH₃ | CN | CH | |
| O | H | H | H | CH₃ | CH(OCH₂CH₃)₂ | CH | |
| O | H | H | H | CH₃ | OCH₂F | CH | |
| O | H | H | H | CH₃ | OCF₃ | CH | |
| O | H | H | H | CH₃ | SCH₂F | CH | |
| O | H | H | H | CH₃ | SCF₃ | CH | |
| O | H | H | H | CH₃ | OCF₂H | CH | |
| O | H | H | H | CH₃ | OCF₂CHClF | CH | |
| O | H | H | H | CH₃ | OCF₂CHBrF | CH | |
| O | H | H | H | CH₃ | OCF₂CHFCF₃ | CH | |
| O | H | H | H | CH₃ | SCF₂H | CH | |
| O | H | H | H | CH₃ | SCF₂CHClF | CH | |
| O | H | H | H | CH₃ | SCF₂CHBrF | CH | |
| O | H | H | H | CH₃ | SCF₂CHFCF₃ | CH | |
| O | H | H | H | CH₃ | OCH₃ | CCH₃ | |
| O | H | H | H | CH₃ | OCH₃ | CCH₂CH₃ | |
| O | H | H | H | CH₃ | OCH₃ | CCl | |
| O | H | H | H | CH₃ | OCH₃ | CBr | |
| O | H | H | H | F | OCH₃ | CH | |
| O | H | H | H | Br | OCH₃ | CH | |
| O | H | H | H | CH₂F | OCH₃ | CH | |
| O | H | H | CH₃ | OCF₂H | OCH₃ | CH | 213–216 |
| O | H | H | H | OCF₃ | OCH₃ | CH | |
| O | H | H | H | CF₃ | OCH₃ | CH | |
| O | H | m-F | H | CH₃ | OCH₃ | CH | |
| O | H | o-Cl | H | CH₃ | OCH₃ | CH | |
| O | H | m-Br | H | CH₃ | OCH₃ | CH | |
| O | H | o-CH₃ | H | CH₃ | OCH₃ | CH | |
| O | H | m-CF₃ | H | CH₃ | OCH₃ | CH | |
| O | H | o-SCH₃ | H | CH₃ | OCH₃ | CH | |
| O | H | m-OCH₃ | H | CH₃ | OCH₃ | CH | |
| O | H | o-OCF₂H | H | CH₃ | OCH₃ | CH | |
| O | CH₃ | H | H | CH₃ | OCH₃ | CH | |
| O | H | H | H | CH₃ | CH₃ | CH | 221–223 |
| O | H | H | H | CH₃ | OCH₃ | CH | 234–236 |
| O | H | H | H | OCH₃ | OCH₃ | CH | |
| O | H | H | H | Cl | OCH₃ | CH | 243–246 |
| O | H | H | H | CH₃ | OCH₃ | N | 202–205 |
| O | H | H | H | OCH₃ | OCH₃ | N | 207–210 |
| O | H | H | CH₃ | CH₃ | CH₃ | CH | 227–229 |
| O | H | H | CH₃ | CH₃ | OCH₃ | CH | 221–223 |
| O | H | H | CH₃ | OCH₃ | OCH₃ | CH | 228–230 |
| O | H | H | CH₃ | Cl | OCH₃ | CH | 246–249 |
| O | H | H | CH₃ | CH₃ | OCH₃ | N | 201–203 |
| O | H | H | CH₃ | OCH₃ | OCH₃ | N | 187–200 |
| O | H | H | CH₂CH₃ | OCH₃ | OCH₃ | CH | 209–211 |
| O | H | H | CH₂CH₂CH₃ | OCH₃ | OCH₃ | CH | |
| O | H | H | CH₂CH₂CH₂CH₃ | OCH₃ | OCH₃ | CH | |
| O | H | H | H | CH₃ | CH₃ | N | 199–202 |
| O | H | H | H | OCF₂H | OCH₃ | CH | 216–218 |
| O | H | H | Cl | OCH₃ | OCH₃ | CH | |
| O | H | H | Br | OCH₃ | OCH₃ | CH | |

TABLE 22a

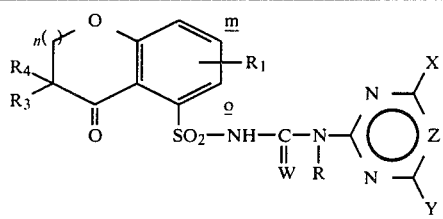

| W | n | R | $R_1$ | $R_3$ | $R_4$ | X | Y | Z | m.p. (°C.) |
|---|---|---|---|---|---|---|---|---|---|
| O | 0 | H | H | H | H | $CH_3$ | $CH_3$ | CH | |
| O | 0 | H | H | H | H | $CH_3$ | $OCH_3$ | CH | |
| O | 0 | H | H | H | H | $OCH_3$ | $OCH_3$ | CH | |
| O | 0 | H | H | H | H | Cl | $OCH_3$ | CH | |
| O | 0 | H | H | H | H | $CH_3$ | $OCH_3$ | N | |
| O | 0 | H | H | H | H | $OCH_3$ | $OCH_3$ | N | |
| O | 0 | H | H | $CH_3$ | H | $CH_3$ | $CH_3$ | CH | |
| O | 0 | H | H | $CH_3$ | H | $CH_3$ | $OCH_3$ | CH | |
| O | 0 | H | H | $CH_3$ | H | $OCH_3$ | $OCH_3$ | CH | |
| O | 0 | H | H | $CH_3$ | H | Cl | $OCH_3$ | CH | |
| O | 0 | H | H | $CH_3$ | H | $CH_3$ | $OCH_3$ | N | |
| O | 0 | H | H | $CH_3$ | H | $OCH_3$ | $OCH_3$ | N | |
| O | 0 | H | H | $CH_3$ | $CH_3$ | $CH_3$ | $CH_3$ | CH | |
| O | 0 | H | H | $CH_3$ | $CH_3$ | $CH_3$ | $OCH_3$ | CH | |
| O | 0 | H | H | $CH_3$ | $CH_3$ | $OCH_3$ | $OCH_3$ | CH | |
| O | 0 | H | H | $CH_3$ | $CH_3$ | Cl | $OCH_3$ | CH | |
| O | 0 | H | H | $CH_3$ | $CH_3$ | $CH_3$ | $OCH_3$ | N | |
| O | 0 | H | H | $CH_3$ | $CH_3$ | $OCH_3$ | $OCH_3$ | N | |
| O | 1 | H | H | H | H | $CH_3$ | $CH_3$ | CH | |
| O | 1 | H | H | H | H | $CH_3$ | $OCH_3$ | CH | |
| O | 1 | H | H | H | H | $OCH_3$ | $OCH_3$ | CH | |
| O | 1 | H | H | H | H | Cl | $CH_3$ | CH | |
| O | 1 | H | H | H | H | $CH_3$ | $OCH_3$ | N | |
| O | 1 | H | H | H | H | $OCH_3$ | $OCH_3$ | N | |
| O | 1 | H | H | $CH_3$ | H | $CH_3$ | $CH_3$ | CH | |
| O | 1 | H | H | $CH_3$ | H | $CH_3$ | $OCH_3$ | CH | |
| O | 1 | H | H | $CH_3$ | H | $OCH_3$ | $OCH_3$ | CH | |
| O | 1 | H | H | $CH_3$ | H | Cl | $CH_3$ | CH | |
| O | 1 | H | H | $CH_3$ | H | $CH_3$ | $OCH_3$ | N | |
| O | 1 | H | H | $CH_3$ | H | $OCH_3$ | $OCH_3$ | N | |
| O | 1 | H | H | $CH_3$ | $CH_3$ | $CH_3$ | $CH_3$ | CH | |
| O | 1 | H | H | $CH_3$ | $CH_3$ | $CH_3$ | $OCH_3$ | CH | |
| O | 1 | H | H | $CH_3$ | $CH_3$ | $OCH_3$ | $OCH_3$ | CH | |
| O | 1 | H | H | $CH_3$ | $CH_3$ | Cl | $CH_3$ | CH | |
| O | 1 | H | H | $CH_3$ | $CH_3$ | $CH_3$ | $OCH_3$ | N | |
| O | 1 | H | H | $CH_3$ | $CH_3$ | $OCH_3$ | $OCH_3$ | N | |
| S | 0 | H | H | H | H | $OCH_3$ | $OCH_3$ | CH | |
| O | 0 | $CH_3$ | H | H | H | $OCH_3$ | $OCH_3$ | N | |
| O | 0 | H | o-F | H | H | $OCH_3$ | $OCH_3$ | CH | |
| O | 0 | H | m-Cl | H | H | $OCH_3$ | $OCH_3$ | CH | |
| O | 0 | H | o-Br | H | H | $OCH_3$ | $OCH_3$ | CH | |
| O | 0 | H | m-$CH_3$ | H | H | $OCH_3$ | $OCH_3$ | CH | |
| O | 0 | H | o-$OCH_3$ | H | H | $OCH_3$ | $OCH_3$ | CH | |
| O | 0 | H | m-$CF_3$ | H | H | $OCH_3$ | $OCH_3$ | CH | |
| O | 0 | H | H | H | $CH_2CH_3$ | $OCH_3$ | $OCH_3$ | CH | |
| O | 0 | H | H | $CH_2CH_2CH_3$ | H | $OCH_3$ | $OCH_3$ | CH | |
| O | 0 | H | H | H | H | $CH_3$ | $CH_3$ | N | |
| O | 0 | H | H | H | H | $CH_3$ | $OCH_2CH_3$ | CH | |
| O | 0 | H | H | H | H | $CH_3$ | $CH_2OCH_3$ | CH | |
| O | 1 | H | H | H | H | $CH_3$ | $CH_2OCH_3$ | CH | |
| O | 0 | H | H | H | H | $CH_3$ | $NH_2$ | CH | |
| O | 0 | H | H | H | H | $CH_3$ | $NHCH_3$ | CH | |
| O | 0 | H | H | H | H | $CH_3$ | $N(CH_3)_2$ | CH | |
| O | 0 | H | H | H | H | $CH_3$ | $CH_2CH_3$ | CH | |
| O | 0 | H | H | H | H | $CH_3$ | $CF_3$ | CH | |
| O | 0 | H | H | H | H | $CH_3$ | $SCH_3$ | CH | |
| O | 0 | H | H | H | H | $CH_3$ | $OCH_2CH=CH_2$ | CH | |
| O | 0 | H | H | H | H | $CH_3$ | $OCH_2C\equiv CH$ | CH | |
| O | 0 | H | H | H | H | $CH_3$ | $OCH_2CF_3$ | CH | |
| O | 0 | H | H | H | H | $CH_3$ | $OCH_2CH_2OCH_3$ | CH | |
| O | 0 | H | H | H | H | $CH_3$ | $CH(OCH_3)_2$ | CH | |
| O | 0 | H | H | H | H | $CH_3$ | $\underset{H}{\overset{\diagup\diagdown}{\underset{O\phantom{xx}O}{C}}}$ | CH | |
| O | 0 | H | H | H | H | $OCH_3$ | $OCH_3$ | $CCH_3$ | |

TABLE 22a-continued

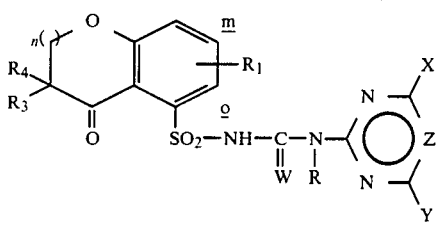

| W | n | R | R₁ | R₃ | R₄ | X | Y | Z | m.p. (°C.) |
|---|---|---|---|---|---|---|---|---|---|
| O | 0 | H | H | H | H | OCH₃ | OCH₃ | CC₂H₅ | |
| O | 0 | H | H | H | H | OCH₃ | OCH₃ | CCl | |
| O | 0 | H | H | H | H | OCH₃ | OCH₃ | CBr | |
| O | 0 | H | H | H | H | F | OCH₃ | CH | |
| O | 0 | H | H | H | H | Br | OCH₃ | CH | |
| O | 0 | H | H | H | H | CH₂F | OCH₃ | CH | |
| O | 0 | H | H | H | H | OCF₂H | OCH₃ | CH | |
| O | 0 | H | H | H | H | OCF₃ | OCH₃ | CH | |
| O | 0 | H | H | H | H | CF₃ | OCH₃ | CH | |
| O | 0 | H | H | H | H | CH₃ | (1,3-dioxane-2-yl) | CH | |
| O | 0 | H | H | H | H | CH₃ | (5-methyl-1,3-dioxan-2-yl) | CH | |
| O | 0 | H | H | H | H | CH₃ | H | CH | |
| O | 0 | H | H | H | H | CH₃ | CN | CH | |
| O | 0 | H | H | H | H | CH₃ | CH(OCH₂CH₃)₂ | CH | |
| O | 0 | H | H | H | H | CH₃ | OCH₂F | CH | |
| O | 0 | H | H | H | H | CH₃ | OCF₃ | CH | |
| O | 0 | H | H | H | H | CH₃ | SCH₂F | CH | |
| O | 0 | H | H | H | H | CH₃ | SCF₃ | CH | |
| O | 0 | H | H | H | H | CH₃ | OCF₂H | CH | |
| O | 0 | H | H | H | H | CH₃ | OCF₂CHClF | CH | |
| O | 0 | H | H | H | H | CH₃ | OCF₂CHBrF | CH | |
| O | 0 | H | H | H | H | CH₃ | OCF₂CHFCF₃ | CH | |
| O | 0 | H | H | H | H | CH₃ | SCF₂H | CH | |
| O | 0 | H | H | H | H | CH₃ | SCF₂CHClF | CH | |
| O | 0 | H | H | H | H | CH₃ | SCF₂CHBrF | CH | |
| O | 0 | H | H | H | H | CH₃ | SCF₂CHFCF₃ | CH | |
| O | 0 | H | H | H | CH₂CH₂CH₃ | OCH₃ | OCH₃ | CH | |
| O | 0 | H | H | H | CH₂CH₂CH₂CH₃ | OCH₃ | OCH₃ | CH | |
| O | 0 | H | m-SCH₃ | H | H | OCH₃ | OCH₃ | CH | |
| O | 0 | H | o-CF₂H | H | H | OCH₃ | OCH₃ | CH | |
| O | 2 | H | H | H | H | CH₃ | CH₃ | CH | |
| O | 2 | H | H | H | H | CH₃ | OCH₃ | CH | |
| O | 2 | H | H | H | H | OCH₃ | OCH₃ | CH | |
| O | 2 | H | H | H | H | Cl | OCH₃ | CH | |
| O | 2 | H | H | H | H | CH₃ | OCH₃ | N | |
| O | 2 | H | H | H | H | OCH₃ | OCH₃ | N | |
| O | 2 | H | H | CH₃ | H | CH₃ | CH₃ | CH | |
| O | 2 | H | H | CH₃ | H | CH₃ | OCH₃ | CH | |
| O | 2 | H | H | CH₃ | H | OCH₃ | OCH₃ | CH | |
| O | 2 | H | H | CH₃ | H | Cl | OCH₃ | CH | |
| O | 2 | H | H | CH₃ | H | CH₃ | OCH₃ | N | |
| O | 2 | H | H | CH₃ | H | OCH₃ | OCH₃ | N | |
| O | 0 | H | H | Cl | Cl | OCH₃ | OCH₃ | CH | |
| O | 0 | H | H | Br | Br | OCH₃ | OCH₃ | CH | |

TABLE 22b

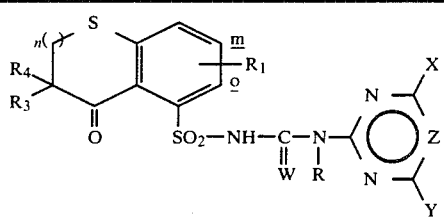

| W | n | R | R1 | R3 | R4 | X | Y | Z | m.p. (°C.) |
|---|---|---|---|---|---|---|---|---|---|
| O | 0 | H | H | H | H | CH3 | CH3 | CH | |
| O | 0 | H | H | H | H | CH3 | OCH3 | CH | |
| O | 0 | H | H | H | H | OCH3 | OCH3 | CH | |
| O | 0 | H | H | H | H | Cl | OCH3 | CH | |
| O | 0 | H | H | H | H | CH3 | OCH3 | N | |
| O | 0 | H | H | H | H | OCH3 | OCH3 | N | |
| O | 0 | H | H | CH3 | H | CH3 | CH3 | CH | |
| O | 0 | H | H | CH3 | H | CH3 | OCH3 | CH | |
| O | 0 | H | H | CH3 | H | OCH3 | OCH3 | CH | |
| O | 0 | H | H | CH3 | H | Cl | OCH3 | CH | |
| O | 0 | H | H | CH3 | H | CH3 | OCH3 | N | |
| O | 0 | H | H | CH3 | H | OCH3 | OCH3 | N | |
| O | 0 | H | H | CH3 | CH3 | CH3 | CH3 | CH | |
| O | 0 | H | H | CH3 | CH3 | CH3 | OCH3 | CH | |
| O | 0 | H | H | CH3 | CH3 | OCH3 | OCH3 | CH | |
| O | 0 | H | H | CH3 | CH3 | Cl | OCH3 | CH | |
| O | 0 | H | H | CH3 | CH3 | CH3 | OCH3 | N | |
| O | 0 | H | H | CH3 | CH3 | OCH3 | OCH3 | N | |
| O | 1 | H | H | H | H | CH3 | CH3 | CH | |
| O | 1 | H | H | H | H | CH3 | OCH3 | CH | |
| O | 1 | H | H | H | H | OCH3 | OCH3 | CH | |
| O | 1 | H | H | H | H | Cl | CH3 | CH | |
| O | 1 | H | H | H | H | CH3 | OCH3 | N | |
| O | 1 | H | H | H | H | OCH3 | OCH3 | N | |
| O | 1 | H | H | CH3 | H | CH3 | CH3 | CH | |
| O | 1 | H | H | CH3 | H | CH3 | OCH3 | CH | |
| O | 1 | H | H | CH3 | H | OCH3 | OCH3 | CH | |
| O | 1 | H | H | CH3 | H | Cl | CH3 | CH | |
| O | 1 | H | H | CH3 | H | CH3 | OCH3 | N | |
| O | 1 | H | H | CH3 | H | OCH3 | OCH3 | N | |
| O | 1 | H | H | CH3 | CH3 | CH3 | CH3 | CH | |
| O | 1 | H | H | CH3 | CH3 | CH3 | OCH3 | CH | |
| O | 1 | H | H | CH3 | CH3 | OCH3 | OCH3 | CH | |
| O | 1 | H | H | CH3 | CH3 | Cl | CH3 | CH | |
| O | 1 | H | H | CH3 | CH3 | CH3 | OCH3 | N | |
| O | 1 | H | H | CH3 | CH3 | OCH3 | OCH3 | N | |
| S | 0 | H | H | H | H | OCH3 | OCH3 | CH | |
| O | 0 | CH3 | H | H | H | OCH3 | OCH3 | N | |
| O | 0 | H | o-F | H | H | OCH3 | OCH3 | CH | |
| O | 0 | H | m-Cl | H | H | OCH3 | OCH3 | CH | |
| O | 0 | H | o-Br | H | H | OCH3 | OCH3 | CH | |
| O | 0 | H | m-CH3 | H | H | OCH3 | OCH3 | CH | |
| O | 0 | H | o-OCH3 | H | H | OCH3 | OCH3 | CH | |
| O | 0 | H | m-CF3 | H | H | OCH3 | OCH3 | CH | |
| O | 0 | H | H | H | CH2CH3 | OCH3 | OCH3 | CH | |
| O | 0 | H | H | CH2CH2CH3 | H | OCH3 | OCH3 | CH | |
| O | 0 | H | H | H | H | CH3 | CH3 | N | |
| O | 0 | H | H | H | H | CH3 | OCH2CH3 | CH | |
| O | 0 | H | H | H | H | CH3 | CH2OCH3 | CH | |
| O | 1 | H | H | H | H | CH3 | CH2OCH3 | CH | |
| O | 0 | H | H | H | H | CH3 | NH2 | CH | |
| O | 0 | H | H | H | H | CH3 | NHCH3 | CH | |
| O | 0 | H | H | H | H | CH3 | N(CH3)2 | CH | |
| O | 0 | H | H | H | H | CH3 | CH2CH3 | CH | |
| O | 0 | H | H | H | H | CH3 | CF3 | CH | |
| O | 0 | H | H | H | H | CH3 | SCH3 | CH | |
| O | 0 | H | H | H | H | CH3 | OCH2CH=CH2 | CH | |
| O | 0 | H | H | H | H | CH3 | OCH2C≡CH | CH | |
| O | 0 | H | H | H | H | CH3 | OCH2CF3 | CH | |
| O | 0 | H | H | H | H | CH3 | OCH2CH2OCH3 | CH | |
| O | 0 | H | H | H | H | CH3 | CH(OCH3)2 | CH | |
| O | 0 | H | H | H | H | CH3 | | CH | |
| O | 0 | H | H | H | H | OCH3 | OCH3 | CCH3 | |

TABLE 22b-continued

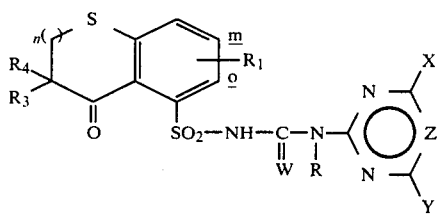

| W | n | R | R$_1$ | R$_3$ | R$_4$ | X | Y | Z | m.p. (°C.) |
|---|---|---|---|---|---|---|---|---|---|
| O | 0 | H | H | H | H | OCH$_3$ | OCH$_3$ | CC$_2$H$_5$ | |
| O | 0 | H | H | H | H | OCH$_3$ | OCH$_3$ | CCl | |
| O | 0 | H | H | H | H | OCH$_3$ | OCH$_3$ | CBr | |
| O | 0 | H | H | H | H | F | OCH$_3$ | CH | |
| O | 0 | H | H | H | H | Br | OCH$_3$ | CH | |
| O | 0 | H | H | H | H | CH$_2$F | OCH$_3$ | CH | |
| O | 0 | H | H | H | H | OCF$_2$H | OCH$_3$ | CH | |
| O | 0 | H | H | H | H | OCF$_3$ | OCH$_3$ | CH | |
| O | 0 | H | H | H | H | CF$_3$ | OCH$_3$ | CH | |
| O | 0 | H | H | H | H | CH$_3$ | (1,3-dioxane) | CH | |
| O | 0 | H | H | H | H | CH$_3$ | (4-methyl-1,3-dioxolane) | CH | |
| O | 0 | H | H | H | H | CH$_3$ | H | CH | |
| O | 0 | H | H | H | H | CH$_3$ | CN | CH | |
| O | 0 | H | H | H | H | CH$_3$ | CH(OCH$_2$CH$_3$)$_2$ | CH | |
| O | 0 | H | H | H | H | CH$_3$ | OCH$_2$F | CH | |
| O | 0 | H | H | H | H | CH$_3$ | OCF$_3$ | CH | |
| O | 0 | H | H | H | H | CH$_3$ | SCH$_2$F | CH | |
| O | 0 | H | H | H | H | CH$_3$ | SCF$_3$ | CH | |
| O | 0 | H | H | H | H | CH$_3$ | OCF$_2$H | CH | |
| O | 0 | H | H | H | H | CH$_3$ | OCF$_2$CHClF | CH | |
| O | 0 | H | H | H | H | CH$_3$ | OCF$_2$CHBrF | CH | |
| O | 0 | H | H | H | H | CH$_3$ | OCF$_2$CHFCF$_3$ | CH | |
| O | 0 | H | H | H | H | CH$_3$ | SCF$_2$H | CH | |
| O | 0 | H | H | H | H | CH$_3$ | SCF$_2$CHClF | CH | |
| O | 0 | H | H | H | H | CH$_3$ | SCF$_2$CHBrF | CH | |
| O | 0 | H | H | H | H | CH$_3$ | SCF$_2$CHFCF$_3$ | CH | |
| O | 0 | H | H | H | CH$_2$CH$_2$CH$_3$ | OCH$_3$ | OCH$_3$ | CH | |
| O | 0 | H | H | H | CH$_2$CH$_2$CH$_2$CH$_3$ | OCH$_3$ | OCH$_3$ | CH | |
| O | 0 | H | m-SCH$_3$ | H | H | OCH$_3$ | OCH$_3$ | CH | |
| O | 0 | H | o-CF$_2$H | H | H | OCH$_3$ | OCH$_3$ | CH | |
| O | 2 | H | H | H | H | CH$_3$ | CH$_3$ | CH | |
| O | 2 | H | H | H | H | CH$_3$ | OCH$_3$ | CH | |
| O | 2 | H | H | H | H | OCH$_3$ | OCH$_3$ | CH | |
| O | 2 | H | H | H | H | Cl | OCH$_3$ | CH | |
| O | 2 | H | H | H | H | CH$_3$ | OCH$_3$ | N | |
| O | 2 | H | H | H | H | OCH$_3$ | OCH$_3$ | N | |
| O | 2 | H | H | CH$_3$ | H | CH$_3$ | CH$_3$ | CH | |
| O | 2 | H | H | CH$_3$ | H | CH$_3$ | OCH$_3$ | CH | |
| O | 2 | H | H | CH$_3$ | H | OCH$_3$ | OCH$_3$ | CH | |
| O | 2 | H | H | CH$_3$ | H | Cl | OCH$_3$ | CH | |
| O | 2 | H | H | CH$_3$ | H | CH$_3$ | OCH$_3$ | N | |
| O | 2 | H | H | CH$_3$ | H | OCH$_3$ | OCH$_3$ | N | |
| O | 0 | H | H | Cl | Cl | OCH$_3$ | OCH$_3$ | CH | |
| O | 0 | H | H | Br | Br | OCH$_3$ | OCH$_3$ | CH | |

TABLE 23a

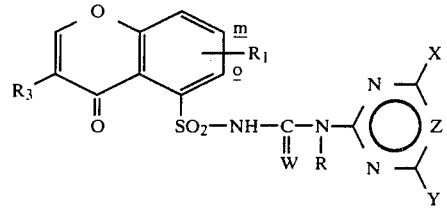

| W | R | R₁ | R₃ | X | Y | Z | m.p. (°C.) |
|---|---|----|----|---|---|---|------------|
| S | H | H | H | OCH$_3$ | OCH$_3$ | CH | |
| O | H | H | H | CH$_3$ | OCH$_2$CH$_3$ | CH | |
| O | H | H | H | CH$_3$ | CH$_2$OCH$_3$ | CH | |
| O | H | H | H | CH$_3$ | NH$_2$ | CH | |
| O | H | H | H | CH$_3$ | NHCH$_3$ | CH | |
| O | H | H | H | CH$_3$ | N(CH$_3$)$_2$ | CH | |
| O | H | H | H | CH$_3$ | CH$_2$CH$_3$ | CH | |
| O | H | H | H | CH$_3$ | CF$_3$ | CH | |
| O | H | H | H | CH$_3$ | SCH$_3$ | CH | |
| O | H | H | H | CH$_3$ | OCH$_2$CH=CH$_2$ | CH | |
| O | H | H | H | CH$_3$ | OCH$_2$C≡CH | CH | |
| O | H | H | H | CH$_3$ | OCH$_2$CF$_3$ | CH | |
| O | H | H | H | CH$_3$ | OCH$_2$CH$_2$OCH$_3$ | CH | |
| O | H | H | H | CH$_3$ | CH(OCH$_3$)$_2$ | CH | |
| O | H | H | H | CH$_3$ | 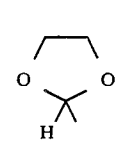 | CH | |
| O | H | H | H | CH$_3$ | 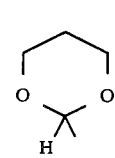 | CH | |
| O | H | H | H | CH$_3$ | 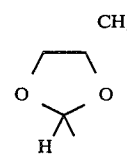 CH$_3$ | CH | |
| O | H | H | H | CH$_3$ | H | CH | |
| O | H | H | H | CH$_3$ | CN | CH | |
| O | H | H | H | CH$_3$ | CH(OCH$_2$CH$_3$)$_2$ | CH | |
| O | H | H | H | CH$_3$ | OCH$_2$F | CH | |
| O | H | H | H | CH$_3$ | OCF$_3$ | CH | |
| O | H | H | H | CH$_3$ | SCH$_2$F | CH | |
| O | H | H | H | CH$_3$ | SCF$_3$ | CH | |
| O | H | H | H | CH$_3$ | OCF$_2$H | CH | |
| O | H | H | H | CH$_3$ | OCF$_2$CHClF | CH | |
| O | H | H | H | CH$_3$ | OCF$_2$CHBrF | CH | |
| O | H | H | H | CH$_3$ | OCF$_2$CHFCF$_3$ | CH | |
| O | H | H | H | CH$_3$ | SCF$_2$H | CH | |
| O | H | H | H | CH$_3$ | SCF$_2$CHClF | CH | |
| O | H | H | H | CH$_3$ | SCF$_2$CHBrF | CH | |
| O | H | H | H | CH$_3$ | SCF$_2$CHFCF$_3$ | CH | |
| O | H | H | H | CH$_3$ | OCH$_3$ | CCH$_3$ | |
| O | H | H | H | CH$_3$ | OCH$_3$ | CCH$_2$CH$_3$ | |
| O | H | H | H | CH$_3$ | OCH$_3$ | CCl | |
| O | H | H | H | CH$_3$ | OCH$_3$ | CBr | |
| O | H | H | H | F | OCH$_3$ | CH | |
| O | H | H | H | Br | OCH$_3$ | CH | |
| O | H | H | H | CH$_2$F | OCH$_3$ | CH | |
| O | H | H | H | OCF$_2$H | OCH$_3$ | CH | |
| O | H | H | H | OCF$_3$ | OCH$_3$ | CH | |
| O | H | H | H | CF$_3$ | OCH$_3$ | CH | |
| O | H | m-F | H | CH$_3$ | OCH$_3$ | CH | |
| O | H | o-Cl | H | CH$_3$ | OCH$_3$ | CH | |
| O | H | m-Br | H | CH$_3$ | OCH$_3$ | CH | |
| O | H | o-CH$_3$ | H | CH$_3$ | OCH$_3$ | CH | |
| O | H | m-CF$_3$ | H | CH$_3$ | OCH$_3$ | CH | |
| O | H | o-SCH$_3$ | H | CH$_3$ | OCH$_3$ | CH | |
| O | H | m-OCH$_3$ | H | CH$_3$ | OCH$_3$ | CH | |

TABLE 23a-continued

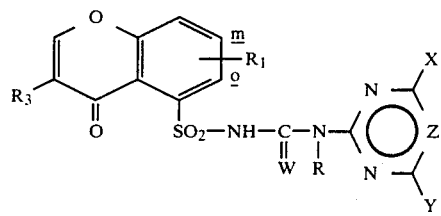

| W | R | R₁ | R₃ | X | Y | Z | m.p. (°C.) |
|---|---|---|---|---|---|---|---|
| O | H | o-OCF₂H | H | CH₃ | OCH₃ | CH | |
| O | CH₃ | H | H | CH₃ | OCH₃ | CH | |
| O | H | H | H | CH₃ | CH₃ | CH | |
| O | H | H | H | CH₃ | OCH₃ | CH | |
| O | H | H | H | OCH₃ | OCH₃ | CH | |
| O | H | H | H | Cl | OCH₃ | CH | |
| O | H | H | H | CH₃ | OCH₃ | N | |
| O | H | H | H | OCH₃ | OCH₃ | N | |
| O | H | H | CH₃ | OCH₃ | OCH₃ | CH | |
| O | H | H | CH₂CH₃ | OCH₃ | OCH₃ | CH | |
| O | H | H | CH₂CH₂CH₃ | OCH₃ | OCH₃ | CH | |
| O | H | H | CH₂CH₂CH₂CH₃ | OCH₃ | OCH₃ | CH | |
| O | H | H | Cl | OCH₃ | OCH₃ | CH | |
| O | H | H | Br | OCH₃ | OCH₃ | CH | |

TABLE 24a

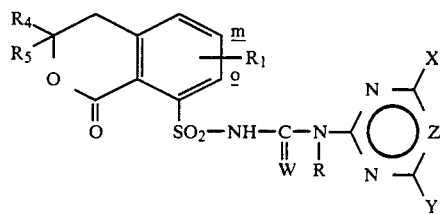

| W | R | R₁ | R₄ | R₅ | X | Y | Z | m.p. (°C.) |
|---|---|---|---|---|---|---|---|---|
| O | H | H | CH₃ | H | CH₃ | CH₃ | CH | 233–237 |
| O | H | H | CH₃ | H | CH₃ | OCH₃ | CH | 198–205 |
| O | H | H | CH₃ | H | OCH₃ | OCH₃ | CH | 204–207 |
| O | H | H | CH₃ | H | CH₃ | CH₃ | N | 212–217 |
| O | H | H | CH₃ | H | CH₃ | OCH₃ | N | 208–212 |
| O | H | H | CH₃ | H | OCH₃ | OCH₃ | N | 212–215 |
| O | H | H | CH₃ | CH₃ | CH₃ | CH₃ | CH | |
| O | H | H | CH₃ | CH₃ | CH₃ | OCH₃ | CH | |
| O | H | H | CH₃ | CH₃ | OCH₃ | OCH₃ | CH | |
| O | H | H | CH₃ | CH₃ | Cl | OCH₃ | CH | |
| O | H | H | CH₃ | CH₃ | CH₃ | OCH₃ | N | |
| O | H | H | CH₃ | CH₃ | OCH₃ | OCH₃ | N | |
| S | H | H | CH₃ | H | OCH₃ | OCH₃ | CH | |
| O | CH₃ | H | CH₃ | H | CH₃ | OCH₃ | CH | 140–143 |
| O | H | o-F | CH₃ | H | OCH₃ | OCH₃ | CH | |
| O | H | m-Cl | CH₃ | H | OCH₃ | OCH₃ | CH | |
| O | H | o-Br | CH₃ | H | OCH₃ | OCH₃ | CH | |
| O | H | m-CH₃ | CH₃ | H | OCH₃ | OCH₃ | CH | |
| O | H | o-OCH₃ | CH₃ | H | OCH₃ | OCH₃ | CH | |
| O | H | m-CF₃ | CH₃ | H | OCH₃ | OCH₃ | CH | |
| O | H | H | CH₃ | CH₂CH₃ | OCH₃ | OCH₃ | CH | |
| O | H | H | CH₂CH₂CH₃ | H | OCH₃ | OCH₃ | CH | |
| O | H | H | CH₃ | H | CH₃ | CH₃ | N | |
| O | H | H | CH₃ | H | CH₃ | OCH₂CH₃ | CH | |
| O | H | H | CH₃ | H | CH₃ | CH₂OCH₃ | CH | |
| O | H | H | CH₃ | H | CH₃ | NH₂ | CH | |
| O | H | H | CH₃ | H | CH₃ | NHCH₃ | CH | |
| O | H | H | CH₃ | H | CH₃ | N(CH₃)₂ | CH | |
| O | H | H | CH₃ | H | CH₃ | CH₂CH₃ | CH | |
| O | H | H | CH₃ | H | CH₃ | CF₃ | CH | |
| O | H | H | CH₃ | H | CH₃ | SCH₃ | CH | |
| O | H | H | CH₃ | H | CH₃ | OCH₂CH=CH₂ | CH | |
| O | H | H | CH₃ | H | CH₃ | OCH₂C≡CH | CH | |
| O | H | H | CH₃ | H | CH₃ | OCH₂CF₃ | CH | |
| O | H | H | CH₃ | H | CH₃ | OCH₂CH₂OCH₃ | CH | |
| O | H | H | CH₃ | H | CH₃ | CH(OCH₃)₂ | CH | |

TABLE 24a-continued

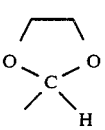

| W | R | R₁ | R₄ | R₅ | X | Y | Z | m.p. (°C.) |
|---|---|---|---|---|---|---|---|---|
| O | H | H | CH₃ | H | CH₃ | (1,3-dioxolan-2-yl) | CH | |
| O | H | H | CH₃ | H | OCH₃ | OCH₃ | CCH₃ | |
| O | H | H | CH₃ | H | OCH₃ | OCH₃ | CC₂H₅ | |
| O | H | H | CH₃ | H | OCH₃ | OCH₃ | CCl | |
| O | H | H | CH₃ | H | OCH₃ | OCH₃ | CBr | |
| O | H | H | CH₃ | H | F | OCH₃ | CH | |
| O | H | H | CH₃ | H | Br | OCH₃ | CH | |
| O | H | H | CH₃ | H | CH₂F | OCH₃ | CH | |
| O | H | H | CH₃ | H | OCF₂H | OCH₃ | CH | |
| O | H | H | CH₃ | H | OCF₃ | OCH₃ | CH | |
| O | H | H | CH₃ | H | CF₃ | OCH₃ | CH | |
| O | H | H | CH₃ | H | CH₃ | (1,3-dioxan-2-yl) | CH | |
| O | H | H | CH₃ | H | CH₃ | (5-methyl-1,3-dioxan-2-yl) | CH | |
| O | H | H | CH₃ | H | CH₃ | H | CH | |
| O | H | H | CH₃ | H | CH₃ | CN | CH | |
| O | H | H | CH₃ | H | CH₃ | CH(OCH₂CH₃)₂ | CH | |
| O | H | H | CH₃ | H | CH₃ | OCH₂F | CH | |
| O | H | H | CH₃ | H | CH₃ | OCF₃ | CH | |
| O | H | H | CH₃ | H | CH₃ | SCH₂F | CH | |
| O | H | H | CH₃ | H | CH₃ | SCF₃ | CH | |
| O | H | H | CH₃ | H | CH₃ | OCF₂H | CH | |
| O | H | H | CH₃ | H | CH₃ | OCF₂CHClF | CH | |
| O | H | H | CH₃ | H | CH₃ | OCF₂CHBrF | CH | |
| O | H | H | CH₃ | H | CH₃ | OCF₂CHFCF₃ | CH | |
| O | H | H | CH₃ | H | CH₃ | SCF₂H | CH | |
| O | H | H | CH₃ | H | CH₃ | SCF₂CHClF | CH | |
| O | H | H | CH₃ | H | CH₃ | SCF₂CHBrF | CH | |
| O | H | H | CH₃ | H | CH₃ | SCF₂CHFCF₃ | CH | |
| O | H | H | H | CH₂CH₂CH₃ | OCH₃ | OCH₃ | CH | |
| O | H | H | H | CH₂CH₂CH₂CH₃ | OCH₃ | OCH₃ | CH | |
| O | H | m-SCH₃ | CH₃ | H | OCH₃ | OCH₃ | CH | |
| O | H | o-CF₂H | CH₃ | H | OCH₃ | OCH₃ | CH | |

TABLE 25a

| W | R | R₁ | R₆ | R₇ | X | Y | Z | m.p. (°C.) |
|---|---|---|---|---|---|---|---|---|
| O | H | H | H | H | CH₃ | CH₃ | CH | |
| O | H | H | H | H | CH₃ | OCH₃ | CH | |
| O | H | H | H | H | OCH₃ | OCH₃ | CH | |
| O | H | H | H | H | Cl | OCH₃ | CH | |
| O | H | H | H | H | CH₃ | CH₃ | N | |
| O | H | H | H | H | OCH₃ | OCH₃ | N | |
| O | H | H | CH₃ | H | CH₃ | CH₃ | CH | |
| O | H | H | H | CH₃ | CH₃ | OCH₃ | CH | |
| O | H | H | CH₃ | H | OCH₃ | OCH₃ | CH | |
| O | H | H | H | CH₃ | Cl | OCH₃ | CH | |
| O | H | H | CH₃ | H | CH₃ | OCH₃ | N | |
| O | H | H | H | CH₃ | OCH₃ | OCH₃ | N | |
| O | H | H | CH₃ | CH₃ | CH₃ | CH₃ | CH | |
| O | H | H | CH₃ | CH₃ | CH₃ | OCH₃ | CH | |
| O | H | H | CH₃ | CH₃ | OCH₃ | OCH₃ | CH | |
| O | H | H | CH₃ | CH₃ | Cl | OCH₃ | CH | |
| O | H | H | CH₃ | CH₃ | CH₃ | OCH₃ | N | |
| O | H | H | CH₃ | CH₃ | OCH₃ | OCH₃ | N | |
| O | H | H | H | H | CH₃ | OCH₂CH₃ | CH | |
| O | H | m-F | H | H | CH₃ | CH₂OCH₃ | CH | |
| O | H | o-Cl | H | H | CH₃ | NH₂ | CH | |
| O | H | m-Br | H | H | CH₃ | NHCH₃ | CH | |
| O | H | o-CH₃ | H | H | CH₃ | N(CH₃)₂ | CH | |
| O | H | m-OCH₃ | H | H | CH₃ | C₂H₅ | CH | |
| O | H | o-CF₃ | H | H | CH₃ | CF₃ | CH | |
| O | H | m-SCH₃ | H | H | CH₃ | SCH₃ | CH | |
| O | H | o-OCF₂H | H | H | CH₃ | OCH₂CH=CH₂ | CH | |
| O | H | o-OCF₂H | H | H | CH₃ | OCH₂C≡CH | CH | |
| O | H | H | H | H | CH₃ | OCH₂CF₃ | CH | |
| O | H | H | H | H | CH₃ | OCH₂CH₂OCH₃ | CH | |
| O | H | H | H | H | CH₃ | CH(OCH₃)₂ | CH | |
| O | H | H | H | H | CH₃ | 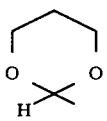 | CH | |
| O | H | H | H | H | CH₃ | 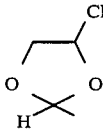 | CH | |
| O | H | H | H | H | CH₃ | (see structure) | CH | |
| O | H | H | H | H | CH₃ | H | CH | |
| O | H | H | H | H | CH₃ | CN | CH | |
| O | H | H | H | H | CH₃ | CH(OCH₂CH₃)₂ | CH | |
| O | H | H | H | H | CH₃ | OCH₂F | CH | |
| O | H | H | H | H | CH₃ | OCF₃ | CH | |
| O | H | H | H | H | CH₃ | SCH₂F | CH | |
| O | H | H | H | H | CH₃ | SCF₃ | CH | |
| O | H | H | H | H | CH₃ | OCF₂H | CH | |
| O | H | H | H | H | CH₃ | OCF₂CHClF | CH | |
| O | H | H | H | H | CH₃ | OCF₂CHBrF | CH | |
| O | H | H | H | H | CH₃ | OCF₂CHFCF₃ | CH | |
| O | H | H | H | H | CH₃ | SCF₂H | CH | |
| O | H | H | H | H | CH₃ | SCF₂CHClF | CH | |
| O | H | H | H | H | CH₃ | SCF₂CHBrF | CH | |
| O | H | H | H | H | CH₃ | SCF₂CHFCF₃ | CH | |
| O | H | H | H | H | CH₂F | CH₃ | CH | |
| O | H | H | H | H | F | OCH₃ | CH | |

TABLE 25a-continued

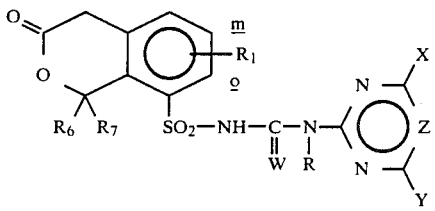

| W | R | R₁ | R₆ | R₇ | X | Y | Z | m.p. (°C.) |
|---|---|---|---|---|---|---|---|---|
| O | H | H | H | H | Br | OCH₃ | CH | |
| O | H | H | H | H | OCF₂H | CH₃ | CH | |
| O | H | H | H | H | OCF₃ | CH₃ | CH | |
| O | H | H | H | H | CF₃ | CH₃ | CH | |
| S | H | H | H | H | OCH₃ | OCH₃ | CH | |
| O | CH₃ | H | H | H | OCH₃ | OCH₃ | N | |
| O | H | H | H | H | CH₃ | CH₃ | CH | |
| O | H | H | H | H | CH₃ | OCH₃ | CH | |
| O | H | H | H | H | OCH₃ | OCH₃ | CH | |
| O | H | H | H | H | Cl | OCH₃ | CH | |
| O | H | H | H | H | CH₃ | OCH₃ | N | |
| O | H | H | H | H | OCH₃ | OCH₃ | N | |
| O | H | H | CH₃ | H | CH₃ | CH₃ | CH | |
| O | H | H | H | CH₃ | CH₃ | OCH₃ | CH | |
| O | H | H | CH₃ | H | OCH₃ | OCH₃ | CH | |
| O | H | H | H | CH₃ | Cl | OCH₃ | CH | |
| O | H | H | CH₃ | H | CH₃ | OCH₃ | N | |
| O | H | H | H | CH₃ | OCH₃ | OCH₃ | N | |
| O | H | H | CH₃ | CH₃ | CH₃ | CH₃ | CH | |
| O | H | H | CH₃ | CH₃ | CH₃ | OCH₃ | CH | |
| O | H | H | CH₃ | CH₃ | OCH₃ | OCH₃ | CH | |
| O | H | H | CH₃ | CH₃ | Cl | OCH₃ | CH | |
| O | H | H | CH₃ | CH₃ | CH₃ | OCH₃ | N | |
| O | H | H | CH₃ | CH₃ | OCH₃ | OCH₃ | N | |
| O | H | H | H | H | CH₃ | CH₃ | CH | |
| O | H | H | H | H | CH₃ | OCH₃ | CH | |
| O | H | H | H | H | OCH₃ | OCH₃ | CH | |
| O | H | H | H | H | Cl | OCH₃ | CH | |
| O | H | H | H | H | CH₃ | OCH₃ | N | |
| O | H | H | H | H | OCH₃ | OCH₃ | N | |

TABLE 25b

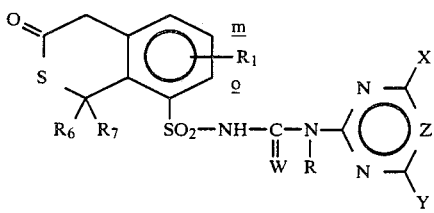

| W | R | R₁ | R₆ | R₇ | X | Y | Z | m.p. (°C.) |
|---|---|---|---|---|---|---|---|---|
| O | H | H | H | H | CH₃ | CH₃ | CH | |
| O | H | H | H | H | CH₃ | OCH₃ | CH | |
| O | H | H | H | H | OCH₃ | OCH₃ | CH | |
| O | H | H | H | H | Cl | OCH₃ | CH | |
| O | H | H | H | H | CH₃ | OCH₃ | N | |
| O | H | H | H | H | OCH₃ | OCH₃ | N | |
| O | H | H | CH₃ | H | CH₃ | CH₃ | CH | |
| O | H | H | H | CH₃ | CH₃ | OCH₃ | CH | |
| O | H | H | CH₃ | H | OCH₃ | OCH₃ | CH | |
| O | H | H | H | CH₃ | Cl | OCH₃ | CH | |
| O | H | H | CH₃ | H | CH₃ | OCH₃ | N | |
| O | H | H | H | CH₃ | OCH₃ | OCH₃ | N | |
| O | H | H | CH₃ | CH₃ | CH₃ | CH₃ | CH | |
| O | H | H | CH₃ | CH₃ | CH₃ | OCH₃ | CH | |
| O | H | H | CH₃ | CH₃ | OCH₃ | OCH₃ | CH | |
| O | H | H | CH₃ | CH₃ | Cl | OCH₃ | CH | |
| O | H | H | CH₃ | CH₃ | CH₃ | OCH₃ | N | |
| O | H | H | CH₃ | CH₃ | OCH₃ | OCH₃ | N | |
| O | H | H | H | H | CH₃ | OCH₂CH₃ | CH | |
| O | H | m-F | H | H | CH₃ | OCH₂OCH₃ | CH | |
| O | H | o-Cl | H | H | CH₃ | NH₂ | CH | |
| O | H | m-Br | H | H | CH₃ | NHCH₃ | CH | |
| O | H | o-CH₃ | H | H | CH₃ | N(CH₃)₂ | CH | |

TABLE 25b-continued

| W | R | R$_1$ | R$_6$ | R$_7$ | X | Y | Z | m.p. (°C.) |
|---|---|---|---|---|---|---|---|---|
| O | H | m-OCH$_3$ | H | H | CH$_3$ | C$_2$H$_5$ | CH | |
| O | H | o-CF$_3$ | H | H | CH$_3$ | CF$_3$ | CH | |
| O | H | m-SCH$_3$ | H | H | CH$_3$ | SCH$_3$ | CH | |
| O | H | o-OCF$_2$H | H | H | CH$_3$ | OCH$_2$CH=CH$_2$ | CH | |
| O | H | o-OCF$_2$H | H | H | CH$_3$ | OCH$_2$C≡CH | CH | |
| O | H | H | H | H | CH$_3$ | OCH$_2$CF$_3$ | CH | |
| O | H | H | H | H | CH$_3$ | OCH$_2$CH$_2$OCH$_3$ | CH | |
| O | H | H | H | H | CH$_3$ | CH(OCH$_3$)$_2$ | CH | |
| O | H | H | H | H | CH$_3$ | (1,3-dioxolan-2-yl) | CH | |
| O | H | H | H | H | CH$_3$ | (1,3-dioxan-2-yl) | CH | |
| O | H | H | H | H | CH$_3$ | (5-methyl-1,3-dioxan-2-yl) | CH | |
| O | H | H | H | H | CH$_3$ | H | CH | |
| O | H | H | H | H | CH$_3$ | CN | CH | |
| O | H | H | H | H | CH$_3$ | CH(OCH$_2$CH$_3$)$_2$ | CH | |
| O | H | H | H | H | CH$_3$ | OCH$_2$F | CH | |
| O | H | H | H | H | CH$_3$ | OCF$_3$ | CH | |
| O | H | H | H | H | CH$_3$ | SCH$_2$F | CH | |
| O | H | H | H | H | CH$_3$ | SCF$_3$ | CH | |
| O | H | H | H | H | CH$_3$ | OCF$_2$H | CH | |
| O | H | H | H | H | CH$_3$ | OCF$_2$CHClF | CH | |
| O | H | H | H | H | CH$_3$ | OCF$_2$CHBrF | CH | |
| O | H | H | H | H | CH$_3$ | OCF$_2$CHFCF$_3$ | CH | |
| O | H | H | H | H | CH$_3$ | SCF$_2$H | CH | |
| O | H | H | H | H | CH$_3$ | SCF$_2$CHClF | CH | |
| O | H | H | H | H | CH$_3$ | SCF$_2$CHBrF | CH | |
| O | H | H | H | H | CH$_3$ | SCF$_2$CHFCF$_3$ | CH | |
| O | H | H | H | H | CH$_2$F | CH$_3$ | CH | |
| O | H | H | H | H | F | OCH$_3$ | CH | |
| O | H | H | H | H | Br | OCH$_3$ | CH | |
| O | H | H | H | H | OCF$_2$H | CH$_3$ | CH | |
| O | H | H | H | H | OCF$_3$ | CH$_3$ | CH | |
| O | H | H | H | H | CF$_3$ | CH$_3$ | CH | |
| S | H | H | H | H | OCH$_3$ | OCH$_3$ | CH | |
| O | CH$_3$ | H | H | H | OCH$_3$ | OCH$_3$ | N | |
| O | H | H | H | H | CH$_3$ | CH$_3$ | CH | |
| O | H | H | H | H | CH$_3$ | OCH$_3$ | CH | |
| O | H | H | H | H | OCH$_3$ | OCH$_3$ | CH | |
| O | H | H | H | H | Cl | OCH$_3$ | CH | |
| O | H | H | H | H | CH$_3$ | OCH$_3$ | N | |
| O | H | H | H | H | OCH$_3$ | OCH$_3$ | N | |
| O | H | H | CH$_3$ | H | CH$_3$ | CH$_3$ | CH | |
| O | H | H | H | CH$_3$ | CH$_3$ | CH$_3$ | CH | |
| O | H | H | CH$_3$ | H | OCH$_3$ | OCH$_3$ | CH | |
| O | H | H | H | CH$_3$ | Cl | OCH$_3$ | CH | |
| O | H | H | CH$_3$ | H | CH$_3$ | OCH$_3$ | N | |
| O | H | H | H | CH$_3$ | OCH$_3$ | OCH$_3$ | N | |
| O | H | H | CH$_3$ | CH$_3$ | CH$_3$ | CH$_3$ | CH | |
| O | H | H | CH$_3$ | CH$_3$ | CH$_3$ | OCH$_3$ | CH | |
| O | H | H | CH$_3$ | CH$_3$ | OCH$_3$ | OCH$_3$ | CH | |
| O | H | H | CH$_3$ | CH$_3$ | Cl | OCH$_3$ | CH | |
| O | H | H | CH$_3$ | CH$_3$ | CH$_3$ | OCH$_3$ | N | |

TABLE 25b-continued

| W | R | R₁ | R₆ | R₇ | X | Y | Z | m.p. (°C.) |
|---|---|---|---|---|---|---|---|---|
| O | H | H | CH₃ | CH₃ | OCH₃ | OCH₃ | N | |
| O | H | H | H | H | CH₃ | CH₃ | CH | |
| O | H | H | H | H | CH₃ | OCH₃ | CH | |
| O | H | H | H | H | OCH₃ | OCH₃ | CH | |
| O | H | H | H | H | Cl | OCH₃ | CH | |
| O | H | H | H | H | CH₃ | OCH₃ | N | |
| O | H | H | H | H | OCH₃ | OCH₃ | N | |

TABLE 26

| W | R | R₁ | R₂ | R₆ | R₇ | X | Y | Z | m.p. (°C.) |
|---|---|---|---|---|---|---|---|---|---|
| O | H | H | H | H | H | CH₃ | CH₃ | CH | |
| O | H | H | H | H | H | CH₃ | OCH₃ | CH | |
| O | H | H | H | H | H | OCH₃ | OCH₃ | CH | |
| O | H | H | H | H | H | Cl | OCH₃ | CH | |
| O | H | H | H | H | H | CH₃ | OCH₃ | N | |
| O | H | H | H | H | H | OCH₃ | OCH₃ | N | |
| O | H | H | H | CH₃ | H | CH₃ | CH₃ | CH | |
| O | H | H | H | H | CH₃ | CH₃ | OCH₃ | CH | |
| O | H | H | H | CH₃ | H | OCH₃ | OCH₃ | CH | |
| O | H | H | H | H | CH₃ | Cl | OCH₃ | CH | |
| O | H | H | H | CH₃ | H | CH₃ | OCH₃ | N | |
| O | H | H | H | H | CH₃ | OCH₃ | OCH₃ | N | |
| O | H | H | H | CH₃ | CH₃ | CH₃ | CH₃ | CH | |
| O | H | H | H | CH₃ | CH₃ | CH₃ | OCH₃ | CH | |
| O | H | H | H | CH₃ | CH₃ | OCH₃ | OCH₃ | CH | |
| O | H | H | H | CH₃ | CH₃ | Cl | OCH₃ | CH | |
| O | H | H | H | CH₃ | CH₃ | CH₃ | OCH₃ | N | |
| O | H | H | H | CH₃ | CH₃ | OCH₃ | OCH₃ | N | |
| O | H | H | H | H | H | CH₃ | OCH₂CH₃ | CH | |
| O | H | m-F | H | H | H | CH₃ | CH₂OCH₃ | CH | |
| O | H | o-Cl | H | H | H | CH₃ | NH₂ | CH | |
| O | H | m-Br | H | H | H | CH₃ | NHCH₃ | CH | |
| O | H | o-CH₃ | H | H | H | CH₃ | N(CH₃)₂ | CH | |
| O | H | m-OCH₃ | H | H | H | CH₃ | C₂H₅ | CH | |
| O | H | o-CF₃ | H | H | H | CH₃ | CF₃ | CH | |
| O | H | m-SCH₃ | H | H | H | CH₃ | SCH₃ | CH | |
| O | H | o-OCF₂H | H | H | H | CH₃ | OCH₂CH=CH₂ | CH | |
| O | H | o-OCF₂H | H | H | H | CH₃ | OCH₂C≡CH | CH | |
| O | H | H | H | H | H | CH₃ | OCH₂CF₃ | CH | |
| O | H | H | H | H | H | CH₃ | OCH₂CH₂OCH₃ | CH | |
| O | H | H | H | H | H | CH₃ | CH(OCH₃)₂ | CH | |
| O | H | H | H | H | H | CH₃ | (1,3-dioxolan-2-yl) | CH | |
| O | H | H | H | H | H | CH₃ | (1,3-dioxan-2-yl) | CH | |

TABLE 26-continued

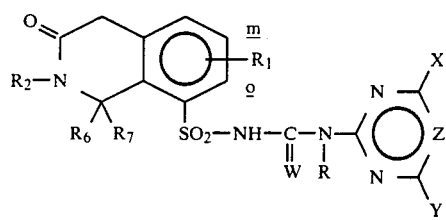

| W | R | $R_1$ | $R_2$ | $R_6$ | $R_7$ | X | Y | Z | m.p. (°C.) |
|---|---|---|---|---|---|---|---|---|---|
| O | H | H | H | H | H | $CH_3$ | ![CH3 dioxolane group] | CH | |
| O | H | H | $CH_3$ | H | H | $CH_3$ | H | CH | |
| O | H | H | $CH_3$ | H | H | $CH_3$ | CN | CH | |
| O | H | H | $CH_3$ | H | H | $CH_3$ | $CH(OCH_2CH_3)_2$ | CH | |
| O | H | H | $CH_3$ | H | H | $CH_3$ | $OCH_2F$ | CH | |
| O | H | H | $CH_3$ | H | H | $CH_3$ | $OCF_3$ | CH | |
| O | H | H | $CH_3$ | H | H | $CH_3$ | $SCH_2F$ | CH | |
| O | H | H | $CH_3$ | H | H | $CH_3$ | $SCF_3$ | CH | |
| O | H | H | $CH_3$ | H | H | $CH_3$ | $OCF_2H$ | CH | |
| O | H | H | $CH_3$ | H | H | $CH_3$ | $OCF_2CHClF$ | CH | |
| O | H | H | $CH_3$ | H | H | $CH_3$ | $OCF_2CHBrF$ | CH | |
| O | H | H | $CH_3$ | H | H | $CH_3$ | $OCF_2CHFCF_3$ | CH | |
| O | H | H | $CH_3$ | H | H | $CH_3$ | $SCF_2H$ | CH | |
| O | H | H | $CH_3$ | H | H | $CH_3$ | $SCF_2CHClF$ | CH | |
| O | H | H | $CH_3$ | H | H | $CH_3$ | $SCF_2CHBrF$ | CH | |
| O | H | H | $CH_3$ | H | H | $CH_3$ | $SCF_2CHFCF_3$ | CH | |
| O | H | H | $CH_3$ | H | H | $CH_2F$ | $CH_3$ | CH | |
| O | H | H | H | H | H | F | $OCH_3$ | CH | |
| O | H | H | H | H | H | Br | $OCH_3$ | CH | |
| O | H | H | H | H | H | $OCF_2H$ | $CH_3$ | CH | |
| O | H | H | H | H | H | $OCF_3$ | $CH_3$ | CH | |
| O | H | H | H | H | H | $CF_3$ | $CH_3$ | CH | |
| S | H | H | H | H | H | $OCH_3$ | $OCH_3$ | CH | |
| O | $CH_3$ | H | H | H | H | $OCH_3$ | $OCH_3$ | N | |
| O | H | H | $CH_3$ | H | H | $CH_3$ | $CH_3$ | CH | |
| O | H | H | $CH_3$ | H | H | $CH_3$ | $OCH_3$ | CH | |
| O | H | H | $CH_3$ | H | H | $OCH_3$ | $OCH_3$ | CH | |
| O | H | H | $CH_3$ | H | H | Cl | $OCH_3$ | CH | |
| O | H | H | $CH_3$ | H | H | $CH_3$ | $OCH_3$ | N | |
| O | H | H | $CH_3$ | H | H | $OCH_3$ | $OCH_3$ | N | |
| O | H | H | $CH_3$ | $CH_3$ | H | $CH_3$ | $CH_3$ | CH | |
| O | H | H | $CH_3$ | H | $CH_3$ | $CH_3$ | $OCH_3$ | CH | |
| O | H | H | $CH_3$ | $CH_3$ | H | $OCH_3$ | $OCH_3$ | CH | |
| O | H | H | $CH_3$ | H | $CH_3$ | Cl | $OCH_3$ | CH | |
| O | H | H | $CH_3$ | $CH_3$ | H | $CH_3$ | $OCH_3$ | N | |
| O | H | H | $CH_3$ | H | $CH_3$ | $OCH_3$ | $OCH_3$ | N | |
| O | H | H | $CH_3$ | $CH_3$ | $CH_3$ | $CH_3$ | $CH_3$ | CH | |
| O | H | H | $CH_3$ | $CH_3$ | $CH_3$ | $CH_3$ | $OCH_3$ | CH | |
| O | H | H | $CH_3$ | $CH_3$ | $CH_3$ | $OCH_3$ | $OCH_3$ | CH | |
| O | H | H | $CH_3$ | $CH_3$ | $CH_3$ | Cl | $OCH_3$ | CH | |
| O | H | H | $CH_3$ | $CH_3$ | $CH_3$ | $CH_3$ | $OCH_3$ | N | |
| O | H | H | $CH_3$ | $CH_3$ | $CH_3$ | $OCH_3$ | $OCH_3$ | N | |
| O | H | H | $CH_2CH_3$ | H | H | $CH_3$ | $CH_3$ | CH | |
| O | H | H | $CH_2CH_3$ | H | H | $CH_3$ | $OCH_3$ | CH | |
| O | H | H | $CH_2CH_3$ | H | H | $OCH_3$ | $OCH_3$ | CH | |
| O | H | H | $CH_2CH_3$ | H | H | Cl | $OCH_3$ | CH | |
| O | H | H | $CH_2CH_3$ | H | H | $CH_3$ | $OCH_3$ | N | |
| O | H | H | $CH_2CH_3$ | H | H | $OCH_3$ | $OCH_3$ | N | |

TABLE 27a

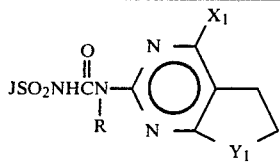

| J | W₁ | n | R | R₁ | R₂ | R₃ | R₄ | R₅ | X₁ | Y₁ | m.p. (°C.) |
|---|---|---|---|---|---|---|---|---|---|---|---|
| J-1 | — | 0 | H | H | CH₃ | — | — | H | CH₃ | O | 201–203 |
| J-1 | — | 0 | H | H | CH₃ | — | — | H | OCH₃ | O | |
| J-1 | — | 0 | H | H | CH₃ | — | — | H | CH₃ | CH₂ | |
| J-1 | — | 0 | H | H | CH₃ | — | — | H | OCH₃ | CH₂ | |
| J-2 | — | 0 | H | H | — | — | — | H | CH₃ | O | |
| J-2 | — | 0 | H | H | — | — | — | H | OCH₃ | O | |
| J-2 | — | 0 | H | H | — | — | — | H | CH₃ | CH₂ | |
| J-2 | — | 0 | H | H | — | — | — | H | OCH₃ | CH₂ | |
| J-3 | — | 0 | H | H | CH₃ | — | — | H | CH₃ | O | |
| J-3 | — | 0 | H | H | CH₃ | — | — | H | OCH₃ | O | |
| J-3 | — | 0 | H | H | CH₃ | — | — | H | CH₃ | CH₂ | |
| J-3 | — | 0 | H | H | CH₃ | — | — | H | OCH₃ | CH₂ | |
| J-4 | — | 0 | H | H | — | — | — | H | CH₃ | O | |
| J-4 | — | 0 | H | H | — | — | — | H | OCH₃ | O | |
| J-4 | — | 0 | H | H | — | — | — | H | CH₃ | CH₂ | |
| J-4 | — | 0 | H | H | — | — | — | H | OCH₃ | CH₂ | |
| J-5 | — | 0 | H | H | — | — | — | H | CH₃ | O | |
| J-5 | — | 0 | H | H | — | — | — | H | OCH₃ | O | |
| J-5 | — | 0 | H | H | — | — | — | H | CH₃ | CH₂ | |
| J-5 | — | 0 | H | H | — | — | — | H | OCH₃ | CH₂ | |
| J-6 | — | 0 | H | H | — | CH₃ | CH₃ | H | CH₃ | O | |
| J-6 | — | 0 | H | H | — | CH₃ | CH₃ | H | OCH₃ | O | |
| J-6 | — | 0 | H | H | — | CH₃ | CH₃ | H | CH₃ | CH₂ | |
| J-6 | — | 0 | H | H | — | CH₃ | CH₃ | H | OCH₃ | CH₂ | |
| J-7 | — | 0 | H | H | CH₃ | — | — | H | CH₃ | O | |
| J-7 | — | 0 | H | H | CH₃ | — | — | H | OCH₃ | O | |
| J-7 | — | 0 | H | H | CH₃ | — | — | H | CH₃ | CH₂ | |
| J-7 | — | 0 | H | H | CH₃ | — | — | H | OCH₃ | CH₂ | |
| J-8 | — | 0 | H | H | — | — | — | H | CH₃ | O | |
| J-8 | — | 0 | H | H | — | — | — | H | OCH₃ | O | |
| J-8 | — | 0 | H | H | — | — | — | H | CH₃ | CH₂ | |
| J-8 | — | 0 | H | H | — | — | — | H | OCH₃ | CH₂ | |
| J-9 | — | 0 | H | H | — | — | — | H | CH₃ | O | |
| J-9 | — | 0 | H | H | — | — | — | H | OCH₃ | O | |
| J-9 | — | 0 | H | H | — | — | — | H | CH₃ | CH₂ | |
| J-9 | — | 0 | H | H | — | — | — | H | OCH₃ | CH₂ | |
| J-10 | O | 0 | H | H | — | — | — | H | CH₃ | O | |
| J-10 | O | 0 | H | H | — | — | — | H | OCH₃ | O | |
| J-10 | O | 0 | H | H | — | — | — | H | CH₃ | CH₂ | |
| J-10 | O | 0 | H | H | — | — | — | H | OCH₃ | CH₂ | |
| J-22 | O | 0 | H | H | — | H | H | — | OCH₃ | CH₂ | |
| J-23 | — | — | H | H | — | H | H | — | OCH₃ | CH₂ | |
| J-24 | — | — | H | H | — | — | — | CH₃ | H | CH₃ | O | 136–141 |
| J-10 | S | 0 | H | H | — | — | — | H | CH₃ | O | |
| J-10 | S | 0 | H | H | — | — | — | H | OCH₃ | O | |
| J-10 | S | 0 | H | H | — | — | — | H | CH₃ | CH₂ | |
| J-10 | S | 0 | H | H | — | — | — | H | OCH₃ | CH₂ | |

TABLE 27b

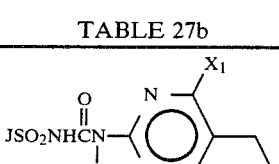

| J | W₁ | n | R | R₁ | R₂ | R₅ | R₆ | R₇ | X₁ | Y₁ | m.p. (°C.) |
|---|---|---|---|---|---|---|---|---|---|---|---|
| J-11 | O | 0 | H | H | — | — | H | H | CH₃ | O | |
| J-11 | O | 0 | H | H | — | — | H | H | OCH₃ | O | |
| J-11 | O | 0 | H | H | — | — | H | H | CH₃ | CH₂ | |
| J-11 | S | 0 | H | H | — | — | H | H | OCH₃ | CH₂ | |
| J-12 | — | 0 | H | H | — | H | H | H | CH₃ | O | |
| J-12 | — | 0 | H | H | — | H | H | H | OCH₃ | O | |
| J-12 | — | 0 | H | H | — | H | H | H | CH₃ | CH₂ | |

TABLE 27b-continued

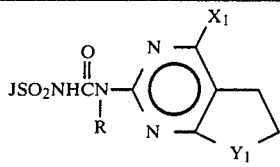

| J | W₁ | n | R | R₁ | R₂ | R₅ | R₆ | R₇ | X₁ | Y₁ | m.p. (°C.) |
|---|---|---|---|---|---|---|---|---|---|---|---|
| J-12 | — | 0 | H | H | — | H | H | H | OCH₃ | CH₂ | |
| J-13 | — | — | H | H | CH₃ | — | — | — | CH₃ | O | |
| J-13 | — | — | H | H | CH₃ | — | — | — | OCH₃ | O | |
| J-13 | — | — | H | H | CH₃ | — | — | — | OCH₃ | CH₂ | |
| J-14 | — | — | H | H | — | — | — | — | CH₃ | O | |
| J-14 | — | — | H | H | — | — | — | — | OCH₃ | O | |
| J-14 | — | — | H | H | — | — | — | — | CH₃ | CH₂ | |
| J-14 | — | — | H | H | — | — | — | — | OCH₃ | CH₂ | |
| J-15 | — | — | H | H | CH₃ | — | — | — | CH₃ | O | |
| J-15 | — | — | H | H | CH₃ | — | — | — | OCH₃ | O | |
| J-15 | — | — | H | H | CH₃ | — | — | — | CH₃ | CH₂ | |
| J-15 | — | — | H | H | CH₃ | — | — | — | OCH₃ | CH₂ | |
| J-16 | — | — | H | H | — | — | — | — | CH₃ | O | |
| J-16 | — | — | H | H | — | — | — | — | OCH₃ | O | |
| J-16 | — | — | H | H | — | — | — | — | CH₃ | CH₂ | |
| J-16 | — | — | H | H | — | — | — | — | OCH₃ | CH₂ | |
| J-17 | — | — | H | H | — | — | — | — | CH₃ | O | |
| J-17 | — | — | H | H | — | — | — | — | OCH₃ | O | |
| J-17 | — | — | H | H | — | — | — | — | CH₃ | CH₂ | |
| J-17 | — | — | H | H | — | — | — | — | OCH₃ | CH₂ | |
| J-18 | — | — | H | H | CH₃ | — | — | — | CH₃ | O | |
| J-18 | — | — | H | H | CH₃ | — | — | — | OCH₃ | O | |
| J-18 | — | — | H | H | CH₃ | — | — | — | CH₃ | CH₂ | |
| J-18 | — | — | H | H | CH₃ | — | — | — | OCH₃ | CH₂ | |
| J-19 | — | — | H | H | — | — | — | — | CH₃ | O | |
| J-19 | — | — | H | H | — | — | — | — | OCH₃ | O | |
| J-19 | — | — | H | H | — | — | — | — | CH₃ | CH₂ | |
| J-19 | — | — | H | H | — | — | — | — | OCH₃ | CH₂ | |
| J-20 | — | — | H | H | CH₃ | — | — | — | CH₃ | O | |
| J-20 | — | — | H | H | CH₃ | — | — | — | OCH₃ | O | |
| J-20 | — | — | H | H | CH₃ | — | — | — | CH₃ | CH₂ | |
| J-20 | — | — | H | H | CH₃ | — | — | — | OCH₃ | CH₂ | |
| J-21 | — | — | H | H | — | — | — | — | CH₃ | O | |
| J-21 | — | — | H | H | — | — | — | — | OCH₃ | O | |
| J-21 | — | — | H | H | — | — | — | — | CH₃ | CH₂ | |
| J-21 | — | — | H | H | — | — | — | — | OCH₃ | CH₂ | |
| J-25 | O | — | H | H | — | — | H | H | CH₃ | O | |
| J-25 | O | — | H | H | — | — | H | H | OCH₃ | O | |
| J-25 | O | — | H | H | — | — | H | H | CH₃ | CH₂ | |
| J-25 | O | — | H | H | — | — | H | H | OCH₃ | CH₂ | |
| J-25 | S | — | H | H | — | — | H | H | CH₃ | O | |
| J-25 | S | — | H | H | — | — | H | H | OCH₃ | O | |
| J-26 | — | — | H | H | CH₃ | — | H | H | CH₃ | O | |
| J-26 | — | — | H | H | CH₃ | — | H | H | OCH₃ | O | |
| J-26 | — | — | H | H | CH₃ | — | H | H | CH₃ | CH₂ | |
| J-26 | — | — | H | H | CH₃ | — | H | H | OCH₃ | CH₂ | |

TABLE 28a

| J | W₁ | n | R | R₁ | R₂ | R₃ | R₄ | R₅ | X₁ | m.p. (°C.) |
|---|---|---|---|---|---|---|---|---|---|---|
| J-1 | — | 0 | H | H | CH₃ | — | — | H | CH₃ | |
| J-1 | — | 0 | H | H | CH₃ | — | — | H | OCH₃ | |
| J-2 | — | 0 | H | H | — | — | — | H | CH₃ | |
| J-2 | — | 0 | H | H | — | — | — | H | OCH₃ | |
| J-3 | — | 0 | H | H | CH₃ | — | — | H | CH₃ | |
| J-3 | — | 0 | H | H | CH₃ | — | — | H | OCH₃ | |
| J-4 | — | 0 | H | H | — | — | — | H | CH₃ | |
| J-4 | — | 0 | H | H | — | — | — | H | OCH₃ | |

TABLE 28a-continued

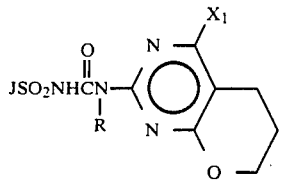

| J | W₁ | n | R | R₁ | R₂ | R₃ | R₄ | R₅ | X₁ | m.p. (°C.) |
|---|---|---|---|---|---|---|---|---|---|---|
| J-5 | — | 0 | H | H | — | — | — | H | CH₃ | |
| J-5 | — | 0 | H | H | — | — | — | H | OCH₃ | |
| J-6 | — | 0 | H | H | — | CH₃ | CH₃ | H | CH₃ | |
| J-6 | — | 0 | H | H | — | CH₃ | CH₃ | H | OCH₃ | |
| J-7 | — | 0 | H | H | CH₃ | — | — | H | CH₃ | |
| J-7 | — | 0 | H | H | CH₃ | — | — | H | OCH₃ | |
| J-8 | — | 0 | H | H | — | — | — | H | CH₃ | |
| J-8 | — | 0 | H | H | — | — | — | H | OCH₃ | |
| J-9 | — | 0 | H | H | — | — | — | H | CH₃ | |
| J-9 | — | 0 | H | H | — | — | — | H | OCH₃ | |
| J-10 | O | 0 | H | H | — | — | — | H | CH₃ | |
| J-10 | O | 0 | H | H | — | — | — | H | OCH₃ | |
| J-22 | O | 0 | H | H | — | H | H | — | OCH₃ | |
| J-23 | — | — | H | H | — | H | H | — | OCH₃ | |
| J-24 | — | — | H | H | — | — | CH₃ | H | OCH₃ | |
| J-10 | S | 0 | H | H | — | — | — | H | CH₃ | |
| J-10 | S | 0 | H | H | — | — | — | H | OCH₃ | |

TABLE 28b

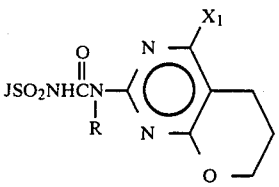

| J | W₁ | n | R | R₁ | R₂ | R₅ | R₆ | R₇ | X₁ | m.p. (°C.) |
|---|---|---|---|---|---|---|---|---|---|---|
| J-11 | O | 0 | H | H | — | — | H | H | CH₃ | |
| J-11 | O | 0 | H | H | — | — | H | H | OCH₃ | |
| J-12 | — | 0 | H | H | — | H | H | H | CH₃ | |
| J-12 | — | 0 | H | H | — | H | H | H | OCH₃ | |
| J-13 | — | — | H | H | CH₃ | — | — | — | CH₃ | |
| J-13 | — | — | H | H | CH₃ | — | — | — | OCH₃ | |
| J-14 | — | — | H | H | — | — | — | — | CH₃ | |
| J-14 | — | — | H | H | — | — | — | — | OCH₃ | |
| J-15 | — | — | H | H | CH₃ | — | — | — | CH₃ | |
| J-15 | — | — | H | H | CH₃ | — | — | — | OCH₃ | |
| J-16 | — | — | H | H | — | — | — | — | CH₃ | |
| J-16 | — | — | H | H | — | — | — | — | OCH₃ | |
| J-17 | — | — | H | H | — | — | — | — | CH₃ | |
| J-17 | — | — | H | H | — | — | — | — | OCH₃ | |
| J-18 | — | — | H | H | CH₃ | — | — | — | CH₃ | |
| J-18 | — | — | H | H | CH₃ | — | — | — | OCH₃ | |
| J-19 | — | — | H | H | — | — | — | — | CH₃ | |
| J-19 | — | — | H | H | — | — | — | — | OCH₃ | |
| J-20 | — | — | H | H | CH₃ | — | — | — | CH₃ | |
| J-20 | — | — | H | H | CH₃ | — | — | — | OCH₃ | |
| J-21 | — | — | H | H | — | — | — | — | CH₃ | |
| J-21 | — | — | H | H | — | — | — | — | OCH₃ | |
| J-25 | O | — | H | H | — | — | H | H | CH₃ | |
| J-25 | O | — | H | H | — | — | H | H | OCH₃ | |
| J-25 | S | — | H | H | — | — | H | H | CH₃ | |
| J-25 | S | — | H | H | — | — | H | H | OCH₃ | |
| J-26 | — | — | H | H | CH₃ | — | H | H | CH₃ | |
| J-26 | — | — | H | H | CH₃ | — | H | H | OCH₃ | |

TABLE 29a

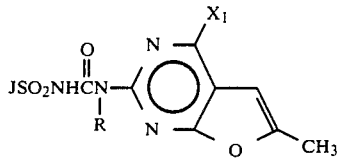

| J | W₁ | n | R | R₁ | R₂ | R₃ | R₄ | R₅ | X₁ | m.p. (°C.) |
|---|---|---|---|---|---|---|---|---|---|---|
| J-1 | — | 0 | H | H | CH₃ | — | — | H | CH₃ | 220–222 |
| J-1 | — | 0 | H | H | CH₃ | — | — | H | OCH₃ | |
| J-2 | — | 0 | H | H | — | — | — | H | CH₃ | |
| J-2 | — | 0 | H | H | — | — | — | H | OCH₃ | |
| J-3 | — | 0 | H | H | CH₃ | — | — | H | CH₃ | |
| J-3 | — | 0 | H | H | CH₃ | — | — | H | OCH₃ | |
| J-4 | — | 0 | H | H | — | — | — | H | CH₃ | |
| J-4 | — | 0 | H | H | — | — | — | H | OCH₃ | |
| J-5 | — | 0 | H | H | — | — | — | H | CH₃ | |
| J-5 | — | 0 | H | H | — | — | — | H | OCH₃ | |
| J-6 | — | 0 | H | H | — | CH₃ | CH₃ | H | CH₃ | |
| J-6 | — | 0 | H | H | — | CH₃ | CH₃ | H | OCH₃ | |
| J-7 | — | 0 | H | H | CH₃ | — | — | H | CH₃ | |
| J-7 | — | 0 | H | H | CH₃ | — | — | H | OCH₃ | |
| J-8 | — | 0 | H | H | — | — | — | H | CH₃ | |
| J-8 | — | 0 | H | H | — | — | — | H | OCH₃ | |
| J-9 | — | 0 | H | H | — | — | — | H | CH₃ | |
| J-9 | — | 0 | H | H | — | — | — | H | OCH₃ | |
| J-10 | O | 0 | H | H | — | — | — | H | CH₃ | |
| J-10 | O | 0 | H | H | — | — | — | H | OCH₃ | |
| J-22 | O | 0 | H | H | — | H | H | — | OCH₃ | |
| J-23 | — | — | H | H | — | H | H | — | OCH₃ | |
| J-24 | — | — | H | H | — | — | CH₃ | H | OCH₃ | |

TABLE 29b

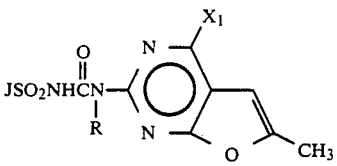

| J | W₁ | n | R | R₁ | R₂ | R₅ | R₆ | R₇ | X₁ | m.p. (°C.) |
|---|---|---|---|---|---|---|---|---|---|---|
| J-11 | O | 0 | H | H | — | — | H | H | CH₃ | |
| J-11 | O | 0 | H | H | — | — | H | H | OCH₃ | |
| J-12 | — | 0 | H | H | — | H | H | H | CH₃ | |
| J-12 | — | 0 | H | H | — | H | H | H | OCH₃ | |
| J-13 | — | — | H | H | CH₃ | — | — | — | CH₃ | |
| J-13 | — | — | H | H | CH₃ | — | — | — | OCH₃ | |
| J-14 | — | — | H | H | — | — | — | — | CH₃ | |
| J-14 | — | — | H | H | — | — | — | — | OCH₃ | |
| J-15 | — | — | H | H | CH₃ | — | — | — | CH₃ | |
| J-15 | — | — | H | H | CH₃ | — | — | — | OCH₃ | |
| J-16 | — | — | H | H | — | — | — | — | CH₃ | |
| J-16 | — | — | H | H | — | — | — | — | OCH₃ | |
| J-17 | — | — | H | H | — | — | — | — | CH₃ | |
| J-17 | — | — | H | H | — | — | — | — | OCH₃ | |
| J-18 | — | — | H | H | CH₃ | — | — | — | CH₃ | |
| J-18 | — | — | H | H | CH₃ | — | — | — | OCH₃ | |
| J-19 | — | — | H | H | — | — | — | — | CH₃ | |
| J-19 | — | — | H | H | — | — | — | — | OCH₃ | |
| J-20 | — | — | H | H | CH₃ | — | — | — | CH₃ | |
| J-20 | — | — | H | H | CH₃ | — | — | — | OCH₃ | |
| J-21 | — | — | H | H | — | — | — | — | CH₃ | |
| J-21 | — | — | H | H | — | — | — | — | OCH₃ | |
| J-25 | O | — | H | H | — | — | H | H | CH₃ | |
| J-25 | O | — | H | H | — | — | H | H | OCH₃ | |
| J-26 | — | — | H | H | CH₃ | — | H | H | CH₃ | |
| J-26 | — | — | H | H | CH₃ | — | H | H | OCH₃ | |

TABLE 30a

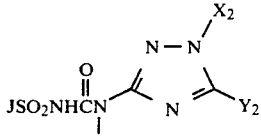

| J | W₁ | n | R | R₁ | R₂ | R₃ | R₄ | R₅ | X₂ | Y₂ | m.p. (°C.) |
|---|---|---|---|---|---|---|---|---|---|---|---|
| J-1 | — | 0 | H | H | CH₃ | — | — | H | CH₃ | CH₃ | |
| J-1 | — | 0 | H | H | CH₃ | — | — | H | CH₃ | OCH₃ | 208–210 |
| J-1 | — | 0 | H | H | CH₃ | — | — | H | CH₃ | OCH₂CH₃ | |
| J-1 | — | 0 | H | H | CH₃ | — | — | H | CH₃ | SCH₃ | |
| J-2 | — | 0 | H | H | — | — | — | H | CH₃ | CH₃ | |
| J-2 | — | 0 | H | H | — | — | — | H | CH₃ | OCH₃ | |
| J-2 | — | 0 | H | H | — | — | — | H | CH₃ | OCH₂CH₃ | |
| J-2 | — | 0 | H | H | — | — | — | H | CH₃ | SCH₃ | |
| J-3 | — | 0 | H | H | CH₃ | — | — | H | CH₃ | CH₃ | |
| J-3 | — | 0 | H | H | CH₃ | — | — | H | CH₃ | OCH₃ | |
| J-3 | — | 0 | H | H | CH₃ | — | — | H | CH₃ | OCH₂CH₃ | |
| J-3 | — | 0 | H | H | CH₃ | — | — | H | CH₃ | SCH₃ | |
| J-4 | — | 0 | H | H | — | — | — | H | CH₃ | CH₃ | |
| J-4 | — | 0 | H | H | — | — | — | H | CH₃ | OCH₃ | |
| J-4 | — | 0 | H | H | — | — | — | H | CH₃ | OCH₂CH₃ | |
| J-4 | — | 0 | H | H | — | — | — | H | CH₃ | SCH₃ | |
| J-5 | — | 0 | H | H | — | — | — | H | CH₃ | CH₃ | |
| J-5 | — | 0 | H | H | — | — | — | H | CH₃ | OCH₃ | |
| J-5 | — | 0 | H | H | — | — | — | H | CH₃ | OCH₂CH₃ | |
| J-5 | — | 0 | H | H | — | — | — | H | CH₃ | SCH₃ | |
| J-6 | — | 0 | H | H | — | CH₃ | CH₃ | H | CH₃ | CH₃ | |
| J-6 | — | 0 | H | H | — | CH₃ | CH₃ | H | CH₃ | OCH₃ | |
| J-6 | — | 0 | H | H | — | CH₃ | CH₃ | H | CH₃ | OCH₂CH₃ | |
| J-6 | — | 0 | H | H | — | CH₃ | CH₃ | H | CH₃ | SCH₃ | |
| J-7 | — | 0 | H | H | CH₃ | — | — | H | CH₃ | CH₃ | |
| J-7 | — | 0 | H | H | CH₃ | — | — | H | CH₃ | OCH₃ | |
| J-7 | — | 0 | H | H | CH₃ | — | — | H | CH₃ | OCH₂CH₃ | |
| J-7 | — | 0 | H | H | CH₃ | — | — | H | CH₃ | SCH₃ | |
| J-8 | — | 0 | H | H | — | — | — | H | CH₃ | CH₃ | |
| J-8 | — | 0 | H | H | — | — | — | H | CH₃ | OCH₃ | |
| J-8 | — | 0 | H | H | — | — | — | H | CH₃ | OCH₂CH₃ | |
| J-8 | — | 0 | H | H | — | — | — | H | CH₃ | SCH₃ | |
| J-9 | — | 0 | H | H | — | — | — | H | CH₃ | CH₃ | |
| J-9 | — | 0 | H | H | — | — | — | H | CH₃ | OCH₃ | |
| J-9 | — | 0 | H | H | — | — | — | H | CH₃ | OCH₂CH₃ | |
| J-9 | — | 0 | H | H | — | — | — | H | CH₃ | SCH₂ | |
| J-10 | O | 0 | H | H | — | — | — | H | CH₃ | CH₃ | |
| J-10 | O | 0 | H | H | — | — | — | H | CH₃ | OCH₃ | |
| J-10 | O | 0 | H | H | — | — | — | H | CH₃ | OCH₂CH₃ | |
| J-10 | O | 0 | H | H | — | — | — | H | CH₃ | SCH₃ | |
| J-22 | O | 0 | H | H | — | H | H | — | CH₃ | OCH₃ | |
| J-23 | — | — | H | H | — | H | H | — | CH₃ | OCH₃ | |
| J-24 | — | — | H | H | — | — | CH₃ | H | CH₃ | OCH₃ | |

TABLE 30b

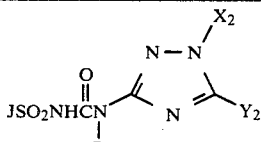

| J | W₁ | n | R | R₁ | R₂ | R₅ | R₆ | R₇ | X₂ | Y₂ | m.p. (°C.) |
|---|---|---|---|---|---|---|---|---|---|---|---|
| J-11 | O | 0 | H | H | — | — | H | H | CH₃ | CH₃ | |
| J-11 | O | 0 | H | H | — | — | H | H | CH₃ | OCH₃ | |
| J-11 | O | 0 | H | H | — | — | H | H | CH₃ | OCH₂CH₃ | |
| J-11 | O | 0 | H | H | — | — | H | H | CH₃ | SCH₃ | |
| J-12 | — | 0 | H | H | — | H | H | H | CH₃ | CH₃ | |
| J-12 | — | 0 | H | H | — | H | H | H | CH₃ | OCH₃ | |
| J-12 | — | 0 | H | H | — | H | H | H | CH₃ | OCH₂CH₃ | |
| J-12 | — | 0 | H | H | — | H | H | H | CH₃ | SCH₃ | |
| J-13 | — | — | H | H | CH₃ | — | — | — | CH₃ | CH₃ | |
| J-13 | — | — | H | H | CH₃ | — | — | — | CH₃ | OCH₃ | |
| J-13 | — | — | H | H | CH₃ | — | — | — | CH₃ | OCH₂CH₃ | |
| J-13 | — | — | H | H | CH₃ | — | — | — | CH₃ | SCH₃ | |
| J-14 | — | — | H | H | — | — | — | — | CH₃ | CH₃ | |
| J-14 | — | — | H | H | — | — | — | — | CH₃ | OCH₃ | |
| J-14 | — | — | H | H | — | — | — | — | CH₃ | OCH₂CH₃ | |
| J-14 | — | — | H | H | — | — | — | — | CH₃ | SCH₃ | |
| J-15 | — | — | H | H | CH₃ | — | — | — | CH₃ | CH₃ | |

TABLE 30b-continued

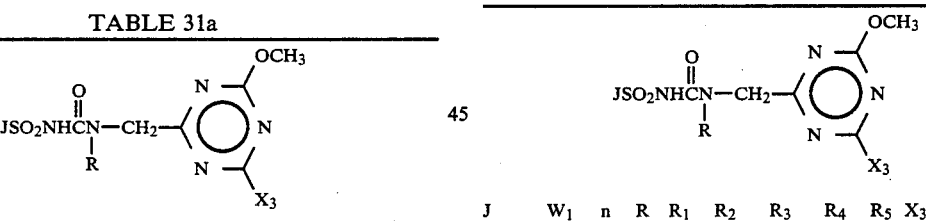

| J | W₁ | n | R | R₁ | R₂ | R₅ | R₆ | R₇ | X₂ | Y₂ | m.p. (°C.) |
|---|---|---|---|---|---|---|---|---|---|---|---|
| J-15 | — | — | H | H | CH₃ | — | — | — | CH₃ | OCH₃ | |
| J-15 | — | — | H | H | CH₃ | — | — | — | CH₃ | OCH₂CH₃ | |
| J-15 | — | — | H | H | CH₃ | — | — | — | CH₃ | SCH₃ | |
| J-16 | — | — | H | H | — | — | — | — | CH₃ | CH₃ | |
| J-16 | — | — | H | H | — | — | — | — | CH₃ | OCH₃ | |
| J-16 | — | — | H | H | — | — | — | — | CH₃ | OCH₂CH₃ | |
| J-16 | — | — | H | H | — | — | — | — | CH₃ | SCH₃ | |
| J-17 | — | — | H | H | — | — | — | — | CH₃ | CH₃ | |
| J-17 | — | — | H | H | — | — | — | — | CH₃ | OCH₃ | |
| J-17 | — | — | H | H | — | — | — | — | CH₃ | OCH₂CH₃ | |
| J-17 | — | — | H | H | — | — | — | — | CH₃ | SCH₃ | |
| J-18 | — | — | H | H | CH₃ | — | — | — | CH₃ | CH₃ | |
| J-18 | — | — | H | H | CH₃ | — | — | — | CH₃ | OCH₃ | |
| J-18 | — | — | H | H | CH₃ | — | — | — | CH₃ | OCH₂CH₃ | |
| J-18 | — | — | H | H | CH₃ | — | — | — | CH₃ | SCH₃ | |
| J-19 | — | — | H | H | — | — | — | — | CH₃ | CH₃ | |
| J-19 | — | — | H | H | — | — | — | — | CH₃ | OCH₃ | |
| J-19 | — | — | H | H | — | — | — | — | CH₃ | OCH₂CH₃ | |
| J-19 | — | — | H | H | — | — | — | — | CH₃ | SCH₂ | |
| J-20 | — | — | H | H | CH₃ | — | — | — | CH₃ | CH₃ | |
| J-20 | — | — | H | H | CH₃ | — | — | — | CH₃ | OCH₃ | |
| J-20 | — | — | H | H | CH₃ | — | — | — | CH₃ | OCH₂CH₃ | |
| J-20 | — | — | H | H | CH₃ | — | — | — | CH₃ | SCH₃ | |
| J-21 | — | — | H | H | — | — | — | — | CH₃ | CH₃ | |
| J-21 | — | — | H | H | — | — | — | — | CH₃ | OCH₃ | |
| J-21 | — | — | H | H | — | — | — | — | CH₃ | OCH₂CH₃ | |
| J-21 | — | — | H | H | — | — | — | — | CH₃ | SCH₂ | |
| J-25 | O | — | H | H | — | — | H | H | CH₃ | CH₃ | |
| J-25 | O | — | H | H | — | — | H | H | CH₃ | OCH₃ | |
| J-25 | O | — | H | H | — | — | H | H | CH₃ | OCH₂CH₃ | |
| J-25 | O | — | H | H | — | — | H | H | CH₃ | SCH₃ | |
| J-26 | — | — | H | H | CH₃ | — | H | H | CH₃ | CH₃ | |
| J-26 | — | — | H | H | CH₃ | — | H | H | CH₃ | OCH₃ | |
| J-26 | — | — | H | H | CH₃ | — | H | H | CH₃ | OCH₂CH₃ | |
| J-26 | — | — | H | H | CH₃ | — | H | H | CH₃ | SCH₃ | |

TABLE 31a

JSO₂NHCN(R)—CH₂—[ring with OCH₃, N, N, X₃]

| J | W₁ | n | R | R₁ | R₂ | R₃ | R₄ | R₅ | X₃ | m.p. (°C.) |
|---|---|---|---|---|---|---|---|---|---|---|
| J-1 | — | 0 | H | H | CH₃ | — | — | H | CH₃ | |
| J-1 | — | 0 | H | H | CH₃ | — | — | H | OCH₃ | |
| J-2 | — | 0 | H | H | — | — | — | H | CH₃ | |
| J-2 | — | 0 | H | H | — | — | — | H | OCH₃ | |
| J-3 | — | 0 | H | H | CH₃ | — | — | H | CH₃ | |
| J-3 | — | 0 | H | H | CH₃ | — | — | H | OCH₃ | |
| J-4 | — | 0 | H | H | — | — | — | H | CH₃ | |
| J-4 | — | 0 | H | H | — | — | — | H | OCH₃ | |
| J-5 | — | 0 | H | H | — | — | — | H | CH₃ | |
| J-5 | — | 0 | H | H | — | — | — | H | OCH₃ | |
| J-6 | — | 0 | H | H | — | CH₃ | CH₃ | H | CH₃ | |
| J-6 | — | 0 | H | H | — | CH₃ | CH₃ | H | OCH₃ | |
| J-7 | — | 0 | H | H | CH₃ | — | — | H | CH₃ | |
| J-7 | — | 0 | H | H | CH₃ | — | — | H | OCH₃ | |
| J-8 | — | 0 | H | H | — | — | — | H | CH₃ | |
| J-8 | — | 0 | H | H | — | — | — | H | OCH₃ | |
| J-9 | — | 0 | H | H | — | — | — | H | CH₃ | |
| J-9 | — | 0 | H | H | — | — | — | H | OCH₃ | |
| J-10 | O | 0 | H | H | — | — | — | H | CH₃ | |
| J-10 | O | 0 | H | H | — | — | — | H | OCH₃ | |
| J-22 | O | 0 | H | H | — | H | H | — | CH₃ | |
| J-23 | — | — | H | H | — | H | H | — | CH₃ | |

TABLE 31a-continued

| J | W₁ | n | R | R₁ | R₂ | R₃ | R₄ | R₅ | X₃ | m.p. (°C.) |
|---|---|---|---|---|---|---|---|---|---|---|
| J-24 | — | — | H | H | — | — | CH₃ | H | CH₃ | |

TABLE 31b

| J | W₁ | n | R | R₁ | R₂ | R₅ | R₆ | R₇ | X₃ | m.p. (°C.) |
|---|---|---|---|---|---|---|---|---|---|---|
| J-11 | O | 0 | H | H | — | — | H | H | CH₃ | |
| J-11 | O | 0 | H | H | — | — | H | H | OCH₃ | |
| J-12 | — | 0 | H | H | — | H | H | H | CH₃ | |
| J-12 | — | 0 | H | H | — | H | H | H | OCH₃ | |
| J-13 | — | — | H | H | CH₃ | — | — | — | CH₃ | |
| J-13 | — | — | H | H | CH₃ | — | — | — | OCH₃ | |
| J-14 | — | — | H | H | — | — | — | — | CH₃ | |
| J-14 | — | — | H | H | — | — | — | — | OCH₃ | |
| J-15 | — | — | H | H | CH₃ | — | — | — | CH₃ | |

TABLE 31b-continued $$JSO_2NHCN-CH_2-\underset{R}{\overset{O}{\|}}\left\langle\bigcirc\right\rangle\underset{N}{\overset{N \longrightarrow}{\underset{X_3}{\longrightarrow}}}OCH_3$$

| J    | $W_1$ | n | R | $R_1$ | $R_2$ | $R_5$ | $R_6$ | $R_7$ | $X_3$ | m.p. (°C.) |
|------|-------|---|---|-------|-------|-------|-------|-------|-------|------------|
| J-15 | —     | — | H | H     | $CH_3$ | —    | —    | —    | $OCH_3$ | |
| J-16 | —     | — | H | H     | —     | —    | —    | —    | $CH_3$  | |
| J-16 | —     | — | H | H     | —     | —    | —    | —    | $OCH_3$ | |
| J-17 | —     | — | H | H     | —     | —    | —    | —    | $CH_3$  | |
| J-17 | —     | — | H | H     | —     | —    | —    | —    | $OCH_3$ | |
| J-18 | —     | — | H | H     | $CH_3$ | —    | —    | —    | $CH_3$  | |
| J-18 | —     | — | H | H     | $CH_3$ | —    | —    | —    | $OCH_3$ | |
| J-19 | —     | — | H | H     | —     | —    | —    | —    | $CH_3$  | |
| J-19 | —     | — | H | H     | —     | —    | —    | —    | $OCH_3$ | |
| J-20 | —     | — | H | H     | $CH_3$ | —    | —    | —    | $CH_3$  | |
| J-20 | —     | — | H | H     | $CH_3$ | —    | —    | —    | $OCH_3$ | |
| J-21 | —     | — | H | H     | —     | —    | —    | —    | $CH_3$  | |
| J-21 | —     | — | H | H     | —     | —    | —    | —    | $OCH_3$ | |
| J-25 | O     | — | H | H     | —     | —    | H    | H    | $CH_3$  | |
| J-25 | O     | — | H | H     | —     | —    | H    | H    | $OCH_3$ | |
| J-26 | —     | — | H | H     | $CH_3$ | —    | H    | H    | $CH_3$  | |
| J-26 | —     | — | H | H     | $CH_3$ | —    | H    | H    | $OCH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 32

|  | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–7ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EAMPLE 10

Wettable Powder

| | |
|---|---|
| N—[(4-chloro-6-methoxypyrimidin-2-yl)aminocarbonyl]-2,3-dihydro-2-methyl-1,2-benzisothiazole-7-sulfonamide, 1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 11

Wettable Powder

| | |
|---|---|
| N—[(4,6-dimethoxypyrimidin-2-yl)aminocarbonyl]-2,3-dihydro-2-methyl-1,2-benzisothiazole-7-sulfonamide, 1,1-dioxide | 50% |
| sodium alkylnaphthalenesulfonate | 2% |
| low viscosity methyl cellulose | 2% |

| | |
|---|---|
| -continued | |
| diatomaceous earth | 46% |

The ingredients are blended, coarsely hammer-milled and then air-milled to produce particles essentially all below 10 microns in diameter. The product is reblended before packaging.

EXAMPLE 12

Granule

| | |
|---|---|
| Wettable Powder of Example 11 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 13

Extruded Pellet

| | |
|---|---|
| N—[(4-methoxy-6-methylpyrimidin-2-yl)aminocarbonyl]-2,3-dihydro-2-propyl-1,2-benzisothiazole-7-sulfonamide, 1,1-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

Oil Suspension

| | |
|---|---|
| N—[(4,6-dimethoxy-1,3,5-triazin-2-yl)aminocarbonyl]-3,4-dihydro-2-methyl-2H—1,2-benzothiazine-8-sulfonamide, 1,1-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 15

Wettable Powder

| | |
|---|---|
| N—[(4-methoxy-6-methylpyrimidin-2-yl)aminocarbonyl]-2,3-dihydro-2-(1-methylethyl)-1,2-benzisothiazole-7-sulfonamide, 1,1-dioxide | 20% |
| sodium alkylnaphthalenesulfonate | 4% |
| sodium ligninsulfonate | 4% |
| low viscosity methyl cellulose | 3% |

| | |
|---|---|
| -continued | |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 16

Low Strength Granule

| | |
|---|---|
| N—[(4,6-dimethoxypyrimidin-2-yl)aminocarbonyl]-1,3-dihydro-3-oxoisobenzofuran-4-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 17

Aqueous Suspension

| | |
|---|---|
| N—[(4-methoxy-6-methyl-1,3,5-triazin-2-yl)aminocarbonyl]-2,3-dihydro-2-(1-methylethyl)-1,2-benzisothiazole-7-sulfonamide, 1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 18

Solution

| | |
|---|---|
| N—[(4-methoxy-6-methyl-1,3,5-triazin-2-yl)aminocarbonyl]-2,3-dihydro-2-methyl-1,2-benzisothiazole-7-sulfonamide, 1,1-dioxide, sodium salt | 5% |
| water | 95% |

The salt is added directly to the water with stirring to produce the solution, which may then be packaged for use.

EXAMPLE 19

Low Strength Granule

| | |
|---|---|
| N—[(4-methoxy-6-methylpyrimidin-2-yl)aminocarbonyl]-1,3-dihydro-2-methyl-1-oxo-1H—isoindole-7-sulfonamide, | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 20

Granule

| | |
|---|---|
| N—[(4-methoxy-6-methyl-1,3,5-triazin-2-yl)aminocarbonyl]-2,3-dihydro-2-ethyl-1,2-benzisothiazole-7-sulfonamide, 1,1-dioxide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 21

High Strength Concentrate

| | |
|---|---|
| N—[(4-chloro-6-methoxypyrimidin-2-yl)aminocarbonyl]-2,3-dihydro-2-methyl-1,2-benzisothiazole-7-sulfonamide, 1,1-dioxide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 22

Wetable Powder

| | |
|---|---|
| N—[(4-chloro-6-methoxypyrimidin-2-yl)aminocarbonyl]-2,3-dihydro-2-methyl-1,2-benzisothiazole-7-sulfonamide, 1,1-dioxide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 23

Wettable Powder

| | |
|---|---|
| N—[(4,6-dimethoxypyrimidin-2-yl)aminocarbonyl]-2,3-dihydro-2-methyl-1,2-benzisothiazole-7-sulfonamide, 1,1-dioxide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 24

Oil Suspension

| | |
|---|---|
| N—[(4-methoxymethyl-6-methylpyrimidin-2-yl)aminocarbonyl]-2,3-dihydro-2-methyl-1,2-benzisothiazole-7-sulfonamide, 1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures, or on fallow land. Alternatively, some of the subject compounds should be useful for the selective pre- or post-emergence weed control in crops, especially wheat, cotton and soy- beans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.001 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types. They also may be used in combination with mefluidide.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), sicklepod (Cassia obtusifolia), morningglory Ipomoea sp.), cocklebur (Xanthium pensylvanicum), sorghum, corn, soybean, sugar beet, rice, wheat, purple nutsedge (Cyperus rotundus) tubers, and in certain cases, cotton were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effects;
L=lodging;
U=unusual pigmentation;
X=axillary stimulation; and
6Y=abscised flowers or buds.

The data show that most of the compounds tested highly active herbicides with growth modifying properties and that some of the compounds tested provide selective weed control in crops such as wheat, cotton and soybeans.

Compounds

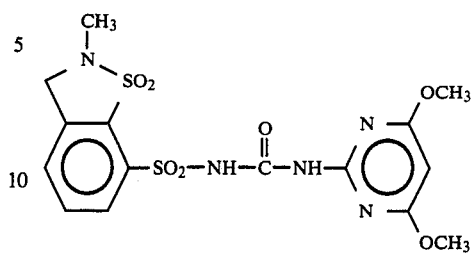

Compound 1

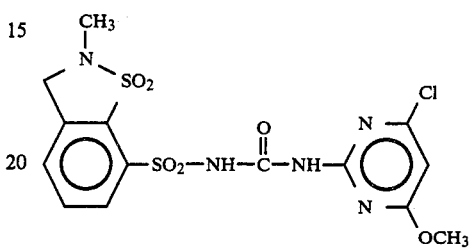

Compound 2

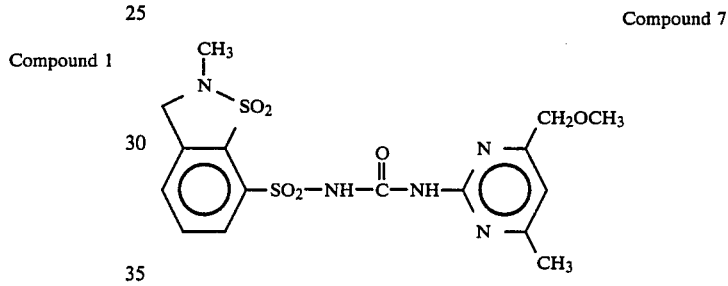

Compound 3

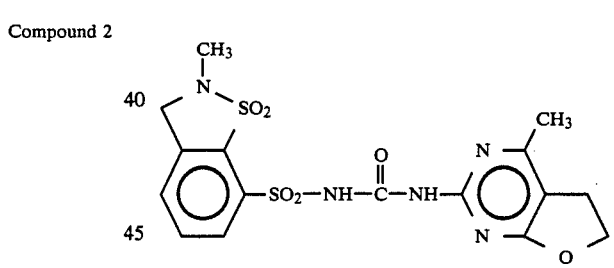

Compound 4

-continued
Compounds

Compound 5

Compound 6

Compound 7

Compound 8

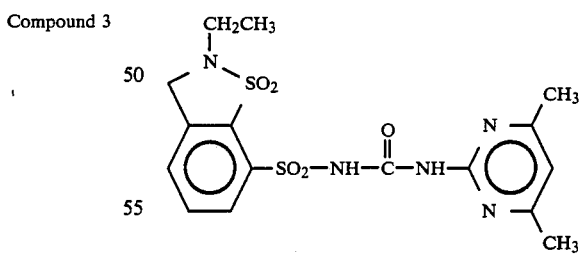

Compound 9

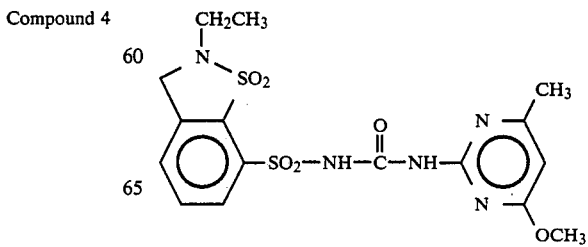

Compound 10

-continued
Compounds
Compound 11
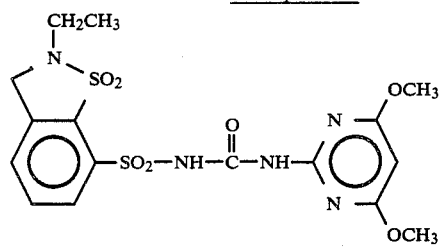
Compound 12
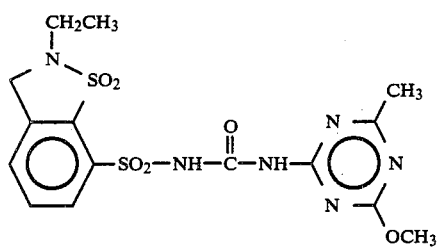
Compound 13
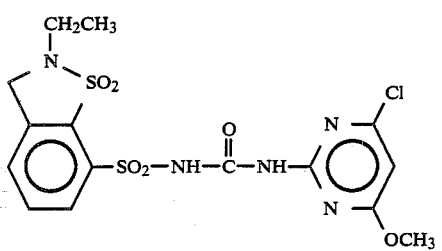
Compound 14
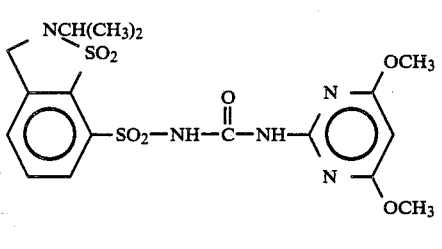
Compound 15
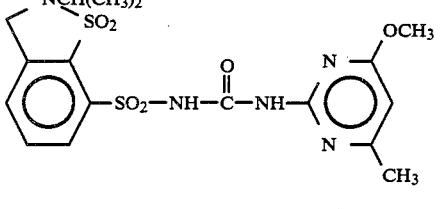
Compound 16
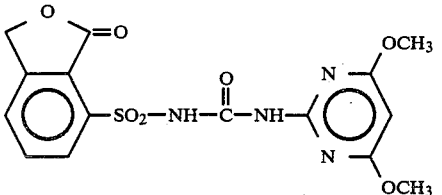
Compound 17
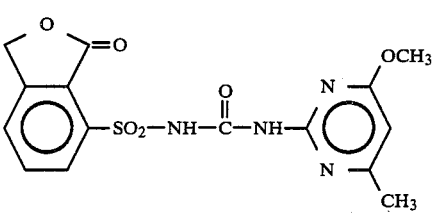
-continued
Compounds
Compound 18
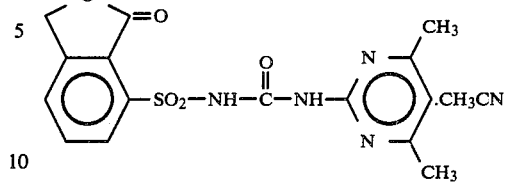
Compound 19
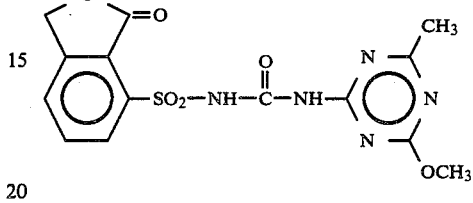
Compound 20
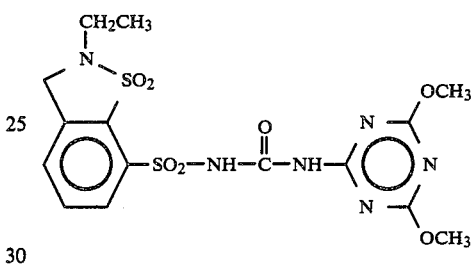
Compound 21
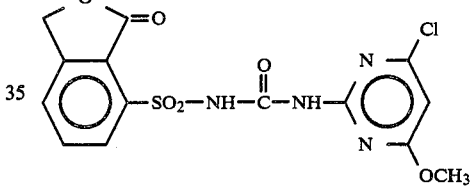
Compound 22
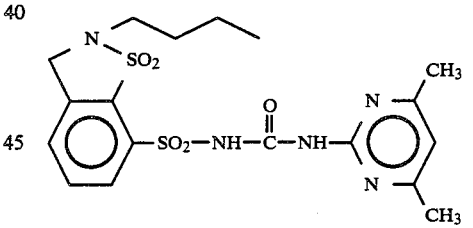
Compound 23
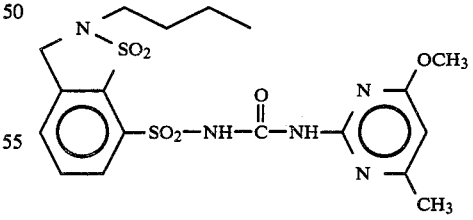
Compound 24
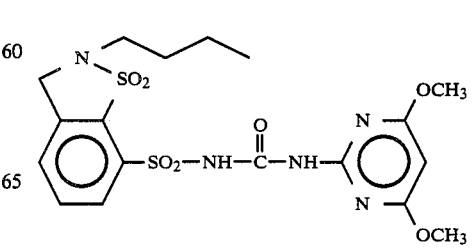

-continued
Compounds
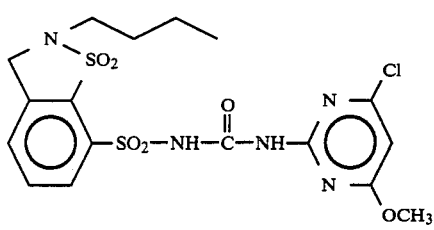<br>
Compound 25
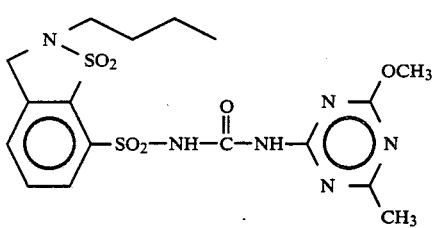<br>
Compound 26
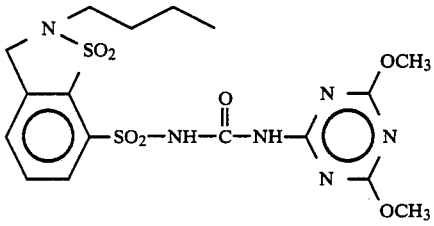<br>
Compound 27
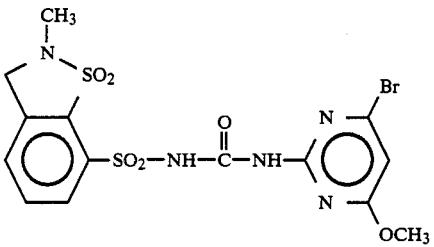<br>
Compound 28
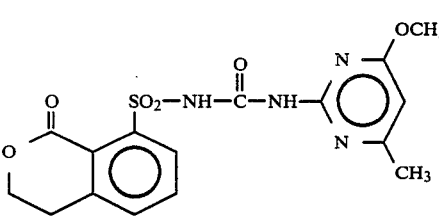<br>
Compound 29
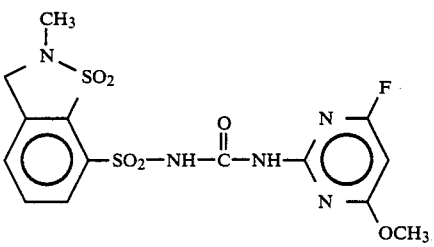<br>
Compound 30
-continued
Compounds
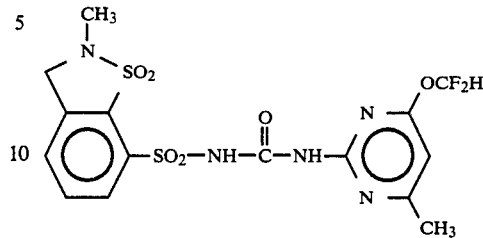<br>
Compound 31
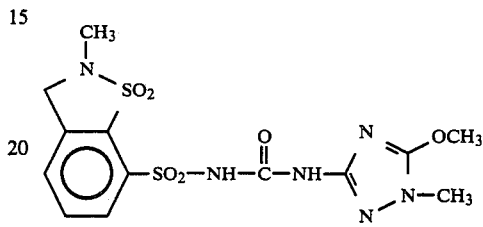<br>
Compound 32
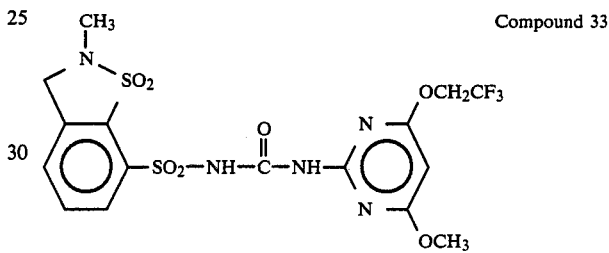<br>
Compound 33
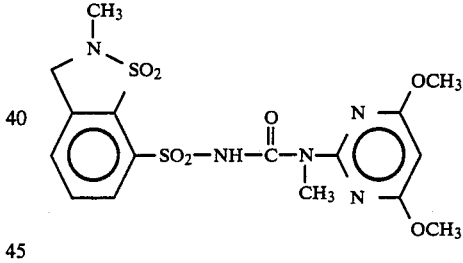<br>
Compound 34
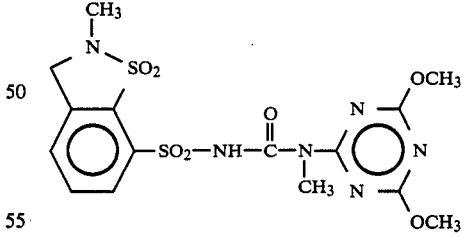<br>
Compound 35
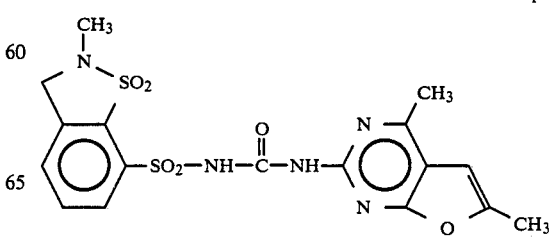<br>
Compound 36

-continued
Compounds
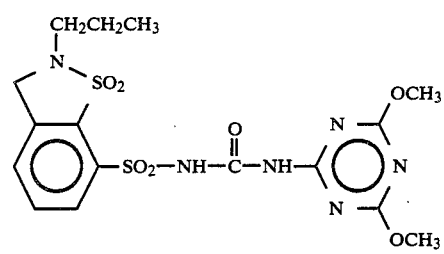 Compound 37
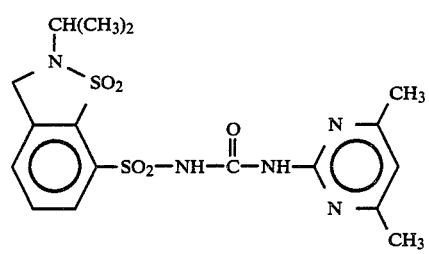 Compound 38
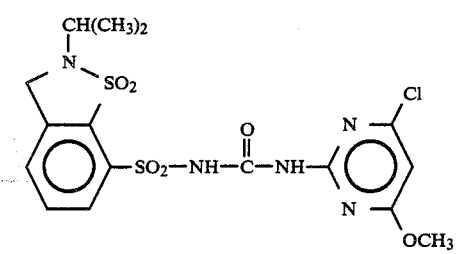 Compound 39
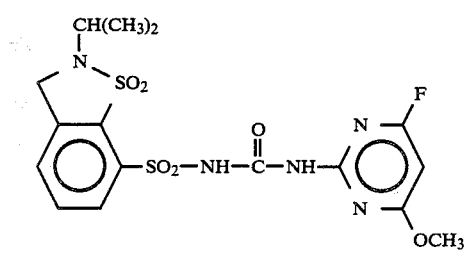 Compound 40
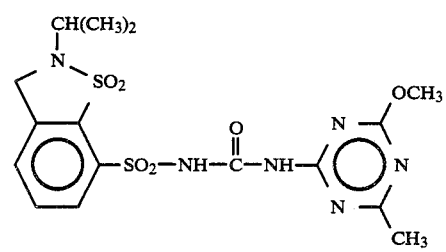 Compound 41
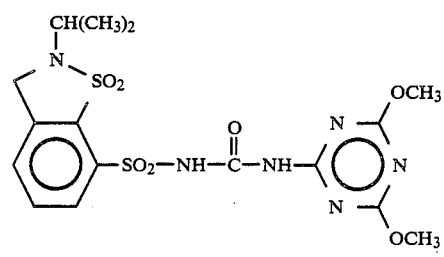 Compound 42
-continued
Compounds
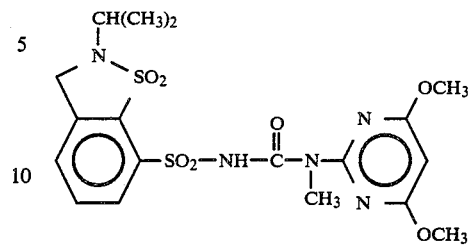 Compound 43
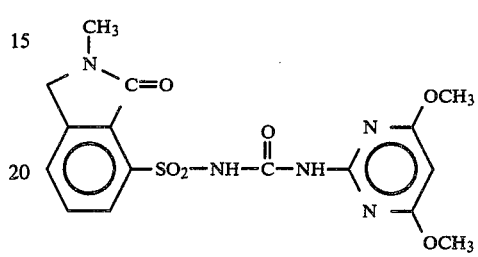 Compound 44
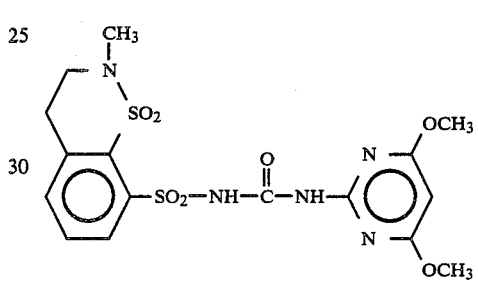 Compound 45
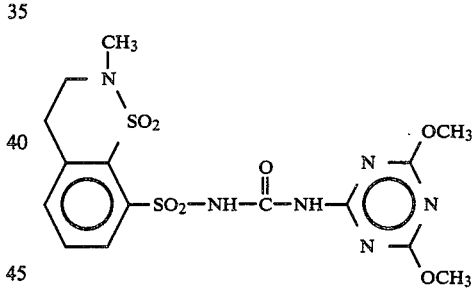 Compound 46
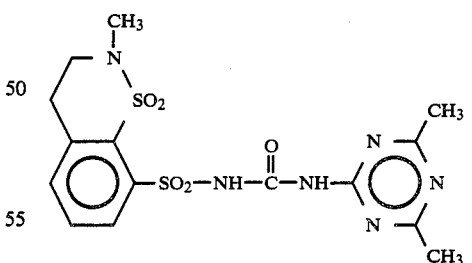 Compound 47
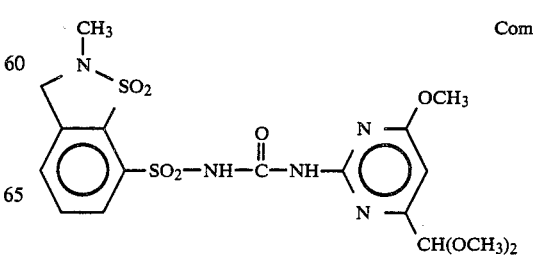 Compound 48

-continued
Compounds
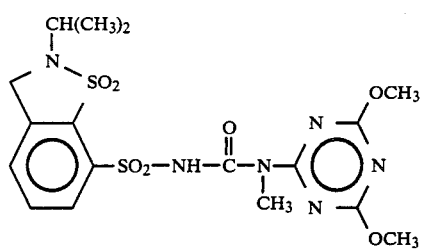
Compound 49
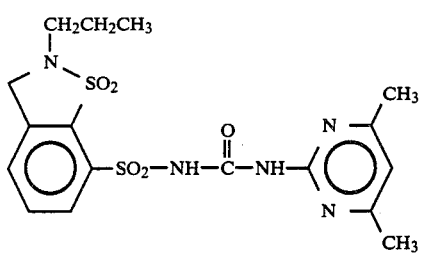
Compound 50
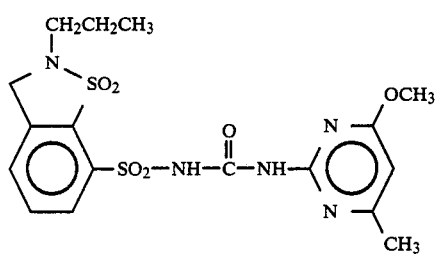
Compound 51
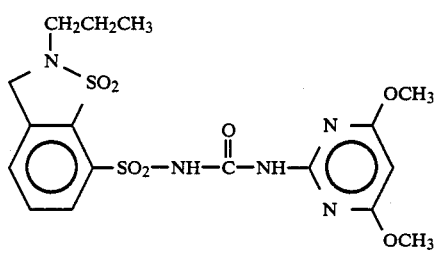
Compound 52
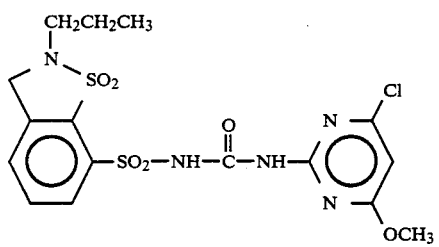
Compound 53
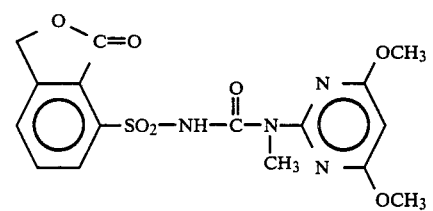
Compound 54
-continued
Compounds
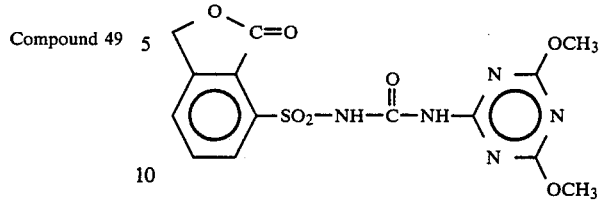
Compound 55
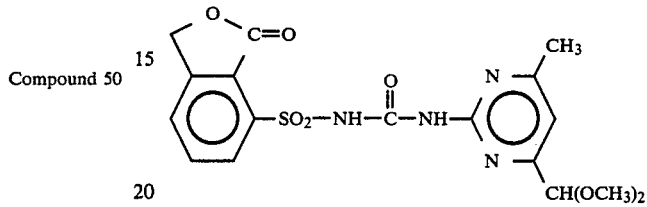
Compound 56
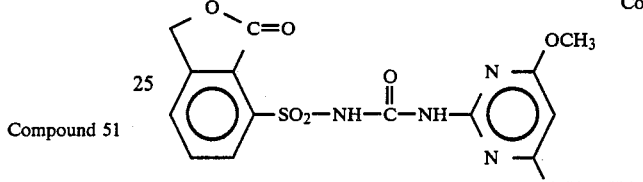
Compound 57
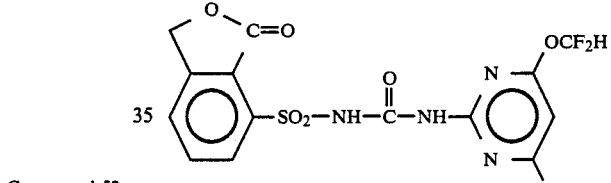
Compound 58
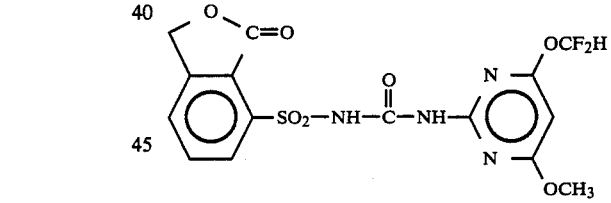
Compound 59
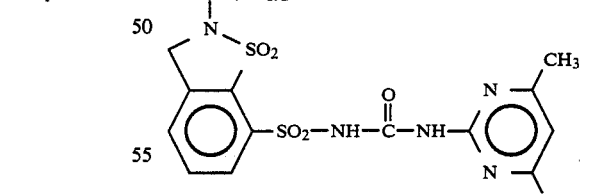
Compound 60
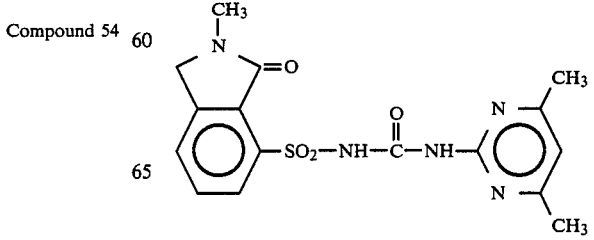
Compound 61

-continued
Compounds
Compound 62
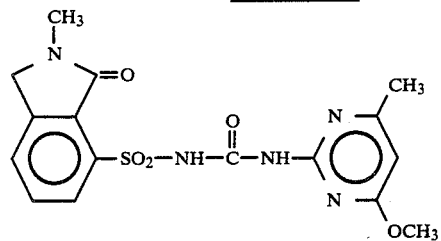
Compound 63
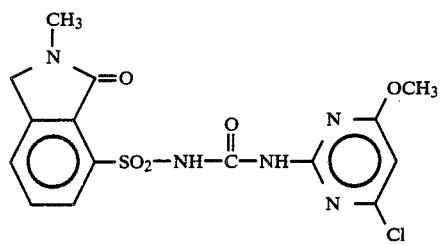
Compound 64
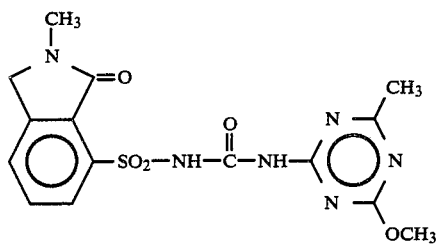
Compound 65
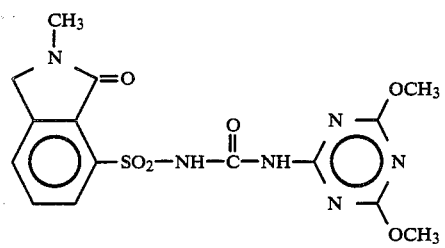
Compound 66
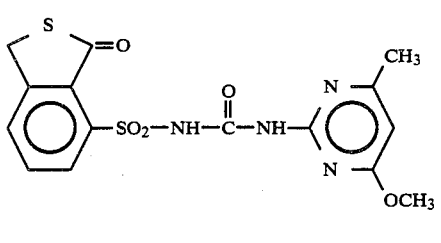
Compound 67
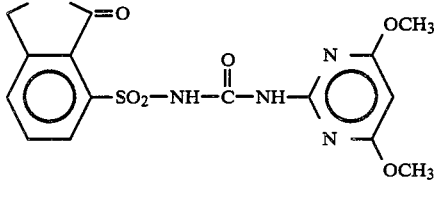
Compound 68
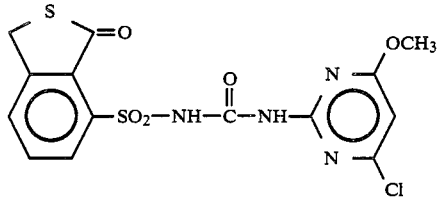
-continued
Compounds
Compound 69
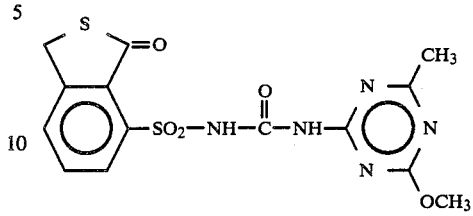
Compound 70
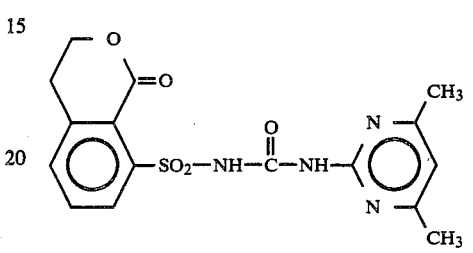
Compound 71
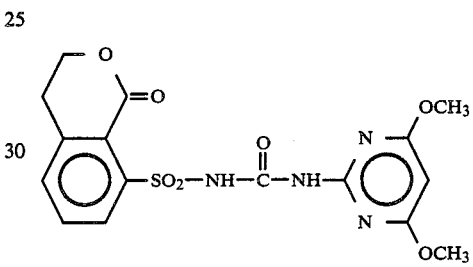
Compound 72
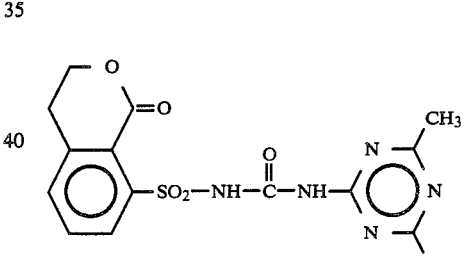
Compound 73
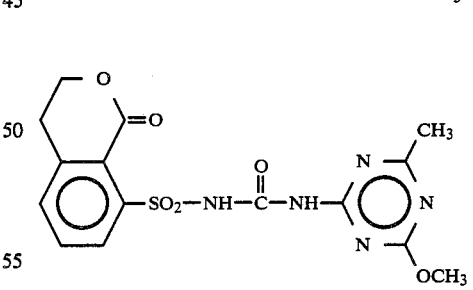
Compound 74
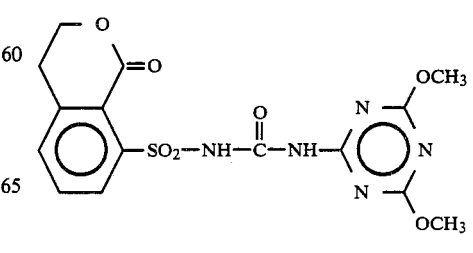

-continued
Compounds
Compound 75
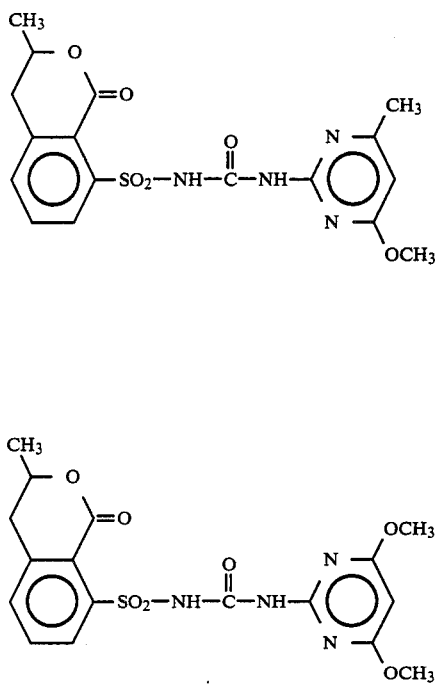
Compound 76
Compound 77
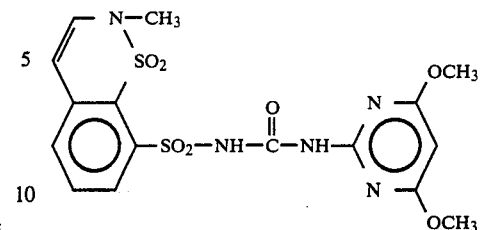
Compound 78
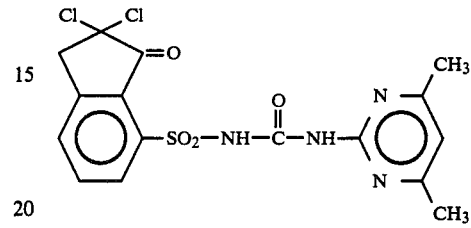
Compound 79
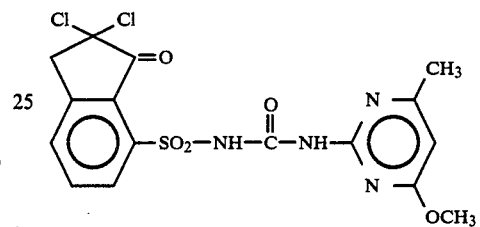
Compound 80
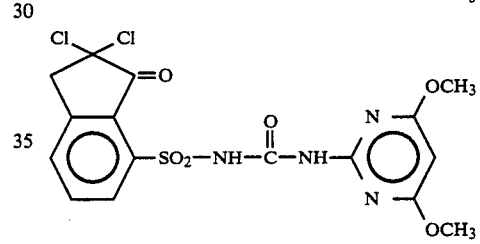

TABLE A

POST-EMERGENCE

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 | Cmpd. 12 | Cmpd. 13 | Cmpd. 14 | Cmpd. 15 | Cmpd. 16 | Cmpd. 17 | Cmpd. 18 |
|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 |
| Bush bean | 6C,9G,6Y | 9C | 4C,SG | 4C,7G,6Y | 9C | 2C,7H | 5C,9G | 5C,9G,6Y | 4C,9H | 5C,9G | 9C | 4C,8G | 4C,8G | 3C,9G | 3C,9H | 10C | — | — |
| Cotton | 5C,9G | 6C,9G | 4C,5H | 2C,3H | 6C,9G | 9C | 5C,9G | 2C,2H | 4C,8H | 10C | 9C | 5C,9G | 4C,8G | 4C,8G | 5C,9G | 9C | 10C | 10C |
| Morningglory | 6C,9G | 10C | 2C,5G | 1C | 9C | 10C | 9C | 2C,4G | 3C,7H | 9C | 9C | 2C,5G | 8H | 4C,9G | 4C,9H | 10C | 10C | 10C |
| Cocklebur | 6C,9G | 9C | 2C,7G | 4G | 9C | 10C | 5C,8G | 1C,3G | 3C,7H | 9C | 10C | 3C,5H | 3G | 9G | 5C,9G | 9C | 9C | 9C |
| Sicklepod | 4C,9G | 9C | 2C,5G | 3C,8G | 9C | 10C | 3C,9G | 3C | 4C,9G | 10C | 2C,9G | 5G | 3C,7G | 5G | 9G | 4C,9G | 10C | 5C,9G |
| Nutsedge | 9C | 9C | 6G | 8G | 10C | 9C | 6C,9G | 2C,5G | 5C,9G | 9C | 9C | 2C,5G | 5C,9G | 5C,9G | 9G | 5C,9G | 10C | 5C,9G |
| Crabgrass | 9C | 9C | 2G | 2C,7G | 9C | 4C,9G | 9C | 5C,9H | 9C | 9C | 9C | 5C,9H | 5C,9G | 5C,9H | 6C,9G | 9C | 9C | 9C |
| Barnyardgrass | 9C | 9C | 5C,9H | 9C | 9C | 9C | 9C | 2C,9G | 5C,9G | 10C | 9C | 6C,9G | 2C,9G | 6C,9G | 6C,9G | 9C | 9C | 9C |
| Wild Oats | 9C | 9C | 3C,9G | 9C | 9C | 4C,9G | 9C | 5C,5G | 6C,9G | 10C | 9C | 5U,9C | 5C,9G | 4U,9G | 6C,9G | 9C | 9C | 9C |
| Wheat | 9C | 9C | 9C | 4C,9G | 9C | 9C | 9C | 5C,9G | 4C,9H | 10C | 9C | 5C,9G | 10C | 5C,9G | 5U,9C | 9C | 5U,9C | 10C |
| Corn | 9C | 9C | 6C,9G | 9C | 9C | 9C | 5U,9C | 3U,9G | 5C,9G | 10C | 10C | 5U,9G | 2C,5G | 4U,9G | 5U,9G | 9C | 6C,9G | 6C,9G |
| Soybean | 5C,9G | 6C,9G | 3C,9G | 3C,8H | 6C,9G | 3C,9G | 5C,9G | 4C,9G | 2C,9G,5X | 5C,9G | 9C | 3C,8G,5X | 5C,9G | 5C,9G | 5C,9G | 9C | 9C | 9C |
| Rice | 6C,9G | 6C,9G | 3C,9G | 5C,9G | 9C | 6C,9G | 5C,9G | 5C,9G | 6C,9G | 10C | 6C,9G | 5C,9G | 2C,9G | 3C,9G | 5C,9G | 4U,9C | 4U,9G | 9C |
| Sorghum | 5C,9G | 9C | 2C,9G | 2C,9G | 10C | 9C | 4C,9G | 4C,9G | 4C,9H | 9C | 9C | 9C | 5C,9G | 2C,9G | 5C,9G | 9C | 9C | 9C |
| Sugar beet | 9C | 9C | 3C,9G | 4C,9G | 9C | 9C | 9C | 2C,8G | 4C,8H | 9C | 9C | 9C | 9C | 5C,9G | 9C | 9C | 9C | 9C |

| | Cmpd. 19 | Cmpd. 20 | Cmpd. 21 | Cmpd. 22 | Cmpd. 23 | Cmpd. 24 | Cmpd. 25 | Cmpd. 26 | Cmpd. 27 | Cmpd. 28 | Cmpd. 29 | Cmpd. 30 | Cmpd. 31 | Cmpd. 32 | Cmpd. 33 | Cmpd. 34 | Cmpd. 35 | Cmpd. 36 | Cmpd. 37 | Cmpd. 38 |
|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 2000 | 50 | 50 | 50 | 50 | 50 | 50 |
| Bush bean | — | — | — | — | — | — | — | — | — | — | — | — | — | 50 | — | — | — | — | — | — |
| Cotton | 10C | 3C,7H | 9C | 0 | 4C,9H | 4C,9G | 2C,7H | 0 | 0 | 9C | 5C,9G | 6C,9G | 3C,8H | 0 | 1C | 9C | 9C | 4G | 4C,8G | 0 |
| Morningglory | 10C | 2C,5H | 9C | 0 | 4C,8H | 5C,9G | 2C,4G | 3G | 0 | 9C | 9C | 5C,9G | 3C,7H | 0 | 2C | 4C,9H | 5C,9G | 2C,8G | 2C,8H | 1C |
| Cocklebur | 10C | 2G | 9C | 3G | 2C,7H | 4C,9H | 4G | 3G | 0 | 9C | 10C | 10C | 7G | 0 | 1C | 5C,9G | 2C,7G | 6G | 2C,5G | 2G |
| Sicklepod | 10C | 3C,6H | 9C | 0 | 4C,8G | 2C,6G | 2C,2G | 3G | 0 | 5C,9G | 9C | 2C,8G | 8G | 0 | 0 | 2C,4G | 10C | 3C,8H | 4C,4H | 1C |
| Nutsedge | 9C | 1C,2G | 9C | 0 | 2C,8G | 9C | 0 | 2G | 0 | 10C | 10C | 2C | 2C,5G | 0 | 2C,6H | 4C,9G | 1C | 9C | 3G | 2C,8G |
| Crabgrass | 9C | 3G | 6C,9G | 2C,5G | 4C,9G | 9C | 2C,8G | 5C,9H | 3C,8H | 10C | 10C | 5C,9G | 4G | 0 | 2C,7G | 0 | 3C,8H | 3C,9G | 9C | 2C,9H |
| Barnyardgrass | 5C,9G | 3C,9H | 9C | 5C,9H | 9C | 9C | 9C | 9C | 3C,8G | 9C | 10C | 9C | 2C,8G | 0 | 2C,7G | 3C,8H | 3C,9G | 3C,9G | 9C | 5C,9G |
| Wild Oats | 5C,9G | 5C,9G | 5C,9G | 9C | 9C | 2C,5G | 9C | 0 | 2C,8H | 10C | 5C,9G | 9C | 2C,3G | 0 | 2C,4G | 3C,9G | 9C | 5C,9G | 5C,9G | 9C |
| Wheat | 6C,9G | 5C,9G | 10C | 2C,8G | 2G | 10C | 6C,9H | 3U,9G | 1C | 10C | 5C,9G | 9C | 2C,6H | 0 | 9C | 3H,5L | 3H,5L | 10C | 6U,9C | 2C,7H |
| Corn | 9C | 5C,9G | 10C | 2U,8H | 7U,9C | 4C,9G | 4C,8H | 0 | 2C,7G | 2C,7G | 10C | 5C,9G | 2H | 0 | 0 | 4C,8H | 4C,9G | 3C,8H | 4C,8G | 2G |
| Soybean | 6C,9G | 2C,2H | 5C,9G | 2C,5G | 5C,9G | 4C,9G | 4C,9G | 5C,9G | 1C | 9C | 5C,9G | 5C,9G | 5G | 0 | 4C,9G | 4C,9G | 4C,9G | 3C,9G | 5C,9G | 5C,9G |
| Rice | 6C,9G | 5C,9G | 6C,9G | 4C,9G | 6C,9G | 5C,9G | 7C,9H | 5C,9G | 7G | 9C | 6C,9G | 6C,9G | 9C | 0 | 0 | 3H,5L | 9G | 5U,9G | 4C,9G | 2G |
| Sorghum | 9C | 3C,9H | 9C | 4C,9H | 5C,9G | 8C,9H | 3C,9H | 3C,9H | 2C,6G | 9C | 4C,9H | 2C,9G | 2C,8H | 0 | 2C,9G | 2U,9H | 9G | 2C,9G | 4C,9G | 4C,9H |
| Sugar beet | 9C | 3C,7G | 9C | 0 | 0 | 9C | 1C | 0 | 0 | 9C | 4C,8H | 9C | 0 | 0 | 2C,3G | 9C | 5C,9G | 9C | 9C | 0 |

| | Cmpd. 39 | Cmpd. 40 | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 | Cmpd. 50 | Cmpd. 51 | Cmpd. 52 | Cmpd. 53 | Cmpd. 54 | Cmpd. 55 | Cmpd. 56 | Cmpd. 57 | Cmpd. 58 | Cmpd. 59 |
|---|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 | 50 | 50 | 50 |
| Bush bean | — | 0 | 0 | — | — | — | — | — | — | — | — | — | — | — | — | — | — | — | — | — | — |
| Cotton | 5G | 3H | 5G | 0 | 2C,5G | 6C,9G | 10C | 5C,9G | 0 | 3C,8H | 7G | 3G | 3C,9G | 3C,9G | 3C,9G | 2C,7G | 3C,9G | 2C,8G | 2C,8H | 5G | 10C |
| Morningglory | 2C,3G | 4G | 5G | 0 | 2G | 6C,9G | 5C,9G | 4C,9G | 1C | 2C,7H | 2C,5G | 1H | 3C,8G | 9C | 3C,8G | 3C,7G | 3C,7G | 4C,8G | 5C,9G | 3C,7G | 9C |
| Cocklebur | 4G | 1C | 3G | 0 | 3G | 9C | 9C | 9C | 1C | 3C,8H | 4H | 2C,4G | 3C,9G | 9C | 4C,9H | 3G | 5C,9G | 5C,9G | 5C,9G | 2C,8H | 9C |
| Sicklepod | 4G | 5C,9G | 2G | 0 | 2G | 9C | 3C,9G | 5C,9G | 0 | 1C,3H | 2G | 2C | 3C,9G | 9C | 3C,7G | 1C,2G | 3C,8G | 3C,9H | 2C,5G | 6G | 9C |
| Nutsedge | 8G | 5C,9G | 2G | 0 | 5G | 9C | 9C | 2C,8G | 0 | 3C,8G | 0 | 2C | 6C,9G | 9C | 9C | 1C,3G | 2C,8G | 6C,9G | 2C,9G | 8G | 9C |
| Crabgrass | 5C,9G | 9C | 3G | 2G | 6G | 3C,9G | 9C | 2C,9G | 0 | 2H | 7H | 3C,9G | 9C | 9C | 9C | 2G | 2C,8H | 3C,8G | 2C,3H | 7G | 9C |
| Barnyardgrass | 9C | 9C | 4C,9H | 3C,8H | 2C,8H | 5C,9G | 9C | 9C | 3C,7H | 4C,9H | 7H | 9C | 9C | 9C | 9C | 9C | 0 | 4C,9H | 4C,9H | 3C,9H | 7G |
| Wild Oats | 10C | 6C,9G | 4C,9H | 3C,9H | 4C,8H | 9C | 9C | 9C | 2C,5G | 5C,9G | 3C,9H | 3C,9G | 9C | 9C | 10C | 9C | 2C,8H | 5C,9G | 9C | 2C,6G | 10C |
| Wheat | 5C,9G | 9C | 9C | 3C,9H | 9C | 10C | 10C | 10C | 6G | 9C | 5C,9H | 9C | 9C | 9C | 9C | 9C | 0 | 5C,9G | 9C | 2C,6G | 4C,9G |
| Corn | 8G | 9G | 9C | | 9C | | | | | | | | | | | | 0 | | | | 9C |

TABLE A-continued

| | Cmpd. 60 | Cmpd. 61 | Cmpd. 62 | Cmpd. 63 | Cmpd. 64 | Cmpd. 65 | Cmpd. 66 | Cmpd. 67 | Cmpd. 68 | Cmpd. 69 | Cmpd. 70 | Cmpd. 71 | Cmpd. 72 | Cmpd. 73 | Cmpd. 74 | Cmpd. 75 | Cmpd. 76 | Cmpd. 77 | Cmpd. 78 | Cmpd. 79 | Cmpd. 80 |
|---|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 | 50 | 50 | 50 |
| Corn | 5C,9G | 5C,9G | 2C,8H | 0 | 2C,9H | 9C | 9C | 10C | 2C,8H | 2C,8H | 2C,5H | 3U,9G | 5C,9G | 9C | 9C | 2C,9H | 9C | 9C | 9C | 3C,9H | 10C |
| Soybean | 1C,3H | 2C,8H | 0 | 0 | 6H | 5C,9H | 9C | 5C,9G | 0 | 2C,7G | 2C,7H | 2C,7G | 3C,9G | 9C | 4C,9G | 3C,8H | 4C,9H | 4C,9H | 4C,9G | 2H,5G | 9C |
| Rice | 9C | 9C | 3C,9G | 9C | 4C,9G | 6C,9G | 6C,9G | 5C,9G | 3C,8H | 6C,9G | 4C,9G | 5C,9G | 6C,9G | 9C | 9C | 4C,9G | 9C | 9C | 4C,9G | 3C,9G | 9C |
| Sorghum | 9C | 3C,9G | 3C,9H | 0 | 3C,8H | 9C | 9C | 10C | 3C,8H | 6H | 2C,7H | 4U,9G | 3C,9H | 9C | 10C | 3C,6G | 10C | 4C,9H | 5C,9G | 3U,9G | 10C |
| Sugar beet | 4C,9H | 2C,5G | 0 | 0 | 2C | 9C | 9C | 9C | 1C | 2C,5G | 2C,3G | 9C | 2C,6G | 9C | 9C | 5C,9G | 9C | 9C | 9C | 5G | 9C |

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 | Cmpd. 12 | Cmpd. 13 | Cmpd. 14 | Cmpd. 15 | Cmpd. 16 | Cmpd. 17 | Cmpd. 18 | Cmpd. 19 | Cmpd. 20 |
|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 | 50 | 50 |
| Bush bean | — | — | — | — | — | — | — | — | — | — | — | — | — | — | — | — | — | — | — | — |
| Cotton | 0 | 0 | 9G,2C | 8G | 2C,5G | 9C | 9C | 1C | 3C,8H | 9C | 10E | 7H | 9C | 9G | 2C,6H | 9H | 9H | 10C | 9G | 4C,9H |
| Morningglory | 0 | 0 | 3C,8H | 1C,3G | 2C | 9H | 9H | 2C,8G | 2C,3H | 9H | 9H | 0 | 9H | 8H | 2C,3H | 9H | 9H | 5G | 9H | 4C,9H |
| Cocklebur | 0 | 0 | 9C | 3C,9H | 3C,7H | 9G | 9G | 3G | 5C,8G | 10E | 9G | 7G | 8G | 8G | 8G | 9C | 9C | 5G | 9C | 4C,9H |
| Sicklepod | 0 | 0 | 3C,8H | 3G | 2C | 10E | 10E | 1C,3G | 5C,9G | 10E | 10E | 2G | 10E | 10E | 10E | 10E | 10E | 3C,6G | 3C,8G | 4C,9G |
| Nutsedge | 0 | 2C,8G | 2C,8H | 5G | 4G | 5C,9H | 4C,9G | 2C | 10C | 9C | 6C,9H | 4C,5G | 5C,9G | 4C,8G | 5C,8G | 5C,9G | 5C,9G | 2C | 5C,9H | 3C,8G |
| Crabgrass | 0 | 0 | 2C,8G | 0 | 0 | 3C,9H | 9H | 2C,7G | 10C | 9C | 10H | 2C,9G | 10H | 2C,8H | 9H | 9H | 9C | 2C | 10H | 9G |
| Barnyardgrass | 0 | 2H | 4C,9G | 1C | 1H | 2C,8G | 5C,9H | 2C,8G | 10C | 9C | 5C,9G | 4C,2G | 5C,9G | 2C,8G | 4C,9H | 5C,9G | 2C,8H | 2C,8G | 6C,9H | 2C,9H |
| Wild Oats | 0 | 0 | 5C,9H | 2C,8G | 2C,9H | 4C,9H | 4C,9H | 2C,7H | 10C | 10C | 10H | 2C,9G | 4C,9H | 2C,8G | 3C,9G | 9H | 5C,9G | 3C,9H | 5C,9H | 5C,9G |
| Wheat | 0 | 0 | 5C,9H | 8G | 1H | 2C,8G | 9H | 1C | 2U,8G | 5C,9H | 9H | 1C,2H | 5C,9H | 1C,1H | 2C,4G | 5C,9H | 10H | 5C,9G | 10H | 2C,9H |
| Corn | 0 | 2H | 4G | 3C,9G | 3G | 4C,9H | 5C,9H | 3C | 3C | 10C | 10H | 1C,2H | 2C,3G | 10E | 3C,9G | 9C | 9H | 9C | 6C,9H | 3G |
| Soybean | 0 | 10E | 9C | 10E | 2C,9H | 6H | 4C,5H | 5C,9H | 10E | 10E | 9H | 10E | 10E | 10E | 2C,4G | 10E | 10E | 10E | 9H | 10E |
| Rice | 0 | 10E | 10E | 2C,9G | 10C | 6C,9H | 10E | 2C,5G | 10E | 10C | 10E | 5C,9H | 7C,9H | 2C,9G | 4C,9G | 10E | 10E | 4U,9G | 10E | 5C,9H |
| Sorghum | 5C,9H | 6C,9H | 4C,9G | 2C,9H | 4C,9H | 6C,9H | 5C,9H | 7G | 10C | 10C | 2C,9G | 5G | 9C | 3C,9G | 4C,9G | 9H | 10C | 4C,9G | 10C | 8G |
| Sugar beet | 5C,9G | 5C,9G | 8G | 4C,9G | 5C,9G | 10E | 3C,9G | — | 3C,4H | — | — | — | 8G | 2G | 3G | 9H | 5C,9G | 3C,9G | 3C,9G | 3G |
| Cotton | — | — | — | — | 3C,8H | — | — | — | — | — | — | — | — | — | — | — | — | — | — | — |

PRE-EMERGENCE

| | Cmpd. 21 | Cmpd. 22 | Cmpd. 23 | Cmpd. 24 | Cmpd. 25 | Cmpd. 26 | Cmpd. 27 | Cmpd. 28 | Cmpd. 29 | Cmpd. 30 | Cmpd. 31 | Cmpd. 32 | Cmpd. 33 | Cmpd. 34 | Cmpd. 35 | Cmpd. 36 | Cmpd. 37 | Cmpd. 38 | Cmpd. 39 | Cmpd. 40 |
|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 / 2000 | 50 | 50 | 50 | 50 | 50 | 50 | 50 | 50 |
| Morningglory | 9H | 2C,4G | 4C,8H | 5C,9G | 4C,8G | 0 | 0 | 9G | 9G | 9H | 8H | 10C | 1C | 3C,8H | 2C | 2C,8G | 8H | 0 | 3G | 2C,2H |
| Cocklebur | 9H | 0 | 5C,9H | 9H | 2C,5G | 2C,3G | 0 | 9H | 2C,9H | 8H | 9H | 9H | 4H | 2C,8H | 2C,7H | 3C,9H | 9H | 0 | 3G | 6H |
| Sicklepod | 8G | 0 | 2C,5G | 3C,9H | 2C | 0 | 0 | 3G | 9C | 9G | 5C,9G | 9C | 0 | 8G | 2G | 4C,8G | 6G | 9C | 3G | 8G |
| Nutsedge | 2C,9G | 2C,9H | 8G | 10E | 8G | 3G | 0 | 3G | 10E | 10E | 7G | 3G | 0 | 0 | 10E | 10E | 3G | 10E | 8G | 0 |
| Crabgrass | 10E | 10E | 6G | 10E | 3C,8G | 2H | 2G | 10E | 6C,9H | 4C,7G | 6G | 0 | 8G | 0 | 0 | 3C,7G | 0 | 9C | 3C,8G | 7G |
| Barnyardgrass | 2C,5G | 2C,6G | 6G | 5C,9G | 3C,9H | — | 0 | 5C,9G | 9C | 5C,9H | 4C,8H | 4C,6H | 0 | 0 | 0 | 5C,9H | 3C,8H | 1H | 3C,8H | 4G |
| Wild oats | 5C,9H | 2C | 3C,8H | 5C,9H | — | — | — | 6C,9H | 6C,9H | — | — | — | 0 | 0 | 0 | — | — | — | 4C,9H | 3C,8H |

TABLE A-continued

| | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 | Cmpd. 50 | Cmpd. 51 | Cmpd. 52 | Cmpd. 53 | Cmpd. 54 | Cmpd. 55 | Cmpd. 56 | Cmpd. 57 | Cmpd. 58 | Cmpd. 59 | Cmpd. 60 |
|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 | 50 | 50 |
| Wild Oats | 2C,9G | 5C,9H | 5C,9H | 6C,9H | 3C,8G | 4G | 5G | 2C,5G | 6C,9H | 5C,9H | 9G | 9G | 0 | 0 | 0 | 3C,9G | 5C,9G | 2C | 3C,9G | 2C,9G |
| Wheat | 4C,9H | 5G | 0 | 2C,9G | 3C,8G | 0 | 0 | 0 | 10E | 5C,9H | 9G | 9H | 0 | 0 | 0 | 10H | 3C,9G | 0 | 7G | 8G |
| Corn | 2C,9H | 3C,8H | 2C,9G | 5C,9H | 3C,9H | 2C,7G | 3G | 3C,9H | 10E | 9H | 3C,9H | 3U,9G | 2C,8H | 0 | 2G | 9H | 5C,9H | 2G | 9G | 3C,8G |
| Soybean | 9H | 2C | 4C,7H | 4C,8G | 3C,6H | 3C,7H | 2C,7G | 3C,6G | 9H | 2C,7H | 1C,3G | 4G | 0 | 0 | 0 | 3C,8G | 2C | 0 | 1C,3G | 2G |
| Rice | 10E | 5C,9H | 10E | 10E | 10E | 3C,7H | 0 | 10E | 10E | 10E | 10E | 3C,8G | 2C,8H | 5G | 0 | 10E | 10E | 5G | 10E | 10E |
| Sorghum | 10H | 3C,6H | 3C,9H | 2C,9H | 5C,9H | 9H | 2C,7G | 10H | 10H | 10H | 9H | 3C,9H | 8H | 2C,8G | 7H | 6C,9H | 6C,9H | 0 | 10H | 5C,9H |
| Sugar beet | 3C,9G | 5G | 3C,8H | 9C | 8G | 0 | 0 | 10E | 6C,9G | 5C,9G | 7G | 8G | 0 | 2C,8G | 2C,9H | 9G | 4C,9G | 0 | 7G | 5G |
| Cotton | 3C,9G | 1C | 6G | 9G | 6G | 0 | 0 | 9G | 9G | 9G | 10E | 8G | 0 | 2G | 2G | 8G | 7G | 0 | 2G | 1C |

| | Cmpd. 61 | Cmpd. 62 | Cmpd. 63 | Cmpd. 64 | Cmpd. 65 | Cmpd. 66 | Cmpd. 67 | Cmpd. 68 | Cmpd. 69 | Cmpd. 70 | Cmpd. 71 | Cmpd. 72 | Cmpd. 73 | Cmpd. 74 | Cmpd. 75 | Cmpd. 76 | Cmpd. 77 | Cmpd. 78 | Cmpd. 79 | Cmpd. 80 |
|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 | 50 | 50 |
| Morningglory | 2C | 0 | 3H | 9G | 9H | 9G | 1C | 0 | 0 | 3H | 9G | 9G | 8G | 9H | 0 | 9G | 9H | 8G | 9G | 0 |
| Cocklebur | 0 | 0 | 2H | 9H | 9H | 8H | 0 | 0 | 0 | 1H | 9H | 9H | 9H | 9H | 0 | 0H | 2C,8H | 2C,8H | 9H | 0 |
| Sicklepod | 0 | 0 | 0 | 8G | 9G | 9G | 0 | 0 | 0 | 0 | 8G | 8G | 7G | 9C | 0 | 6G | 1C | 8G | 5C,9G | 0 |
| Nutsedge | 0 | 0 | 0 | 5G | 10E | 8G | 0 | 0 | 0 | 0 | 3C,8H | 10E | 10E | 10E | 0 | 0 | 2C,6G | 8G | 10E | 0 |
| Crabgrass | 0 | 0 | 0 | 0 | 5C,9G | 2C,7G | 4C,6G | 0 | 0 | 0 | 5C,9H | 6C,9H | 6C,9H | 9C | 0 | 2C,2G | 2C,2G | 3C,6G | 1C,3G | 0 |
| Barnyardgrass | 2H | 0 | 0 | 0 | 9H | 3C,9H | 4C,9H | 1C | 0 | 7G | 2C,9H | 5C,9H | 6C,9H | 5C,9H | 5C,9G | 2C,3H | 2C,3H | 4C,9H | 5C,9H | 0 |
| Wild Oats | 2C,4G | 2G | 3G | 2C,6H | 5C,9H | 3C,8G | 4C,9H | 0 | 0 | 2G | 9C | 6C,9H | 4C,9G | 10E | 0 | 4C,4H | 5C,9H | 2C,8H | 5C,8G | 0 |
| Wheat | 8G | 2G | 2G | 2C,5G | 9H | 9H | 4C,9H | 3C,9H | 0 | 2C,8G | 2C,5H | 10E | 3C,8G | 9C | 5C,9G | 2C,9G | 9C | 4C,9H | 5C,9G | 0 |
| Corn | 4G | 0 | 2G | 9G | 9G | 5C,9G | 4C,9H | 9H | 0 | 2C,5H | 2C,9H | 4C,9H | 3C,9H | 5C,9H | 10E | 3C,9H | 9G | 2C,8G | 5C,9H | 0 |
| Soybean | 0 | 0 | 3G | 9G | 1C,9G | 10E | 4C,5H | 4G | 0 | 3C,7G | 4C,9H | 3C,6H | 5G | 10H | 10E | 4C,6G | 9G | 3C,9H | 3C,9H | 0 |
| Rice | 5G | 0 | 0 | 2C,3G | 2C,5G | 5C,9H | 4C,5H | 9H | 0 | 0 | 3C,6G | 3C,7H | 10E | 9C | 9H | 9H | 2C,3G | 1C,6G | 3C,8H | 0 |
| Sorghum | 2G | 0 | 0 | 5C,9H | 5C,9H | 4C,9G | 2C,6H | 2C,9H | 0 | 5C,9H | 5C,9H | 10E | 10E | 10E | 10E | 2C,9H | 5C,9H | 10E | 10E | 0 |
| Sugar beet | 0 | 0 | 0 | 5C,9G | 5C,9H | 5C,9G | 2C,8G | 3C,4H | 0 | 3C,7G | 3C,7G | 6C,9G | 6C,9G | 10C | 9G | 5C,9G | 5C,9H | 2C,8H | 9C | 0 |
| Cotton | 0 | 0 | 0 | 8G | 9G | 8G | 1C | 0 | 0 | 3G | 8G | 3C,9G | 8G | 9G | 9G | 7G | 8G | 8G | 9G | 0 |

| | Cmpd. 61 | Cmpd. 62 | Cmpd. 63 | Cmpd. 64 | Cmpd. 65 | Cmpd. 66 | Cmpd. 67 | Cmpd. 68 | Cmpd. 69 | Cmpd. 70 | Cmpd. 71 | Cmpd. 72 | Cmpd. 73 | Cmpd. 74 | Cmpd. 75 | Cmpd. 76 | Cmpd. 77 | Cmpd. 78 | Cmpd. 79 | Cmpd. 80 |
|---|---|---|---|---|---|---|---|---|---|---|---|---|---|---|---|---|---|---|---|---|
| Rate g/ha | 50 | 50 | 50 | 50 | 50 | 50 | 50 | 50 | 50 | 50 | 50 | 50 | 50 | 50 | 50 | 50 | 50 | 50 | 50 | 50 |
| Morningglory | 0 | 9G | 5G | 2C,6G | 2C,4H | 10C | 5C,9G | 9G | 5C,9G | 9C | 9C | 10C | 9C | 9H | 9C | 9C | 9C | 2C,7G | 4C,9G | 9G |
| Cocklebur | 0 | 2C,9H | 8H | 8H | 7H | 2C,9H | 4C,9H | 9H | 9H | 9C | 9H | 9H | 9H | 9H | 4C,9G | 9H | 5C,9H | 9H | 3C,9H | 9H |
| Sicklepod | 0 | 3C,6H | 4G | 5G | 3C,5G | 5C,9G | 2C,9G | 8G | 9C | 9C | 9C | 9C | 9C | 9C | 9G | 9C | 9C | 3C,8G | 5C,9G | 5C,9G |
| Nutsedge | 0 | 5G | 4G | 0 | 0 | 9G | 10E | 2C,7G | 7G | 10E | 10E | 10E | 5C,9G | 10E | 9G | 9G | 10E | 2C,5G | 2C,8G | 8G |
| Crabgrass | 0 | 3C,7G | 5G | 0 | 2C | 3C,8G | 4C,6G | 1C | 4C,9G | 6C,9H | 5C,9H | 9C | 9C | 9C | 9C | 4C,9G | 2C,5G | 2C,3H | 5C,9G | 2C,9G |
| Barnyardgrass | 0 | 3C,9H | 9H | 2C,6H | 2C,4H | 9H | 4C,9H | 3C,9H | 4C,9H | 5C,9H | 9C | 2C,9H | 9C | 5C,9H | 9C | 5C,9H | 4C,9H | 3C,9H | 5C,9H | 2C,8G |
| Wild Oats | 0 | 4C,9G | 9H | 2C,6H | 3C,7G | 9H | 4C,9H | 1C | 4C,9G | 6C,9H | 9C | 7C,9H | 9C | 9C | 9C | 9C | 9G | 2C,9G | 4C,9G | 9H |
| Wheat | 0 | 5C,9G | 1C,3G | 9G | 9G | 5C,9G | 4C,9H | 4G | 2C,5G | 2C,8G | 5C,9H | 10H | 10C | 10C | 5C,9G | 9C | 10H | 2C,9G | 10H | 2C,9H |
| Corn | 0 | 2C,9G | 2C,8G | 2C,6H | 1C,9G | 10E | 10E | 9H | 3C,9H | 10H | 10H | 10H | 10H | 9C | 10E | 5C,9H | 5C,9H | 2C,8G | 3C,9H | 4C,9H |
| Soybean | 0 | 2C,9G | 2C,9G | 2C,5G | 2C,5G | 4C,9G | 5C,9H | 4G | 3C,9H | 10H | 4C,9H | 10H | 5C,9H | 9C | 10E | 8H | 4C,9H | 2G | 3C,9H | 2C,9H |
| Rice | 0 | 2C,7H | 1H | 10E | 5C,9H | 10E | 2C,6H | 9H | 3C,9H | 9H | 10E | 3C,9H | 3C,9H | 9H | 9H | 10E | 10E | 9H | 10E | 3C,7H |
| Sorghum | 0 | 5C,9H | 10E | 2C,3G | 2C,9H | 7C,9H | 10E | 3C,9H | 7C,9H | 10E | 10E | 10E | 10E | 10E | 10E | 10H | 10E | 3C,9H | 10E | 10E |
| Sugar beet | 0 | 5C,9G | 2C,9H | 5C,9H | 5C,9H | 3C,9G | 9G | 2C,9G | 5C,9G | 10C | 10C | 10E | 10C | 10C | 9C | 6C,9G | 9C | 2C,8G | 10C | 4C,9H |
| Cotton | 0 | 8G | 5G | 5G | 2G | 9G | 9G | 8G | 9G | 9C | 9C | 9G,4C | 9G | 9C | 9G | 9C | 9C | 8G | 9G | 9G |

Test B

Two plastic bulb pans were filled with fertilized and limed Woodstown sandy loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

Test C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, corn, rice, wheat, velvetleaf (*Abutilon theophrasti*), sesbania (*Sesbania exaltata*), sicklepod (*Cassia, obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*) and wild oats (*Avena fatua*). Sugar beets were grown separately in soil in a paper cut (12 cm diameter by 13 cm deep). All plants were sprayed approximately 14 days after planting. Additional plant species are sometimes added to this standard test in order to evaluate unusual selectivity.

TABLE B

PRE-EMERGENCE ON WOODSTOWN SANDY LOAM

| | Compound 1 | | | | | Compound 2 | | | | | Compound 5 | |
|---|---|---|---|---|---|---|---|---|---|---|---|---|
| Rate g/ha | 1 | 4 | 16 | 62 | 250 | 1 | 4 | 16 | 62 | 250 | 4 | 31 |
| Crabgrass | 0 | 0 | 4G | 7G | 8G | 0 | 3G | 8G | 8G | 9G | 10C | 10C |
| Barnyardgrass | 0 | 0 | 2G | 8G | 9G | 0 | 0 | 7G | 8G | 9G | 10C | 10C |
| Sorghum | — | — | — | — | — | — | — | — | — | — | 10C | 10C |
| Wild Oats | 0 | 0 | 2G | 7G | 9G | 0 | 0 | 6G | 8G | 8G | 9G | 9G |
| Johnsongrass | 0 | 0 | 8G | 8G | 9G | 0 | 0 | 8G | 7G | 9G | 9G | 10C |
| Dallisgrass | — | — | — | — | — | — | — | — | — | — | 9G | 10C |
| Giant foxtail | 0 | 0 | 7G | 9G | 9G | 4G | 9G | 9G | 8G | 9G | 9G | 10C |
| Ky. bluegrass | — | — | — | — | — | — | — | — | — | — | 10C | 10C |
| Cheatgrass | — | — | — | — | — | — | — | — | — | — | 9G | 10C |
| Sugar beets | 0 | 3G | 7G | 7G | 9G | 6G | 7G | 8G | 9G | 9G | 10C | 10C |
| Corn | 3G | 3G | 9G | 9G | 10G | 5G | 8G | 8G | 10G | 10G | 10C | 10C |
| Mustard | — | — | — | — | — | — | — | — | — | — | 8G | 9G |
| Cocklebur | 0 | 5G | 7G | 8G | 8G | 0 | 7G | 8G | 9G | 9G | 6G | 9G |
| Pigweed | — | — | — | — | — | — | — | — | — | — | — | — |
| Nutsedge | 6G | 9G | 10G | 10G | 10G | 8G | 9G | 10G | 10G | 10G | 10C | 10C |
| Cotton | 0 | 0 | 0 | 3G | 9G | 0 | 0 | 8G | 9G | 9G | 7G | 9G |
| Morningglory | 0 | 0 | 6G | 8G | 9G | 0 | 3G | 7G | 9G | 9G | 9G | 9G |
| Sicklepod | 0 | 0 | 2G | 8G | 9G | 0 | 4G | 7G | 9G | 7G | 7G | 9G |
| Teaweed | 0 | 0 | 0 | 2G | 9G | 0 | 0 | 8G | 9G | 9G | 6G | 9G |
| Velvetleaf | 0 | 1G | 6G | 6G | 9G | 0 | 0 | 8G | 9G | 9G | 6G | 9C |
| Jimsonweed | 0 | 0 | 6G | 9G | 9G | 0 | 7G | 8G | 9G | 9G | 8G | 9G |
| Soybean | 0 | 0 | 2G | 1G | 9G | 0 | 3G | 7G | 9G | 9G | 7G,5H | 9G |
| Rice | 8G | 9G | 10G | 10G | 10G | 9G | 9G | 10G | 10G | 10G | 10C | 10C |
| Wheat | 0 | 2G | 8G | 9G | 9G | 8G | 9G | 9G | 10G | 10G | 10C | 10C |

TABLE C

Over-the-Top Soil/Foliage Treatment

| | Compound 1 | | | | Compound 2 | | | | Compound 5 | | | | |
|---|---|---|---|---|---|---|---|---|---|---|---|---|---|
| Rate g/ha | 1 | 4 | 16 | 62 | 1 | 4 | 16 | 62 | 1 | 4 | 4 | 16 | 16 | 62 |
| Soybeans | 2G | 0 | 10C | 10C | 8G | 10G | 10G | 10G | 8G | 10G | 10C | 10G | 10C | 10C |
| Velvetleaf | 0 | 8C | 9G | 9C | 0 | 9G | 9C | 9C | 8G | 10G | 9C | 10G | 10C | 10C |
| Sesbania | 2G | 2G | 7G | 7G | 5G | 7G | 8G | 10C | — | — | — | — | — | — |
| Sicklepod | 2G | 4G | 4G | 9G | 5G | 7G | 9G | 10G | 6G | 10G | 9G | 10G | 10C | 10C |
| Cotton | 3G | 3G | 4G | 7G | 0 | 8G | 9G | 10G | 7G | 10G | 10C | 10G | 10C | 10C |
| Morningglory | 3G | 8G | 9G | 10G | 7G | 9G | 9G | 10G | 5G | 9G | 8G | 10G | 9G | 10C |
| Alfalfa | — | — | — | — | — | — | — | — | — | — | — | — | — | — |
| Jimsonweed | 0 | 0 | — | — | 0 | — | — | — | 7G | 10G | 9G | 10G | 10C | 10C |
| Cocklebur | 2G | 2G | 9G | 10G | 0 | 5G | 10G | 10C | 5G | 7G | 9C | 10G | 10C | 10C |
| Sunflower | — | — | — | — | — | — | — | — | — | — | — | — | — | — |
| Mustard | — | — | — | — | — | — | — | — | — | — | — | — | — | — |

TABLE C-continued

Over-the-Top Soil/Foliage Treatment

| | | | | | | | | | | | | | | |
|---|---|---|---|---|---|---|---|---|---|---|---|---|---|---|
| Sugar beets | 8G | 10G | 10G | 10C | 7G | 10G | 10C | 10C | 10G | 10G | 10C | 10G | 10C | 10C |
| Corn | 6U | 10C | 10C | 10C | 7C | 10C | 10C | 10U | 9G | 10G | 9C | 10G | 9C | 10C |
| Crabgrass | 0 | 4G | 7G | 8G | 2G | 7G | 9C | 8C | 8G | 10G | 9G | 10G | 10C | 10C |
| Rice | 3C | 7G | 8C | 8C | 5G | 8C | 9C | 8G | 6G | 10G | 9C | 10G | 9C | 10C |
| Nutsedge | 5H | 6G | 6C | 6G | 0 | 1G | 2G | 5C | 0 | 8G | 7G | 10G | 7G | 8G |
| Barnyardgrass | 5G | 8C | 10G | 10C | 6G | — | 9C | 9C | 8G | 10G | 10C | 10G | 10C | 10C |
| Wheat | 2G | 4G | 6C | 7C | 3G | 4G | 5G | 6C | 8G | 9G | 7G | 10G | 7G | 8G |
| Giant foxtail | 3G | 6G | 6G | 7G | 4G | 7G | 8G | 7C | 8G | 9G | 10C | 10G | 10C | 10G |
| Wild Oats | 2G | 6G | 8G | 9C | 6G | 6G | 8C | 7G | 7G | 9G | 7G | 10G | 8C | 8G |
| Sorghum | — | — | — | — | — | — | — | — | — | — | — | — | — | — |
| Johnsongrass | 6U | 9U | 10C | 10C | 8U | 10U | 10U | 10U | 10G | 10G | 10C | 10G | 10C | 10C |
| Field Bindweed | — | — | — | — | — | — | — | — | — | — | — | — | — | — |

| | Compound 6 | | | | Compound 7 | | | |
|---|---|---|---|---|---|---|---|---|
| Rate g/ha | 1 | 4 | 16 | 62 | 1 | 4 | 16 | 62 |
| Soybeans | 2G | 8G | 9G | 10G | 0 | 5G | 10G | 10G |
| Velvetleaf | 4G | 8G | 9C | 9G | 1C | 5C | 8G | 8G |
| Sesbania | 6G | 7G | 8G | 10G | 2G | 4G | 7G | 8G |
| Sicklepod | 2G | 6G | 9G | 10G | 2G | 8G | 8G | — |
| Cotton | 0 | 3G | 7G | 10G | 3G | 7G | 7G | 9G |
| Morningglory | 2G | 6G | 9G | 10G | 0 | 4G | 8G | 9G |
| Alfalfa | — | — | — | — | — | — | — | — |
| Jimsonweed | 0 | 3G | 8G | — | 0 | 7G | — | — |
| Cocklebur | 0 | 0 | 5G | 10C | 0 | 3G | 6G | — |
| Sunflower | — | — | — | — | — | — | — | — |
| Mustard | — | — | — | — | — | — | — | — |
| Sugar beets | 5G | 10C | 10G | 10C | 3G | 7C | 10G | 10G |
| Corn | 6C | 9G | 10U | 10U | 4G | 7U | 10U | 10U |
| Crabgrass | 0 | 3G | 7G | 8G | 0 | 2G | 7G | 8G |
| Rice | 3G | 6G | 8C | 8C | 3G | 8G | 8C | 8C |
| Nutsedge | 0 | 0 | 4G | 4G | 0 | 0 | 4G | 3G |
| Barnyardgrass | 6C | 9G | 9G | 9G | 4G | 6G | 9G | 9G |
| Wheat | 0 | 0 | 0 | 4G | 1G | 6G | 7C | 7C |
| Giant foxtail | 0 | 0 | 5G | 6G | 3G | 5G | 7C | 8G |
| Wild Oats | 0 | 0 | 0 | 5G | 0 | 4G | 7G | 8G |
| Sorghum | — | — | — | — | — | — | — | — |
| Johnsongrass | 10U | 10U | 10U | 10U | 8U | 9U | 10C | 10C |
| Field Bindweed | — | — | — | — | — | — | — | — |

Test D

Post-emergence phase

Two round pans (25 cm diameter by 12.5 cm deep) were filled with Woodstown sandy loam soil. One pan was planted with sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Pre-emergence phase

Two round pans (25 cm diameter by 12.5 cm deep) were filled with Woodstown sandy loam soil. One pan was planted with sugar beets, nutsedge, crabgrass, sicklepod, teaweed, jimsonweed, velvetleaf and giant foxtail. The other pan was planted with wheat, cotton, rice, corn, soybeans, wild oats, cocklebur, morningglory, johnsongrass and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for response utilizing the rating system as described above for Test A. The data are given in Table D.

It will be seen that the compounds tested have utility for weed control in cotton.

TABLE D

| | PRE-EMERGENCE | | | | | | | | POST-EMERGENCE | | | | | | | |
|---|---|---|---|---|---|---|---|---|---|---|---|---|---|---|---|---|
| | Compound 14 | | | | Compound 15 | | | | Compound 14 | | | | Compound 15 | | | |
| Rate g/ha | 4 | 16 | 62 | 250 | 4 | 16 | 62 | 250 | 1 | 4 | 16 | 62 | 1 | 4 | 16 | 62 |
| Corn | 0 | 3G | 6G | 8G | 0 | 0 | 0 | 0 | 3G | 9G | 10C | 10C | 0 | 6G | 10C | 10C |
| Wheat | 0 | 2G | 8G | 9G | 0 | 0 | 8G | 10G | 0 | 3G | 8G | 8G | 0 | 0 | 9C | 10C |
| Rice | 3G | 8G | 10G | 10G | 0 | 6G | 10G | 10G | 0 | 5G | 9G | 10G | 3G | 8G | 10C | 10C |
| Soybean | 0 | 2G | 6G | 8G | 0 | 0 | 2G | 4G | 3G | 9G | 9G | 9G | 0 | 7G | 9G | 10C |
| Cotton | 0 | 3G | 4G | 6G | 0 | 0 | 0 | 0 | 0 | 2G | 3G | 4G | 0 | 0 | 0 | 0 |
| Sugar beet | 0 | 3G | 7G | 9G | 0 | 0 | 3G | 9G | 0 | 6G | 10G | 10G | 0 | 4G | 10G | 10C |
| Crabgrass | 0 | 5G | 8G | 9G | 4G | 7G | 8G | 9G | 0 | 5G | 10C | 10G | 3G | 7G | 10C | 10C |
| Johnsongrass | 0 | 3G | 9G | 9G | 0 | 3G | 7G | 8G | 0 | 5G | 9C | 10C | 0 | 3G | 10C | 10C |
| Barnyardgrass | 0 | 3G | 8G | 9G | 0 | 0 | 8G | 8G | 0 | 5G | 9C | 9C | 0 | 7G | 9C | 10C |
| Nutsedge | 0 | 2G | 7G | 9G | 0 | 0 | 8G | 0 | 0 | 0 | 4G | 6G | 0 | 0 | 5G | 6G |
| Giant Foxtail | — | — | — | — | 0 | 3G | 7G | 9G | 0 | 0 | 3G | 9G | 0 | 3G | 8G | 10C |

TABLE D-continued

| | PRE-EMERGENCE | | | | | | | | POST-EMERGENCE | | | | | | | |
|---|---|---|---|---|---|---|---|---|---|---|---|---|---|---|---|---|
| | Compound 14 | | | | Compound 15 | | | | Compound 14 | | | | Compound 15 | | | |
| Rate g/ha | 4 | 16 | 62 | 250 | 4 | 16 | 62 | 250 | 1 | 4 | 16 | 62 | 1 | 4 | 16 | 62 |
| Wild Oats | 0 | 3G | 8G | 8G | 0 | 4G | 8G | 8G | 0 | 4G | 9G | 9G | 0 | 5G | 9C | 10C |
| Cocklebur | 0 | 4G | 5G | 7G | 0 | 0 | 0 | 0 | 0 | 2G | 5G | 8G | 0 | 0 | 0 | 5G |
| Morningglory | 0 | 0 | 0 | 3G | 0 | 0 | 2G | 5G | 2G | 4G | 5G | 7G | 0 | 0 | 7G | 8G |
| Teaweed | 0 | 2G | 6G | 8G | 0 | 5G | 6G | 6G | 0 | 5G | 9G | 10G | 0 | 0 | 3G | 10C |
| Sicklepod | 0 | 4G | 4G | 5G | 0 | 0 | 4G | 9G | 0 | 3G | 7G | 8G | 0 | 5G | 10G | 10C |
| Jimsonweed | 0 | 0 | 4G | 8G | 0 | 0 | 4G | 6G | 0 | 3G | 7G | 10G | 0 | 0 | 0 | 5G |
| Velvetleaf | 0 | 0 | 0 | 3G | 0 | 0 | 0 | 0 | 0 | 3G | 3G | 8G | 0 | 0 | 7G | 8G |

Test E

This test was conducted to evaluate compounds for potential utility in fallow weed control. Plastic pots lined with polyethylene bags were filled with Woodstown sandy loam and planted to kochia (*Kochia scoparia*) and Russian thistle (*Salsola kali*). About 10 days later, seeds of wheat (*Triticum aestivum*), wild oats (*Avena fatua*), cheatgrass (*Bromus secalinus*) and green foxtail (*Setaria lutescens*) were planted in the same pots. After an additional 10 days, wheat, barley, corn and sorghum were planted. Immediately after the last planting, the test chemical, dissolved in a non-phytotoxic solvent, was applied to the soil surface and the foliage of the emerged plants.

Twenty one days after treatment, all species were rated utilizing the rating system as described for Test A. The response data are summarized in Table E. It will be seen that all species are killed or seriously injured at very low rates of application of compound No. 5, regardless of whether the treatments were applied pre- or post-emergence.

TABLE E

| | Compound 5 | |
|---|---|---|
| Rate g/ha | 4 | 1 |
| Post-Emergence | | |
| Russian thistle | 10C | 10C |
| Kochia | 10C | 2G |
| Cheatgrass | 6G | 1G |
| Green foxtail | 9G,9C | 2G |
| Wild Oats | 9G | 4G |
| Volunteer Wheat | 8G,2C | 2G |
| Pre-Emergence | | |
| Wheat | 8G,8C | 4G |
| Barley | 10C | 6G |
| Corn | 4G | 1G |
| Sorghum | 10C | 5G |

What is claimed is:

1. A compound of the formula:

$$J-SO_2NHCNA \overset{W}{\underset{R}{\|}}$$

wherein J is

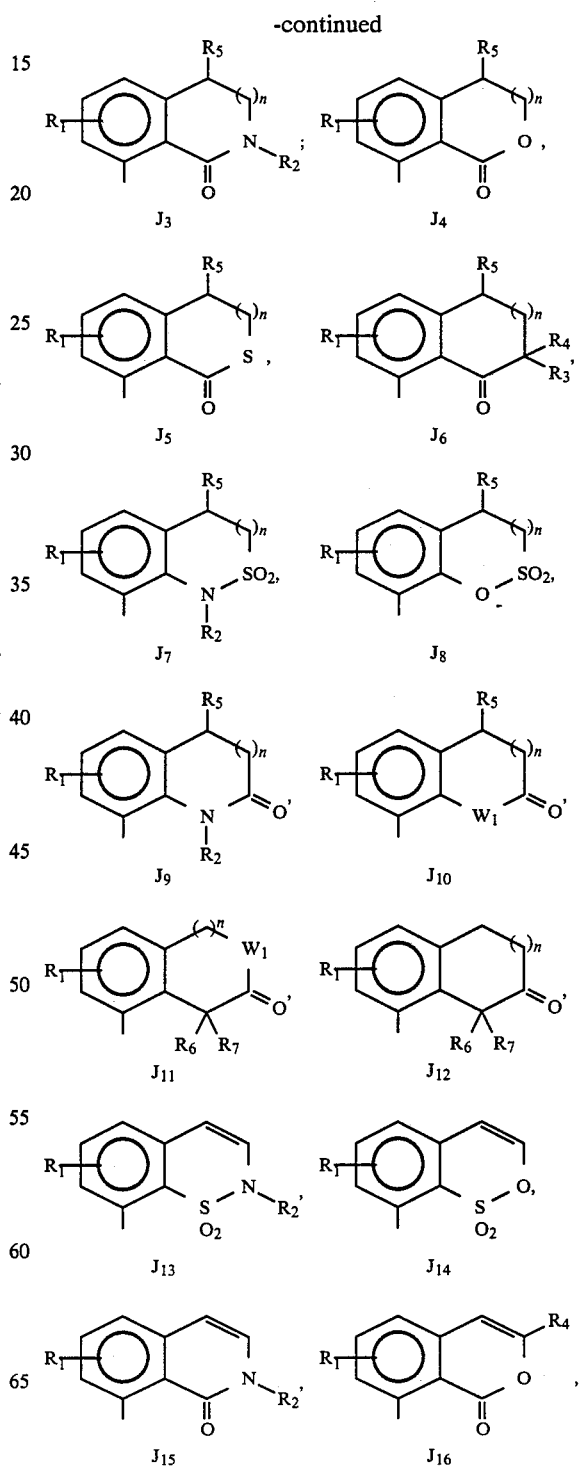

-continued

J₁₇, J₁₈, J₁₉, J₂₀, J₂₁, J₂₂, J₂₃, J₂₄, J₂₅, J₂₆ n is 0, 1 or 2
W is O or S;
W₁ is O or S;
R is H or CH₃;
R₁ is H, F, Cl, Br, CH₃, OCH₃, CF₃, SCH₃ or OCF₂H;
R₂ is H or C₁-C₄ alkyl;
R₃ and R₄ are independently H, C₁-C₄ alkyl, Cl or Br;
R₅ is H or CH₃;
R₆ is H or Ch₃;
R₇ is H or Ch₃;
A is -continued X is CH₃, OCH₃, OCH₂CH₃, Cl, F, Br, OCF₂H, CH₂F or CF₃;
Y is H, CH₃, OCH₃, OC₂H₅, CH₂OCH₃, NH₂, NHCH₃, N(CH₃)₂, C₂H₅, CF₃, SCH₃, OCH₂CH=CH₂, OCH₂C≡CH, OCH₂CF₃, CN, N₃, OCH₂CH₂OCH₃, CH₂SCH₃, CR₆(QCH₃)₂, CH₆(QCH₂CH₃)₂ or QCF₂T where Q is O or S and T is H, CHClF, CHBrF or CHFCH₃;
Z is CH, CCH₃, CC₂H₅, CCl or CBr;
Y₁ is O or CH₂;
X₁ is CH₃, OCH₃, OC₂H₅ or OCF₂H;
provided that
(a) when W is S, then R is H, A is Z is CH, and Y is CH₃, OCH₃, OC₂H₅, CH₂OCH₃, C₂H₅, CF₃, SCH₃, OCH₂CH=CH₂, OCH₂C≡CH, OCH₂CF₃, OCH₂CH₂OCH₃, CH(OCH₃)₂ or (b) the total number of carbon atoms in R₃ and R₄ is less than or equal to 4;
(c) when X is Cl, F or Br, then Z is CH and Y is OCH₃, OC₂H₅, NH₂, NHCH₃, N(CH₃)₂ or OCF₂H;
(d) when R₅ is CH₃, then n is O;
(e) when J is J₂₄, then R₄ and R₅ are not both H and R₄ is not Cl or Br;
and their agriculturally suitable salts.

2. Compounds of claim 1 where W is O, R₂ is H or C₁-C₃ alkyl, R₃ and R₄ are independently H or C₁-C₃ alkyl and R₁ is bonded to the ortho or meta position of the ring relative to the sulfonylurea moiety.

3. Compounds of claim 2 where R₁ is H, F, Cl, Br, CH₃, OCH₃, CF₃ or SCH₃; Y is CH₃, OCH₃, OC₂H₅, CH₂OCH₃, NH₂, NHCH₃, N(CH₃)₂, C₂H₅, CF₃, SCH₃, OCH₂CH=CH₂, OCH₂C≡CH, OCH₂CF₃, OCH₂CH₂OCH₃, CR₆(OCH₃)₂, CR₆(OCH₂CH₃)₂ or OCF₂H; and Z is CH.

4. Compounds of claim 3 where $R_1$ is H, $R_5$ is H, A is

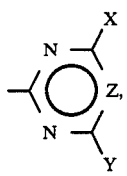

X is $CH_3$, $OCH_3$, Cl, Br, $CH_2F$ or $OCF_2H$; and Y is $CH_3$, $OCH_3$, $OC_2H_5$, $CH_2OCH_3$, $CF_3$, $OCH_2CF_3$, $CH(OCH_3)_2$,

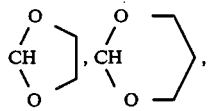

$CH(OCH_2CH_3)_2$ or $OCF_2H$.

5. Compounds of claim 4 where R is H, Y is $CH_3$ or $OCH_3$ and X is $CH_3$, $OCH_3$, Cl or Br.
6. Compounds of claim 5 where J is $J_1$.
7. Compounds of claim 5 where J is $J_2$.
8. Compounds of claim 5 where J is $J_3$.
9. Compounds of claim 5 where J is $J_4$.
10. Compounds of claim 5 where J is $J_5$.
11. Compounds of claim 5 where J is $J_6$.
12. Compounds of claim 5 where J is $J_7$.
13. Compounds of claim 5 where J is $J_8$.
14. Compounds of claim 5 where J is $J_9$.
15. Compounds of claim 5 where J is $J_{10}$.
16. Compounds of claim 5 where J is $J_{11}$.
17. Compounds of claim 5 where J is $J_{12}$.
18. Compounds of claim 5 where J is $J_{13}$.
19. Compounds of claim 5 where J is $J_{14}$.
20. Compounds of claim 5 where J is $J_{15}$.
21. Compounds of claim 5 where J is $J_{16}$.
22. Compounds of claim 5 where J is $J_{17}$.
23. Compounds of claim 5 where J is $J_{18}$.
24. Compounds of claim 5 where J is $J_{19}$.
25. Compounds of claim 5 where J is $J_{20}$.
26. Compounds of claim 5 where J is $J_{21}$.
27. Compounds of claim 5 where J is $J_{22}$.
28. Compounds of claim 5 where J is $J_{23}$.
29. Compounds of claim 5 where J is $J_{24}$.
30. Compounds of claim 5 where J is $J_{25}$.
31. Compounds of claim 5 where J is $J_{26}$.
32. The compound of claim 1 which is N-[(4,6-dimethoxypyrimidin-2-yl)aminocarbonyl]-2,3-dihydro-2-methyl-1,2-benzisothiazole-7-sulfonamide, 1,1-dioxide.
33. The compound of claim 1 which is N-[(4-methoxymethyl-6-methylpyrimidin-2-yl)aminocarbonyl]-2,3-dihydro-2-methyl-1,2-benzisothiazole-7-sulfonamide, 1,1-dioxide.
34. The compound of claim 1 which is N-[(4-chloro-6-methoxypyrimidin-2-yl)aminocarbonyl]-2,3-dihydro-2-methyl-1,2-benzisothiazole-7-sulfonamide, 1,1-dioxide.
35. The compound of claim 1 which is N-[(4-methoxy-6-methylpyrimidin-2-yl)aminocarbonyl]-2,3-dihydro-2-(1-methylethyl)-1,2-benzisothiazole-7-sulfonamide, 1,1-dioxide.
36. The compound of claim 1 which is N-[(4-methoxy-6-methylpyrimidin-2-yl)aminocarbonyl]-2,3-dihydro-2-propyl-1,2-benzisothiazole-7-sulfonamide, 1,1-dioxide.
37. The compound of claim 1 which is N-[(4,6-dimethoxypyrimidin-2-yl)aminocarbonyl]-1,3-dihydro-3-oxoisobenzofuran-4-sulfonamide.
38. The compound of claim 1 which is N-[(4-methoxy-6-methylpyrimidin-2-yl)aminocarbonyl]-1,3-dihydro-2-methyl-1-oxo-1H-isoindole-7-sulfonamide.
39. The compound of claim 1 which is N-[(4-bromo-6-methoxypyrimidin-2-yl)aminocarbonyl]-2,3-dihydro-2-methyl-1,2-benzisothiazole-7-sulfonamide, 1,1-dioxide.
40. A composition suitable for controlling the growth of undesired vegetation which comprises an effective amount of a compound of claim 1 and at least one of the following: surfactant, solid or liquid inert diluent.
41. A composition suitable for controlling the growth of undesired vegetation which comprises an effective amount of a compound of claim 2 and at least one of the following: surfactant, solid or liquid inert diluent.
42. A composition suitable for controlling the growth of undesired vegetation which comprises an effective amount of a compound of claim 3 and at least one of the following: surfactant, solid or liquid inert diluent.
43. A composition suitable for controlling the growth of undesired vegetation which comprises an effective amount of a compound of claim 4 and at least one of the following: surfactant, solid or liquid inert diluent.
44. A composition suitable for controlling the growth of undesired vegetation which, comprises an effective amount of a compound of claim 5 and at least one of the following: surfactant, solid or liquid inert diluent.
45. A composition suitable for controlling the growth of undesired vegetation which comprises an effective amount of a compound of claim 6 and at least one of the following: surfactant, solid or liquid inert diluent.
46. A composition suitable for controlling the growth of undesired vegetation which comprises an effective amount of a compound of claim 7 and at least one of the following: surfactant, solid or liquid inert diluent.
47. A composition suitable for controlling the growth of undesired vegetation which, comprises an effective amount of a compound of claim 8 and at least one of the following: surfactant, solid or liquid inert diluent.
48. A method for controlling the growth of undesired vegetation which comprises applying to the locus to be protected an effective amount of a compound of claim 1.
49. A method for controlling the growth of undesired vegetation which comprises applying to the locus to be protected an effective amount of a compound of claim 2.
50. A method for controlling the growth of undesired vegetation which comprises applying to the locus to be protected an effective amount of a compound of claim 3.
51. A method for controlling the growth of undesired vegetation which comprises applying to the locus to be protected an effective amount of a compound of claim 4.
52. A method for controlling the growth of undesired vegetation which comprises applying to the locus to be protected an effective amount of a compound of claim 5.
53. A method for controlling the growth of undesired vegetation which comprises applying to the locus to be protected an effective amount of a compound of claim 6.

54. A method for controlling the growth of undesired vegetation which comprises applying to the locus to be protected an effective amount of a compound of claim 7.

55. A method for controlling the growth of undesired vegetation which comprises applying to the locus to be protected an effective amount of a compound of claim 8.

56. The species of claim 1 which is 2-butyl-2,3-dihydro-N-[(4-methoxy-6-methylpyrimidin-2-yl)aminocarbonyl]-1,2-benzisothiazole-7-sulfonamide, 1,1-dioxide.

57. The species of claim 1 which is 2-butyl-2,3-dihydro-N-[(4,6-dimethoxyprimidin-2-yl)aminocarbonyl]-1,2-benzisothiazole-7-sulfonamide, 1,1-dioixde.

58. A compound of claim 1 which is 6-chloro-N-[(4,6-dimethoxypyrimidin-2-yl)aminocarbonyl]-3,4-dihydro-3-methyl-1-oxo-1H-2-benzopyran-8-sulfonamide.

59. The compound of claim 1 which is 2propyl-2,3-dihydro-N-[(4-chloro-6-methoxypyrimidin-2-yl)aminocarbonyl]-1,2-benzisothiazole-7-sulfonamide, 1,1-dioxide.

* * * * *